(12) United States Patent
Glossop et al.

(10) Patent No.: US 8,486,992 B2
(45) Date of Patent: Jul. 16, 2013

(54) CARBOXAMIDE DERIVATIVES AS MUSCARINIC RECEPTOR ANTAGONISTS

(75) Inventors: Paul Alan Glossop, Sandwich (GB);
Simon John Mantell, Sandwich (GB);
Anthony Wood, Sandwich (GB);
Christine Anne Louise Watson, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 206 days.

(21) Appl. No.: 12/828,732

(22) Filed: Jul. 1, 2010

(65) Prior Publication Data
US 2011/0251164 A1    Oct. 13, 2011

Related U.S. Application Data

(60) Continuation of application No. 12/556,285, filed on Sep. 9, 2009, now Pat. No. 8,268,881, which is a division of application No. 11/522,840, filed on Sep. 18, 2006, now Pat. No. 7,772,223.

(60) Provisional application No. 60/719,468, filed on Sep. 21, 2005, provisional application No. 60/719,467, filed on Sep. 21, 2005, provisional application No. 60/719,477, filed on Sep. 21, 2005.

(51) Int. Cl.
*A61K 31/40* (2006.01)
*A61K 31/423* (2006.01)
*A61K 31/445* (2006.01)

(52) U.S. Cl.
USPC .......................... 514/424; 548/541

(58) Field of Classification Search
USPC .......................... 514/424; 548/541
See application file for complete search history.

(56) References Cited

U.S. PATENT DOCUMENTS

| 2,886,574 | A | 5/1959 | Aspergren et al. | 260/326.3 |
| 4,219,559 | A | 8/1980 | Janssens et al. | 424/267 |
| 5,070,087 | A | 12/1991 | Teng et al. | 514/212.01 |
| 6,673,908 | B1 * | 1/2004 | Stanton, Jr. | 536/22.1 |
| 6,814,953 | B2 * | 11/2004 | Banerjee et al. | 424/45 |

FOREIGN PATENT DOCUMENTS

| EP | 0365093 | 4/1990 |
| EP | 0948964 | * 10/1999 |
| EP | 1325921 | 7/2003 |
| EP | 1375508 | 1/2004 |
| JP | 11100366 | 4/1999 |
| WO | WO 9709973 | 3/1997 |
| WO | WO 0187839 | 11/2001 |
| WO | WO 03053966 | 7/2003 |
| WO | WO 2004026836 | 4/2004 |

OTHER PUBLICATIONS

Herner et al. "Combined ipratropium . . . " EMBASE No. 11190774 (2000).*
Gross "The combination . . . " Regulatory focus p. 43-46 (2009).*
Nelson "Symbicort . . . " PMID 11858561 (2002).*
Cheney et al., J. Org. Chem, vol. 17, pp. 770-777, 1952.
Angeli et al., Bioorganic and Medicinal Chemistry, vol. 5, No. 4, pp. 731-737, 1997.
XP-002419978, Chemical Abstracts Service, Makosza, Mieczyslaw et al.
XP-002419977, Database Beilstein, Beilstein Insitut Zur Foerderung der Chemischen Wissenschaften, BRN 1520424, Abstract.

* cited by examiner

*Primary Examiner* — Celia Chang
(74) *Attorney, Agent, or Firm* — Lisa A. Samuels

(57) ABSTRACT

The invention relates to compounds of formula

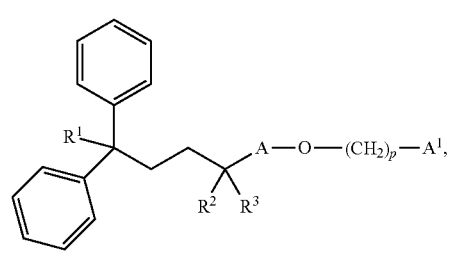

(I)

processes and intermediates for their preparation, their use as muscarinic antagonists and pharmaceutical composition containing them.

4 Claims, No Drawings

CARBOXAMIDE DERIVATIVES AS MUSCARINIC RECEPTOR ANTAGONISTS

CROSS-REFERENCE TO RELATED APPLICATIONS

This application is a continuation of U.S. application Ser. No. 12/556/285 filed Sep. 9, 2009 now U.S. Pat. No. 8,268,881 which claims priority from divisional U.S. application Ser. No. 11/522,840, filed Sep. 18, 2006 now U.S. Pat. No. 7,772,223, which claims priority from U.S. Provisional Application No. 60/719,468, filed Sep. 21, 2005; 60/719,467, filed Sep. 21, 2005; and 60/719,477, filed Sep. 21, 2005.

BACKGROUND OF THE INVENTION

Cholinergic muscarinic receptors are members of the G-protein coupled receptor super-family and are further divided into 5 subtypes, $M_1$ to $M_5$. Muscarinic receptor subtypes are widely and differentially expressed in the body. Genes have been cloned for all 5 sub-types and of these, $M_1$, $M_2$ and $M_3$ receptors have been extensively pharmacologically characterized in animal and human tissue. $M_1$ receptors are expressed in the brain (cortex and hippocampus), glands and in the ganglia of sympathetic and parasympathetic nerves. $M_2$ receptors are expressed in the heart, hindbrain, smooth muscle and in the synapses of the autonomic nervous system. $M_3$ receptors are expressed in the brain, glands and smooth muscle. In the airways, stimulation of $M_3$ receptors evokes contraction of airway smooth muscle leading to bronchoconstriction, while in the salivary gland $M_3$ receptor stimulation increases fluid and mucus secretion leading to increased salivation. $M_2$ receptors expressed on smooth muscle are understood to be pro-contractile while pre-synaptic $M_2$ receptors modulate acetylcholine release from para-sympathetic nerves. Stimulation of $M_2$ receptors expressed in the heart produces bradycardia.

Short and long-acting muscarinic antagonists are used in the management of asthma and COPD; these include the short acting agents Atrovent® (ipratropium bromide) and Oxivent® (oxitropium bromide) and the long acting agent Spiriva® (tiotropium bromide). These compounds produce bronchodilation following inhaled administration. In addition to improvements in spirometric values, anti-muscarinic use in chronic obstructive pulmonary disease (COPD) is associated with improvements in health status and quality of life scores. As a consequence of the wide distribution of muscarinic receptors in the body, significant systemic exposure to muscarinic antagonists is associated with effects such as dry mouth, constipation, mydriasis, urinary retention (all predominantly mediated via blockade of $M_3$ receptors) and tachycardia (mediated by blockade of $M_2$ receptors). A commonly reported side-effect following inhaled administration of therapeutic dose of the current, clinically used non-selective muscarinic antagonists is dry-mouth and while this is reported as only mild in intensity it does limit the dose of inhaled agent given.

Accordingly, there is still a need for improved $M_3$ receptor antagonists that would have an appropriate pharmacological profile, for example in term of potency, pharmacokinetics or duration of action. In this context, the present invention relates to novel $M_3$ receptor antagonists. In particular, there is a need for $M_3$ receptor antagonists that would have a pharmacological profile suitable for an administration by the inhalation route.

The scientific literature discloses many compounds having a muscarinic receptor antagonist activity. As a matter of example, EP0948964A1 discloses compounds of formula

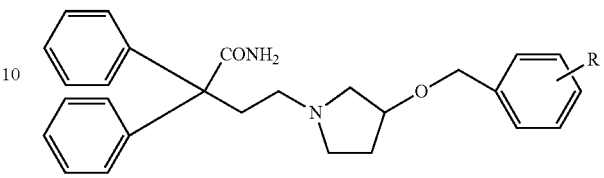

I in which R denotes a hydrogen atom, a halogen atom or a lower alkoxy group.

SUMMARY OF THE INVENTION

The invention relates to a compound of formula (I)

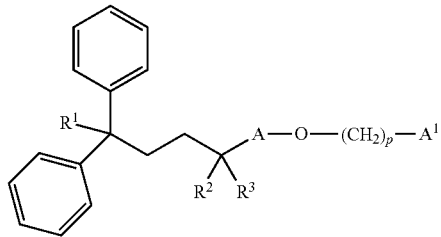

(I)

wherein, $R^1$ is CN or $CONH_2$;

A is selected from

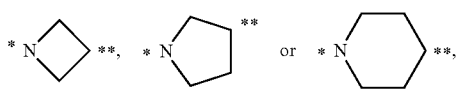

wherein * and  represent the attachment points,  being linked to the oxygen, $R^2$ and $R^3$ are methyl, or, where A is a group of formula

$R^2$ and $R^3$ may also together form with the carbon atom to which they are linked a cyclopentane ring;

p is 0 or 1;

$A^1$ is selected from a) phenyl optionally substituted with 1, 2 or 3 groups independently selected from halo, CN, $CF_3$, $OR^4$, $SR^4$, $OCF_3$, $(C_1-C_4)$alkyl and phenyl optionally substituted with OH;

b) naphthyl optionally substituted with 1 or 2 groups independently selected from halo, CN, $CF_3$, $OR^4$, $SR^4$, $OCF_3$ and $(C_1-C_4)$alkyl;

c) a 9 or 10-membered bicyclic aromatic heterocyclic group, containing from 1, 2 or 3 heteroatoms independently selected from O, S or N, said heterocyclic group being optionally substituted with 1 or 2 substituents independently selected from $OR^4$, $(C_1-C_4)$alkyl and halo;

$R^4$ is H or $(C_1-C_4)$alkyl;

or, if appropriate, the pharmaceutically acceptable salts or solvates thereof.

DETAILED DESCRIPTION OF THE INVENTION

In the here above general formula (I), $(C_1-C_4)$alkyl denote a straight-chain or branched group containing 1, 2, 3 or 4 carbon atoms. This also applies if they carry substituents or occur as substituents of other radicals, for example in O—$(C_1-C_4)$alkyl radicals, S—$(C_1-C_4)$alkyl radicals etc. . . . Examples of suitable $(C_1-C_4)$alkyl radicals are methyl, ethyl, n-propyl, iso-propyl, n-butyl, iso-butyl, sec-butyl, tert-butyl . . . . Examples of suitable O—$(C_1-C_4)$alkyl radicals are methoxy, ethoxy, n-propyloxy, iso-propyloxy, n-butyloxy, iso-butyloxy, sec-butyloxy and tert-butyloxy . . . .

Examples of 9 or 10-membered bicyclic aromatic heterocyclic group, containing from 1, 2 or 3 heteroatoms independently selected from O, S or N are indolyl, isoindolyl, quinolyl, isoquinolyl, benzofuranyl, isobenzofuranyl, benzothienyl, isobenzothienyl, quinazolyl, quinoxalyl, phthalazinyl, benzothiazolyl, benzoxazolyl, benzisothiazolyl, benzisoxazolyl, benzimidazolyl, indazolyl, benzotriazolyl, benzoxadiazolyl, benzisoxadiazolyl, benzothiadiazolyl and benzisothiadiazolyl.

Preferred 9 or 10-membered bicyclic aromatic heterocyclic groups are benzoxazolyl, benzothiazolyl, benzofuranyl, benzothienyl, isoquinolyl and quinolyl. Benzoxazolyl is particularly preferred.

Halo denotes a halogen atom selected from the group consisting of fluoro, chloro, bromo and iodo. Preferred halo groups are fluoro and chloro.

In the above compounds of formula (I) and in the intermediates useful for their preparation, the following definitions are preferred:

Preferably, $R^1$ is $CONH_2$.
Preferably, $R^4$ is H or $CH_3$.
Preferably, $A^1$ is phenyl optionally substituted with 1, 2 or 3 groups independently selected from F, Cl, $CF_3$, OH, $OCH_3$, $OCF_3$ and $CH_3$. More preferably, $A^1$ is phenyl optionally substituted with 1 or 2 groups independently selected from F, Cl, $CF_3$, OH, $OCH_3$, $OCF_3$ and $CH_3$.
Preferably, $A^1$ is naphthyl optionally substituted with OH.
Preferably, $A^1$ is benzoxazolyl.
Preferably, $R^2$ and $R^3$ are methyl.
In a preferred embodiment, p is 0.
In another preferred embodiment, p is 1.
In a preferred embodiment, the compound of formula (I) wherein A is a group of formula

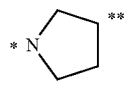

has the below (R) configuration:

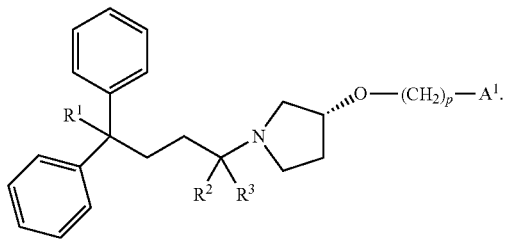

In a preferred embodiment, the compounds of formula (I) wherein A is a group of formula

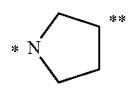

has the below (S) configuration:

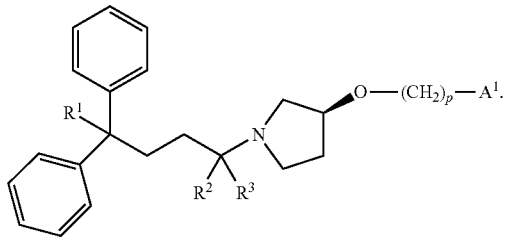

Preferred compounds according to the invention are:
5-Methyl-5-[(3S)-3-phenoxypyrrolidin-1-yl]-2,2-diphenylhexanenitrile;
5-Methyl-5-[(3S)-3-phenoxypyrrolidin-1-yl]-2,2-diphenylhexanamide;
5-Methyl-5-[(3R)-3-phenoxypyrrolidin-1-yl]-2,2-diphenylhexanenitrile;
5-Methyl-5-[(3R)-3-phenoxypyrrolidin-1-yl]-2,2-diphenylhexanamide;
5-[(3S)-3-(3-Methoxyphenoxy)pyrrolidin-1-yl]-5-methyl-2,2-diphenylhexanenitrile;
5-[(3S)-3-(3-methoxyphenoxy)pyrrolidin-1-yl]-5-methyl-2,2-diphenylhexanamide;
5-[(3S)-3-(3-Hydroxyphenoxy)pyrrolidin-1-yl]-5-methyl-2,2-diphenylhexanamide;
5-[(3R)-3-(Benzyloxy)pyrrolidin-1-yl]-5-methyl-2,2-diphenylhexanenitrile;
5-[(3R)-3-(Benzyloxy)pyrrolidin-1-yl]-5-methyl-2,2-diphenylhexanamide;
5-[(3S)-3-(Benzyloxy)pyrrolidin-1-yl]-5-methyl-2,2-diphenylhexanenitrile;
5-[(3S)-3-(Benzyloxy)pyrrolidin-1-yl]-5-methyl-2,2-diphenylhexanamide;
5-[(3R)-3-(3-Methoxyphenoxy)pyrrolidin-1-yl]-5-methyl-2,2-diphenylhexanamide;
5-[(3R)-3-(3-Hydroxyphenoxy)pyrrolidin-1-yl]-5-methyl-2,2-diphenylhexanamide;
5-Methyl-5-[(3S)-3-(3-methylphenoxy)pyrrolidin-1-yl]-2,2-diphenylhexanamide;
5-[(3R)-3-(1,3-Benzoxazol-6-yloxy)pyrrolidin-1-yl]-5-methyl-2,2-diphenylhexanamide;
5-[(3S)-3-(4-Chlorophenoxy)pyrrolidin-1-yl]-5-methyl-2,2-diphenylhexanamide;

5-[(3S)-3-(3-Bromophenoxy)pyrrolidin-1-yl]-5-methyl-2,2-diphenylhexanamide;
5-{(3S)-3-[(3'-Hydroxybiphenyl-4-yl)oxy]pyrrolidin-1-yl}-5-methyl-2,2-diphenylhexanamide;
5-{(3S)-3-[(3'-Hydroxybiphenyl-3-yl)oxy]pyrrolidin-1-yl}-5-methyl-2,2-diphenylhexanamide;
5-{(3S)-3-[(6-Hydroxy-2-naphthyl)oxy]pyrrolidin-1-yl}-5-methyl-2,2-diphenylhexanamide;
5-[(3S)-3-(2-Hydroxyphenoxy)pyrrolidin-1-yl]-5-methyl-2,2-diphenylhexanamide;
5-[(3S)-3-(4-methoxyphenoxy)pyrrolidin-1-yl]-5-methyl-2,2-diphenylhexanamide;
5-[(3S)-3-(4-hydroxyphenoxy)pyrrolidin-1-yl]-5-methyl-2,2-diphenylhexanamide;
5-[(3S)-3-(4-trifluoromethyl-phenoxy)pyrrolidin-1-yl]-5-methyl-2,2-diphenylhexanamide;
5-[(3R)-3-(4-Trifluoromethyl-phenoxy)pyrrolidin-1-yl]-5-methyl-2,2 diphenylhexanenitrile;
5-[(3R)-3-(4-trifluoromethyl-phenoxy)pyrrolidin-1-yl]-5-methyl-2,2-diphenylhexanamide;
5-[(3R)-3-(3-chloro-4-methoxy-phenoxy)pyrrolidin-1-yl]-5-methyl-2,2-diphenylhexanenitrile;
5-[(3R)-3-(3-chloro-4-methoxy-phenoxy)pyrrolidin-1-yl]-5-methyl-2,2-diphenylhexanamide;
5-[(3S)-3-(3-Hydroxy-5-methyl-phenoxy)-pyrrolidin-1-yl]-5-methyl-2,2-diphenyl-hexanoic acid amide;
5-[(3S)-3-(3-Hydroxy-2-methyl-phenoxy)-pyrrolidin-1-yl]-5-methyl-2,2-diphenyl-hexanoic acid amide;
5-[(3S)-3-(2,4-Dichloro-5-Hydroxy-phenoxy)-pyrrolidin-1-yl]-5-methyl-2,2-diphenyl-hexanoic acid amide;
5-[(3S)-3-(4,5-Dichloro-2-Hydroxy-phenoxy)-pyrrolidin-1-yl]-5-methyl-2,2-diphenyl-hexanoic acid amide;
5-[(3S)-3-(3-Chloro-5-methoxy-phenoxy)-pyrrolidin-1-yl]-5-methyl-2,2-diphenyl-hexanoic acid amide;
5-[(3S)-3-(3-Chloro-5-hydroxy-phenoxy)-pyrrolidin-1-yl]-5-methyl-2,2-diphenyl-hexanoic acid amide;
5-[(3S)-3-(4-Chloro-2-Methoxy-phenoxy)-pyrrolidin-1-yl]-5-methyl-2,2-diphenyl-hexanoic acid amide;
5-[(3S)-3-(4-Chloro-2-Hydroxy-phenoxy)-pyrrolidin-1-yl]-5-methyl-2,2-diphenyl-hexanoic acid amide;
5-[(3S)-3-(2-Chloro-3-Methoxy-phenoxy)-pyrrolidin-1-yl]-5-methyl-2,2-diphenyl-hexanoic acid amide;
5-[(3S)-3-(2-Chloro-3-Hydroxy-phenoxy)-pyrrolidin-1-yl]-5-methyl-2,2-diphenyl-hexanoic acid amide;
5-[(3S)-3-(4-Chloro-3-Hydroxy-phenoxy)-pyrrolidin-1-yl]-5-methyl-2,2-diphenyl-hexanoic acid amide;
5-[(3S)-3-(2-Chloro-5-Hydroxy-phenoxy)-pyrrolidin-1-yl]-5-methyl-2,2-diphenyl-hexanoic acid amide;
5-[(3R)-3-(3-Chloro-2-Methoxy-phenoxy)-pyrrolidin-1-yl]-5-methyl-2,2-diphenyl-hexanenitrile;
5-[(3R)-3-(3-Chloro-2-Methoxy-phenoxy)-pyrrolidin-1-yl]-5-methyl-2,2-diphenyl-hexanoic acid amide;
5-[(3R)-3-(3-Chloro-2-Hydroxy-phenoxy)-pyrrolidin-1-yl]-5-methyl-2,2-diphenyl-hexanoic acid amide;
5-[(3S)-3-(3-Hydroxy-2,5-dimethyl-phenoxy)-pyrrolidin-1-yl]-5-methyl-2,2-diphenyl-hexanoic acid amide;
5-[(3S)-3-(3-Fluoro-5-Methoxy-phenoxy)-pyrrolidin-1-yl]-5-methyl-2,2-diphenyl-hexanoic acid amide;
5-[(3S)-3-(3-Fluoro-5-Hydroxy-phenoxy)-pyrrolidin-1-yl]-5-methyl-2,2-diphenyl-hexanoic acid amide;
5-[(3R)-3-(3-Methoxy-5-trifluoromethyl-phenoxy)-pyrrolidin-1-yl]-5-methyl-2,2-diphenyl-hexanenitrile;
5-[(3R)-3-(3-Methoxy-5-trifluoromethyl-phenoxy)-pyrrolidin-1-yl]-5-methyl-2,2-diphenyl-hexanoic acid amide;
5-[(3R)-3-(3-Hydroxy-5-trifluoromethyl-phenoxy)-pyrrolidin-1-yl]-5-methyl-2,2-diphenyl-hexanoic acid amide;
5-[(3S)-3-(4-Fluoro-3-Methoxy-phenoxy)-pyrrolidin-1-yl]-5-methyl-2,2-diphenyl-hexanoic acid amide;
5-[(3S)-3-(2-Fluoro-3-Methoxy-phenoxy)-pyrrolidin-1-yl]-5-methyl-2,2-diphenyl-hexanoic acid amide;
5-[(3S)-3-(4-Fluoro-3-Hydroxy-phenoxy)-pyrrolidin-1-yl]-5-methyl-2,2-diphenyl-hexanoic acid amide;
5-[(3S)-3-(2-Fluoro-3-Hydroxy-phenoxy)-pyrrolidin-1-yl]-5-methyl-2,2-diphenyl-hexanoic acid amide;
5-[(3R)-3-(3-Hydroxy-benzyloxy)-pyrrolidin-1-yl]-5-methyl-2,2-diphenyl-hexanoic acid amide;
5-{(3S)-3-[(3-Bromobenzyl)oxy]pyrrolidin-1-yl}-5-methyl-2,2-diphenylhexanenitrile;
5-{(3S)-3-[(3'-Hydroxybiphenyl-3-yl)methoxy]pyrrolidin-1-yl}-5-methyl-2,2-diphenylhexanenitrile;
5-[(3S)-3-(Biphenyl-3-ylmethoxy)pyrrolidin-1-yl]-5-methyl-2,2-diphenylhexanenitrile;
5-{(3S)-3-[(2'-Hydroxybiphenyl-3-yl)methoxy]pyrrolidin-1-yl}-5-methyl-2,2-diphenylhexanenitrile;
5-{(3S)-3-[(4-Bromobenzyl)oxy]pyrrolidin-1-yl}-5-methyl-2,2-diphenylhexanenitrile;
5-{(3S)-3-[(3'-Hydroxybiphenyl-4-yl)methoxy]pyrrolidin-1-yl}-5-methyl-2,2-diphenylhexanenitrile;
5-{(3S)-3-[(3'-Hydroxybiphenyl-3-yl)methoxy]pyrrolidin-1-yl}-5-methyl-2,2-diphenylhexanamide;
5-{(3S)-3-[(4'-Hydroxybiphenyl-3-yl)methoxy]pyrrolidin-1-yl}-5-methyl-2,2-diphenylhexanenitrile;
5-{(3S)-3-[(4'-Hydroxybiphenyl-3-yl)methoxy]pyrrolidin-1-yl}-5-methyl-2,2-diphenylhexanamide;
5-{(3S)-3-[(2'-Hydroxybiphenyl-3-yl)methoxy]pyrrolidin-1-yl}-5-methyl-2,2-diphenylhexanamide;
5-{(3S)-3-[(3'-Hydroxybiphenyl-4-yl)methoxy]pyrrolidin-1-yl}-5-methyl-2,2-diphenylhexanamide;
5-[(3S)-3-(Biphenyl-3-ylmethoxy)pyrrolidin-1-yl]-5-methyl-2,2-diphenylhexanamide;
5-[(3R)-3-(4-Fluoro-3-hydroxy-benzyloxy)-pyrrolidin-1-yl]-5-methyl-2,2-diphenylhexanamide;
5-[(3S)-3-(3-Cyano-5-hydroxy-phenoxy)-pyrrolidin-1-yl]-5-methyl-2,2-diphenylhexanamide;
5-[(3S)-3-(2-Cyano-5-methoxy-phenoxy)-pyrrolidin-1-yl]-5-methyl-2,2-diphenylhexanamide;
5-{(3S)-3-[(7-Hydroxy-2-naphthyl)oxy]pyrrolidin-1-yl}-5-methyl-2,2-diphenylhexanamide;
5-[(3S)-3-(4-Phenylphenoxy)pyrrolidin-1-yl]-5-methyl-2,2-diphenylhexanamide;
5-[(3R)-3-(3-chloro-4-hydroxyphenoxy)pyrrolidin-1-yl]-5-methyl-2,2-diphenylhexanamide;
5-[(3R)-3-(3-Fluoro-5-methoxy-phenoxy)-pyrrolidin-1-yl]-5-methyl-2,2-diphenylhexanamide;
5-[(3R)-3-(3-Fluoro-5-hydroxy-phenoxy)-pyrrolidin-1-yl]-5-methyl-2,2-diphenyl-hexanamide;
5-[(3R)-3-(2-Fluoro-3-methoxy-phenoxy)-pyrrolidin-1-yl]-5-methyl-2,2-diphenylhexanamide;
5-[(3R)-3-(2-Fluoro-3-hydroxy-phenoxy)-pyrrolidin-1-yl]-5-methyl-2,2-diphenylhexanamide;
5-[(3R)-3-(2-Chloro-3-methoxy-phenoxy)-pyrrolidin-1-yl]-5-methyl-2,2-diphenylhexanamide;
5-[(3R)-3-(2-Chloro-3-hydroxy-phenoxy)-pyrrolidin-1-yl]-5-methyl-2,2-diphenylhexanamide;
5-[(3R)-3-(4-Chloro-3-hydroxy-benzyloxy)-pyrrolidin-1-yl]-5-methyl-2,2-diphenylhexanamide;
5-[(3R)-3-(3-methoxy-4-chloro-phenoxy)pyrrolidin-1-yl]-5-methyl-2,2-diphenylhexanenitrile;
5-[(3R)-3-(3-methoxy-4-chloro-phenoxy)pyrrolidin-1-yl]-5-methyl-2,2-diphenylhexanamide;
5-[(3R)-3-(3-hydroxy-4-chloro-phenoxy)pyrrolidin-1-yl]-5-methyl-2,2-diphenylhexanamide;

5-[(3R)-3-(3-hydroxy-4-cyano-phenoxy)-pyrrolidin-1-yl]-5-methyl-2,2-diphenylhexanamide;
5-[(3S)-3-(3-methoxy-benzyloxy)pyrrolidin-1-yl]-5-methyl-2,2-diphenylhexanamide;
5-[(3R)-3-(2-Chloro-3-hydroxy-benzyloxy)-pyrrolidin-1-yl]-5-methyl-2,2-diphenylhexanamide;
5-Methyl-5-(4-phenoxypiperidin-1-yl)-2,2-diphenylhexanenitrile;
5-{4-[(3-Bromobenzyl)oxy]piperidin-1-yl}-5-methyl-2,2-diphenylhexanenitrile;
5-{4-[(3-Hydroxybenzyl)oxy]piperidin-1-yl}-5-methyl-2,2-diphenylhexanenitrile;
5-[4-(Benzyloxy)piperidin-1-yl]-5-methyl-2,2-diphenylhexanenitrile;
5-Methyl-5-(4-phenoxypiperidin-1-yl)-2,2-diphenylhexanamide;
5-{4-[(3-Bromobenzyl)oxy]piperidin-1-yl}-5-methyl-2,2-diphenylhexanamide;
5-[4-(Benzyloxy)piperidin-1-yl]-5-methyl-2,2-diphenylhexanamide;
5-[4-(2,4-Dichloro-5-hydroxy-phenoxy)-piperidin-1-yl]-5-methyl-2,2-diphenylhexanoic acid amide;
5-[4-(4-Cyano-2,5-difluoro-phenoxy)-piperidin-1-yl]-5-methyl-2,2-diphenylhexanoic acid amide;
5-[4-(3-hydroxyphenoxy)piperidin-1-yl]-5-methyl-2,2-diphenylhexanamide;
5-[4-(3-hydroxy-2-methylphenoxy)piperidin-1-yl]-5-methyl-2,2-diphenylhexanamide;
5-{4-[(3'-hydroxybiphenyl-3-yl)methoxy]piperidin-1-yl}-5-methyl-2,2-diphenylhexanenitrile;
5-{4-[(3'-hydroxybiphenyl-3-yl)methoxy]piperidin-1-yl}-5-methyl-2,2-diphenylhexanamide;
5-[3-(3-Methoxyphenoxy)azetidin-1-yl]-5-methyl-2,2-diphenylhexanenitrile;
5-[3-(3-Methoxyphenoxy)azetidin-1-yl]-5-methyl-2,2-diphenylhexanamide;
5-[3-(Benzyloxy)azetidin-1-yl]-5-methyl-2,2-diphenylhexanenitrile;
5-[3-(Benzyloxy)azetidin-1-yl]-5-methyl-2,2-diphenylhexanamide;
5-Methyl-5-(3-phenoxyazetidin-1-yl)-2,2-diphenylhexanenitrile;
5-Methyl-5-(3-phenoxyazetidin-1-yl)-2,2-diphenylhexanamide;
5-[3-(4-Methoxyphenoxy)azetidin-1-yl]-5-methyl-2,2-diphenylhexanenitrile;
5-[3-(4-Methoxyphenoxy)azetidin-1-yl]-5-methyl-2,2-diphenylhexanamide;
5-[3-(4-hydroxyphenoxy)azetidin-1-yl]-5-methyl-2,2-diphenylhexanamide;
5-[3-(3-Hydroxyphenoxy)azetidin-1-yl]-5-methyl-2,2-diphenylhexanamide;
5-[3-(2-Hydroxyphenoxy)azetidin-1-yl]-5-methyl-2,2-diphenylhexanamide;
5-{3-(2,4-Dichloro-5-hydroxy-phenoxy)-azetidin-1-yl}-5-methyl-2,2-diphenylhexanamide;
5-{3-(4,5-Dichloro-2-hydroxy-phenoxy)-azetidin-1-yl}-5-methyl-2,2-diphenylhexanamide;
5-[3-(4-Chloro-3-methoxy-phenoxy)-azetidin-1-yl]-5-methyl-2,2-diphenyl-hexanenitrile;
5-{3-(4-Chloro-3-methoxy-phenoxy)-azetidin-1-yl]-5-methyl-2,2-diphenylhexanamide;
5-{3-(4-Chloro-3-hydroxy-p henoxy)-azetidin-1-yl}-5-methyl-2,2-diphenylhexanamide;
5-[3-(3-Hydroxy-benzyloxy)-azetidin-1-yl]-5-methyl-2,2-diphenyl-hexanoic acid amide;
5-[3-(2-Chloro-5-methoxy-phenoxy)-azetidin-1-yl]-5-methyl-2,2-diphenyl-hexanenitrile;
5-[3-(2-Chloro-5-methoxy-phenoxy)-azetidin-1-yl]-5-methyl-2,2-diphenyl-hexanoic acid amide;
5-[3-(2-Chloro-5-hydroxy-phenoxy)-azetidin-1-yl]-5-methyl-2,2-diphenyl-hexanoic acid amide;
5-[3-(3-Fluoro-5-methoxy-phenoxy)-azetidin-1-yl]-5-methyl-2,2-diphenyl-hexanenitrile;
5-[3-(3-Fluoro-5-methoxy-phenoxy)-azetidin-1-yl]-5-methyl-2,2-diphenyl-hexanamide;
5-{3-(3-Fluoro-5-hydroxy-phenoxy)-azetidin-1-yl}-5-methyl-2,2-diphenyl-hexanamide;
5-[3-(3-Chloro-5-methoxy-phenoxy)-azetidin-1-yl]-5-methyl-2,2-diphenyl-hexanenitrile;
5-[3-(3-Chloro-5-methoxy-phenoxy)-azetidin-1-yl]-5-methyl-2,2-diphenyl-hexanamide;
5-{3-(3-Chloro-5-hydroxy-p henoxy)-azetidin-1-yl}-5-methyl-2,2-diphenyl-hexanamide;
5-[3-(4-Fluoro-2-methoxy-phenoxy)-azetidin-1-yl]-5-methyl-2,2-diphenyl-hexanenitrile;
5-[3-(4-Fluoro-2-methoxy-phenoxy)-azetidin-1-yl]-5-methyl-2,2-diphenyl-hexanamide;
5-{3-(4-Fluoro-2-hydroxy-phenoxy)-azetidin-1-yl}-5-methyl-2,2-diphenyl-hexanamide;
5-[3-(2,6-Dichloro-3-hydroxy-benzyloxy)-azetidin-1-yl]-5-methyl-2,2-diphenyl-hexanoic acid amide;
4-{1-[3-(3-Methoxy-phenoxy)-azetidin-1-yl]-cyclopentyl}-2,2-diphenyl-butyronitrile;
4-{1-[3-(3-Methoxy-phenoxy)-azetidin-1-yl]-cyclopentyl}-2,2-diphenyl-butyramide;
4-{1-[3-(3-Hydroxy-phenoxy)-azetidin-1-yl]-cyclopentyl}-2,2-diphenyl-butyramide;
5-[3-(2-Fluoro-3-methoxy-phenoxy)-azetidin-1-yl]-5-methyl-2,2-diphenyl-hexanenitrile;
5-[3-(2-Fluoro-3-methoxy-phenoxy)-azetidin-1-yl]-5-methyl-2,2-diphenyl-hexanoic acid amide;
5-[3-(2-Fluoro-3-hydroxy-phenoxy)-azetidin-1-yl]-5-methyl-2,2-diphenyl-hexanoic acid amide;
5-[3-(2-Fluoro-5-methoxy-phenoxy)-azetidin-1-yl]-5-methyl-2,2-diphenyl-hexanenitrile;
5-[3-(2-Fluoro-5-methoxy-phenoxy)-azetidin-1-yl]-5-methyl-2,2-diphenyl-hexanoic acid amide;
5-[3-(2-Fluoro-5-hydroxy-phenoxy)-azetidin-1-yl]-5-methyl-2,2-diphenyl-hexanoic acid amide;
5-[3-(4-Chloro-3-hydroxy-benzyloxy)-azetidin-1-yl]-5-methyl-2,2-diphenyl-hexanoic acid amide;
4-{1-[3-(4-Chloro-3-hydroxy-phenoxy)-azetidin-1-yl]-cyclopentyl}-2,2-diphenyl-butyramide;
5-[3-(3-Bromo-5-methoxy-phenoxy)-azetidin-1-yl]-5-methyl-2,2-diphenyl-hexanenitrile;
5-[3-(3-Bromo-5-methoxy-phenoxy)-azetidin-1-yl]-5-methyl-2,2-diphenyl-hexanoic acid amide;
5-[3-(3-Bromo-5-hydroxy-phenoxy)-azetidin-1-yl]-5-methyl-2,2-diphenyl-hexanoic acid amide;
4-{1-[3-(3-Fluoro-4-methoxy-phenoxy)-azetidin-1-yl]-cyclopentyl}-2,2-diphenyl-butyronitrile;
4-{1-[3-(3-Fluoro-4-methoxy-phenoxy)-azetidin-1-yl]-cyclopentyl}-2,2-diphenyl-butyramide;
4-{1-[3-(3-Fluoro-4-hydroxy-phenoxy)-azetidin-1-yl]-cyclopentyl}-2,2-diphenyl-butyramide;
5-[3-(3-Chloro-4-hydroxy-benzyloxy)-azetidin-1-yl]-5-methyl-2,2-diphenyl-hexanoic acid amide;
5-[3-(4-Chloro-2-hydroxy-benzyloxy)-azetidin-1-yl]-5-methyl-2,2-diphenyl-hexanoic acid amide;
5-[3-(2-Chloro-3-hydroxy-benzyloxy)-azetidin-1-yl]-5-methyl-2,2-diphenyl-hexanoic acid amide;

5-[3-(3,5-Dihydroxy-phenoxy)-azetidin-1-yl]-5-methyl-2,2-diphenyl-hexanoic acid amide;
5-[3-(3-Hydroxy-phenoxy)-azetidin-1-yl]-5-methyl-2,2-diphenyl-hexanenitrile;
5-{3-[(4-Hydroxybenzyl)oxy]azetidin-1-yl}-5-methyl-2,2-diphenylhexanenitrile; and,
5-[3-(4-Hydroxy-benzyloxy)-azetidin-1-yl]-5-methyl-2,2-diphenyl-hexanoic acid amide.

More preferred compounds are:
5-Methyl-5-[(3S)-3-phenoxypyrrolidin-1-yl]-2,2-diphenyl-hexanamide;
5-Methyl-5-[(3R)-3-phenoxypyrrolidin-1-yl]-2,2-diphenyl-hexanamide;
5-[(3S)-3-(3-Hydroxyphenoxy)pyrrolidin-1-yl]-5-methyl-2,2-diphenylhexanamide;
5-[(3R)-3-(3-Hydroxyphenoxy)pyrrolidin-1-yl]-5-methyl-2,2-diphenylhexanamide;
5-[(3S)-3-(3-Fluoro-5-Hydroxy-phenoxy)-pyrrolidin-1-yl]-5-methyl-2,2-diphenyl-hexanoic acid amide;
5-[(3S)-3-(2-Fluoro-3-Hydroxy-phenoxy)-pyrrolidin-1-yl]-5-methyl-2,2-diphenyl-hexanoic acid amide;
5-[(3R)-3-(2-Fluoro-3-hydroxy-phenoxy)-pyrrolidin-1-yl]-5-methyl-2,2-diphenylhexanamide;
5-[(3R)-3-(2-Chloro-3-hydroxy-phenoxy)-pyrrolidin-1-yl]-5-methyl-2,2-diphenylhexanamide;
5-Methyl-5-(4-phenoxypiperidin-1-yl)-2,2-diphenylhexanamide;
5-[4-(3-hydroxyphenoxy)piperidin-1-yl]-5-methyl-2,2-diphenylhexanamide;
5-Methyl-5-(3-phenoxyazetidin-1-yl)-2,2-diphenylhexanamide;
5-[3-(3-Hydroxyphenoxy)azetidin-1-yl]-5-methyl-2,2-diphenylhexanamide;
5-{3-(4-Chloro-3-hydroxy-p henoxy)-azetidin-1-yl}-5-methyl-2,2-diphenylhexanamide;
5-{3-(3-Fluoro-5-hydroxy-phenoxy)-azetidin-1-yl}-5-methyl-2,2-diphenylhexanamide;
5-{3-(3-Chloro-5-hydroxy-p henoxy)-azetidin-1-yl}-5-methyl-2,2-diphenylhexanamide;
4-{1-[3-(3-Hydroxy-phenoxy)-azetidin-1-yl]-cyclopentyl}-2,2-diphenyl-butyramide;
5-[3-(2-Fluoro-3-hydroxy-phenoxy)-azetidin-1-yl]-5-methyl-2,2-diphenyl-hexanoic acid amide;
5-[3-(2-Fluoro-5-hydroxy-phenoxy)-azetidin-1-yl]-5-methyl-2,2-diphenyl-hexanoic acid amide; and,
5-[3-(4-Chloro-3-hydroxy-benzyloxy)-azetidin-1-yl]-5-methyl-2,2-diphenyl-hexanoic acid amide.

Most preferred compounds are:
5-[(3S)-3-(3-Hydroxyphenoxy)pyrrolidin-1-yl]-5-methyl-2,2-diphenylhexanamide;
5-[(3R)-3-(3-Hydroxyphenoxy)pyrrolidin-1-yl]-5-methyl-2,2-diphenylhexanamide;
5-[(3R)-3-(2-Fluoro-3-hydroxy-phenoxy)-pyrrolidin-1-yl]-5-methyl-2,2-diphenylhexanamide;
5-[3-(3-Hydroxyphenoxy)azetidin-1-yl]-5-methyl-2,2-diphenylhexanamide;
5-{3-(4-Chloro-3-hydroxy-p henoxy)-azetidin-1-yl}-5-methyl-2,2-diphenylhexanamide;
5-{3-(3-Fluoro-5-hydroxy-phenoxy)-azetidin-1-yl}-5-methyl-2,2-diphenylhexanamide;
5-{3-(3-Chloro-5-hydroxy-p henoxy)-azetidin-1-yl}-5-methyl-2,2-diphenylhexanamide;
4-{1-[3-(3-Hydroxy-phenoxy)-azetidin-1-yl]-cyclopentyl}-2,2-diphenyl-butyramide;
5-[3-(2-Fluoro-3-hydroxy-phenoxy)-azetidin-1-yl]-5-methyl-2,2-diphenyl-hexanoic acid amide;
5-[3-(2-Fluoro-5-hydroxy-phenoxy)-azetidin-1-yl]-5-methyl-2,2-diphenyl-hexanoic acid amide; and,
5-[3-(4-Chloro-3-hydroxy-benzyloxy)-azetidin-1-yl]-5-methyl-2,2-diphenyl-hexanoic acid amide.

The invention also relates to processes for the preparation of the compounds of formula (I) as well as intermediates useful for their preparation. In particular, the invention relates to the below intermediates:

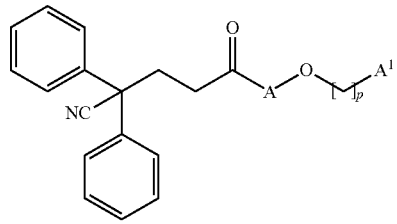

(1)

wherein A, p and $A^1$ are as defined in compounds of formula (I);

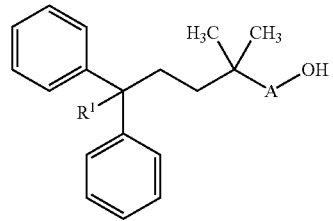

(2)

wherein A and $R^1$ are as defined in compounds of formula (I);

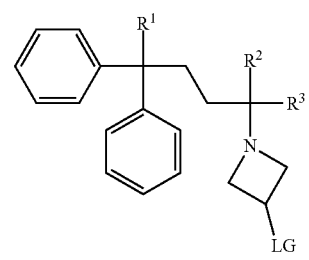

(3)

wherein $R^1$, $R^2$ and $R^3$ are as defined in compounds of formula (I) and LG is a suitable leaving group such as mesylate or tosylate;

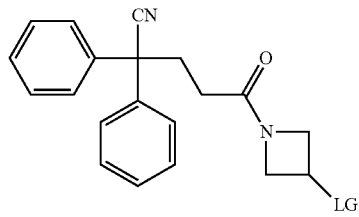

(XXIV)

wherein LG is a suitable leaving group such as mesylate or tosylate; and,

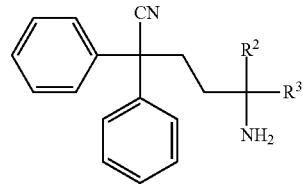

(XVII)

wherein $R^2$ and $R^3$ are as defined in compounds of formula (I).

Compound of formula (I) may be prepared in a variety of ways. The routes below illustrate one such way of preparing these compounds; the skilled person will appreciate that other routes may be equally as practicable.

Compounds of formula (I) where A is

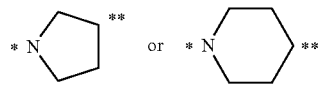 [SMILES: C1CCNC1 ; C1CCNCC1]

may be prepared according to the routes disclosed below:

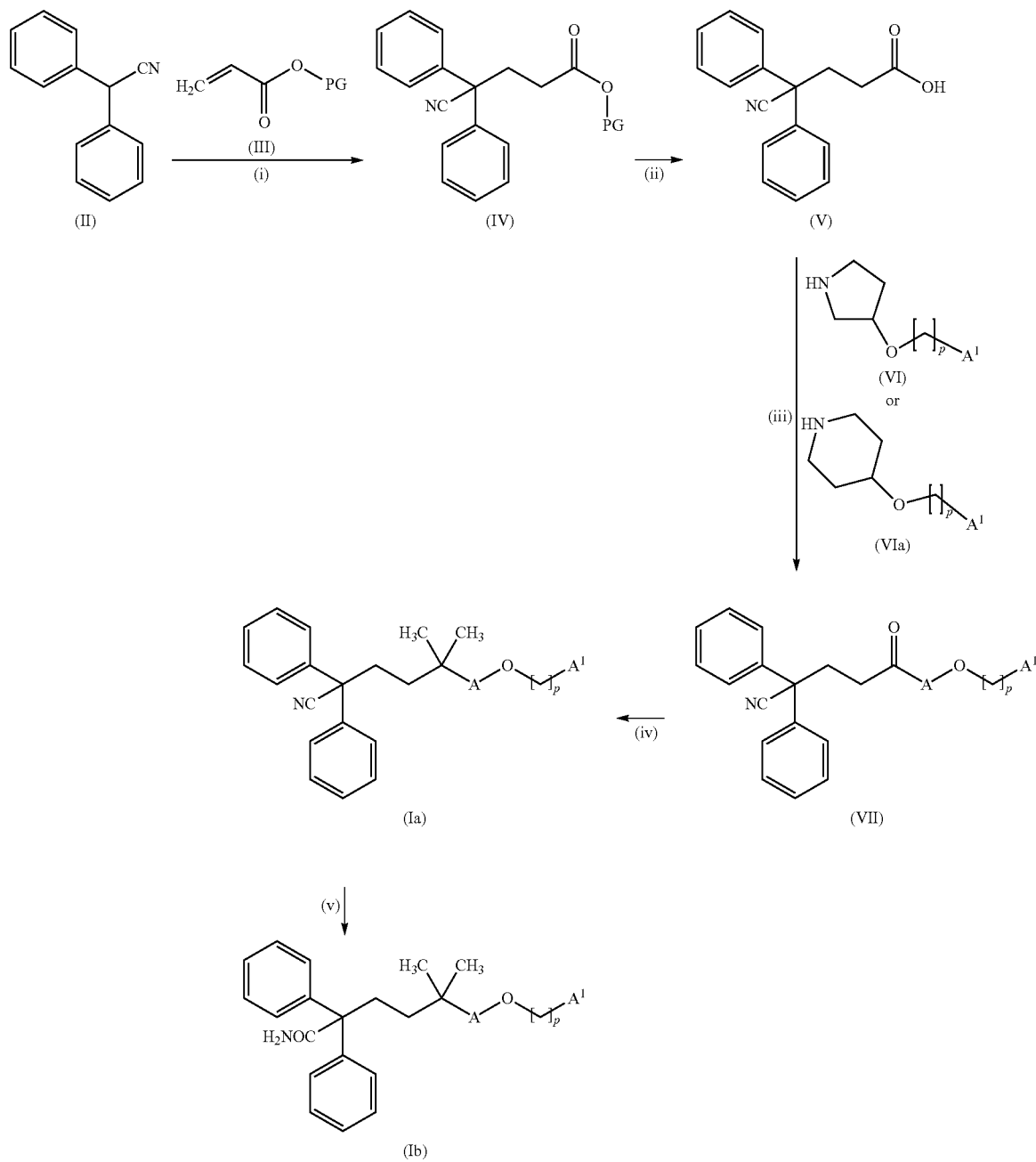

Wherein A is

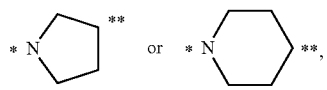 [SMILES: C1CCNC1 ; C1CCNCC1]

A¹ and p are as defined above for the compounds of formula (I), and,
PG is a suitable carboxyl-protecting group such as methyl or tert-butyl and is typically tert-butyl.

Compound of formula (II) is commercially available.

Compounds of formula (III) are either commercially available or their preparation is known from the literature.

Compounds of formula (IV) may be prepared from compounds of formula (II) and (III) by process step (i): compound (II) is treated with compound (III) in the presence of a suitable base such as potassium hydroxide or sodium hydroxide, in a suitable solvent such as methanol, ethanol or tert-butanol, at a temperature between 25° C. and elevated temperature for 6-24 hours. Typical conditions comprise of 1.0 equivalent of compound (II), 0.05 eq of potassium hydroxide and 1.0 equivalent of compound (III) in tert-butanol at a temperature between 25-60° C. for up to 24 hours.

Compounds of formula (V) may be prepared from compounds of formula (IV) by process step (ii). De-protection of compound (IV) may be achieved using standard methodology as described in "Protecting Groups in Organic Synthesis" by T. W. Greene and P. Wutz. When PG is tert butyl, typical conditions comprise of 1.0 equivalent of compound (IV) in the presence of hydrochloric acid (4M in dioxan), in dichloromethane, at room temperature for up to 18 hours.

Compound of formula (VI) may be prepared as described in scheme 2:

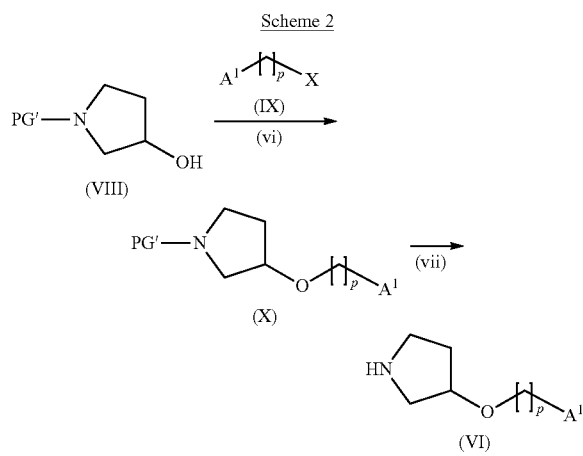

Compounds of formula (VIa) are either commercially available or can be prepared as described in scheme 2a

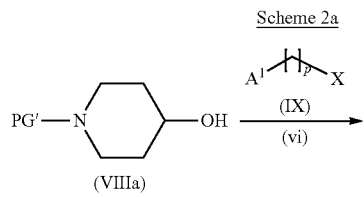

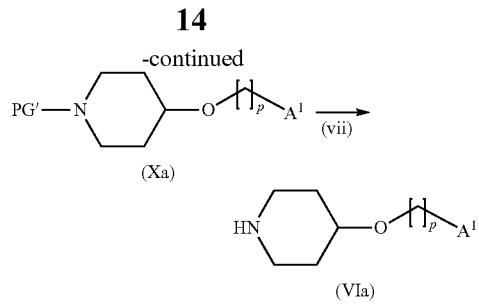

wherein A¹ and p are as defined above for the compounds of formula (I). In some cases, A¹ may be protected with a suitable protecting group. For example, when A¹ contains a phenol, it may be protected by a suitable hydroxyl protecting group.

PG' is a suitable amino protecting group such as tertbutoxycarbonyl (BOC), benzyloxycarbonyl (CBz) and is typically BOC.

X is a suitable functional group such as hydroxy, fluoro, bromo, chloro, iodo, O-mesylate or O-tosylate and is typically hydroxy or bromo.

When PG' is BOC, compounds of formula (VIII) and (VIIIa) are commercially available.

Compounds of general formula (IX) are either commercially available, known in the literature, or may be prepared as illustrated in schemes 3-5.

Scheme 3

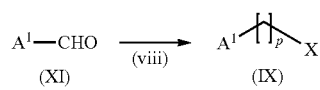

wherein A¹ is as defined above for the compounds of formula (I) or may be optionally protected.

Compounds of formula (IX) where A¹ is as defined for compounds of formula (I), p is 0 and X is OH, may be prepared from compounds of formula (XI) by Baeyer-Villiger oxidation and subsequent hydrolysis (process step (viii)). Typical conditions comprise reaction of 1.0 equivalent of compound (XI) with 3.0 equivalents of 3-chloroperoxybenzoic acid, in a suitable solvent such as dichloromethane, at room temperature for 18 hours, and subsequent treatment of this product with a suitable base such as triethylamine, in a suitable solvent such as methanol, at room temperature for 18 hrs.

Scheme 4

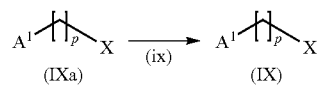

Compounds of formula (IX) where A¹ contains a suitably protected phenol, p is 0 and X is OH may be prepared from compounds of formula (IXa) where A¹ contains a phenol, p is 0 and X is OH, by addition of a suitable phenol protecting group such as benzyl, by process step (ix). Typical conditions comprise reaction of 1.0 equivalent of compound (IXa) with 1.0 equivalent of benzyl bromide and 1.0 equivalent of a suitable base such as caesium carbonate, in a suitable solvent such as dimethylformamide, at 80° C. for 30 minutes.

Alternatively, compounds of formula (IX) where A¹ contains a suitably protected phenol, p is 0 and X is OH may be prepared from compounds of formula (IXa) where A¹ contains a suitably protected phenol, p is 0 and X is OMe, by mono-deprotection using conditions described in "Protecting Groups in Organic Synthesis" by T. W. Greene and P. Wutz.

Compounds of formula (IX) where A¹ contains a suitably protected phenol, p is 0 and X is F, may be prepared from compounds of formula (IXa) where A¹ contains a phenol, p is 0 and X is F, by addition of a suitable phenol protecting group such as methyl, by process step (ix). Typical conditions comprise reaction of 1.0 equivalent of compound (IXa) with 2.0 equivalents of methyl iodide and 1.0 equivalent of a suitable base such as potassium carbonate, in a suitable solvent such as tetrahydrofuran, at room temperature for 3 hours.

Compounds of formula (X) where p is 0 may be prepared from compounds of formulae (VIII), and (IX) where X is OH and p is 0, by a Mitsunobu reaction, between compounds (VIII) and (IX) in the presence of a suitable phosphine such as tri-ⁿbutyl phosphine or triphenyl phosphine and a suitable azo compound such as diethylazodicarboxylate, diisopropylazodicarboxylate or di-tert-butylazodicarboxylate, in a solvent such as dichloromethane, tetrahydrofuran or N,N-dimethylformamide, at temperatures between 25-115° C., for 1-48 hours, by process step (vi). Typical conditions comprise of 1.0 equivalent of compound (VIII), 1.0 equivalent of compound (IX) 1.0-1.2 equivalents of triphenylphosphine and 1.0-1.2 equivalents of di-isopropylazodicarboxylate, in tetrahydrofuran, at 25° C. for up to 18 hours. Compounds of formula (Xa)

Scheme 5

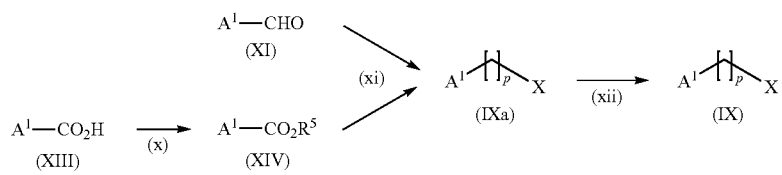

wherein A¹ is as defined above for the compounds of formula (I) or may be optionally protected.

Compounds of formula (IXa) where p is 1 and X is OH may be prepared from compounds of formula (XI) by reduction of the aldehyde with a suitable reducing agent such as sodium borohydride, by process step (xi). Typical conditions comprise reaction of 1.0 equivalent of compound (XI) with 1.0 equivalent of sodium borohydride, in a suitable solvent such as ethanol, at room temperature for 18 hours.

Compounds of formula (XIV) where R⁵ represents a suitable acid protecting group such as methyl, ethyl or allyl may be prepared from compounds of formula (XIII) by addition of a suitable protecting group such as allyl, by process step (x). Typical conditions comprise reaction of 1.0 equivalent of compound (XIII) with 2.0 equivalents of allyl bromide and 2.0 equivalents of a suitable base such as potassium carbonate, in a suitable solvent such as dimethylformamide, at room temperature for 18 hours.

Compounds of formula (IXa) where p is 1 and X is OH may be prepared from compounds of formula (XIV) by reduction of the ester with a suitable reducing agent such as lithium aluminium hydride, by process step (xi). Typical conditions comprise reaction of 1.0 equivalent of compound (XIV) with 2.0 equivalent of lithium aluminium hydride, in a suitable solvent such as tetrahydrofuran, at 0° C. to room temperature over 5 hours.

Compounds of formula (IX) where p is 1 and X is halo may be prepared from compounds of formula (IXa) where p is 1 and X is OH, by halogenation of the primary alcohol using a suitable reagent such as thionyl chloride, dibromotriphenylphosphorane or iodine plus triphenyl phosphine, preferably thionyl chloride or dibromotriphenylphosphorane, in a suitable solvent such as dichloromethane or acetonitrile, by process step (xii). When X is bromo, Typical conditions comprise reaction of 1.0 equivalent of compound (IXa) with 1.0 equivalent of dibromotriphenylphosphorane, in a suitable solvent such as acetonitrile, at room temperature for 18 hours. When X is chloro, Typical conditions comprise reaction of 1.0 equivalent of compound (IXa) with 2.5 equivalent of thionyl chloride in dichloromethane at room temperature for 10 minutes.

where p is 0 may be prepared from compounds of formula (VIIIa) and (IX) using the same conditions.

Compounds of formula (X) where p is 1 may be prepared from compounds of formulae (VIII), and (IX) where X is halo and p is 1, by treatment of compound (VIII) with a suitable strong base such sodium hydride or potassium tert-butoxide followed by quench with compound (IX), in a suitable solvent such as tetrahydrofuran or dimethyl formamide, at a temperature between 0° C. and room temperature, for 1-18 hours, by process step (vi). Typical conditions comprise of 1.0 equivalent of compound (VIII), 1.0 equivalent of sodium hydride and 1.0 equivalent of compound (IX), in tetrahydrofuran, at temperatures between 0-25° C. for up to 18 hours. Compounds of formula (Xa) where p is 1 may be prepared from compounds of formula (VIIIa) and (IX) using the same conditions.

Compounds of formula (VI) may be prepared from compounds of formula (X) by process step (vii). De-protection of compound (X) may be achieved using standard methodology as described in "Protecting Groups in Organic Synthesis" by T. W. Greene and P. Wutz. When PG' is BOC typical conditions comprise of 1.0 equivalent of compound (X) in the presence of hydrochloric acid (4M in dioxan), in dichloromethane, at room temperature for up to 18 hours. Compounds of formula (VIa) may be prepared from compounds of formula (Xa) and using the same conditions.

Compounds of formula (VII) may be prepared from compounds of formulae (V) and (VI) or (VIa) by process step (iii), coupling of (V) and (VI) or (VIa) in the presence of a suitable coupling agent such as 1-(3-dimethylaminopropyl)-3-ethylcarbodiimide hydrochloride, N,N'-carbonyldiimidazole, N,N'-dicyclohexylcarbodiimide, optionally in the presence of a catalyst such as 1-hydroxybenzotriazole hydrate or 1-hydroxy-7-azabenzotriazole, and optionally in the presence of a tertiary amine base such as N-methylmorpholine, triethylamine or N,N-diisopropylethylamine, in a suitable solvent such as N,N-dimethylformamide, tetrahydrofuran or dimethylsulfoxide, under ambient conditions for 1-48 hours. Typical conditions comprise of 1.0 equivalent of compound (V), 1.0 equivalent of compound (VI) or (Via) and 1.0-1.2 equivalents of 1-(3-dimethylaminopropyl)-3-ethylcarbodiimide hydrochloride, 1.0-1.2 equivalents of 1-hydroxybenzotriazole hydrate and 1.0-1.2 equivalents triethylamine in dichloromethane, at room temperature for 18 hours.

Compounds of formula (Ia) may be prepared from compounds of formula (VII) by process step (iv). Compound (Ia) may be prepared in analogy to the methods of Denton and Wood (Synlett, 1999, 1, 55); Compound (VII) is typically pre-activated with a suitable Lewis acid such as titanium chloride or zirconium chloride then treated with an excess of a suitable organometallic reagent such as MeMgCl or MeMgBr, in a suitable solvent such as tetrahydrofuran or diethyl ether, at a temperature between −78° C. to 25° C., for 1-18 hours. Typical conditions comprise of 1.0 equivalent of compound (VII), 2 equivalents of zirconium chloride and 9.0 equivalents of MeMgCl in tetrahydrofuran, at −30° C. for 4-8 hours.

Compounds of formula (Ib) may be prepared from compounds of formula (Ia) by hydrolysis of compound (Ia) with an excess of potassium hydroxide in 3-methyl-3-pentanol, at elevated temperature for up to 24 hours (process step (v)). Typical conditions comprise of 1.0 equivalent of compound (Ia) and 20 equivalents of potassium hydroxide in 3-methyl-3-pentanol at elevated temperature for up to 24 hours.

In a further embodiment, when p is 1, compounds of formula (I) can be further functionalised to provide compounds of formula (Ic), as described in scheme 6

Scheme 6

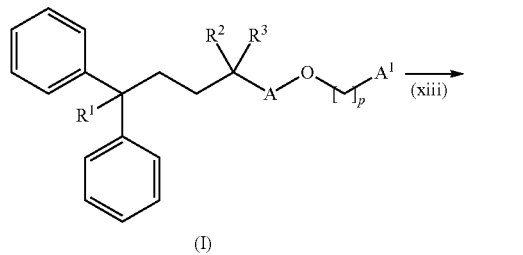

(I)

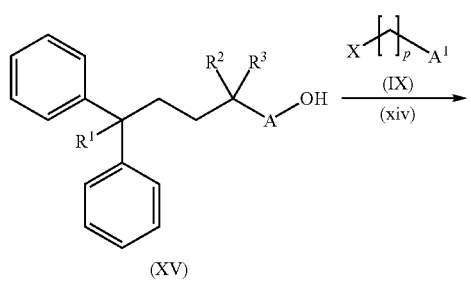

(XV)

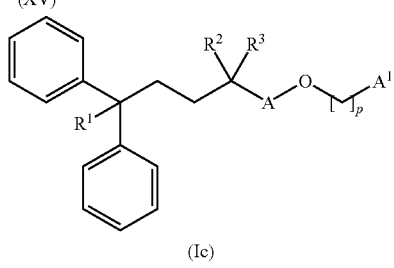

(Ic)

wherein A is

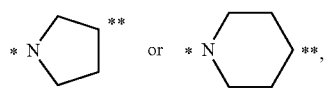 [SMILES: C1CCNC1 ; C1CCNCC1]

and,
$R^2$ and $R^3$ are methyl.

Compounds of formula (XV) may be prepared from compounds of formula (I) where p is 1, by process step (xiii). When $R^1$ is CN, cleavage of the benzyl ether group is typically achieved by treatment of compound (I) with an excess of iron (III) chloride, in a suitable solvent such as dichloromethane, under ambient conditions for 1-8 hours to provide compounds of formula (XV). When $R^1$ is $CONH_2$ treatment of compound (I) with hydrogen gas, in the presence of a suitable hydrogenation catalyst such as 20% $Pd(OH)_2$ or 10% Pd/C, optionally in the presence of a suitable acid such as hydrochloric acid, in a suitable solvent such as methanol, ethanol or tetrahydrofuran, at elevated temperature for 1-18 hours, provides compounds of formula (XV).

Compounds of formula (Ic) where p is 0 may be prepared from compounds of formula (XV) and compounds of formula (IX) where p is 0 and X is OH by process step (xiv)—using the conditions disclosed for step (vi).

Compounds of formula (Ic) where p is 0 may be prepared from compounds of formula (XV) and a compound of formula (IX) where p is 0 and X is F, by process step (xiv)—treatment of compound (XV) with a suitable strong base such sodium hydride or potassium tert-butoxide followed by quench with compound (IX), in a suitable solvent such as tetrahydrofuran or N,N-dimethylformamide, at a temperature between 0° C. and elevated temperature, for 1-96 hours. Typical conditions comprise of 1.0 equivalent of compound (XV), 1.0 to 2.0 equivalents of sodium hydride and 1.0 equivalent of compound (IX), in N,N-dimethylformamide, at temperatures between 0-60° C. for 18-96 hours.

Compounds of formula (Ic) where p is 1 may be prepared from compounds of formula (XV) and a compound of formula (IX) where p is 1 and X is Cl, Br, I, O-mesylate or O-tosylate by process step (xiv), treatment of compound (XV) with a suitable strong base such sodium hydride or potassium tert-butoxide followed by quench with compound (IX), in a suitable solvent such as tetrahydrofuran or N,N-dimethylformamide, at a temperature between 0° C. and elevated temperature, for 1-96 hours. Typical conditions comprise of 1.0 equivalent of compound (XV), 1.0 to 2.0 equivalents of sodium hydride and 1.0 equivalent of compound (IX), in N,N-dimethylformamide, at temperatures between 0-60° C. for 18-96 hours.

In a further embodiment, compounds of formula (I) can be further functionalised to provide compounds of formula (Id), as described in scheme 7:

Scheme 7

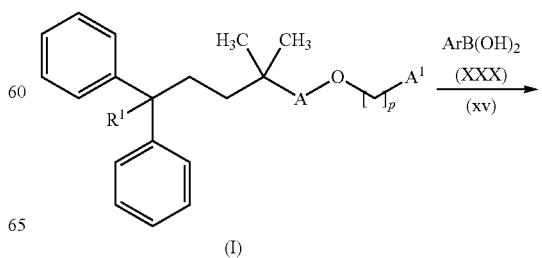

(I)

-continued

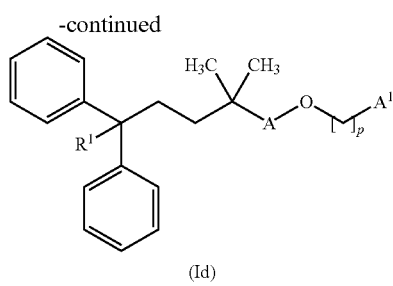
(Id)

wherein A is

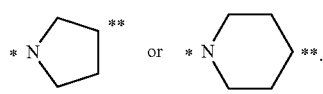 [SMILES: C1CCNC1 ; C1CCNCC1]

Compounds of formula (Id) where $A^1$ represents phenyl substituted with phenyl optionally substituted with OH, may be prepared from compounds of formula (I) where $A^1$ is phenyl substituted with Cl, Br or I, by process step (xv), Suzuki coupling reaction with compound (XXX) in a suitable solvent, such as 1,4-dioxane or tetrahydrofuran, in the presence of water, a suitable base such as sodium carbonate or caesium carbonate, and a palladium catalyst such as [1,1'-bis (diphenylphosphino)ferrocene]palladium (II) chloride or tetrakis(triphenyl phosphine)palladium(0). Suzuki coupling reactions can be carried out as described in the literature: Suzuki, A. Pure & Appl. Chem. 1985, 57, 1749 and references contained within; Angew. Chem. Int. Ed. 2002, 41, 4176 and references contained within. Typical conditions comprise 1.0 equivalent of compound (I), 2.0 equivalents of compound (XXX), 2.0 equivalents of sodium carbonate and 0.05 equivalents of palladium catalyst in tetrahydrofuran and water, at elevated temperature for up to 16 hours.

Compound (XVI) is either commercially available or may be prepared by methods described in the literature.

Compounds of formula (Ic) and (Id) where $R^1$ is $CONH_2$ may also be prepared from compounds of formula (Ic) and (Id) where $R^1$ is CN, by hydrolysis with an excess of potassium hydroxide in 3-methyl-3-pentanol, at elevated temperature for up to 24 hours. Typical conditions comprise of 1.0 equivalent of compound (Ic) or (Id) where $R^1$ is CN and 20 equivalents of potassium hydroxide in 3-methyl-3-pentanol at reflux for up to 24 hours.

Compounds of formula (I) where A is

may be prepared according to the routes disclosed below:

Scheme 8

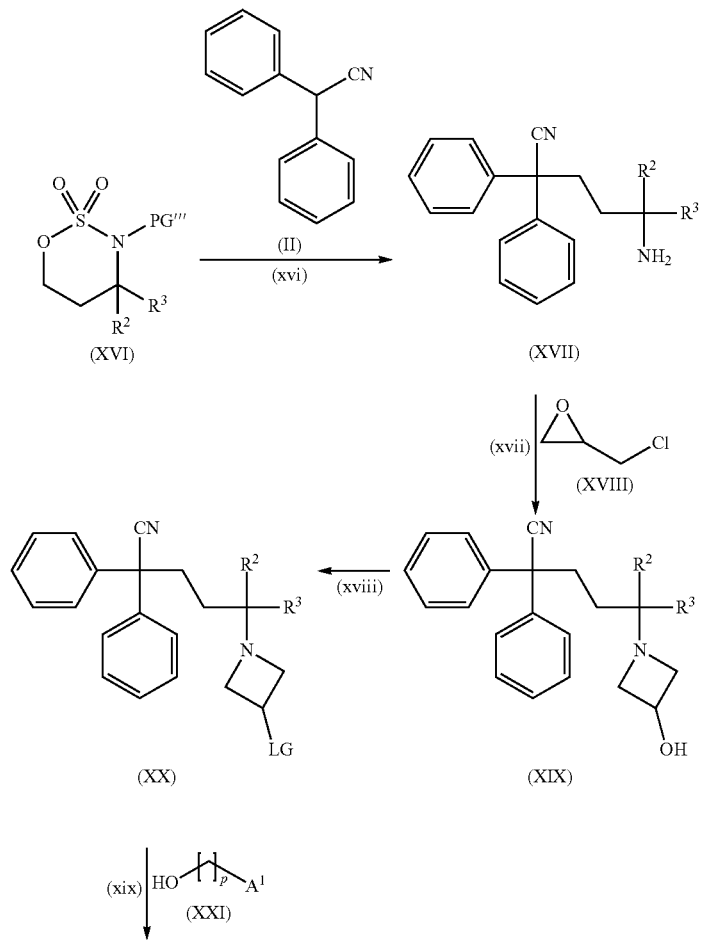

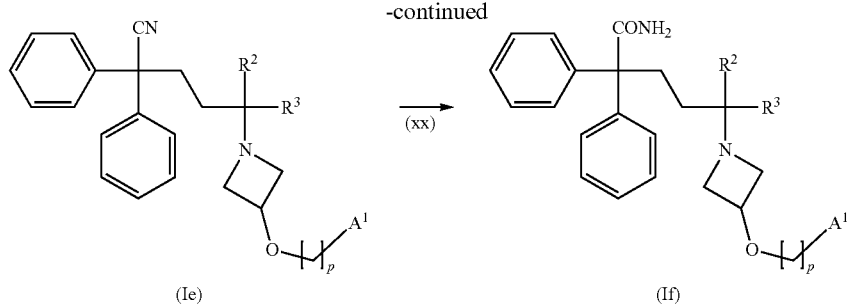

(Ie)  (If)

wherein LG represents a suitable leaving group such as mesylate or tosylate and is preferably mesylate.

Compounds of formula (XVI) may be prepared as described in WO2003037327, page 83. PG''' represents a protecting group such as tert-butoxycarbonyl or benzyloxycarbonyl and is preferably tert-butoxycarbonyl. Alternatively, compounds of formula (XVI) may be prepared according to the following process:

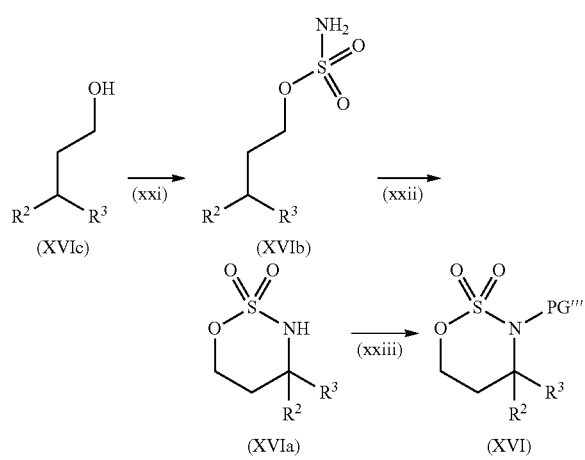

Compounds of formula (XVIc) are commercially available or known in the literature. Compounds of formula (XVIb) may be prepared from compounds of formula (XVIc) by reaction of compounds (XVIc) with chlorosulfonyl isocyanate, formic acid and pyridine, in a suitable solvent such as dichloromethane, at low temperature for 2 hours (process step (xxi)). Typical conditions comprise 1.0 equivalent of compound (XVIc), 1.5 equivalents of chlorosulfonyl isocyanate, 1.5 equivalents of formic acid and 1.5 equivalents of pyridine in dichloromethane, at low temperature for 2 hours.

Compounds of formula (XVIa) may be prepared from compounds of formula (XVIb) by reaction of compounds (XVIb) with magnesium oxide, iodobenzene diacetate and rhodium acetate dimer in a suitable solvent such as dichloromethane at room temperature for up to 24 hours (process step (xxii)). Typical conditions comprise reaction of 1.0 equivalent of compound (XVIb), 2.3 equivalent of magnesium dioxide, 1.1 equivalent of iodobenzene diacetate and 0.02 equivalent of rhodium acetate dimer in dichloromethane at room temperature for 18 hours.

Compounds of formula (XVI) may be prepared from compounds of formula (XVIa) by incorporation of a suitable protecting group such as tert-butoxycarbonyl or benzyloxycarbonyl, preferably tert-butoxycarbonyl, using conditions described in "Protecting Groups in Organic Synthesis" by T. W. Greene and P. Wutz. Typical conditions comprise reaction of 1.0 equivalent of compound (XVIa), 1.2 equivalents of di-tert-butyl dicarbonate, 2.0 equivalents of triethylamine and 0.2 equivalents of 4-dimethylaminopyridine in dichloromethane, at room temperature for 3 hours.

Compounds of formula (XVII) may be prepared from compounds of formula (II) and compounds of formula (XVI) by process step (xvi)—
1) Reaction of compounds (II) and (XVI) in the presence of a strong base such as potassium tert butoxide or sodium hydride, in a suitable solvent such as N,N-dimethylformamide or dimethylsulfoxide, under ambient conditions or at elevated temperature for up to 18 hours.
2) Removal of the protecting group (when used) using suitable conditions such as 4N hydrochloric acid in dioxan or trifluoroacetic acid or hydrogenation in the presence of catalytic palladium, as described in "Protecting Groups in Organic Synthesis" by T. W. Greene and P. Wutz.

Typical conditions comprise of 1.2 equivalents of compound (II), 1.0 equivalent of compound (XVI) and 1.2 equivalents of potassium tert butoxide in N,N-dimethylformamide, under ambient conditions for up to 18 hours, followed by treatment with 4N hydrochloric acid in dioxane.

Compounds of formula (XVIII) are commercially available.

Compounds of formula (XIX) may be prepared from compounds of formula (XVII) and (XVIII) by process step (xvii)—heterocycle formation can be achieved by nucleophilic addition of compound (XVIII) by compound (XVII) followed by in situ ring closure, in a suitable solvent such as methanol or ethanol, at elevated temperature for up to 48 hours. Typical conditions comprise of 1.0 equivalent of compound (XVII) and 1.1 equivalents of compound (XVIII) in methanol, at elevated temperature for up to 48 hours.

Compounds of formula (XX) may be prepared from compounds of formula (XIX) by process step (xviii)—introduction of a suitable leaving group (LG), such as mesylate or tosylate groups by reaction of compound (XIX) with mesyl chloride/anhydride or tosyl chloride, in the presence of a suitable base such as Hünig's base, triethylamine or pyridine, optionally in a suitable solvent such as dichloromethane or diethyl ether, at low temperature for 1-2 hours. Typical conditions comprise of 1.0 equivalent of compound (XIX) and 3 equivalents of mesyl chloride in pyridine at low temperature for up to 1-2 hours.

Compounds of general formula (XXI) are either commercially available or are known in the literature. Compounds of formula (XXI) containing a phenol group may be protected by addition of a suitable phenol protecting group such as allyl.

Typical conditions comprise reaction of 1.0 equivalent of compound (XXI) containing a phenol with 1.0 equivalent of allyl bromide and 1.0 equivalent of a suitable base such as potassium carbonate, in a suitable solvent such as dimethylformamide, at room temperature for 18 hours.

Alternatively, compounds of formula (XXI) may be prepared by mono-deprotection of a bis-protected phenol using conditions described in "Protecting Groups in Organic Synthesis" by T. W. Greene and P. Wutz.

Compounds of formula (Ie) can be prepared from compounds of general formula (XX) and (XXI) by treatment of compound (XXI) with a suitable base such caesium carbonate or sodium carbonate followed by quench with compound (XX), in a suitable solvent such as N,N-dimethylformamide or dimethylsulfoxide, at elevated temperature for up to 18 hours (process step (xix)). Typical conditions comprise of 1.0 equivalent of compound (XX), 3.0 equivalents of caesium carbonate and 3.0 equivalent of compound (XXI), in N,N-dimethylformamide, at elevated temperature for up to 18 hours.

In a further embodiment, compounds of formula (If) may be prepared from compounds of formula (Ie) by hydrolysis of compound (Ie) with an excess of potassium hydroxide in 3-methyl-3-pentanol, at elevated temperature for up to 24 hours (process step (xx)). Typical conditions comprise of 1.0 equivalent of compound (Ie) and 20 equivalents of potassium hydroxide in 3-methyl-3-pentanol at elevated temperature for up to 24 hours.

Alternatively compounds of formula (I) where A is

and $R^2$ and $R^3$ are methyl may be prepared as described in scheme 9.

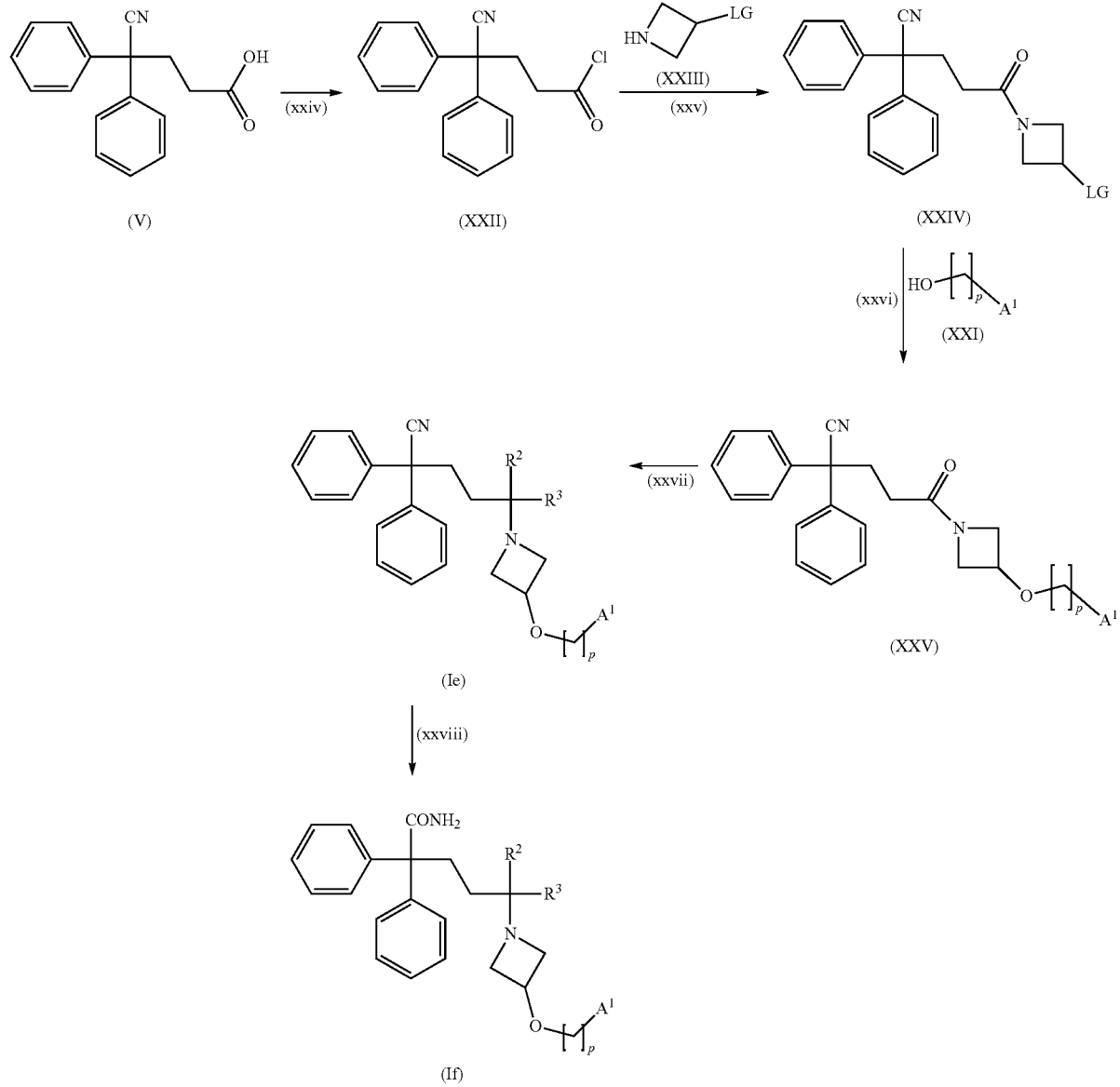

wherein LG represents a suitable leaving group such as mesylate or tosylate and is preferably mesylate.

Compounds of general formula (V) may be prepared as described in WO97/24325. Compounds of formula (XXII) may be prepared from compounds of general formula (V) by process step (xxiv): carboxylic acid (V) may be treated with a suitable chlorinating agent such as thionyl chloride or oxalyl chloride, in a suitable solvent such as N,N-dimethylformamide, acetonitrile or dichloromethane, under ambient conditions for up to 8 hours. Typical conditions comprise of 1.0 equivalent of compound (V) and 2 equivalents of oxalyl chloride in N,N-dimethylformamide, at room temperature for 2 hours.

Compounds of formula (XXIII) may be prepared as described in J. Org. Chem. 1991, 56, 6729-30.

Compounds of general formula (XXIV) may be prepared from compounds of general formula (XXII) and (XXIII) by process step (xxv): compound (XXII) undergoes nucleophilic substitution with compound (XXIII), in the presence of a tertiary amine base such as N-methylmorpholine, triethylamine or N,N-diisopropylethylamine, in a suitable solvent such as N,N-dimethylformamide, tetrahydrofuran or dichloromethane, at low temperature for 1-8 hours. Typical conditions comprise of 1 equivalent of compound (XXII), 1 equivalent of compound (XXIII) and 3 equivalents of triethylamine in dichloromethane, at low temperature for 1 hour. Compounds of general formula (XXV) may be prepared from compounds of general formulae (XXIV) and (XXI) by process step (xxvi) using the conditions described for step (xix) in scheme 8.

Compounds of formula (Ie) may be prepared from compounds of formula (XXV) using the conditions disclosed for step (iv) of scheme 1.

Compounds of formula (If) may be prepared from compounds of formula (Ie) using the conditions disclosed for step (xx) of scheme 8.

Alternatively, compounds of formula (I) may be prepared as disclosed in scheme 1, using an intermediate of formula (VIb)

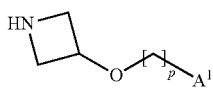

(VIb)

which is commercially available or known in the literature.

Typical conditions for step (iii) comprise of 1.0 equivalent of compound (V), 1.2 equivalent of compound (VIb), 1.0-1.2 equivalents of 1-(3-dimethylaminopropyl)-3-ethylcarbodiimide hydrochloride, 1.0-1.2 equivalents of 1-hydroxybenzotriazole hydrate and 2.5 equivalents of N,N-diisopropylethylamine in dichloromethane, at room temperature for 18 hours.

Alternatively, a compound of formula (Ie) wherein p is 1 may be prepared as described in scheme 10:

Scheme 10

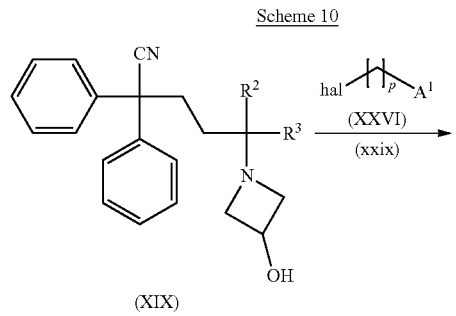

(XIX)

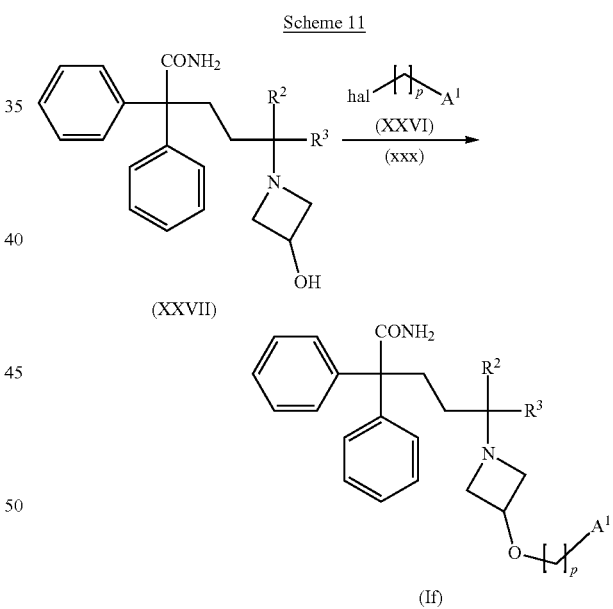

wherein p is 1 and Hal represents halo and is typically chloro or bromo, preferably chloro. Compound of formula (XXVI) may be prepared as disclosed in scheme 5.

Compounds of general formula (Ie) may be prepared from compounds of general formulae (XIX) and (XXVI) by treatment of compound (XIX) with a suitable strong base such sodium hydride or potassium tert-butoxide followed by quench with compound (XXVI), in a suitable solvent such as tetrahydrofuran, at a temperature between 0° C. and room temperature, for 1-8 hours. Typical conditions comprise of 1.0 equivalent of compound (XIX), 1.2 equivalents of sodium hydride and 1.5 equivalents of compound (XXVI), in tetrahydrofuran, at temperatures between 0-25° C. for up to 1-2 hours.

Alternatively, compounds of formula (If) may be prepared as described in scheme 11.

wherein Hal represents halo and is typically chloro or bromo, preferably chloro.

Compounds of formula (XXVII) are prepared from compounds of formula (If), where $A^1$ represents phenyl and p=1, by removal of the benzyl group using standard hydrogenation conditions as described in "Protecting Groups in Organic Synthesis" by T. W. Greene and P. Wutz.

Compounds of formula (If) are prepared from compounds of formula (XXVII) and compounds of formula (XXVI), using the conditions disclosed in step (xxix).

Alternatively, compounds of formula (If) may be prepared as described in scheme 12.

Scheme 12

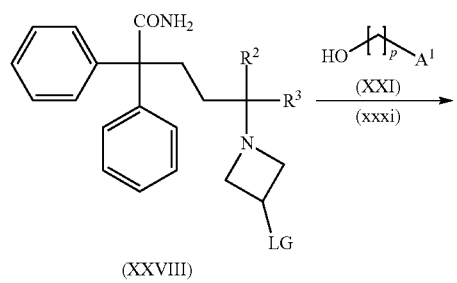

(XXVIII)

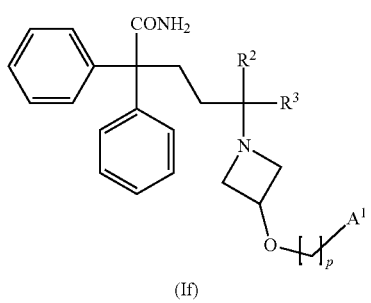

(If)

wherein LG represents a suitable leaving group such as mesylate or tosylate and is preferably mesylate.

Compounds of formula (XXVIII) can be prepared from compounds of formula (XXVII) by process step (xviii), as described in scheme 8.

Compounds of formula (If) can be prepared from compounds of formula (XXVIII) and compounds of formula (XXI) by process step (xix), as described in scheme 8.

Alternatively, compounds of formula (XIX) may be prepared as described in scheme 13.

Scheme 13

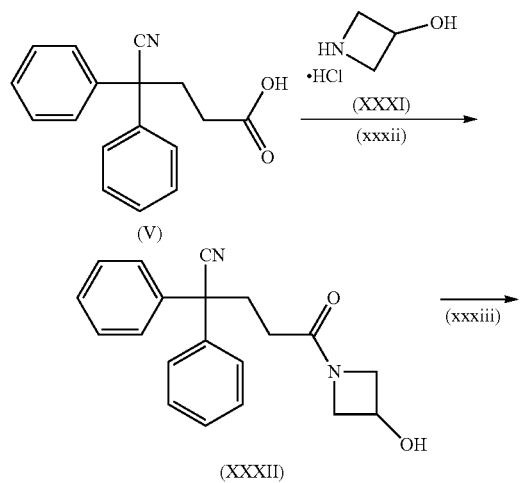

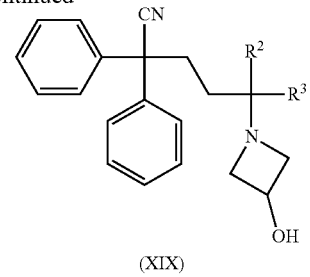

(XIX)

wherein $R^2$ and $R^3$ represent methyl.

Compound of formula (XXXI) is commercially available.

Compound of formula (XXXII) can be prepared from compound of formula (V) and compound of formula (XXXI) using the conditions disclosed for step (iii) of scheme 1.

Compounds of formula (XIX) can be prepared from compound of formula (XXXII) using the conditions disclosed for step (iv) of scheme 1.

When $A^1$ contains a suitably protected phenol, compounds of formula (I) are deprotected to provide the corresponding phenol. Suitable protecting groups (PG") include methyl, benzyl, allyl and tert-butyldimethylsilyl (TBDMS). De-protection may be achieved using standard methodology as described in "Protecting Groups in Organic Synthesis" by T. W. Greene and P. Wutz.

When PG" is methyl, Typical conditions of this procedure comprise of 1.0 equivalent of protected compound of formula (I) and 1-4 equivalents of 1M boron tribromide in dichloromethane, in a suitable solvent such as dichloromethane, at ambient temperature for 1-18 hours.

When PG" is allyl Typical conditions of this procedure comprise of 1.0 equivalent of protected compound of formula (I) and 20 equivalents of potassium hydroxide in 3-methyl-3-pentanol at reflux for 1-24 hrs, followed by isolation of the residue and treatment with hydrochloric acid (4M in dioxan), in water, at 60° C. for 20 mins. Alternative conditions of this procedure comprise of 1.0 equivalent of protected compound of formula (I), 6 equivalents of sodium borohydride and 0.1 equivalents of tetrakis(triphenylphosphine)palladium(0) in tetrahydrofuran at elevated temperature for 30 minutes.

When PG" is TBDMS, Typical conditions of this procedure comprise of 1.0 equivalent of protected compound of formula (I) and 10 equivalents of ammonium fluoride in methanol and water at 50° C. for 18-24 hrs.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include
(i) where the compound of formula (I) contains a carboxylic acid functionality (—COOH), an ester thereof, for example, a compound wherein the hydrogen of the carboxylic acid functionality of the compound of formula (I) is replaced by (C$_1$-C$_8$)alkyl;
(ii) where the compound of formula (I) contains an alcohol functionality (—OH), an ether thereof, for example, a compound wherein the hydrogen of the alcohol functionality of the compound of formula (I) is replaced by (C$_1$-C$_6$)alkanoyloxymethyl; and
(iii) where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula I.

Also included within the scope of the invention are metabolites of compounds of formula that is, compounds formed in vivo upon administration of the drug. Some examples of metabolites in accordance with the invention include (i) where the compound of formula (I) contains a methyl group, an hydroxymethyl derivative thereof (—$CH_3$ -> —$CH_2OH$):
(ii) where the compound of formula (I) contains an alkoxy group, an hydroxy derivative thereof (—OR -> —OH);
(iii) where the compound of formula (I) contains a tertiary amino group, a secondary amino derivative thereof (—$NR^1R^2$ -> —$NHR^1$ or —$NHR^2$);
(iv) where the compound of formula (I) contains a secondary amino group, a primary derivative thereof (—$NHR^1$ -> —$NH_2$);
(v) where the compound of formula (I) contains a phenyl moiety, a phenol derivative thereof (—Ph -> —PhOH); and
(vi) where the compound of formula (I) contains an amide group, a carboxylic acid derivative thereof (—$CONH_2$ -> COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of formula II as hereinbefore defined, all salts, solvates and complexes thereof and all solvates and complexes of salts thereof as defined hereinbefore for compounds of formula I. The invention includes all polymorphs of the aforementioned species and crystal habits thereof.

When preparing compounds of formula (I) in accordance with the invention, it is open to a person skilled in the art to routinely select the form of compound of formula II which provides the best combination of features for this purpose. Such features include the melting point, solubility, processability and yield of the intermediate form and the resulting ease with which the product may be purified on isolation.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof).

Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line* 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™ etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula I, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

The compounds of formula (I) are particularly suitable for an administration by inhalation The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, oral administration may require a total daily dose of from 0.1 mg to 1000 mg, while an intravenous dose may only require from 0.001 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

The compounds of formula (I) have the ability to interact with muscarinic receptors and thereby have a wide range of therapeutic applications, as described further below, because of the essential role which muscarinic receptors play in the physiology of all mammals.

Thus the invention relates to the use of the compounds of formula (I) for the manufacture of a medicament for the treatment or the prevention of diseases, disorders, and conditions in which the M3 receptor is involved. The invention further relates to a method of treatment of a mammal, including a human being, with a M3 antagonist including treating said mammal with an effective amount of a compound of the formula (I) or with a pharmaceutically acceptable salt, derived form or composition thereof.

Therefore, a further aspect of the present invention relates to the compounds of formula (I), or pharmaceutically acceptable salts, derived forms or compositions thereof, for use in the treatment of diseases, disorders, and conditions in which muscarinic receptors are involved. Examples of such diseases, disorders, and conditions are Inflammatory Bowel Disease, Irritable Bowel Disease, diverticular disease, motion sickness, gastric ulcers, radiological examination of the bowel, symptomatic treatment of BPH (benign prostatic hyperplasia), NSAID induced gastric ulceration, urinary Incontinence (including urgency, frequency, urge incontinence, overactive bladder, nocturia and Lower urinary tract symptoms), cycloplegia, mydriatics, parkinsons disease.

More specifically, the present invention also concerns the compounds of formula (I), or pharmaceutically acceptable salts, derived forms or compositions thereof, for use in the treatment of diseases, disorders, and conditions selected from the group consisting of:

chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

More specifically, the present invention also concerns the compounds of formula (I), or pharmaceutically acceptable salts, derived forms or compositions thereof, for use in the treatment of COPD or asthma.

Suitable examples of other therapeutic agents which may be used in combination with the compound(s) of formula (I), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) short or long acting $\beta_2$ agonists,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκB pathway, e.g. IKK inhibitors,
(w) modulators of cytokine signalling pathways such as p38 MAP kinase or syk kinase,
(x) Agents that can be classed as mucolytics or anti-tussive,
(y) Antibiotics,
(z) HDAC inhibitors, and,
(aa) P13 kinase inhibitors.
(bb) CXCR2 antagonists.

According to the present invention, combination of the compounds of formula (I) with:
H3 antagonists,
$\beta_2$ agonists,
PDE4 inhibitors,
steroids, especially glucocorticosteroids,
Adenosine A2a receptor agonists,
Modulators of cytokine signalling pathways such as p38 MAP kinase or syk kinase, or,
Leukotriene antagonists (LTRAs) including antagonists of $LTB_4$, $LTC_4$, $LTD_4$, and $LTE_4$, are preferred.

According to the present invention, combination of the compounds of formula (I) with:
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
β2 agonists including in particular salbutamol, terbutaline, bambuterol, fenoterol, salmeterol, formoterol, tulobuterol and their salts.
are further preferred.

The following examples illustrate the preparation of the compounds of the formula (I):

PREPARATION 1 tert-Butyl 4-cyano-4,4-diphenylbutanoate

A suspension of diphenylacetonitrile (38.6 g, 200 mmol) in tert-butanol (200 ml) was warmed to 60° C. for 30 minutes. The resulting solution was cooled to 50° C. and a solution of potassium hydroxide (0.6 g, 10.69 mmol) in methanol (2 mL) was added. tert-Butyl acrylate (30 mL, 200 mmol) was then added dropwise and the mixture was stirred at 50° C. for 2 hours and at room temperature for 18 hours. Further potassium hydroxide (0.6 g, 10.69 mmol) was added and the mixture was re-warmed to 50° C. for 3 hours. The reaction mixture was then concentrated in vacuo and the residue was diluted with diethyl ether (300 mL), washed with water (200 mL), dried over sodium sulfate and concentrated in vacuo to afford the title compound as a white solid in 90% yield, 57.95 g.

$^1$HNMR(400 MHz, $CD_3OD$) δ: 1.41(s, 9H), 2.29(t, 2H), 2.72(t, 2H), 7.29-7.33(m, 1H), 1H), 7.36-7.42(m, 9H); LRMS APCI m/z 322 $[M+H]^+$

PREPARATION 2

4-Cyano-4,4-diphenylbutanoic acid

A mixture of the product of preparation 1 (57.5 g, 179.13 mmol) in hydrochloric acid (4N in dioxan, 500 mL) was stirred at room temperature for 18 hours. The reaction mixture was concentrated in vacuo and the residue was treated with warm diisopropyl ether (150 mL) then cooled to room temperature. The resulting solid was filtered off, washing through with diisopropyl ether (2×30 mL), and dried under vacuum to afford the title compound as crystalline white solid in 77% yield, 36.45 g.

$^1$HNMR(400 MHz, CD$_3$OD) δ: 2.35(t, 2H), 2.76(t, 2H), 7.30-7.44(m, 10H); LRMS APCI m/z 266 [M+H]$^+$

PREPARATION 3 tert-Butyl (3S)-3-phenoxypyrrolidine-1-carboxylate

Di-isopropylazodicarboxylate (5.7 mL, 29.38 mmol) was added to an ice-cooled solution of (R)-(–)-N-boc-3-pyrrolidinol (5 g, 26.71 mmol), phenol (2.51 g, 26.71 mmol) and triphenyl phosphine (7.71 g, 29.38 mmol) in tetrahydrofuran (70 mL) and the mixture was stirred at room temperature for 18 hours. The reaction mixture was then concentrated in vacuo and the residue was twice triturated with diethyl ether and filtered. The filtrate was washed with 1N sodium hydroxide solution (20 mL), dried over sodium sulfate and concentrated in vacuo. Purification of the residue by column chromatography on silica gel, eluting with pentane:ethyl acetate, 90:10 to 83:17, afforded the title compound as a colourless oil in 75% yield, 5.27 g.

$^1$HNMR(400 MHz, CD$_3$OD) δ: 1.45(m, 9H), 2.10-2.16(m, 2H), 3.40-3.59(m, 4H), 4.95-4.97(m, 1H), 6.88-6.95(m, 3H), 7.24-7.28(m, 2H)

PREPARATION 4 tert-Butyl (3S)-3-(3-methoxyphenoxy)pyrrolidine-1-carboxylate

The title compound was prepared from (R)-(–)-N-boc-3-pyrrolidinol and 3-methoxyphenol, using the same method as that described for preparation 3, as a gum in 81% yield.

$^1$HNMR(400 MHz, CD$_3$OD) δ: 1.45(m, 9H), 2.14(bs, 2H), 3.40-3.58(m, 4H), 3.75(s, 3H), 4.95(m, 1H), 6.45-6.54(m, 3H), 7.14-7.18(m, 1H)

PREPARATION 5 tert-Butyl (3S)-3-(benzyloxy)pyrrolidine-1-carboxylate

Sodium hydride (60% dispersion in mineral oil, 2.13 g, 53.41 mmol) was added portionwise to an ice-cooled solution of (S)-(–)-N-boc-3-pyrrolidinol (10 g, 53.41 mmol) in tetrahydrofuran (100 mL) and the mixture was stirred at 0° C. for 1 hour. Benzyl bromide (6.4 mL, 53.41 mmol) and tetrahydrofuran (50 mL) were added and the mixture was stirred for 6 hours allowing the temperature to rise to 25° C. The reaction mixture was then slowly diluted with water (50 mL), concentrated in vacuo and the aqueous residue was extracted with ethyl acetate (3×70 mL). The combined organic solution was washed with brine (30 mL), dried over sodium sulfate and concentrated in vacuo to give an orange oil. This oil was purified by column chromatography on silica gel, eluting with dichloromethane:methanol:0.88 ammonia, 100:0:0 to 90:10:1. The appropriate fractions were evaporated under reduced pressure and the residue was further purified by column chromatography on silica gel, eluting with pentane:ethyl acetate, 66:33, to afford the title compound as a colourless oil in 74% yield, 10.93 g.

$^1$HNMR(400 MHz, CD$_3$OD) δ: 1.45(s, 9H), 1.91-2.00(m, 1H), 2.02-2.08(m, 1H), 3.35-3.44(m, 4H), 4.13-4.17(m, 1H), 4.51-4.52(m, 2H), 7.24-7.29(m, 1H), 7.30-7.32(m, 4H); LRMS APCI m/z 278 [M+H]$^+$

PREPARATION 6 tert-Butyl (3R)-3-(benzyloxy)pyrrolidine-1-carboxylate

The title compound was prepared from (R)-(–)-N-boc-3-pyrrolidinol and benzyl bromide, using the same method as that described for preparation 5. The crude compound was purified by column chromatography on silica gel, eluting with dichloromethane:methanol:0.88 ammonia, 95:5:0.5, to afford the desired product in 97% yield.

$^1$HNMR(400 MHz, CD$_3$OD) δ: 1.46(s, 3H), 1.92-2.02(m, 1H), 2.03-2.10(m, 1H), 3.35-3.48(m, 4H), 4.14-4.19(m, 1H), 4.49-4.57(m, 2H), 7.24-7.33(m, 5H)

PREPARATION 7

(3S)-3-Phenoxypyrrolidine hydrochloride

A mixture of the product of preparation 3 (5.25 g, 19.96 mmol) in hydrochloric acid (4N in dioxan, 50 mL) was stirred at room temperature for 2 hours. The reaction mixture was then concentrated in vacuo to afford the title compound as a white solid in 100% yield.

$^1$HNMR(400 MHz, CD$_3$OD) δ: 2.29-2.33(m, 2H), 3.42-3.56(m, 4H), 5.18-5.21(m, 1H), 6.95-7.01(m, 3H), 7.29-7.32(m, 2H); LRMS APCI m/z 164 [M+H]$^+$

PREPARATION 8

(3S)-3-(3-Methoxyphenoxy)pyrrolidine

A mixture of the product of preparation 4 (3.19 g, 10.8 mmol) in hydrochloric acid (4N in dioxan, 27 mL) was stirred at room temperature for 3 hours. The reaction mixture was then concentrated in vacuo and the residue was purified by column chromatography using an (solute® SCX-2 cartridge, eluting with methanol followed by 1M ammonia in methanol, to afford the title compound as a yellow oil in 85% yield, 1.77 g.

$^1$HNMR(400 MHz, CD$_3$OD) δ: 1.91-1.98(m, 1H), 2.02-2.11(m, 1H), 2.85-2.91(m, 1H), 3.02-3.08(m, 3H), 3.75(s, 3H), 4.85-4.89(m, 1H), 6.43-6.51(m, 3H), 7.12-7.16(m, 1H); LRMS APCI m/z 194 [M+H]$^+$

PREPARATION 9

(3S)-3-(Benzyloxy)pyrrolidine hydrochloride

The title compound was prepared from the product of preparation 5, using the same method as that described for preparation 7, as a solid in 100% yield.

$^1$HNMR(400 MHz, CD$_3$OD) δ: 2.02-2.12(m, 1H), 2.22-2.29(m, 1H), 3.26-3.46(m, 4H), 4.35-4.37(m, 1H), 4.55(s, 2H), 7.25-7.37(m, 5H); LRMS APCI m/z 178 [M+H]$^+$

PREPARATION 10

(3R)-3-(Benzyloxy)pyrrolidine hydrochloride

The title compound was prepared from the product of preparation 6, using the same method as that described for preparation 7, as a solid in 100% yield.

¹HNMR(400 MHz, CDCl₃) δ: 1.96-2.05(m, 1H), 2.20-2.15(m, 1H), 3.49-3.32(m, 4H), 4.23-4.25(m, 1H), 4.44-4.54 (m, 2H), 7.26-7.36(m, 5H), 9.74-9.88(m, 2H); LRMS APCI m/z 178 [M+H]⁺

PREPARATION 11

5-Oxo-5-[(3S)-3-phenoxypyrrolidin-1-yl]-2,2-diphenylpentanenitrile

A mixture of the products of preparations 2 (2.40 g, 9.05 mmol) and 7 (1.99 g, 9.96 mmol), 1-(3-dimethylaminopropyl)-3-ethylcarbodiimide hydrochloride (1.55 g, 9.96 mmol), 1-hydroxybenzotriazole hydrate (1.35 g, 9.96 mmol) and triethylamine (1.38 mL, 9.96 mmol) in dichloromethane (40 mL) was stirred at room temperature for 18 hours. The reaction mixture was then diluted with dichloromethane (100 mL), washed with 1M hydrochloric acid (70 mL), 1M sodium hydroxide solution (30 mL) and brine (30 mL), dried over sodium sulfate and concentrated in vacuo. The residue was re-crystallised from hot ethanol to afford the title compound as a crystalline solid in 76% yield, 2.83 g.

¹HNMR(400 MHz, CD₃OD) δ: 2.07-2.21(m, 2H), 2.33-2.38(m, 1H), 2.43-2.47(m, 1H), 2.69-2.84(m, 2H), 3.44-3.55 (m, 2H), 3.58-3.67(m, 2H), 4.96-5.04(m, 1H), 6.89(d, 2H), 6.93-6.96(m, 1H), 7.24-7.46(m, 12H); LRMS APCI m/z 412 [M+H]⁺

PREPARATION 12

5-Oxo-5-[(3R)-3-phenoxypyrrolidin-1-yl]-2,2-diphenylpentanenitrile

The title compound was prepared from (3R)-3-phenoxypyrrolidine (WO 2005/061457) and the product of preparation 2, using the same method as that described for preparation 11, to afford the title compound in 41% yield.

PREPARATION 13

5-[(3S)-3-(3-Methoxyphenoxy)pyrrolidin-1-yl]-5-oxo-2,2-diphenylpentanenitrile

The title compound was prepared from the products of preparations 2 and 8, using the same method as that described for preparation 11. The crude compound was purified by column chromatography on silica gel, eluting with dichloromethane:methanol:0.88 ammonia, 98:2:0.2 to 95:5:0.5, to afford the desired product as a colourless oil in quantitative yield.

¹HNMR(400 MHz, CD₃OD) δ: 2.03-2.20(m, 2H), 2.32-2.37(m, 1H), 2.43-2.47(m, 1H), 2.66-2.84(m, 2H), 3.44-3.67 (m, 4H), 3.74(s, 3H), 4.94-5.00(m, 1H), 6.44-6.55(m, 3H), 7.13-7.19(m, 1H), 7.28-7.46(m, 10H); LRMS APCI m/z 412 [M+H]⁺

PREPARATION 14

5-[(3S)-3-(Benzyloxy)pyrrolidin-1-yl]-5-oxo-2,2-diphenylpentanenitrile

The title compound was prepared from the products of preparation 2 and 9, using the same method as that described for preparation 11, as a pale orange solid in 70% yield.

¹HNMR(400 MHz, CD₃OD) δ: 1.86-2.15(m, 2H), 2.32-2.43(m, 2H), 2.75-2.82(m, 2H), 3.35-3.62(m, 4H), 4.14-4.21 (m, 1H), 4.45-4.56(m, 2H), 7.22-7.44(m, 15H); LRMS APCI m/z 412 [M+H]⁺

PREPARATION 15

5-[(3R)-3-(Benzyloxy)pyrrolidin-1-yl]-5-oxo-2,2-diphenylpentanenitrile

N,N'-Carbonyldiimidazole (27 g, 162 mmol) was added to a solution of the product of preparation 2 (36 g, 135 mmol) in tetrahydrofuran (600 mL) and the mixture was stirred for 3 hours at room temperature. A solution of the product of preparation 10 (31 g, 141.75 mmol) in tetrahydrofuran (300 mL) was added and the mixture was stirred at room temperature for 18 hours. The reaction mixture was then filtered, washing through with tetrahydrofuran, and the filtrate was concentrated in vacuo. The residue was partitioned between water (200 mL) and ethyl acetate (600 mL) and the organic layer was separated, washed with water, 2N hydrochloric acid (2×100 mL) and brine, dried over magnesium sulfate and concentrated in vacuo. Trituration of the residue with diethyl ether then afforded the title compound in 83% yield, 48.2 g.

¹HNMR(400 MHz, CD₃OD) δ: 1.87-2.15(m, 2H), 2.32-2.44(m, 2H), 2.74-2.82(m, 2H), 3.35-3.61(m, 4H), 4.14-4.22 (m, 1H), 4.46-4.57(m, 2H), 7.23-7.44(m, 15H); LRMS APCI m/z 425 [M+H]⁺

PREPARATION 16

5-[(3S)-3-Hydroxypyrrolidin-1-yl]-5-methyl-2,2-diphenylhexanamide

Iron (III) chloride (1.57 g, 9.70 mmol) was added to a solution of the product of example 11 (385 mg, 0.84 mmol) in dichloromethane (10 mL) and the mixture was stirred at room temperature for 3 hours. The reaction was quenched by the addition of 2M hydrochloric acid (6 mL), filtered through Arbocel® and the filtrate was basified with 0.88 ammonia solution (20 mL). The layers of the filtrate were separated and the aqueous solution was extracted with dichloromethane (2×25 mL). The combined organic solution was dried over sodium sulfate, concentrated in vacuo and purification of the residue by column chromatography on silica gel, eluting with ethyl acetate:methanol:0.88 ammonia, 95:5:0.5 to 85:15:1.5, afforded the title compound as a brown gum in 60% yield, 415 mg.

¹HNMR(400 MHz, CD₃OD) δ: 0.99(s, 6H), 1.23-1.27(m, 2H), 1.56-1.64(m, 1H), 1.89-1.98(m, 1H), 2.40-2.44(m, 3H), 2.47-2.52(m, 1H), 2.61-2.67(m, 1H), 2.74-2.78(m, 1H), 4.17-4.22(m, 1H), 7.22-7.26(m, 2H), 7.29-7.33(m, 4H), 7.37(d, 4H); LRMS APCI m/z 367 [M+H]⁺

PREPARATION 17

5-[(3R)-3-Hydroxypyrrolidin-1-yl]-5-methyl-2,2-diphenylhexanamide

1N Hydrochloric acid (10.95 mL, 10.95 mmol) and 20% Pd(OH)₂ (1 g) were added to a solution of the product of example 9 (5 g, 10.95 mmol) in ethanol (250 mL) and the mixture was stirred at 50° C., under 50 psi of hydrogen gas, for 4 hours. The reaction mixture was then filtered through Arbocel® and the filtrate was concentrated in vacuo to give a white foam. The foam was re-dissolved in ethanol (250 mL), 20% Pd(OH)₂ (1 g) was added and the mixture was stirred at 50° C., under 50 psi of hydrogen gas, for 24 hours. The reaction mixture was then filtered through Arbocel®, washing through with ethanol, and the filtrate was concentrated in vacuo. The residue was suspended in 0.88 ammonia, extracted with ethyl acetate (3×50 mL) and the combined organic solution was washed with brine (50 mL), dried over sodium sulfate and concentrated in vacuo to afford the title compound as a white foam in 90% yield, 3.63 g.

$^1$HNMR(400 MHz, CD$_3$OD) δ: 0.99(s, 6H), 1.23-1.27(m, 2H), 1.56-1.63(m, 1H), 1.89-1.96(m, 1H), 2.39-2.44(m, 3H), 2.46-2.52(m, 1H), 2.61-2.67(m, 1H), 2.74-2.78(m, 1H), 4.17-4.22(m, 1H), 7.22-7.26(m, 2H), 7.29-7.33(m, 4H), 7.36-7.39 (m, 4H); LRMS APCI m/z 367 [M+H]$^+$

PREPARATION 18

5-[(3S)-3-Hydroxypyrrolidin-1-yl]-5-methyl-2,2-diphenylhexanenitrile

Iron (III) chloride (1.33 g, 8.22 mmol) was added to a solution of the product of example 10 (1.2 g, 2.74 mmol) in dichloromethane (25 mL) and the mixture was stirred at room temperature for 3 hours. The solvent was removed in vacuo and the residue was partitioned between 2M hydrochloric acid (aq) (20 mL) and diethyl ether (30 mL). The aqueous layer was separated and basified to pH14 with solid sodium hydroxide. The resulting brown precipitate was collected by filtration and purified by column chromatography on silica gel, eluting with dichloromethane:methanol:0.88 ammonia, 95:5:0.5 to 85:15:1.5, to afford the title compound as a colourless gum in 50% yield, 475 mg.

$^1$HNMR(400 MHz, CD$_3$OD) δ: 1.11(s, 6H), 1.52-1.56(m, 2H), 1.69-1.76(m, 1H), 1.95-2.04(m, 1H), 2.53-2.57(m, 2H), 2.62-2.65(m, 1H), 2.69-2.76(m, 1H), 2.83-2.95(m, 2H), 4.27-4.31(m, 1H), 7.29-7.33(m, 2H), 7.36-7.45(m, 8H); LRMS APCI m/z 349 [M+H]$^+$

PREPARATION 19

5-{(3S)-3-[(6-{[tert-Butyl(dimethyl)silyl]oxy}-2-naphthyl)oxy]pyrrolidin-1-yl}-5-methyl-2,2-diphenylhexanamide 1,1'-Azobis(N,N'-dimethylformamide) (95 mg, 0.553 mmol) was added to an ice-cooled solution of triphenyl phosphine (145 mg, 0.553 mmol), 6-(tert-Butyldimethylsilyloxy)-2-naphthol [(102 mg, 0.372 mmol) EP625510, p 13] and the product from preparation 17 (150 mg, 0.41 mmol) in tetrahydrofuran (5 mL) and the mixture was heated at 60° C. for 18 hrs. Additional triphenyl phosphine (145 mg, 0.553 mmol) and 1,1'-Azobis(N,N'-dimethylformamide) (95 mg, 0.553 mmol) were added and heating continued for a further 18 hrs. The mixture was concentrated in vacuo and the residue purified using an Isolute® SCX-2 cartridge, eluting with methanol, then with 0.25M ammonia in methanol. Basic fractions were concentrated in vacuo and further purified using a RediSep® silica gel cartridge, eluting with dichloromethane:methanol:0.88 ammonia (100:0:0 to 92:8:0.8) to afford the title compound in 20% yield, 46 mg.

$^1$HNMR(400 MHz, CD$_3$OD) δ: 0.24(s, 6H), 0.95(s, 3H), 1.04(s, 9H), 1.06(s, 3H) 1.15-1.29(m, 2H), 1.88-1.99(m, 1H), 2.11-2.22(m, 1H), 2.30-2.52(m, 2H), 2.54-2.62(m, 1H), 2.64-2.69(m, 1H), 2.72-2.82(m, 1H), 2.82-2.90(m, 1H), 4.83-4.89 (m, 1H), 6.96-7.06(m, 2H), 7.12-7.34(m, 12H), 7.53-7.57(m, 1H), 7.60-7.65(m, 1H); LRMS APCI m/z 623 [M+H]$^+$

PREPARATION 20

5-[(3R)-3-Hydroxypyrrolidin-1-yl]-5-methyl-2,2-diphenylhexanenitrile

Iron (III) chloride (13.3 g, 82.192 mmol) was added to a solution of the product of example 8 (9 g, 20.548 mmol) in dichloromethane (200 mL) and the mixture was stirred at room temperature for 1 hour. The reaction was quenched by addition of 2M hydrochloric acid (150 mL) and stirred for 30 minutes. The organic layer was separated and the aqueous re-extracted with a further 100 ml dichloromethane. The combined organic layers were dried over sodium sulphate and concentrated in vacuo. Purification by column chromatography on silica gel, eluting with dichloromethane:methanol: 0.88 ammonia, 95:5:0.5 to 90:1:1.0, afforded the title compound as a pale brown foam in 89% yield, 6.37 g.

$^1$HNMR(400 MHz, CD$_3$OD) δ: 1.18(s, 6H), 1.58-1.62(m, 2H), 1.76-1.84(m, 1H), 1.96-2.05(m, 1H), 2.55-2.59(m, 2H), 2.74-2.81(m, 1H), 2.87-2.93(m, 1H), 2.98-3.06(m, 2H), 4.32-4.36(m, 1H), 7.30-7.34(m, 2H), 7.37-7.46(m, 8H); LRMS APCI m/z 349 [M+H]$^+$

PREPARATION 21

2-Chloro-3-Methoxyphenol

3-Chloroperoxybenzoic acid (760 mg, 4.396 mmol) was added portionwise to a solution of 2-Chloro-3-Methoxybenzaldehyde (500 mg, 2.931 mmol) in dichloromethane (12 ml) and the mixture was stirred for 3 hours at room temperature. Further 3-chloroperoxybenzoic acid (760 mg, 4.396 mmol) was added and mixture allowed to stir for 18 hrs. The solution was diluted with 12 ml dichloromethane and washed with saturated sodium sulphite solution (15 ml) and saturated sodium hydrogen carbonate solution (15 ml). The organic layer was dried over sodium sulphate and concentrated in vacuo to a yellow gum. The residue was dissolved in methanol (12 ml), triethylamine (0.05 ml) was added and the mixture stirred for 18 hours at room temperature. The solution was concentrated in vacuo, dissolved in diethyl ether (20 ml) and extracted with 1N sodium hydroxide (20 ml). The aqueous layer was acidified to pH1 by dropwise addition of 2N hydrochloric acid and extracted with diethyl ether (2×25 ml). These combined organic layers were dried over sodium sulphate and concentrated in vacuo to afford the title compound as a brown gum in 70% yield, 325 mg.

$^1$HNMR(400 MHz, CD$_3$OD) δ: 3.83(s, 3H), 6.52-6.54(d, 2H), 7.01-7.06(t, 1H)

PREPARATION 22

1-Chloro-3-Fluoro-2-Methoxybenzene

Methyl iodide (850 μl, 13.646 mmol) and potassium carbonate (943 mg, 6.824 mmol) were added to 2-chloro-6-fluorophenol (1.0 g, 6.824 mmol) in tetrahydrofuran (10 ml) and the mixture was stirred at room temperature for 3 hours. The reaction mixture was partitioned between diethyl ether (50 ml) and water (50 ml). The organic phase was extracted and further washed with water (2×20 ml) then dried over sodium sulphate and concentrated in vacuo to afford the title compound as a colourless liquid in 94% yield, 1.03 g.

$^1$HNMR(400 MHz, CD$_3$OD) δ: 3.90-3.91(s, 3H), 7.01-7.12(m, 2H), 7.18-7.21(m, 1H)

PREPARATION 23

3-Fluoro-5-Methoxyphenol

Boron tribromide (1M in dichloromethane, 9 mL, 89.985 mmol) was added drop wise to an ice-cooled solution of 3,5-dimethoxy fluorobenzene (3 ml, 22.496 mmol) in dichloromethane (20 mL) and the mixture was stirred at 0° C. to room temperature for 4 hours. The solution was cooled to 0° C., further boron tribromide (4 ml, 44.992 mmol) was added and stirring continued, warming to room temperature for an additional 18 hours. The reaction was quenched with 0.88 ammonia solution and stirred at room temperature for 90 minutes. The organic layer was separated and extracted with 2N sodium hydroxide (30 ml), which was then acidified to pH1 by drop wise addition of concentrated hydrochloric acid. The aqueous layer was then re-extracted with dichloromethane (3×15 mL), the combined organic solution was dried over sodium sulfate and concentrated in vacuo to afford the title compound as a white solid in 54% yield, 1.72 g.

$^1$HNMR(400 MHz, CD$_3$OD) δ: 3.72(s, 3H), 6.07-6.15(m, 3H)

PREPARATION 24

1-Fluoro-3-Methoxy-5-Trifluoromethyl-benzene

The title compound was prepared from 3-fluoro-5-trifluoromethylphenol, using the same method as that described for preparation 22 to afford a colourless oil in 90% yield.

$^1$HNMR(400 MHz, CD$_3$OD) δ: 3.84(s, 3H), 6.92-6.97(m, 2H), 7.00(s, 1H)

PREPARATION 25

4-Fluoro-3-Methoxyphenol

The title compound was prepared from 4-fluoro-3-methoxybenzaldehyde, using the same method as that described for preparation 21, to afford a brown oil in 55% yield.

$^1$HNMR(400 MHz, CD$_3$OD) δ: 3.79(s, 3H), 6.23-6.27(m, 1H), 6.47-6.50(dd, 1H), 6.81-6.86(m, 1H)

PREPARATION 26

2-Fluoro-3-Methoxyphenol

The title compound was prepared from 2-fluoro-3-methoxybenzaldehyde, using the same method as that described for preparation 21, to afford a brown oil in 33% yield.

$^1$HNMR(400 MHz, CD$_3$OD) δ: 3.82(s, 3H), 6.47-6.55(m, 2H), 6.82-6.87(t, 1H)

PREPARATION 27

1-Allyloxy-3-bromomethyl-benzene

To a solution of (3-allyloxy-phenyl)-methanol (Tetrahedron, 2000, 56(13), 1873-1882) (1.07 g, 6.49 mmol) in THF (7 mls) at 3° C. was added carbon tetrabromide (2.69 g, 8.11 mmol) then triphenylphosphine (2.13 g, 8.11 mmol) in THF (2 mls). The reaction mixture was stirred at 5° C. for 1 hour. The reaction mixture was filtered and concentrated in vacuo. The residue was washed with pentane to give a yellow solid which was purified by column chromatography on silica gel, eluting with pentane:ethyl acetate, 100:0, to 95:5 to afford the title compound as a pale yellow oil in 24% yield, 350 mg.

$^1$HNMR(400 MHz, CDCl$_3$) δ: 4.47 (s, 2H), 4.51-4.60 (m, 2H), 5.26-5.35 (m, 1H), 5.37-5.47 (m, 1H), 5.99-6.11 (m, 1H), 6.82-6.90 (m, 1H), 6.92-7.01 (m, 2H), 7.21-7.30 (m, 1H).

PREPARATION 28

5-[(3R)-3-(3-Allyloxy-benzyloxy)-pyrrolidin-1-yl]-5-methyl-2,2-diphenyl-hexanenitrile The product of preparation 20 (179 mg, 0.514 mmol) in dimethylformamide (3 ml) was added drop wise to an ice-cooled solution of sodium hydride (60% dispersion in mineral oil, 31 mg, 0.770 mmol) in dimethylformamide (1 ml). After stirring for 1 hour the product of preparation 27 (175 mg, 0.514 mmol) in dimethylformamide (1 ml) was added and the mixture was allowed to warm to room temperature for 18 hours. The reaction mixture was then re-cooled to 0° C. and further sodium hydride (60% dispersion in mineral oil, 31 mg, 0.770 mmol) added, with stirring at room temperature for an additional 3 hours. The solution was quenched by dropwise addition of water, concentrated in vacuo and partitioned between ethyl acetate (10 ml) and water (10 ml). The organic layer was extracted and washed with water (10 ml), then dried over sodium sulphate and concentrated in vacuo. Purification by column chromatography on silica gel, eluting with dichloromethane:methanol:0.88 ammonia, 97:3:0.3, afforded the title compound as a pale yellow gum in 43% yield, 108 mg.

$^1$HNMR(400 MHz, CD$_3$OD) δ: 1.03(s, 3H), 1.05(s, 3H), 1.44-1.51(m, 2H), 1.78-1.85(m, 1H), 1.93-2.01(m, 1H), 2.50-2.55(m, 3H), 2.64-2.78(m, 3H), 4.03-4.08(m, 1H), 4.43(s, 2H), 4.50-4.55(m, 2H), 5.20-5.24(m, 1H), 5.34-5.41(m, 1H), 5.98-6.09(m, 1H), 6.79-6.84(m, 1H), 6.87-6.94(m, 2H), 7.18-7.21(t, 1H), 7.26-7.43(m, 10H); LRMS ESI m/z 495 [M+H]$^+$

PREPARATION 29

5-Methyl-2,2-diphenyl-5-[(3R)-3-(3-propenyloxy-benzyloxy)-pyrrolidin-1-yl]-hexanoicacid amide The title compound was prepared from the product of preparation 28, using the same method as that described for example 2, with the addition of further potassium hydroxide (2 eq) after 20 hours and continued heating for an additional 4 hrs to afford product as a yellow gum in 88% yield.

$^1$HNMR(400 MHz, CD$_3$OD) δ: 0.99(s, 3H), 1.01(s, 3H), 1.23-1.28(m, 2H), 1.67-1.69(d, 3H), 1.74-1.82(m, 1H), 1.88-1.95(m, 1H), 2.40-2.44(m, 2H), 2.47-2.53(m, 1H), 2.55-2.74 (m, 3H), 3.99-4.04(m, 1H), 4.42(s, 2H), 4.85-4.87(m, 1H), 6.40-6.42(d, 1H), 6.88-6.90(d, 1H), 6.96-6.99(m, 2H), 7.21-7.38(m, 11H); LRMS ESI m/z 513 [M+H]$^+$

PREPARATION 30

3-Allyloxy-4-fluoro-benzoic acid allyl ester

Allyl bromide (3.04 ml, 35.2 mmol) was added dropwise to a suspension of 4-fluoro-3-hydroxybenzoic acid (2.5 g, 16.0 mmol) and potassium carbonate (4.43 g, 32.03 mmol) in dimethylformamide (50 ml) at room temperature and the mixture was stirred for 18 hrs. The solvent was removed in vacuo and the residue partitioned between diethyl ether (30 ml) and water (30 ml). The aqueous layer was separated and extracted with further diethyl ether (2×20 ml). The combined organic layers were washed with water (3×10 ml), dried over sodium sulfate and concentrated in vacuo to afford the title compound as a colourless liquid in 100% yield, 3.82 g.

¹HNMR(400 MHz, CDCl₃) δ: 4.65-4.66(d, 2H), 4.80-4.82 (d, 2H), 5.28-5.48(m, 4H), 5.98-6.12(m, 2H), 7.10-7.14(dd, 1H), 7.65-7.69(m, 2H); LRMS APCI m/z 237 [M+H]⁺

PREPARATION 31

(3-Allyloxy-4-fluoro-phenyl)-methanol

A solution of the product of preparation 30 (2.0 g, 8.47 mmol) in tetrahydrofuran (30 ml) was added dropwise over 20 minutes to a solution of lithium aluminium hydride in tetrahydrofuran (1M, 16.9 ml, 16.9 mmol) at 0° C. under a nitrogen atmosphere, and the solution allowed to warm to room temperature over 5 hrs. The mixture was cooled to 0° C. and quenched by sequential dropwise addition of water (1 ml), aqueous sodium hydroxide solution (2M, 2 ml) and water (3 ml), and the mixture stirred at room temperature for 18 hrs. The mixture was filtered through Celite® and the filter pad washed with ethyl acetate (3×20 ml). The filtrate was separated and the organic layer washed with brine (10 ml), dried over sodium sulfate and concentrated in vacuo to afford the title compound as a colourless liquid in 100% yield, 1.75 g.

¹HNMR(400 MHz, CDCl₃) δ: 4.61-4.63(m, 4H), 5.29-5.32(d, 1H), 5.41-5.45(d, 1H), 6.02-6.11(m, 1H), 6.85-6.89 (m, 1H), 7.00-7.07(m, 2H); LRMS APCI m/z 165 [M−OH]⁺

PREPARATION 32

2-Allyloxy-4-bromomethyl-1-fluorobenzene

Dibromotriphenylphosphorane (2.3 g, 5.43 mmol) was added to a solution of the product from preparation 31 (900 mg, 4.94 mmol) in acetonitrile (40 ml) at room temperature and the solution stirred for 18 hrs. The solvent was removed in vacuo and the residue purified by column chromatography on silica gel, eluting with pentane:ethyl acetate (80:20) to afford the title compound as a colourless liquid in 31% yield, 380 mg.

¹HNMR(400 MHz, CDCl₃) δ: 4.44(s, 2H), 4.61-4.63(m, 2H), 5.30-5.34(m, 1H), 5.41-5.47(m, 1H), 6.02-6.11(m, 1H), 6.91-6.94(m, 1H), 6.99-7.05(m, 2H); LRMS APCI m/z 165 [M−Br]⁺

PREPARATION 33

5-[(3R)-3-(3-Allyloxy-4-fluoro-benzyloxy)-pyrrolidin-1-yl]-5-methyl-2,2-diphenylhexanenitrile Sodium hydride (62 mg, 1.55 mmol) was added portionwise to an ice-cooled solution of the product of preparation 20 (270 mg, 0.775 mmol) in dimethylformamide (3 ml) under a nitrogen atmosphere. After stirring for 1.5 hrs a solution of the product of preparation 32 (380 mg, 1.55 mmol) in dimethylformamide (2 ml) was added and the mixture was allowed to warm to room temperature and stirred for 18 hours. The solvent was removed in vacuo and the residue partitioned between ethyl acetate (10 ml) and saturated sodium hydrogen carbonate solution (5 ml). The aqueous layer was separated and extracted with further ethyl acetate (10 ml). The combined organic layers were washed with water (5 ml), brine (5 ml), dried over sodium sulphate and concentrated in vacuo. The residue was purified by column chromatography on silica gel, eluting with dichloromethane:methanol:0.88 ammonia (99:1:0.1 to 98:2:0.2 to 95:5:0.5) to afford the title compound as a yellow oil in 38% yield, 150 mg.

¹HNMR(400 MHz, CD₃OD) δ: 1.03(s, 3H), 1.06(s, 3H), 1.44-1.53(m, 2H), 1.78-1.86(m, 1H), 1.93-2.02(m, 1H), 2.50-2.57(m, 3H), 2.67-2.79(m, 3H), 4.03-4.07(m, 1H), 4.41(s, 2H), 4.56-4.58(m, 2H), 5.22-5.26(m, 1H), 5.36-5.41(m, 1H), 5.99-6.08(m, 1H), 6.85-6.88(m, 1H), 6.98-7.06(m, 2H), 7.28-7.43(m, 10H); LRMS ESI m/z 513 [M+H]⁺

PREPARATION 34

5-[(3R)-3-(4-Fluoro-3-propenyloxy-benzyloxy)-pyrrolidin-1-yl]-5-methyl-2,2-diphenylhexanamide The title compound was prepared from the product of preparation 33, using the same method as that described for example 2 to afford a colourless oil in 100% yield.

¹HNMR(400 MHz, CD₃OD) δ: 1.02(s, 3H), 1.04(s, 3H), 1.23-1.32(m, 2H), 1.69-1.71(d, 3H), 1.77-1.86(m, 1H), 1.89-1.97(m, 1H), 2.40-2.82(m, 6H), 4.02-4.07(m, 1H), 4.39(s, 2H), 4.88-4.95(m, 1H), 6.37-6.40(m, 1H), 6.95-6.99(m, 1H), 7.04-7.11(m, 2H), 7.22-7.38(m, 10H); LRMS ESI m/z 531 [M+H]⁺

PREPARATION 35

3-Benzyloxy-5-hydroxy-benzonitrile

Caesium carbonate (2.41 g, 7.4 mmol) was added to a solution of 3,5-dihydroxy benzonitrile (1.0 g, 7.4 mmol) in dimethylformamide (5 ml) at room temperature and the mixture stirred for 10 minutes. Benzyl bromide (0.880 ml, 7.4 mmol) was added dropwise and the mixture heated at 80° C. for 30 minutes. The solvent was removed in vacuo, the residue treated with water (10 ml), acidified with aqueous hydrochloric acid (2M) and extracted with ethyl acetate (3×25 ml). The combined organic layers were washed with water (2×10 ml), brine (10 ml), dried over sodium sulphate and concentrated in vacuo. The residue was purified by column chromatography, eluting with ethyl acetate/pentane (20:80 to 50:50) to afford the title compound as a white solid in 26% yield, 445 mg.

¹HNMR(400 MHz, CD₃OD) δ: 5.07(s, 2H), 6.67-6.70(m, 2H), 6.80(d, 1H), 7.29-7.43(m, 5H); LRMS ESI m/z 224 [M]⁻

PREPARATION 36

5-[(3S)-3-(3-Benzyloxy-5-cyano-phenoxy)-pyrrolidin-1-yl]-5-methyl-2,2-diphenylhexanamide Diisopropyl azodicarboxylate (215 μL, 1.09 mmol) was added dropwise to an ice-cooled solution of triphenyl phosphine (286 mg, 1.09 mmol), the product from preparation 35 (369 mg, 1.64 mmol) and the product from preparation 17 (200 mg, 0.546 mmol) in tetrahydrofuran (10 mL), and the mixture was stirred at room temperature for 18 hours. The mixture was concentrated in vacuo and purified using an Isolute® SCX-2 cartridge, eluting with methanol, then with 1M ammonia in methanol. Basic fractions were concentrated in vacuo and further purified by column chromatography on silica gel, eluting with dichloromethane:methanol: 0.88 ammonia (98:2:0.2 to 97:3:0.3) to afford the title compound as an orange foam in 25% yield, 80 mg.

¹HNMR(400 MHz, CD₃OD) δ: 0.98(s, 3H), 1.02(s, 3H), 1.20-1.28(m, 3H), 1.81-1.87(m, 1H), 2.07-2.16(m, 1H), 2.34-2.83(m, 5H), 4.74-4.79(m, 1H), 5.10(s, 2H), 6.72-6.74(m, 2H), 6.93(s, 1H), 7.20-7.43(m, 15H); LRMS ESI m/z 574 [M+H]⁺

PREPARATION 37

5-{(3S)-3-[(7-{[tert-Butyl(dimethyl)silyl]oxy}-2-naphthyl)oxy]pyrrolidin-1-yl}-5-methyl-2,2-diphenylhexanamide A solution of 1,1'-Azobis(N,N'-dimethylformamide) (109 mg, 0.630 mmol) in tetrahydrofuran (2 ml) was added dropwise to an ice-cooled solution of triphenyl phosphine (165 mg, 0.630 mmol), 7-[[dimethyl(1,1-dimethylethyl)silyl]oxy] naphthalen-2-ol [(115 mg, 0.420 mmol), Journal of Medicinal Chemistry, 1993, Vol. 36, No. 22, p 3316] and the product from preparation 17 (171 mg, 0.467 mmol) in tetrahydrofuran (3 mL), and the mixture was stirred at room temperature for 72 hours, then 60° C. for 18 hrs. The mixture was concentrated in vacuo and the residue purified using an Isolute® SCX-2 cartridge, eluting with methanol, then with 0.5M ammonia in methanol. Basic fractions were concentrated in vacuo and further purified using a RediSep® silica gel cartridge, eluting with dichloromethane:methanol:0.88 ammonia (100:0:0 to 92:8:0.8) to afford the title compound as a colourless gum in 34% yield, 90 mg.

$^1$HNMR(400 MHz, CD$_3$OD) δ: 0.25(s, 6H), 0.95-1.10(m, 15H), 1.19-1.33(m, 2H), 1.95(m, 1H), 2.18(m, 1H), 2.34-2.52(m, 2H), 2.56-2.75(m, 2H), 2.76-2.86(m, 1H), 2.87-2.94 (m, 1H), 4.90(m, 1H), 6.83-6.96(m, 3H), 7.12(m, 1H), 7.13-7.36(m, 10H), 7.58-7.66(m, 2H); LRMS APCI m/z 623 [M+H]$^+$

PREPARATION 38

3-Methoxy-4-chloro-benzoic acid allyl ester

Potassium carbonate (4.44 g, 32.156 mmol) and allyl bromide (2.78 ml, 32.156 mmol) were added to a stirred solution of 4-chloro-3-methoxybenzoic acid (3 g, 16.078 mmol) in N,N-dimethylformamide (30 ml) and allowed to stir at room temperature for 18 hours. The reaction mixture was partitioned between diethyl ether (200 ml) and water (150 ml), the organic phase extracted and further washed with water (150 ml), dried over sodium sulfate and concentrated in vacuo to afford the title compound as an orange oil in 98% yield, 3.57 g.

$^1$HNMR(400 MHz, CD$_3$OD) δ: 3.92(s, 3H), 4.79-4.82(d, 2H), 5.26-5.29(d, 1H), 5.37-5.42(d, 1H), 6.00-6.10(m, 1H), 7.44-7.46(d, 1H), 7.56-7.59(dd, 1H), 7.62-7.63(d, 1H); LRMS ESI m/z 227 [M+H]$^+$

PREPARATION 39

3-Hydroxy-4-chloro-benzoic acid

Boron tribromide (1M in dichloromethane, 31 mL, 31.504 mmol) was added to an ice-cooled solution of the product of preparation 38 (3.56 g, 15.752 mmol) in dichloromethane (30 mL) and the mixture was stirred at 0° C. to room temperature for 18 hours. The reaction was quenched with 0.88 ammonia solution and stirred at room temperature for 90 minutes. The reaction mixture was acidified to pH 1 by dropwise addition of 2N hydrochloric acid (aq) and extracted with diethyl ether (2×50 mL). The combined organic layers were dried over sodium sulfate and concentrated in vacuo to afford the title compound as a pale yellow solid in 90% yield, 2.45 g.

$^1$HNMR(400 MHz, CD$_3$OD) δ: 7.36-7.38(d, 1H), 7.44-7.47(dd, 1H), 7.54-7.55(d, 1H); LRMS APCI m/z 171 [M–H]$^-$

PREPARATION 40

3-Allyloxy-4-chloro-benzoic acid allyl ester

Potassium carbonate (4.9 g, 35.057 mmol) and allyl bromide (3.07 ml, 35.507 mmol) were added to a stirred solution of the product of preparation 39 (2.45 g, 14.203 mmol) in N,N-dimethylformamide (30 ml) and allowed to stir at room temperature for 18 hours. The reaction mixture was partitioned between diethyl ether (70 ml) and water (70 ml), the organic phase was then extracted and further washed with water (50 ml), dried over sodium sulfate and concentrated in vacuo. The residue was purified by column chromatography on silica gel, eluting with pentane:ethyl acetate, 100:0 to 90:10, to afford the title compound as a pale orange oil in 74% yield, 2.65 g.

$^1$HNMR(400 MHz, CD$_3$OD) δ: 4.66-4.68(d, 2H), 4.79-4.81(d, 2H), 5.25-5.31(t, 2H), 5.36-5.49(q, 2H), 6.00-6.12(m, 2H), 7.45-7.47(d, 1H), 7.56-7.59(dd, 1H), 7.62(d, 1H)

PREPARATION 41

(3-Allyloxy-4-chloro-phenyl)-methanol

A solution of the product of preparation 40 (2.6 g, 10.30 mmol) in tetrahydrofuran (40 ml) was added dropwise to a stirred solution of lithium aluminium hydride (1M in tetrahydrofuran, 21 ml, 20.60 mmol) over 30 minutes at room temperature and allowed to stir for 18 hours. The reaction mixture was quenched by dropwise addition of water (1 ml), 2M sodium hydroxide (2 ml) and water (3 ml) and allowed to stir for 3 hours. The mixture was then filtered, washing with diethyl ether (2×20 ml) and water (10 ml). The organic phase was extracted, dried over sodium sulfate and concentrated in vacuo to afford the title compound as a colourless oil in 69% yield, 1.4 g.

$^1$HNMR(400 MHz, CD$_3$OD) δ: 4.50(s, 2H), 4.60-4.62(d, 2H), 5.24-5.28(d, 1H), 5.42-5.48(d, 1H), 6.03-6.12(m, 1H), 6.87-6.90(d, 1H), 7.05(s, 1H), 7.29-7.31(d, 1H); LRMS ESI m/z 198 [M+H]$^+$

PREPARATION 42

2-Allyloxy-4-bromomethyl-1-chlorobenzene

Dibromotriphenylphosphorane (3.27 g, 7.758 mmol) was added to a stirred solution of the product of preparation 41 (1.4 g, 7.053 mmol) in acetonitrile (50 ml) and allowed to stir at room temperature for 18 hours. Further dibromotriphenylphosphorane (3.27 g, 7.758 mmol) was added and the reaction mixture stirred at room temperature for a further 6 hours. The solution was then concentrated in vacuo and recrystallised from hot ethyl acetate (25 ml) and diethyl ether (25 ml). The solid was filtered from solution and the filtrate concentrated in vacuo. The residue was purified by column chromatography on silica gel, eluting with pentane:ethyl acetate, 100:0 to 80:20, to afford the title compound as a colourless oil in 48% yield, 890 mg.

$^1$HNMR(400 MHz, CD$_3$OD) δ: 4.52(s, 2H), 4.61-4.63(d, 2H), 5.25-5.29(d, 1H), 5.42-5.48(d, 1H), 6.02-6.11(m, 1H), 6.95-6.98(d, 1H), 7.10(d, 1H), 7.30-7.32(d, 1H)

PREPARATION 43

5-[(3R)-3-(3-Allyloxy-4-chloro-benzyloxy)-pyrrolidin-1-yl]-5-methyl-2,2-diphenylhexanenitrile A solution of the product of preparation 20 (180 mg, 0.515 mmol) in N,N-dimethylformamide (3 ml) was added to an ice-cooled solution of sodium hydride (60% dispersion in mineral oil, 41 mg, 1.032 mmol) in N,N-dimethylformamide (2 mL) and the mixture was stirred at 0° C. for 30 minutes. The product of preparation 42 (270 mg, 1.032 mmol) was added and the mixture was stirred for 18 hours at 0° C. to room temperature. The reaction was ice-cooled, further sodium hydride (41 mg, 1.032 mmol) was added and the mixture was stirred for a further 3 hours at room temperature. The reaction mixture was then quenched with water (3 mL), concentrated in vacuo and the aqueous residue was partitioned between ethyl acetate (30 mL) and water (20 mL). The organic layer was separated and washed with water (2×20 mL), then concentrated in vacuo. The residue was purified by column chromatography on silica gel, eluting with dichloromethane:methanol:0.88 ammonia, 95:5:0.5, to afford the title compound as a brown gum in 62% yield, 170 mg.

$^1$HNMR(400 MHz, $CD_3OD$) δ: 1.02(s, 3H), 1.05(s, 3H), 1.43-1.52(m, 2H), 1.78-1.86(m, 1H), 1.93-2.02(m, 1H), 2.49-2.56(m, 3H), 2.65-2.79(m, 3H), 4.03-4.08(m, 1H), 4.43(s, 2H), 4.56-4.58(d, 2H), 5.22-5.26(d, 1H), 5.39-5.45(d, 1H), 5.99-6.08(m, 1H), 6.85-6.88(dd, 1H), 7.01-7.02(d, 1H), 7.26-7.42(m, 11H); LRMS APCI m/z 529 [M+H]$^+$

PREPARATION 44

5-[(3R)-3-(4-Chloro-3-propenyloxy-benzyloxy)-pyrrolidin-1-yl]-5-methyl-2,2-diphenylhexanamide Potassium hydroxide (340 mg, 6.055 mmol) was added to a solution of the product of preparation 43 (160 mg, 0.303 mmol) in 3-methyl-3-pentanol (7 mL) and the mixture was heated under reflux for 24 hours. The reaction mixture was then cooled to room temperature, concentrated in vacuo and the residue was partitioned between ethyl acetate (25 mL) and water (25 mL). The aqueous layer was separated, extracted with further ethyl acetate (25 mL) and the combined organic layers were dried over sodium sulfate and concentrated in vacuo to afford the title compound as a yellow gum in 97% yield, 161 mg.

$^1$HNMR(400 MHz, $CD_3OD$) δ: 0.97(s, 3H), 0.99(s, 3H), 1.21-1.27(m, 2H), 1.70-1.72(d, 3H), 1.74-1.80(m, 1H), 1.87-1.93(m, 1H), 2.39-2.44(m, 2H), 2.45-2.50(m, 1H), 2.53-2.57 (dd, 1H), 2.59-2.65(q, 1H), 2.68-2.72(m, 1H), 3.98-4.02(m, 1H), 4.39(s, 2H), 4.93-5.00(m, 1H), 6.38-6.40(m, 1H), 6.94-6.97(dd, 1H), 7.04(d, 1H), 7.20-7.39(m, 11H); LRMS APCI m/z 547 [M+H]$^+$

PREPARATION 45

5-[(3R)-3-(3-benzyloxy-4-cyano-phenoxy)pyrrolidin-1-yl]-5-methyl-2,2-diphenylhexanamide Sodium hydride (60% dispersion in mineral oil, 26 mg, 0.656 mmol) was added to an ice-cooled solution of the product of preparation 17 (200 mg, 0.546 mmol) in N,N-dimethylformamide (5 mL) and the mixture was stirred for 60 minutes. 2-Benzyloxy-4-fluoro-benzonitrile (136 mg, 0.601 mmol) was added and the mixture was stirred for 18 hours at room temperature. The reaction mixture was quenched with water (3 mL), concentrated in vacuo and the aqueous residue was partitioned between ethyl acetate (20 mL) and water (15 mL). The aqueous layer was separated and extracted with further ethyl acetate (2×10 mL). The combined organic layers were concentrated in vacuo and the residue was purified by column chromatography on silica gel, eluting with dichloromethane:methanol:0.88 ammonia, 95:5:0.5, to afford the title compound as a white foam in 33% yield, 105 mg.

$^1$HNMR(400 MHz, $CD_3OD$) δ: 0.95(s, 3H), 1.02(s, 3H), 1.19-1.25(m, 2H), 1.79-1.88(m, 1H), 2.07-2.16(m, 1H), 2.33-2.49(m, 2H), 2.51-2.58(m, 2H), 2.67-2.74(m, 1H), 2.79-2.83 (m, 1H), 4.80-4.84(m, 1H), 5.20(s, 2H), 6.49-6.52(dd, 1H), 6.57-6.58(d, 1H), 7.20-7.38(m, 13H), 7.44-7.46(m, 2H), 7.48-7.50(d, 1H); LRMS APCI m/z 574 [M+H]$^+$

PREPARATION 46

(3-Allyloxy-2-chloro-phenyl)-methanol

Sodium borohydride (185 mg, 4.883 mmol) was added to a solution of the product of preparation 99 (800 mg, 4.07 mmol) in ethanol (30 ml) and the mixture stirred at room temperature for 18 hours. The mixture was quenched by addition of water (30 ml) followed by dropwise addition of glacial acetic acid until effervescence ceased. The mixture was then extracted with diethyl ether (2×50 ml) and the combined organic layers were washed with saturated aqueous sodium hydrogen carbonate solution (40 ml), dried over sodium sulfate and concentrated in vacuo to afford the title compound as a colourless gum in 100% yield, 805 mg.

$^1$HNMR(400 MHz, $CD_3OD$) δ: 4.60-4.62(m, 2H), 4.66-4.69(d, 2H), 5.24-5.28(d, 1H), 5.43-5.47(d, 1H), 6.01-6.12 (m, 1H), 6.82-6.84(d, 1H), 7.09-7.12(m, 1H), 7.22-7.26(m, 1H); LRMS ESI m/z 198 [M+H]$^+$

PREPARATION 47

3-Allyloxy-2-chloro-benzyl bromide

Dibromotriphenylphosphorane (1.87 g, 4.431 mmol) was added to a solution of the product of preparation 46 (800 mg, 4.028 mmol) in acetonitrile (30 ml) and the mixture allowed to stir at room temperature for 18 hours. Additional dibromotriphenylphosphorane (1.87 g, 4.431 mmol) was added and the mixture stirred at room temperature for a further 6 hours. The solution was concentrated in vacuo and the residue recrystallised from hot ethyl acetate (15 ml) and diethyl ether (15 ml). The solid was filtered from solution and the filtrate concentrated in vacuo. The residue was purified by column chromatography on silica gel, eluting with pentane:ethyl acetate, 100:0 to 90:10, to afford the title compound as a colourless oil in 27% yield, 285 mg.

$^1$HNMR(400 MHz, $CD_3OD$) δ: 4.61-4.63(m, 2H), 4.65(s, 2H), 5.26-5.29(d, 1H), 5.43-5.49(d, 1H), 6.00-6.11(m, 1H), 7.01-7.03(d, 1H), 7.08-7.10(d, 1H), 7.20-7.24(t, 1H); LRMS APCI m/z 262 [M+H]$^+$

PREPARATION 48

5-[(3R)-3-(3-Allyloxy-2-chloro-benzyloxy)-pyrrolidin-1-yl]-5-methyl-2,2-diphenylhexanenitrile The title compound was prepared from the product of preparation 47 and the product of preparation 20, using the same method as that described for preparation 43, to afford a brown gum in 46% yield.

$^1$HNMR(400 MHz, $CD_3OD$) δ: 1.03(s, 3H), 1.05(s, 3H), 1.45-1.51(m, 2H), 1.81-1.90(m, 1H), 1.95-2.04(m, 1H), 2.50-2.58(m, 3H), 2.65-2.79(m, 3H), 4.07-4.12(m, 1H), 4.49-4.54 (m, 2H), 4.59-4.61(m, 2H), 5.24-5.27(d, 1H), 5.41-5.47(d,

1H), 6.02-6.11(m, 1H), 6.96-6.98(d, 1H), 7.06-7.08(d, 1H), 7.17-7.42(m, 11H); LRMS APCI m/z 529 [M+H]+

PREPARATION 49

5-[(3R)-3-(2-Chloro-3-propenyloxy-benzyloxy)-pyrrolidin-1-yl]-5-methyl-2,2-diphenylhexanamide The title compound was prepared from the product of preparation 48, using the same method as that described for preparation 44, to afford a yellow gum in 100% yield.

$^1$HNMR(400 MHz, CD$_3$OD) δ: 0.98(s, 3H), 1.01(s, 3H), 1.23-1.27(m, 2H), 1.71-1.73(d, 3H), 1.78-1.85(m, 1H), 1.90-1.97(m, 1H), 2.40-2.44(m, 2H), 2.46-2.58(m, 2H), 2.61-2.67(q, 1H), 2.71-2.75(m, 1H), 4.03-4.09(m, 1H), 4.52-4.53(d, 2H), 4.93-5.00(m, 1H), 6.40-6.42(m, 1H), 7.00-7.02(d, 1H), 7.11-7.40(m, 12H); LRMS APCI m/z 547 [M+H]+

PREPARATION 50

5-Oxo-5-(4-phenoxypiperidin-1-yl)-2,2-diphenyl-pentanenitrile

1-Hydroxybenzotriazole hydrate (5.67 g, 42 mmol) and triethylamine (14.88 mL, 107 mmol) were added to 4-cyano-4,4-diphenylbutanoic acid (WO97/24325) (10.39 g, 39 mmol) and 4-phenoxy-piperidine hydrochloride (6.32 g, 36 mmol) in N,N-dimethylformamide (150 mL). The mixture was stirred for 10 minutes. 1-(3-Dimethylaminopropyl)-3-ethylcarbodiimide hydrochloride (8.20 g, 42 mmol) was then added and the mixture was stirred at room temperature for 18 hours. The reaction mixture was then concentrated in vacuo and the residue was partitioned between ethyl acetate (100 mL) and water (100 mL). The organic layer was separated, washed with water (100 mL) and brine (30 mL), dried over magnesium sulfate and concentrated in vacuo. The residue was triturated with diethyl ether, filtered off, washed through with diethyl ether and purified by column chromatography on silica gel, eluting with pentane:ethyl acetate, 75:25 to 50:50, to afford the title compound as a white solid (14.4 g) in a 95% yield.

$^1$HNMR(400 MHz, CDCl$_3$) δ: 1.74-1.90(m, 4H), 2.45-2.49(m, 2H), 2.79-2.83(m, 2H), 3.27-3.33(m, 1H), 3.54-3.61(m, 1H), 3.62-3.74(m, 2H), 4.49-4.53(m, 1H), 6.87-6.91(m, 2H), 6.93-6.98(m, 1H), 7.26-7.43(m, 12H); LRMS APCI m/z 426 [M+H]+

PREPARATION 51 tert-Butyl 4-[(3-bromobenzyl)oxy]piperidine-1-carboxylate

Sodium hydride (60% dispersion in mineral oil, 3.31 g, 83 mmol) was added to an ice-cooled solution of 1-tert-butoxy-carbonyl-4-hydroxy-piperidine (16.64 g, 83 mmol) in tetrahydrofuran (200 mL) and the mixture was stirred at 0° C. for 30 minutes. 3-Bromobenzyl bromide (20.66 g, 83 mmol) was added and the mixture was stirred at room temperature for 18 hours. The reaction was then quenched with water (50 mL) and concentrated in vacuo. The aqueous residue was extracted with ethyl acetate (2×100 mL) and the combined organic phases were washed with brine (100 mL), dried over magnesium sulfate and concentrated in vacuo. Purification of the residue by column chromatography on silica gel, eluting with pentane:ethyl acetate, 90:10 to 80:20, to afford the title compound as a colourless oil in 61% yield, 18.64 g.

$^1$HNMR(400 MHz, CDCl$_3$) δ: 1.45(s, 9H), 1.54-1.62(m, 2H), 1.81-1.88(m, 2H), 3.08-3.14(m, 2H), 3.52-3.58(m, 1H), 3.73-3.79(m, 2H), 4.51(s, 2H), 7.18-7.26(m, 2H), 7.38-7.41(m, 1H), 7.49(m, 1H); LRMS APCI m/z 372 [M+H]+

PREPARATION 52

4-[(3-Bromobenzyl)oxy]piperidine

Hydrochloric acid (4M in dioxan, 340 mL) was added to a solution of the product of preparation 51 (18.64 g, 50 mmol) in dioxan (50 mL) and the mixture was stirred at room temperature for 2.5 hours. The reaction mixture was concentrated in vacuo and the residue was dissolved in 2M aqueous hydrochloric acid (200 mL) and washed with diethyl ether (2×100 mL). The aqueous layer was adjusted to pH10 with 2M aqueous sodium hydroxide solution, extracted with diethyl ether (3×200 mL). The combined organic phases were dried over sodium sulfate and concentrated in vacuo to afford the title compound as a colourless oil in 98% yield, 13.39 g.

$^1$HNMR(400 MHz, CDCl$_3$) δ: 1.45-1.55(m, 2H), 1.92-1.97(m, 2H), 2.58-2.64(m, 2H), 3.07-3.13(m, 2H), 3.42-3.49(m, 1H), 4.51(s, 2H), 7.17-7.27(m, 2H), 7.37-7.40(m, 1H), 7.50(m, 1H); LRMS APCI m/z 270 [M+H]+

PREPARATION 53

5-{4-[(3-Bromobenzyl)oxy]piperidin-1-yl}-5-oxo-2,2-diphenylpentanenitrile

The title compound was prepared from 4-cyano-4,4-diphenylbutanoic acid (WO9724325) and the product of preparation 52 using the same method as that described for preparation 50, in 95% yield.

$^1$HNMR(400 MHz, CDCl$_3$) δ: 1.63(m, 2H), 1.82(m, 2H), 2.46(m, 2H), 2.80(m, 2H), 3.17(m, 1H), 3.35(m, 1H), 3.51-3.64(m, 2H), 3.88(m, 1H), 4.44-4.53(m, 2H), 7.17-7.42(m, 14H); LRMS APCI m/z 519 [M+H]+

PREPARATION 54

5-(4-Hydroxy-piperidin-1-yl)-5-methyl-2,2-diphenyl-hexanoic acid amide

A 1M HCl aqueous solution (9.43 mL, 9.43 mmol) was added to a stirred solution of example 91 in ethanol (250 mL). 20% Palladium (II) hydroxide on carbon (1 g) was added and the resulting mixture stirred under an atmosphere of hydrogen gas (50 psi) at 50° C. for 18 hours. The reaction mixture was filtered through arbocel and then concentrated in vacuo. The residue was dissolved in water (100 mL), the solution adjusted to pH 12 with 2M aqueous sodium hydroxide solution and extracted with ethyl acetate (3×100 mL). The combined organic layers were dried over magnesium sulfate and concentrated in vacuo to yield a white foam in 95% yield, 3.39 g.

$^1$HNMR(400 MHz, CD$_3$OD) δ: 0.97(s, 6H), 1.23-1.27(m, 2H), 1.39-1.48(m, 2H), 1.74-1.78(m, 2H), 2.06-2.11(m, 2H), 2.40-2.44(m, 2H), 2.65-2.68(m, 2H), 3.47(m, 1H), 7.23-7.39(m, 10H); LRMS ESI m/z 381 [M+H]+

PREPARATION 55

5-Amino-5-methyl-2,2-diphenylhexanenitrile

Potassium tert-butoxide (203 mg, 1.81 mmol) and tert-butyl 4,4-dimethyl-1,2,3-oxathiazinane-3-carboxylate 2,2- dioxide [(400 mg, 1.51 mmol), WO2003037327, p 83] were added to a solution of diphenylacetonitrile (349 mg, 1.81 mmol) in N,N-dimethylformamide (5 mL) and the mixture was stirred for 18 hours at room temperature. The reaction mixture was then concentrated in vacuo and the residue was treated with hydrochloric acid (4M in dioxane, 10 mL) and heated at 40° C. for 2.5 hours. The reaction mixture was concentrated in vacuo and the residue was basified with saturated sodium hydrogen carbonate solution and extracted with ethyl acetate (2×30 mL). The combined organic solution was dried over magnesium sulfate, concentrated in vacuo and the residue was purified by column chromatography on silica gel, eluting with dichloromethane:methanol:0.88 ammonia, 90:10:1, to afford the title compound as a colourless oil in 77% yield, 324 mg.
$^1$HNMR(400 MHz, CDCl$_3$) δ: 1.17(m, 6H), 1.48-1.57(m, 2H), 2.20-2.40(brs, 2H), 2.42-2.53(m, 2H), 7.22-7.43(m, 10H); LRMS APCI m/z 279 [M+H]$^+$

PREPARATION 56

5-(3-Hydroxyazetidin-1-yl)-5-methyl-2,2-diphenyl-hexanenitrile

A mixture of (+/-)-epichlorohydrin (1.47 mL, 18.76 mmol) and the product of preparation 55 (4.74 g, 17 mmol) in methanol (50 mL) was heated at 60° C. for 48 hours. The reaction mixture was then concentrated in vacuo and the residue was partitioned between ethyl acetate (50 mL) and sodium hydrogen carbonate solution (30 mL). The aqueous layer was separated and extracted with ethyl acetate (2×50 mL). The combined organic solution was dried over magnesium sulfate, concentrated in vacuo and the residue was purified by column chromatography on silica gel, eluting with dichloromethane:methanol:0.88 ammonia, 100:0:0 to 95:5:0.5, to afford the title compound as a pale yellow oil in 50% yield, 2.86 g.
$^1$HNMR(400 MHz, CDCl$_3$) δ: 0.93(s, 6H), 1.29-1.39(m, 2H), 2.38-2.50(m, 2H), 2.90-3.00(m, 2H), 3.29-3.39(m, 2H), 4.29-4.39(m, 1H), 7.24-7.45(m, 10H); LRMS APCI m/z 335 [M+H]$^+$

PREPARATION 57

1-(4-Cyano-1,1-dimethyl-4,4-diphenylbutyl)azetidin-3-yl methanesulfonate

Methane sulfonyl chloride (3.3 mL, 43 mmol) was added to a solution of the product of preparation 56 (4.82 g, 14.4 mmol) in pyridine (50 mL) cooled to –15° C. The mixture was stirred for 2 hours, allowing the temperature to warm to 0° C., then concentrated in vacuo. The residue was partitioned between ethyl acetate (100 mL) and sodium hydrogen carbonate solution (100 mL) and the organic layer was separated, dried over magnesium sulfate and concentrated in vacuo. Purification of the residue by column chromatography on silica gel, eluting with pentane:ethylacetate/methanol/0.88 ammonia (90/10/1) 2:1, afforded the title compound as a yellow oil in 81% yield, 4.80 g.
$^1$HNMR(400 MHz, CDCl$_3$) δ: 0.95(s, 6H), 1.30-1.41(m, 2H), 2.42-2.55(m, 2H), 2.98(s, 3H), 3.25-3.37(m, 2H), 3.44-3.56(m, 2H), 5.00-5.06(m, 1H), 7.23-7.44(m, 10H); LRMS APCI m/z 413 [M+H]$^+$

PREPARATION 58

Azetidin-3-yl methanesulfonate hydrochloride

A mixture of 1-(diphenylmethyl)azetidin-3-yl methanesulfonate (WO9725322, p 64), (20 g, 63 mmol) and chloroethylchloroformate (10 mL, 95 mmol) in dichloromethane (100 mL) was heated under reflux for 2.5 hours. The reaction mixture was then concentrated in vacuo and the residue was re-dissolved in methanol (100 mL) and heated under reflux for a further 2.5 hours. The mixture was then cooled to room temperature and concentrated in vacuo to afford the title compound as a white solid in quantitative yield, 9.6 g.
$^1$HNMR(400 MHz, DMSO-d$_6$) δ: 3.28(s, 3H), 4.00-4.15 (m, 2H), 4.31(m, 2H), 5.28-5.38(m, 1H); LRMS APCI m/z 152 [M+H]$^+$

PREPARATION 59

4-Cyano-4,4-diphenylbutanoyl chloride

N,N-Dimethylformamide (1 drop) was added to a suspension of 4-cyano-4,4-diphenylbutanoic acid [(7.8 g, 29 mmol), WO97/24325] and oxalyl chloride (5.2 mL, 60 mmol) in dichloromethane (40 mL) and the mixture was stirred at room temperature for 2 hours. The reaction mixture was then concentrated in vacuo and the residue was azeotroped with toluene (3×50 mL) to afford the crude title compound. The material was used in preparation 60 without further purification.

PREPARATION 60

1-(4-Cyano-4,4-diphenylbutanoyl)azetidin-3-yl methanesulfonate

Triethylamine (12.3 mL, 87 mmol) and a solution of the product of preparation 59 (8.23 g, 29 mmol) in dichloromethane were added dropwise to a solution of preparation 58 (5.53 g, 29 mmol) in dichloromethane (50 mL), cooled to –78° C., and the mixture was stirred at this temperature for 1 hour. The reaction mixture was quenched with 2N hydrochloric acid (50 mL) and the organic layer was separated, dried over magnesium sulfate and concentrated in vacuo. Purification of the residue by column chromatography on silica gel, eluting with ethyl acetate:pentane, 50:50 to 100:0, afforded the title compound as a yellow oil in 97% yield, 11.4 g.
$^1$HNMR(400 MHz, CDCl$_3$) δ: 2.17-2.29(m, 2H), 2.71-2.80(m, 2H), 3.05(s, 3H), 4.03-4.20(m, 2H), 4.26-4.38(m, 2H), 5.18-5.22(m, 1H), 7.24-7.45(m, 10H); LRMS APCI m/z 399 [M+H]$^+$

PREPARATION 61

5-{3-[2-(Benzyloxy)phenoxy]azetidin-1-yl}-5-oxo-2,2-diphenylpentanenitrile

The title compound was prepared from the product of preparation 60 and 2-(benzyloxy)phenol, using the same method as that described for example 99, as a yellow oil in 77% yield.
$^1$HNMR(400 MHz, CDCl$_3$) δ: 2.18-2.24(m, 2H), 2.75-2.80(m, 2H), 4.02-4.10(m, 2H), 4.23-4.33(m, 2H), 4.82-4.91 (m, 1H), 5.08(s, 2H), 6.62-6.65(m, 1H), 6.84-6.99(m, 3H), 7.24-7.43(m, 15H); LRMS APCI m/z 503 [M+H]$^+$

PREPARATION 62

5-{3-[2-(Benzyloxy)phenoxy]azetidin-1-yl}-5-methyl-2,2-diphenylhexanenitrile

A solution of the product of preparation 61 (700 mg, 1.39 mmol) in tetrahydrofuran (10 mL) was cooled to –35° C. Zirconium chloride (650 g, 2.78 mmol) was added and the reaction mixture was stirred at −35° C. for 1 hour. Methyl magnesium chloride (3M in tetrahydrofuran, 4.2 mL, 12.6 mmol) was then added dropwise and the mixture was stirred for 3 hours, with the temperature maintained below −20° C. The reaction was quenched with 1N sodium hydroxide solution (10 mL) and the mixture was filtered through Arbocel®, washing through with ethyl acetate. The organic layer of the filtrate was separated, washed with brine (20 mL), dried over magnesium sulfate and concentrated in vacuo. Purification of the residue by column chromatography on silica gel, eluting with pentane:ethyl acetate, 85:15 to 50:50 afforded the title compound as a yellow oil in 10% yield, 69 mg.

$^1$HNMR(400 MHz, CDCl$_3$) δ: 0.98(s, 6H), 1.35-1.42(m, 2H), 2.45-2.58(m, 2H), 3.20-3.32(m, 2H), 3.40-3.55(m, 2H), 4.68-4.78(m, 1H), 5.13(s, 2H), 6.64-6.72(d, 1H), 6.85-6.99 (m, 3H), 7.24-7.48(m, 15H); LRMS ESI m/z 517 [M+H]$^+$

PREPARATION 63

5-{3-[2-(Benzyloxy)phenoxy]azetidin-1-yl}-5-methyl-2,2-diphenylhexanamide

The title compound was prepared from the product of preparation 62, using the same method as that described for example 100, as a colourless gum in 55% yield.

$^1$HNMR(400 MHz, CDCl$_3$) δ: 0.90(s, 6H), 1.15-1.22(m, 2H), 2.42-2.52(m, 2H), 3.18-3.32(m, 2H), 3.40-3.58(m, 2H), 4.65-4.78(m, 1H), 5.13(s, 2H), 5.40-5.60(m, 2H), 6.62-6.70 (m, 1H), 6.82-6.97(m, 3H), 7.23-7.44(m, 15H); LRMS APCI m/z 535 [M+H]$^+$

PREPARATION 64

3-Phenoxyazetidine hydrochloride

10% Pd/C (2.5 g) was added to a solution of 1-(diphenylmethyl)-3-phenoxy-azetidine (27.7 g, 88 mmol) in ethanol (100 mL) and acetic acid (100 mL) and the mixture was stirred at room temperature, under 50 psi of hydrogen, for 24 hours. The reaction mixture was then filtered through Arbocel® and the filtrate was concentrated in vacuo. The residue was dissolved in diethyl ether (200 mL), cooled to 0° C. and treated with hydrochloric acid (1M in diethyl ether, 120 mL). The solvent was then evaporated under reduced pressure and the residue was azeotroped with toluene and triturated with ethyl acetate to afford the title compound as a white solid in 86% yield, 13.99 g.

LRMS APCI m/z 160 [M+H]$^+$

PREPARATION 65

5-Oxo-5-(3-phenoxyazetidin-1-yl)-2,2-diphenylpentanenitrile

A mixture of the product of preparation 64 (1.13 g, 7.6 mmol), 4-cyano-4,4-diphenylbutanoic acid [(2.4 g, 9.12 mmol), WO97/24325], 1-(3-dimethylaminopropyl)-3-ethylcarbodiimide hydrochloride (1.76 g, 9.12 mmol), 1-hydroxybenzotriazole hydrate (1.30 g, 9.12 mmol) and N,N-diisopropylethylamine (5.3 mL, 19 mmol) in dichloromethane (50 mL) was stirred at room temperature for 18 hours. The reaction mixture was then diluted with ethyl acetate (50 mL), washed with 2M hydrochloric acid (30 mL), and sodium hydrogen carbonate solution (30 mL), dried over magnesium sulfate and concentrated in vacuo. Purification of the residue by column chromatography on silica gel, eluting with pentane:ethyl acetate, 100:0 to 0:100, then afforded the title compound as a colourless oil in 75% yield, 2.28 g.

$^1$HNMR(400 MHz, CDCl$_3$) δ: 2.20-2.25(m, 2H), 2.75-2.82(m, 2H), 3.97-4.08(m, 2H), 4.28-4.40(m, 2H), 4.85-4.90 (m, 1H), 6.65-6.74(m, 2H), 6.98-7.04(m, 1H), 7.24-7.43(m, 12H); LRMS APCI m/z 397 [M+H]$^+$

PREPARATION 66 tert-Butyl[4-(iodomethyl)phenoxy]dimethylsilane

Triphenyl phosphine (1.32 g, 5.03 mmol), imidazole (370 mg, 5.47 mmol) and iodine (1.16 g, 4.61 mmol) were added to an ice-cooled solution of 4-(tert-butyldimethylsilyloxy)benzyl alcohol [(1 g, 4.19 mmol), Tet. Lett. (2004), 45, 9617] in tetrahydrofuran (50 mL) and the mixture was stirred at 0° C. for 10 minutes and room temperature for 30 minutes. The reaction mixture was then concentrated in vacuo and the residue was partitioned between ethyl acetate and water. The organic layer was separated, dried over magnesium sulfate and concentrated in vacuo. Purification of the residue by column chromatography on silica gel, eluting with pentane, afforded the title compound in 41% yield, 600 mg.

$^1$HNMR(400 MHz, CDCl$_3$) δ: 0.00 (s, 6H), 0.78 (s, 9H), 4.26 (s, 2H), 6.72-6.98 (m, 2H), 7.22-7.28 (m, 2H)

PREPARATION 67

5-Allyloxy-2,4-dichloro-phenol 4,6-dichlororesorcinol (3.80 g, 21 mmol), allyl bromide (1.82 mL, 21 mmol) and potassium carbonate (2.24 g, 21 mmol) were combined in DMF and stirred at room temperature for 18 hours. The DMF was removed in vacuo and the residue acidified with 2M hydrochloric acid (50 mL) and extracted with ethyl acetate (2×50 mL). The combined organic solution was dried over magnesium sulphate and concentrated in vacuo. The residue was purified by column chromatography on silica gel, eluting with pentane:ethyl acetate 9:1 to 4:1 to afford the title compound as a yellow oil in 27% yield, 1.24 g.

$^1$HNMR(400 MHz, CDCl$_3$) δ: 4.55-4.60 (m, 2H), 5.33-5.52 (m, 2H), 5.95-6.10 (m, 1H), 6.62 (s, 1H), 7.3 (s, 1H); LRMS ESI m/z 217 [M−H]$^-$

PREPARATION 68

5-[3-(5-Allyloxy-2,4-dichloro-phenoxy)-azetidin-1-yl]-5-methyl-2,2-diphenyl-hexanenitrile The title compound was prepared from the products of preparation 67 and preparation 57, using the same method as that described for example 99, as a colourless gum in 93% yield.

$^1$HNMR(400 MHz, CDCl$_3$) δ: 0.98 (s, 6H), 1.31-1.40 (m, 2H), 2.41-2.55 (m, 2H), 3.20-3.25 (m, 2H), 3.48-3.58 (m, 2H), 4.55-4.58 (m, 2H), 4.62-4.75 (m, 1H), 5.32-5.38 (m, 1H), 5.40-5.48 (m, 1H), 5.95-6.10 (m, 1H), 6.28 (s, 1H), 7-25-7.45 (m, 11H); LRMS APCI m/z 535 [M+H]$^+$

PREPARATION 69

2-Allyloxy-4,5-dichloro-phenol

The title compound was prepared from 4,5-dichlorocatechol using the same method as that described for preparation 67, as a pink solid in 62% yield.

¹HNMR(400 MHz, CDCl₃) δ: 4.55-4.60 (m, 2H), 5.35-5.45 (m, 2H), 5.81 (1H, s), 5.95-6.10 (m, 1H), 6.90 (s, 1H), 7.03 (s, 1H); LRMS APCI m/z 217 [M–H]⁻

PREPARATION 70

5-[3-(2-Allyloxy-4,5-dichloro-phenoxy)-azetidin-1-yl]-5-methyl-2,2-diphenyl-hexanenitrile The title compound was prepared from the products of preparation 69 and preparation 57, using the same method as that described for example 99, as a colourless gum in 75% yield.

¹HNMR(400 MHz, CDCl₃) δ: 0.98 (s, 6H), 1.31-1.40 (m, 2H), 2.41-2.55 (m, 2H), 3.15-3.25 (m, 2H), 3.36-3.50 (m, 2H), 4.50-4.58 (m, 2H), 4.60-4.66 (m, 1H), 5.28-5.42 (m, 2H), 5.95-6.10 (m, 1H), 6.65 (s, 1H), 6.95 (s, 1H), 7-25-7.45 (m, 10H); LRMS APCI m/z 535 [M+H]⁺

PREPARATION 71

1-Allyloxy-3-bromomethyl-benzene

To a solution of (3-allyloxy-phenyl)-methanol (Tetrahedron (2000), 56(13), 1873-1882) (1.07 g, 6.49 mmol) in THF (7 mls) at 3° C. was added carbon tetrabromide (2.69 g, 8.11 mmol) then triphenylphosphine (2.13 g, 8.11 mmol) in THF (2 mls). The reaction mixture was stirred at 5° C. for 1 hour. The reaction mixture was filtered and concentrated in vacuo. The residue was washed with pentane to give a yellow solid which was purified by column chromatography on silica gel, eluting with pentane:ethyl acetate, 100:0, to 95:5 to afford the title compound as a pale yellow oil in 24% yield, 350 mg.

¹HNMR(400 MHz, CDCl₃) δ: 4.47 (s, 2H), 4.51-4.60 (m, 2H), 5.26-5.35 (m, 1H), 5.37-5.47 (m, 1H), 5.99-6.11 (m, 1H), 6.82-6.90 (m, 1H), 6.92-7.01 (m, 2H), 7.21-7.30 (m, 1H).

PREPARATION 72

5-[3-(3-Allyloxy-benzyloxy)-azetidin-1-yl]-5-methyl-2,2-diphenyl-hexanenitrile Sodium hydride (60% dispersion in mineral oil, 24 mg, 0.596 mmol) was added portionwise to an ice-cooled solution of the product of preparation 56 (166 mg, 0.496 mmol) in N,N-dimethylformamide (2 mL) and the mixture was stirred at 0° C. for 15 mins. The product of preparation 71 (169 mg, 0.746 mmol) was added and the mixture was stirred for 0.5 hour at 0° C. The reaction mixture was then quenched with 2N hydrochloric acid (2 mL) then basified with saturated sodium hydrogen carbonate solution. The resulting mixture was then partitioned between ethyl acetate (50 mL) and water (10 mL). The aqueous layer was separated and extracted with ethyl acetate (1×50 mL). The combined organic solution was dried over magnesium sulfate, concentrated in vacuo and the residue was purified by column chromatography on silica gel, eluting with dichloromethane:methanol:0.88 ammonia, 100:0:0 to 98:2:0.2 to afford the title compound as a colourless gum in 54% yield, 130 mg.

¹HNMR(400 MHz, CDCl₃) δ: 0.93(s, 6H), 1.26-1.38 (m, 2H), 2.38-2.50 (m, 2H), 2.96-3.10 (m, 2H), 3.18-3.36 (m, 2H), 4.06-4.18 (m, 1H), 4.39 (s, 2H), 4.52-4.58 (m, 2H), 5.25-5.33 (m, 1H), 5.37-5.47 (m, 1H), 6.00-6.11 (m, 1H), 6.81-6.93(m, 3H), 7.20-7.45(m, 11H); LRMS APCI m/z 481 [M+H]⁺

PREPARATION 73

5-Methyl-2,2-diphenyl-5-[3-(3-propenyloxy-benzyloxy)-azetidin-1-yl]-hexanoicacid amide Potassium hydroxide (303 mg, 5.42 mmol) was added to a solution of preparation 72 (130 mg, 0.271 mmol) in 3-methyl-3-pentanol (5 mL) and the mixture was heated under reflux for 24 hours. The reaction mixture was then cooled to room temperature, concentrated in vacuo and the residue was partitioned between ethyl acetate (50 mL) and water (10 mL). The aqueous layer was separated, extracted with ethyl acetate (2×30 mL) and the combined organic solution was dried over magnesium sulfate and concentrated in vacuo to give a colourless gum in 96% yield, 130 mg.

¹HNMR(400 MHz, CDCl₃) δ: 0.87(s, 6H), 1.07-1.19(m, 2H), 1.64-1.76 (m, 3H), 2.37-2.47(m, 2H), 2.94-3.10 (m, 2H), 3.20-3.40(m, 2H), 4.08-4.20(m, 1H), 4.35 (s, 2H), 4.83-4.93 (m, 1H), 5.35-5.65 (d, 2H), 6.34-6.40 (d, 1H), 6.88-6.98(m, 3H), 7.20-7.40 (m, 11H); LRMS APCI m/z 499 [M+H]⁺

PREPARATION 74

3-Allyloxy-2,6-dichloro-benzaldehyde 2,6-dichloro-3-hydroxybenzaldehyde (960 mg, 5.03 mmol) (Synthesis, 2004, 12, 2062), allyl bromide (431 μL, 5.03 mmol) and potassium carbonate (563 mg, 10.06 mmol) were combined in DMF (5 mL) and stirred at room temperature for 18 hours. The DMF was removed in vacuo and the residue partitioned between diethyl ether (50 mL) and water (30 mL). The layers were separated and the aqueous extracted with diethyl ether (2×30 mL). The combined organic solution was dried over magnesium sulphate and concentrated in vacuo to afford the title compound as a yellow solid which was used without further purification in preparation 75.

¹HNMR(400 MHz, CDCl₃) δ: 4.62-4.65 (m, 2H), 5.35-5.38 (m, 1H), 5.45-5.52 (m, 1H), 6.00-6.13 (m, 1H), 7.00-7.04 (m, 1H), 7.27-7.35 (m, 1H), 10.46 (s, 1H); LRMS APCI m/z 232 [M+H]⁺

PREPARATION 75

(3-Allyloxy-2,6-dichloro-phenyl)-methanol

The product of preparation 74 (~5.03 mmol) was dissolved in ethanol (30 mL) and sodium borohydride (284 mg, 7.79 mmol) was added. The reaction mixture was stirred at room temperature for 30 minutes. The reaction was diluted with water (30 mL) and glacial acetic acid was added dropwise until no further effervescence was observed. The mixture was extracted with diethyl ether (2×50 mL). The combined organic extracts were washed with brine, dried over magnesium sulphate and concentrated in vacuo to afford the title compound as a colourless solid which was used without further purification in preparation 76.

¹HNMR(400 MHz, CDCl₃) δ: 4.54-4.64 (m, 2H), 4.98 (s, 2H), 5.33-5.38 (m, 1H), 5.43-5.52 (m, 1H), 5.99-6.11 (m, 1H), 6.83-6.88 (m, 1H), 7.24-7.28 (m, 1H).

PREPARATION 76

1-Allyloxy-2,4-dichloro-3-chloromethyl-benzene

The product of preparation 75 (400 mg, 1.72 mmol) was dissolved in dichloromethane (20 mL) and thionyl chloride (312 μL, 4.29 mmol) was added over 1 minute. The reaction mixture was stirred at room temperature for 10 minutes. The reaction was quenched with water (2×10 mL). The organic layer was dried over magnesium sulphate and concentrated in vacuo to afford the title compound as a yellow solid in 91% yield (390 mg)

$^1$HNMR(400 MHz, CDCl$_3$) δ: 4.54-4.64 (m, 2H), 4.88 (s, 2H), 5.28-5.37 (m, 1H), 5.42-5.50 (m, 1H), 5.99-6.11 (m, 1H), 6.83-6.91 (m, 1H), 7.24-7.33 (m, 1H).

PREPARATION 77

5-[3-(3-Allyloxy-2,6-dichloro-benzyloxy)-azetidin-1-yl]-5-methyl-2,2-diphenyl-hexanenitrile Sodium hydride (60% dispersion in mineral oil, 25 mg, 0.629 mmol) was added portionwise to an ice-cooled solution of the product of preparation 56 (140 mg, 0.419 mmol) in N,N-dimethylformamide (2 mL) and the mixture was stirred at 0° C. for 30 mins. The product of preparation 76 (137 mg, 0.546 mmol) was added in DMF (1 mL) and the mixture was stirred for 18 hour at room temperature. The reaction mixture was then quenched saturated sodium hydrogen carbonate solution (10 mL) and the resulting mixture was extracted with diethyl ether (3×50 mL). The combined organic solution was dried over magnesium sulfate, concentrated in vacuo and the residue was purified by column chromatography on silica gel, eluting with dichloromethane:methanol:0.88 ammonia, 100:0:0 to 98:2:0.2 to afford the title compound as a colourless gum in 87% yield, 200 mg.

$^1$HNMR(400 MHz, CDCl$_3$) δ: 0.95 (s, 6H), 1.28-1.38 (m, 2H), 2.40-2.48 (m, 2H), 3.00-3.10 (m, 2H), 3.20-3.38 (m, 2H), 4.15-4.25 (m, 1H), 4.58-4.62 (m, 2H), 4.68 (s, 2H), 5.26-5.35 (m, 1H), 5.42-5.48 (m, 1H), 6.00-6.08 (m, 1H), 6.82-6.85 (m, 1H), 7.21-7.44 (m, 11H); LRMS APCI m/z 549 [M+H]$^+$

PREPARATION 78

5-(3-{2,6-Dichloro-3-[((E)-propenyl)oxy]-benzyloxy}-azetidin-1-yl)-5-methyl-2,2-diphenyl-hexanoic acid amide Potassium hydroxide (400 mg, 7.14 mmol) was added to a solution of preparation 77 (200 mg, 0.364 mmol) in 3-methyl-3-pentanol (3 mL) and the mixture was heated at 120° C. for 24 hours. The reaction mixture was then cooled to room temperature, concentrated in vacuo and the residue was partitioned between ethyl acetate (50 mL) and water (30 mL). The aqueous layer was separated, extracted with ethyl acetate (2×50 mL) and the combined organic solution was dried over magnesium sulfate and concentrated in vacuo. Recrystallisation from diisopropylether gave the title compound as a colourless solid in 73% yield, 150 mg.

$^1$HNMR(400 MHz, CDCl$_3$) δ: 0.90 (s, 6H), 1.12-1.20 (m, 2H), 1.72-1.78 (m, 3H), 2.40-2.52 (m, 2H), 3.02-3.15 (m, 2H), 3.24-3.40 (m, 2H), 4.15-4.25 (m, 1H), 4.68 (s, 2H), 4.98-5.07 (m, 1H), 5.35-5.63 (br m, 2H), 6.25-6.28 (m, 1H), 6.92-6.95 (m, 1H), 7.21-7.38 (m, 11H); LRMS ESI m/z 567 [M+H]$^+$

PREPARATION 79

Sulfamic acid 2-cyclopentyl-ethyl ester

To chlorosulfonyl isocyanate (275 mL, 3.15 mol) at 0° C. was added formic acid (119 mL, 3.15 mol), dropwise. The resulting solid was allowed to stir at 0° C. for a further 20 minutes. The residue was diluted with dichloromethane (875 mL) and warmed to room temperature for one hour. The reaction mixture was cooled in an ice/salt bath and a solution of 2-cyclopentyl ethanol (240 g, 2.1 mol) in pyridine (255 mL, 3.15 mol) and dichloromethane (2.1 L) was added, keeping the temperature below 7° C. After 2 hours, the reaction was concentrated in vacuo, diluted with ethyl acetate, washed with saturated sodium bicarbonate solution and brine. The organic layer was dried over sodium sulfate, filtered and concentrated in vacuo to give a colourless oil. The residue was purified by column chromatography on silica gel, eluting with 90:10 to 50:50 heptane:ethyl acetate, to afford the title compound as a colourless oil in 95% yield (276 g).

PREPARATION 80

8-Oxa-7-this-6-aza-spiro[4.5]decane 7,7-dioxide

To the product of preparation 79 (276 g, 1.43 mol) in dichloromethane (7.1 L) at room temperature were added magnesium oxide (132.5 g, 3.29 mol), iodobenzene diacetate (507 g, 1.57 mol) and rhodium acetate dimer (12.6 g, 0.028 mol). The reaction mixture was stirred at room temperature for 18 hours. The residue was filtered through a bed of celite and the solvent was removed in vacuo. The residue was purified by column chromatography on silica gel, eluting with 90:10 to 50:50 heptane:ethyl acetate, to afford the title compound as a white crystalline solid in 75% yield (205 g).

$^1$HNMR(400 MHz, CDCl$_3$) δ: 1.63-1.78 (m, 4H), 1.79-2.00 (m, 4H), 2.00-2.11 (m, 2H), 4.64-4.67 (m, 2H), 4.71 (s, 1H); LRMS APCI m/z 214 [M+Na]$^+$

PREPARATION 81

7,7-Dioxo-8-oxa-7lambda*6*-thia-6-aza-spiro[4.5]decane-6-carboxylic acid tert-butylester The product of preparation 80 (1.0 g, 5.23 mmol), di-tert-butyl dicarbonate (1.36 g, 6.24 mmol), triethyamine (1.06 g, 10.5 mmol) and 4-dimethylaminepyridine (126 mg, 1.03 mmol) were combined at room temperature in dichloromethane (50 mL). After 3 hours, the reaction was washed with ammonium chloride (50 mL, sat. aq.) and the organic solution was dried over magnesium sulfate and concentrated in vacuo. The residue was purified by column chromatography on silica gel, eluting with 100:0 to 80:20 pentane:ethyl acetate, to afford the title compound as a colourless oil in 46% yield (700 mg).

$^1$HNMR(400 MHz, CDCl$_3$) δ: 1.48 (s, 9H), 1.48-1.66 (m, 2H), 1.82-1.96 (m, 4H), 2.17-2.33 (m, 4H), 4.57-4.63 (m, 2H).

PREPARATION 82

4-(1-Amino-cyclopentyl)-2,2-diphenyl-butyronitrile

The title compound was prepared from the product of preparation 81 using a similar method to that described for preparation 55, in 67% yield.

$^1$HNMR(400 MHz, CDCl$_3$) δ: 1.43-1.58 (m, 4H), 1.58-1.67 (m, 4H), 1.72-1.80 (m, 2H), 2.49-2.60 (m, 2H), 7.25-7.46 (m, 10H); LRMS APCI m/z 305[M+H]$^+$

PREPARATION 83

4-[1-(3-Hydroxy-azetidin-1-yl)-cyclopentyl]-2,2-diphenyl-butyronitrile

The title compound was prepared from the product of preparation 82 using a similar method to that described for preparation 56, in 52% yield.
$^1$HNMR(400 MHz, CDCl$_3$) δ: 1.25-1.38 (m, 2H), 1.39-1.64 (m, 6H), 1.65-1.78 (m, 2H), 2.42-2.55 (m, 2H), 2.86-2.97 (m, 2H), 3.36-3.40 (m, 2H), 4.29-4.40 (m, 1H), 7.25-7.48 (m, 10H); LRMS APCI m/z 361 [M+H]$^+$

PREPARATION 84

Methanesulfonic acid 1-[1-(3-cyano-3,3-diphenyl-propyl)-cyclopentyl]-azetidin-3-yl ester The title compound was prepared from the product of preparation 83 using a similar method to that described for preparation 57, in 59% yield.
$^1$HNMR(400 MHz, CDCl$_3$) δ: 1.25-1.67 (m, 10H), 2.42-2.52 (m, 2H), 3.00 (s, 3H), 3.15-3.26 (m, 2H), 3.40-3.55 (m, 2H), 4.95-5.05 (m, 1H), 7.27-7.45 (m, 10H); LRMS APCI m/z 439 [M+H]$^+$

PREPARATION 85

5-[3-(3-Allyloxy-4-chloro-benzyloxy)-azetidin-1-yl]-5-methyl-2,2-diphenyl-hexanenitrile The title compound was prepared from the product of preparation 56 and the product of preparation 42 using a similar method to that described for example 101, in 83% yield.
$^1$HNMR(400 MHz, CDCl$_3$) δ: 0.92 (s, 6H), 1.32-1.38 (m, 2H), 2.40-2.48 (m, 2H), 2.97-3.06 (m, 2H), 3.23-3.32 (m, 2H), 4.05-4.16 (m, 1H), 4.36 (s, 2H), 4.58-4.65 (m, 2H), 5.28-5.35 (m, 1H), 5.43-5.63 (m, 1H), 6.02-6.16 (m, 1H), 6.80-6.85 (m, 1H), 6.92 (s, 1H), 7.23-7.42 (m, 11H); LRMS APCI m/z 515 [M+H]$^+$

PREPARATION 86

5-(3-{4-Chloro-3-[((E)-propenyl)oxy]-benzyloxy}-azetidin-1-yl)-5-methyl-2,2-diphenyl-hexanoic acid amide The title compound was prepared from the product of preparation 85 using a similar method to that described for preparation 73, in 75% yield.
LRMS APCI m/z 533 [M+H]$^+$

PREPARATION 87

4-{1-[3-(3-Allyloxy-4-chloro-phenoxy)-azetidin-1-yl]-cyclopentyl}-2,2-diphenyl-butyronitrile The title compound was prepared from the product of preparation 84 and 3-allyloxy-4-chlorophenol (EP78099) using a similar method to that described for example 99, in 82% yield.
$^1$HNMR(400 MHz, CDCl$_3$) δ: 1.25-1.40 (m, 2H), 1.40-1.65 (m, 6H), 1.66-1.77 (m, 2H), 2.46-2.58 (m, 2H), 3.07-3.16 (m, 2H), 3.46-3.58 (m, 2H), 4.55-4.59 (m, 2H), 4.60-4.73 (m, 1H), 5.26-5.35 (m, 1H), 5.43-5.53 (m, 1H), 6.00-6.13 (m, 1H), 6.20-6.28 (m, 1H), 6.42 (s, 1H), 7.19-7.23 (m, 1H), 7.23-7.46 (m, 10H); LRMS APCI m/z 527 [M+H]$^+$

PREPARATION 88

4-[1-(3-{4-Chloro-3-[((E)-propenyl)oxy]-phenoxy}-azetidin-1-yl)-cyclopentyl]-2,2-diphenyl-butyramide The title compound was prepared from the product of preparation 87 using a similar method to that described for preparation 73, in 49% yield.
LRMS APCI m/z 545 [M+H]$^+$

PREPARATION 89

3-Bromo-5-methoxy-phenol 1-bromo-3,5-dimethyoxybenzene (3.0 g, 13.8 mmol) was dissolved in dichloromethane (45 mL) and the solution was cooled to −78° C. Boron tribromide (1M in dichloromethane, 41 mL, 41 mmol) was added and the solution was warmed gradually to room temperature over 18 hours. After cooling to −78° C., the reaction was quenched with water (100 mL). The organics were separated and washed with sodium thiosulphate solution then water, then dried over magnesium sulfate and concentrated in vacuo. The residue was purified by column chromatography on silica gel, eluting with pentane:ethyl acetate 100:0 to 80:20, to afford the title compound in 16% yield (470 mg).
$^1$HNMR(400 MHz, MeOD) δ: 3.76 (s, 3H), 6.28 (s, 1H), 6.53-6.57 (m, 2H).

PREPARATION 90

4-Allyloxy-3-chloro-benzaldehyde

The title compound was prepared from 3-chloro-4-hydroxybenzaldehyde using a similar method to that described for preparation 74, in 96% yield. The material was used without further purification in preparation 91.
$^1$HNMR(400 MHz, CDCl$_3$) δ: 4.68-4.76 (m, 2H), 5.35-5.39 (m, 1H), 5.44-5.56 (m, 1H), 6.02-6.15 (m, 1H), 7.01-7.05 (m, 1H), 7.76-7.79 (m, 1H), 7.93 (s, 1H), 9.86 (s, 1H); LRMS APCI m/z 197 [M+H]$^+$

PREPARATION 91

(4-Allyloxy-3-chloro-phenyl)-methanol

The title compound was prepared from the product of preparation 90 using a similar method to that described for preparation 75, in 100% yield. The material was used without further purification in preparation 92.
$^1$HNMR(400 MHz, CDCl$_3$) δ: 4.61-4.65 (m, 4H), 5.28-5.36 (m, 1H), 5.44-5.52 (m, 1H), 6.02-6.13 (m, 1H), 6.88-6.94 (m, 1H), 7.17-7.20 (m, 1H), 7.40 (s, 1H).

PREPARATION 92

1-Allyloxy-2-chloro-4-chloromethyl-benzene

The title compound was prepared from the product of preparation 91 using a similar method to that described for preparation 76, in 70% yield. The material was used without further purification in preparation 94.

¹HNMR(400 MHz, CDCl₃) δ: 4.52 (s, 2H), 4.60-4.63 (m, 2H), 5.28-5.35 (m, 1H), 5.43-5.54 (m, 1H), 6.01-6.12 (m, 1H), 6.86-6.94 (m, 1H), 7.20-7.24 (m, 1H), 7.42 (s, 1H).

PREPARATION 93

5-(3-Hydroxy-azetidin-1-yl)-5-methyl-2,2-diphenyl-hexanoic acid amide

The product from example 102 (5.2 g, 12.2 mmol), ammonium formate (4.25 g, 92 mmol) and palladium hydroxide 20 wt % Pd on carbon (1.7 g) were combined in ethanol (150 mL) and stirred at reflux for one hour. After cooling, the residue was filtered through Arbocel®, washing with MeOH (50 mL). The filtrate was concentrated in vacuo. The residue was diluted with ethyl acetate (100 mL) and washed with sodium hydrogen carbonate solution (30 mL, sat. aq.). The organic extract was dried over magnesium sulfate and concentrated in vacuo. The title compound was isolated as a colourless foam in 97% yield, 4.2 g.
¹HNMR(400 MHz, CDCl₃) δ: 0.94 (s, 6H), 1.08-1.18 (m, 2H), 2.35-2.45 (m, 2H), 2.85-2.95 (m, 2H), 3.26-3.35 (m, 2H), 4.25-4.35 (m, 1H), 5.56-5.80 (br m, 2H), 7.15-7.40 (m, 10H); LRMS ESI m/z 353 [M+H]⁺

PREPARATION 94

5-[3-(4-Allyloxy-3-chloro-benzyloxy)-azetidin-1-yl]-5-methyl-2,2-diphenyl-hexanoic acid amide The product of preparation 93 (300 mg, 0.85 mmol) was dissolved in DMF at 0° C. (5 mL) and sodium hydride (60% dispersion in oil, 62 mg, 1.6 mmol) added. After 30 minutes, a solution of the product of preparation 92 (210 mg, 1.15 mmol) in DMF (1 mL) was added. After 30 minutes, the reaction was quenched with 2N HCl (20 ml), basified with saturated sodium hydrogen carbonate and the product extracted with ethyl acetate (20 mL). The organic extract was dried over magnesium sulfate and concentrated in vacuo. Purification of the residue by column chromatography on silica gel, eluting with dichloromethane:methanol:0.88 ammonia, 100:0:0 to 90:10:1, afforded the title compound as a colourless oil in 22% yield, 100 mg.
¹HNMR(400 MHz, CDCl₃) δ: 0.92 (s, 6H), 1.11-1.20 (m, 2H), 2.39-2.47 (m, 2H), 2.98-3.08 (m, 2H), 3.23-3.39 (m, 2H), 4.08-4.17 (m, 1H), 4.28 (s, 2H), 4.58-4.63 (m, 2H), 5.27-5.35 (m, 1H), 5.45-5.50 (m, 1H), 5.40-5.60 (br m, 2H), 6.01-6.13 (m, 1H), 6.85-6.92 (m, 1H), 7.07-7.15 (m, 1H), 7.20-7.37 (m, 11H); LRMS ESI m/z 533 [M+H]⁺

PREPARATION 95

2-Allyloxy-4-chloro-benzaldehyde

The title compound was prepared from 4-chloro-2-hydroxybenzaldehyde using a similar method to that described for preparation 74, in 85% yield. The material was used without further purification in preparation 96.
¹HNMR(400 MHz, CDCl₃) δ: 4.62-4.66 (m, 2H), 5.35-5.39 (m, 1H), 5.40-5.46 (m, 1H), 6.02-6.13 (m, 1H), 6.92-6.96 (m, 1H), 7.45-7.51 (m, 1H), 7.80 (s, 1H), 10.45 (s, 1H); LRMS APCI m/z 197 [M+H]⁺

PREPARATION 96

(2-Allyloxy-4-chloro-phenyl)-methanol

The title compound was prepared from the product of preparation 95 using a similar method to that described for preparation 75, in 100% yield. The material was used without further purification in preparation 97.
¹HNMR(400 MHz, CDCl₃) δ: 4.55-4.60 (m, 2H), 4.67 (s, 2H), 5.28-5.35 (m, 1H), 5.38-5.45 (m, 1H), 5.98-6.08 (m, 1H), 6.76-6.83 (m, 1H), 7.17-7.21 (m, 1H), 7.33 (s, 1H).

PREPARATION 97

2-Allyloxy-4-chloro-1-chloromethyl-benzene

The title compound was prepared from the product of preparation 96 using a similar method to that described for preparation 76, in 77% yield. The material was used without further purification in preparation 98
¹HNMR(400 MHz, CDCl₃) δ: 4.57-4.60 (m, 2H), 4.62 (s, 2H), 5.28-5.35 (m, 1H), 5.40-5.47 (m, 1H), 6.00-6.09 (m, 1H), 6.78-6.83 (m, 1H), 7.20-7.25 (m, 1H), 7.37 (s, 1H).

PREPARATION 98

5-[3-(2-Allyloxy-4-chloro-benzyloxy)-azetidin-1-yl]-5-methyl-2,2-diphenyl-hexanoic acid amide The title compound was prepared from the products of preparation 97 and 93 using a similar method to that described for preparation 94, in 18% yield.
¹HNMR(400 MHz, CDCl₃) δ: 0.92 (s, 6H), 1.10-1.98 (m, 2H), 2.38-2.45 (m, 2H), 2.98-3.08 (m, 2H), 3.28-3.39 (m, 2H), 4.10-4.20 (m, 1H), 4.40 (s, 2H), 4.47-4.55 (m, 2H), 5.23-5.32 (m, 1H), 5.35-5.41 (m, 1H), 5.53-5.86 (br m, 2H), 5.97-6.08 (m, 1H), 6.73-6.78 (m, 1H), 7.14-7.20 (m, 1H), 7.20-7.39 (m, 11H); LRMS ESI m/z 533 [M+H]⁺

PREPARATION 99

3-Allyloxy-2-chloro-benzaldehyde

The title compound was prepared from 2-chloro-3-hydroxybenzaldehyde using a similar method to that described for preparation 74, in 100% yield. The material was used without further purification in preparation 100.

PREPARATION 100

(3-Allyloxy-2-chloro-phenyl)-methanol

The title compound was prepared from the product of preparation 99 using a similar method to that described for preparation 31, in 92% yield. The material was used without further purification in preparation 101.
¹HNMR(400 MHz, CDCl₃) δ: 4.62-4.66 (m, 2H), 4.78 (s, 2H), 5.32-5.37 (m, 1H), 5.46-5.52 (m, 1H), 6.02-6.15 (m, 1H), 6.86-6.94 (m, 1H), 7.07-7.14 (m, 1H), 7.20-7.28 (m, 1H).

PREPARATION 101

1-Allyloxy-2-chloro-3-chloromethyl-benzene

The product of preparation 100 (740 mg, 3.73 mmol) was dissolved in dichloromethane (20 mL) and thionyl chloride (678 μL, 9.32 mmol) was added over 1 minute. The reaction mixture was stirred at room temperature for 2 hours. A further 600 μl thionyl chloride was added and the reaction stirred for 1 hour. The reaction was quenched with water (10 mL). The organic layer was washed with saturated sodium hydrogen carbonate solution (20 mL) and water (10 mL), dried over magnesium sulphate and concentrated in vacuo. Purification of the residue by column chromatography on silica gel, eluting with pentane:ethyl acetate 100:0 to 99:1 afforded the title compound as a colourless oil in 21% yield, 168 mg.

$^1$HNMR(400 MHz, CDCl$_3$) δ: 4.59-4.68 (m, 2H), 4.75 (s, 2H), 5.28-5.37 (m, 1H), 5.44-5.55 (m, 1H), 6.00-6.15 (m, 1H), 6.86-6.95 (m, 1H), 7.06-7.13 (m, 1H), 7.17-7.26 (m, 1H).

PREPARATION 102

5-[3-(3-Allyloxy-2-chloro-benzyloxy)-azetidin-1-yl]-5-methyl-2,2-diphenyl-hexanenitrile The title compound was prepared from the products of preparations 101 and 56 using a similar method to that described for example 101, in 69% yield.

$^1$HNMR(400 MHz, CDCl$_3$) δ: 0.95 (s, 6H), 1.29-1.38 (m, 2H), 2.40-2.52 (m, 2H), 3.02-3.15 (m, 2H), 3.24-3.39 (m, 2H), 4.15-4.22 (m, 1H), 4.53 (s, 2H), 4.60-4.64 (m, 2H), 5.28-5.35 (m, 1H), 5.45-5.50 (m, 1H), 6.03-6.15 (m, 1H), 6.86-6.90 (m, 1H), 7.05-7.08 (m, 1H), 7.16-7.23 (m, 1H), 7.23-7.45 (m, 10H); LRMS APCI m/z 515 [M+H]$^+$

PREPARATION 103

5-(3-{2-Chloro-3-[((E)-propenyl)oxy]-benzyloxy}-azetidin-1-yl)-5-methyl-2,2-diphenyl-hexanoic acid amide The title compound was prepared from the product of preparation 102 using a similar method to that described for preparation 78, in 61% yield.

$^1$HNMR(400 MHz, CDCl$_3$) δ: 0.95 (s, 6H), 1.19-1.20 (m, 2H), 1.72-1.78 (m, 3H), 2.40-2.48 (m, 2H), 3.02-3.15 (m, 2H), 3.20-3.42 (m, 2H), 4.13-4.25 (m, 1H), 4.53 (s, 2H), 4.95-5.03 (m, 1H), 5.32-5.60 (br m, 2H), 6.30-6.45 (m, 1H), 6.93-6.97 (m, 1H), 7.12-7.40 (m, 12H); LRMS ESI m/z 533 [M+H]$^+$

PREPARATION 104

Methanesulfonic acid 1-(4-carbamoyl-1,1-dimethyl-4,4-diphenyl-butyl)-azetidin-3-yl ester Methane sulfonyl chloride (102 μL, 1.33 mmol) was added dropwise to a solution of the product of preparation 93 (156 mg, 0.44 mmol) in pyridine (5 mL), cooled to −20° C. The mixture was warmed gradually to 5° C. over 2 hours. Saturated sodium hydrogen carbonate solution (10 mL) was added and the reaction mixture stirred at room temperature for 10 minutes. The residue was extracted with ethyl acetate (3×30 mL) and the combined organics were dried over magnesium sulphate, filtered and concentrated in vacuo. Purification of the residue by column chromatography on silica gel, eluting with pentane:ethylacetate/methanol/0.88 ammonia (90/10/1) 8:1 to 1:2, afforded the title compound as a colourless oil in 74% yield, 142 mg.

$^1$HNMR(400 MHz, CDCl$_3$) δ: 0.88 (s, 6H), 1.08-1.15 (m, 2H), 2.38-2.45 (m, 2H), 2.98 (s, 3H), 3.07-3.22 (m, 2H), 3.36-3.52 (m, 2H), 4.95-5.00 (m, 1H), 5.42-5.53 (br m, 1H), 5.71-5.80 (br m, 1H), 7.23-7.38 (m, 10H); LRMS ESI m/z 431 [M+H]$^+$

PREPARATION 105

5-[3-(3-Benzyloxy-phenoxy)-azetidin-1-yl]-5-methyl-2,2-diphenyl-hexanenitrile

The title compound was prepared from the product of preparation 57 and 3-(benzyloxy)phenol, using the same method as that described in example 99, as a yellow oil in 95% yield.

$^1$HNMR(400 MHz, CDCl$_3$) δ: 0.95 (s, 6H), 1.35-1.42 (m, 2H), 2.40-2.52 (m, 2H), 3.09-3.20 (m, 2H), 3.40-3.52 (m, 2H), 4.61-4.72 (m, 1H), 5.06 (s, 2H), 6.36-6.40 (m, 2H), 6.57-6.62 (m, 1H), 7.10-7.18 (m, 1H), 7.15-7.47 (m, 15H); LRMS APCI m/z 517 [M+H]$^+$

PREPARATION 106

(4-Allyloxy-phenyl)-methanol

The title compound was prepared from the 4-hydroxybenzyl alcohol using a similar method to that described for preparation 74, in 57% yield.

$^1$HNMR(400 MHz, CDCl$_3$) δ: 4.52-4.94 (m, 2H), 4.63 (s, 2H), 5.28-5.35(m, 1H), 5.38-5.45(m, 1H), 6.00-6.12(m, 1H), 6.86-6.94 (m, 2H), 7.24-7.33 (m, 2H).

PREPARATION 107

1-Allyloxy-4-chloromethyl-benzene

The title compound was prepared from the product of preparation 106 using a similar method to that described for preparation 76 in 43% yield.

$^1$HNMR(400 MHz, CDCl$_3$) δ: 4.53-4.58 (m, 4H), 5.25-5.32 (m, 1H), 5.36-5.43 (m, 1H), 6.00-6.12 (m, 1H), 6.86-6.94 (m, 2H), 7.28-7.35 (m, 2H)

PREPARATION 108

5-[3-(4-Allyloxy-benzyloxy)-azetidin-1-yl]-5-methyl-2,2-diphenyl-hexanoic acid amide The title compound was prepared from the products of preparations 107 and 93 using a similar method to that described for preparation 94, in 25% yield.

$^1$HNMR(400 MHz, CDCl$_3$) δ: 0.95 (s, 6H), 1.24-1.28 (m, 2H), 2.35-2.45 (m, 2H), 2.94-3.00 (m, 2H), 3.20-3.28 (m, 2H), 4.05-4.15 (m, 1H), 4.35 (s, 2H), 4.52-4.55 (m, 2H), 5.25-5.28 (m, 1H), 5.36-5.43 (m, 1H), 5.40-5.60 (br m, 2H), 6.00, 6.12 (m, 1H), 6.84-6.89 (m, 2H), 7.20-7.38 (m, 12H); LRMS APCI m/z 499 [M+H]$^+$

EXAMPLE 1

5-Methyl-5-[(3S)-3-phenoxypyrrolidin-1-yl]-2,2-diphenylhexanenitrile

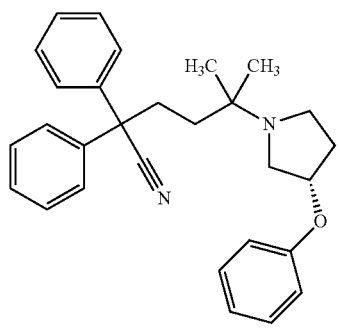 [SMILES: CC(C)(CCC(C#N)(c1ccccc1)c1ccccc1)N1CC[C@H](Oc2ccccc2)C1]

A solution of the product of preparation 11 (3.31 g, 8.07 mmol) in tetrahydrofuran (90 mL) was cooled to −20° C. Zirconium chloride (3.76 g, 16.15 mmol) was added and the reaction mixture was stirred at −20° C. for 1 hour. Methyl magnesium chloride (3M in tetrahydrofuran, 24 mL, 72 mmol) was then added dropwise and the mixture was stirred for 2 hours, with the temperature maintained below −10° C. The reaction was quenched with 1M aqueous sodium hydroxide solution (25 mL) and then filtered through Celite®, washing through with ethyl acetate (2×50 mL). The filtrate was washed with brine (70 mL), concentrated in vacuo and the residue was re-crystallised from hexane/ethyl acetate to afford the title compound as a pale orange crystalline solid in 59% yield, 2 g.

$^{1}$HNMR(400 MHz, CD$_3$OD) δ: 0.99(s, 3H), 1.04(s, 3H), 1.23-1.27(m, 2H), 1.85-1.93(m, 1H), 2.07-2.16(m, 1H), 2.40-2.45(m, 2H), 2.58-2.67(m, 2H), 2.72-2.78(m, 1H), 2.87-2.91 (m, 1H), 4.75-4.79(m, 1H), 6.80(d, 2H), 6.88-6.92(m, 1H), 7.21-7.36(m, 12H); LRMS APCI m/z 425 [M+H]$^{+}$

EXAMPLE 2

5-Methyl-5-[(3S)-3-phenoxypyrrolidin-1-yl]-2,2-diphenylhexanamide

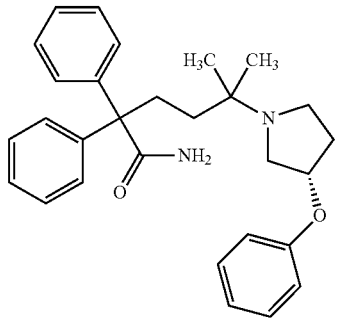 [SMILES: CC(C)(CCC(C(N)=O)(c1ccccc1)c1ccccc1)N1CC[C@H](Oc2ccccc2)C1]

Potassium hydroxide (5.10 g, 91.98 mmol) was added to a solution of the product of example 1 (1.95 g, 4.60 mmol) in 3-methyl-3-pentanol (40 mL) and the mixture was heated under reflux for 24 hours. The reaction mixture was then cooled to room temperature, concentrated in vacuo and the residue was partitioned between ethyl acetate (70 mL) and water (40 mL). The aqueous layer was separated, extracted with ethyl acetate (50 mL) and the combined organic solution was dried over sodium sulfate and concentrated in vacuo. The residue was then re-crystallised from hexane/ethyl acetate and dried under vacuum for 18 hours to afford the title compound as a white solid in 82% yield, 1.66 g.

$^{1}$HNMR(400 MHz, CD$_3$OD) δ: 0.97(s, 3H), 1.02(s, 3H), 1.19-1.33(m, 2H), 1.82-1.91(m, 1H), 2.02-2.17(m, 1H), 2.37-2.47(m, 2H), 2.48-2.64(m, 2H), 2.65-2.75(m, 1H), 2.81-2.89 (m, 1H), 4.75(m, 1H), 6.76-6.83(m, 2H), 6.86-6.92(m, 1H), 7.17-7.38(m, 12H); LRMS APCI m/z 425 [M+H]$^{+}$

EXAMPLE 3

5-Methyl-5-[(3R)-3-phenoxypyrrolidin-1-yl]-2,2-diphenylhexanenitrile

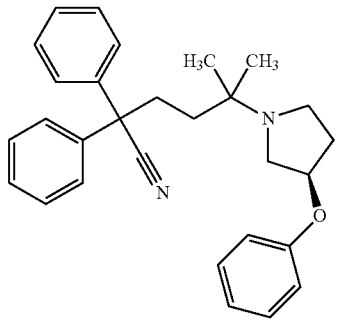 [SMILES: CC(C)(CCC(C#N)(c1ccccc1)c1ccccc1)N1CC[C@@H](Oc2ccccc2)C1]

A solution of the product of preparation 12 (0.84 g, 2.05 mmol) in tetrahydrofuran (15 mL) was cooled to −10° C. Titanium (IV) chloride (0.23 mL, 2.05 mmol) was added and the reaction mixture was stirred at −10° C. for 15 minutes. Methyl magnesium bromide (3M, in diethyl ether, 4.1 mL, 12.3 mmol) was then added dropwise and the mixture was stirred for 10 minutes at temperatures below −5° C. and at room temperature for 18 hours. The reaction mixture was slowly quenched with water (4 mL), diluted with ethyl acetate (20 mL) and then decanted off. The residual solid was extracted with ethyl acetate (3×20 mL) and the combined organic solution was dried over sodium sulphate and concentrated in vacuo. Purification of the residue by column chromatography on silica gel, eluting with ethyl acetate:hexane, 60:40, afforded the title compound in 54% yield, 0.47 g.

LRMS APCI m/z 425 [M+H]$^{+}$

EXAMPLE 4

5-Methyl-5-[(3R)-3-phenoxypyrrolidin-1-yl]-2,2-diphenylhexanamide

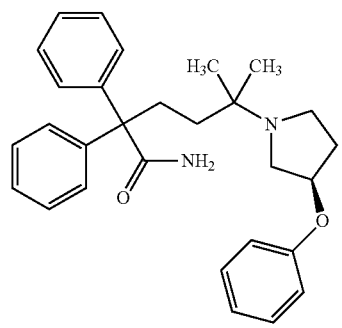 [SMILES: CC(C)(CCC(C(N)=O)(c1ccccc1)c1ccccc1)N1CC[C@@H](Oc2ccccc2)C1]

The title compound was prepared from the product of example 3, using the same method as that described for example 2, in 62% yield.

LRMS APCI m/z 443 [M+H]$^{+}$

EXAMPLE 5

5-[(3S)-3-(3-Methoxyphenoxy)pyrrolidin-1-yl]-5-methyl-2,2-diphenylhexanenitrile

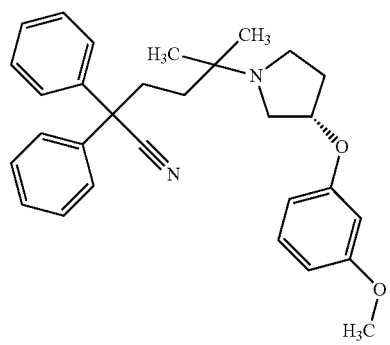 [SMILES: COc1cccc(O[C@H]2CCN(C(C)(C)CCC(C#N)(c3ccccc3)c3ccccc3)C2)c1]

The title compound was prepared from the product of preparation 13, using the same method as that described for example 1. The crude compound was purified by column chromatography on silica gel, eluting with dichloromethane:methanol:0.88 ammonia, 97.5:2.5:0.25 to 95:5:0.5, to afford the desired product as a brown oil in 78% yield.

$^1$HNMR(400 MHz, CD$_3$OD) δ: 1.01(s, 3H), 1.07(s, 3H), 1.43-1.47(m, 2H), 1.86-1.93(m, 1H), 2.08-2.19(m, 1H), 2.47-2.59(m, 3H), 2.65-2.69(m, 1H), 2.73-2.86(m, 2H), 3.73(s, 3H), 4.74-4.79(m, 1H), 6.38-6.43(m, 2H), 6.47-6.50(m, 1H), 7.11-7.15(m, 1H), 7.24-7.42(m, 10H); LRMS APCI m/z 456 [M+H]$^+$

EXAMPLE 6

5-[(3S)-3-(3-methoxyphenoxy)pyrrolidin-1-yl]-5-methyl-2,2-diphenylhexanamide

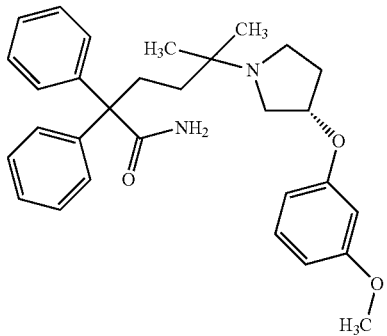 [SMILES: COc1cccc(O[C@H]2CCN(C(C)(C)CCC(C(N)=O)(c3ccccc3)c3ccccc3)C2)c1]

The title compound was prepared from the product of example 5, using the same method as that described for example 2, as a pale yellow gum in 96% yield.

$^1$HNMR(400 MHz, CD$_3$OD) δ: 1.03(s, 3H), 1.08(s, 3H), 1.24-1.30(m, 2H), 1.89-1.98(m, 1H), 2.08-2.16(m, 1H), 2.40-2.46(m, 2H), 2.65-2.76(m, 2H), 2.79-2.88(m, 1H), 2.91-2.98(m, 1H), 3.74(s, 3H), 4.77-4.82(m, 1H), 6.37-6.42(m, 2H), 6.51(dd, 1H), 7.12-7.16(m, 1H), 7.22-7.36(m, 10H); LRMS APCI m/z 474 [M+H]$^+$

EXAMPLE 7

5-[(3S)-3-(3-Hydroxyphenoxy)pyrrolidin-1-yl]-5-methyl-2,2-diphenylhexanamide

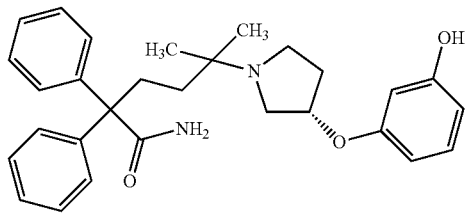 [SMILES: CC(C)(CCC(C(N)=O)(c1ccccc1)c1ccccc1)N1CC[C@H](Oc2cccc(O)c2)C1]

Boron tribromide (1M in dichloromethane, 20.7 mL, 20.7 mmol) was added to an ice-cooled solution of the product of example 6 (2.45 g, 5.18 mmol) in dichloromethane (25 mL) and the mixture was stirred at 0° C. for 20 minutes. The reaction was then quenched with 0.88 ammonia solution and stirred at room temperature for 20 minutes. The reaction mixture was extracted with dichloromethane (3×25 mL) and the combined organic solution was dried over sodium sulfate and concentrated in vacuo. Purification of the residue by column chromatography on silica gel, eluting with pentane:ethyl acetate/methanol/0.88 ammonia (90:10:1), 50:50 to 33:66, afforded the title compound as a white foam in 60% yield, 1.42 g.

$^1$HNMR(400 MHz, CD$_3$OD) δ: 1.06(s, 3H), 1.11(s, 3H), 1.30-1.34(m, 2H), 1.94-2.01(m, 1H), 2.08-2.17(m, 1H), 2.42-2.46(m, 2H), 2.77-2.93(m, 3H), 2.99-3.05(m, 1H), 4.79(m, 1H), 6.30(d, 2H), 6.37-6.40(d, 1H), 7.02-7.06(m, 1H), 7.23-7.36(m, 10H); LRMS APCI m/z 459 [M+H]$^+$

EXAMPLE 8

5-[(3R)-3-(Benzyloxy)pyrrolidin-1-yl]-5-methyl-2,2-diphenylhexanenitrile

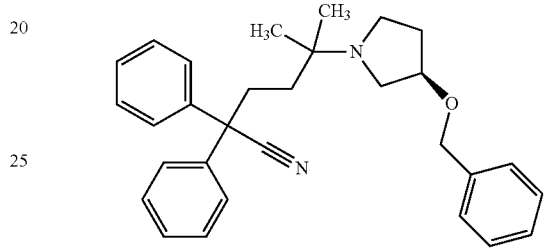

A solution of the product of preparation 15 (40 g, 93 mmol) in tetrahydrofuran (1 L) was cooled to −30° C. Zirconium chloride (44 g, 186 mmol) was added and the reaction mixture was stirred at −30° C. for 1 hour. Methyl magnesium chloride (3M in tetrahydrofuran, 300 mL, 900 mmol) was then added dropwise and the mixture was stirred for 2 hours, with the temperature maintained below −10° C. The reaction was quenched with 1M aqueous sodium hydroxide solution (300 mL) and the mixture was then decanted off. The residual solid was extracted with ethyl acetate (2×500 mL) and the combined organic solution was evaporated under reduced pressure. The residue was then dissolved in dichloromethane (1 L), washed with water (200 mL) and concentrated in vacuo. The crude material was purified by column chromatography on silica gel, eluting with dichloromethane:methanol, 97.5:2.5, and the subsequent residue azeotroped with pentane (2×250 mL), diethyl ether (2×250 mL) and pentane (2×250 mL) to afford the title compound as a solid.

$^1$HNMR(400 MHz, CD$_3$OD) δ: 1.02(s, 3H), 1.04(s, 3H), 1.42-1.54(m, 2H), 1.78-1.86(m, 1H), 1.93-2.02(m, 1H), 2.47-2.60(m, 3H), 2.63-2.77(m, 3H), 4.04-4.08(m, 1H), 4.43-4.49(s, 2H), 7.23-7.43(m, 15H); LRMS APCI m/z 439 [M+H]$^+$

EXAMPLE 9

5-[(3R)-3-(Benzyloxy)pyrrolidin-1-yl]-5-methyl-2,2-diphenylhexanamide

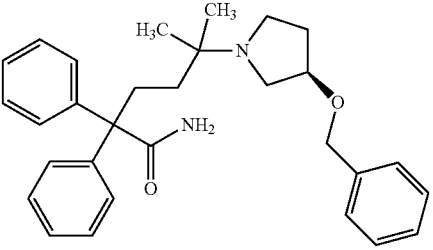 [SMILES: CC(C)(CCC(C(N)=O)(c1ccccc1)c1ccccc1)N1CC[C@@H](OCc2ccccc2)C1]

The title compound was prepared from the product of example 8, using the same method as that described for example 2, as a solid in 89% yield.

$^1$HNMR(400 MHz, CD$_3$OD) δ: 0.99-1.01(m, 6H), 1.24-1.28(m, 2H), 1.75-1.82(m, 1H), 1.88-1.97(m, 1H), 2.40-2.44 (m, 2H), 2.49-2.68(m, 2H), 2.71-2.76(m, 1H), 4.00-4.05(m, 1H), 4.39-4.46(m, 2H), 7.22-7.38(m, 15H); LRMS APCI m/z 425 [M+H]$^+$

EXAMPLE 10

5-[(3S)-3-(Benzyloxy)pyrrolidin-1-yl]-5-methyl-2,2-diphenylhexanenitrile

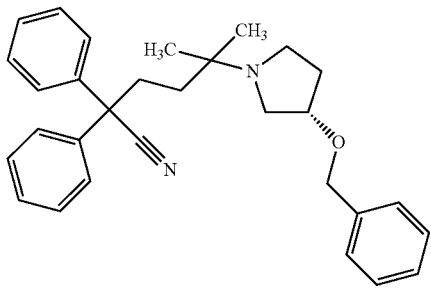 [SMILES: CC(C)(CCC(C#N)(c1ccccc1)c1ccccc1)N1CC[C@H](OCc2ccccc2)C1]

The title compound was prepared from the product of preparation 14, using the same method as that described for example 1. The crude compound was purified by column chromatography on silica gel, eluting with dichloromethane:methanol:0.88 ammonia, 99:1:0.1 to 92:8:0.8, to afford the desired product as a brown oil in 76% yield.

$^1$HNMR(400 MHz, CD$_3$OD) δ: 1.02(s, 3H), 1.04(s, 3H), 1.41-1.55(m, 2H), 1.77-1.85(m, 1H), 1.93-2.01(m, 1H), 2.50-2.55(m, 3H), 2.63-2.77(m, 3H), 4.03-4.08(m, 1H), 4.45(s, 2H), 7.22-7.42(m, 15H); LRMS APCI m/z 439 [M+H]$^+$

EXAMPLE 11

5-[(3S)-3-(Benzyloxy)pyrrolidin-1-yl]-5-methyl-2,2-diphenylhexanamide

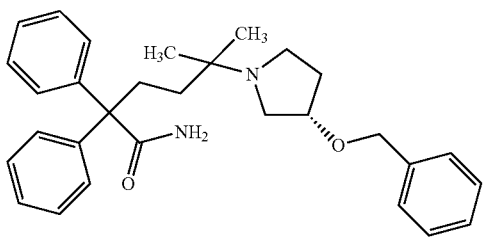 [SMILES: CC(C)(CCC(C(N)=O)(c1ccccc1)c1ccccc1)N1CC[C@H](OCc2ccccc2)C1]

The title compound was prepared from the product of example 10, using the same method as that described for example 2. The crude compound was purified by column chromatography on silica gel, eluting with ethyl acetate:methanol:0.88 ammonia, 98:2:0.2 to afford the desired product as a colourless gum in 78% yield.

$^1$HNMR(400 MHz, CD$_3$OD) δ: 0.98(s, 3H), 1.00(s, 3H), 1.23-1.27(m, 2H), 1.73-1.80(m, 1H), 1.87-1.96(m, 1H), 2.40-2.65(m, 5H), 2.69-2.73(m, 1H), 3.98-4.03(m, 1H), 4.42(m, 2H), 7.22-7.32(m, 11H), 7.35-7.38(m, 4H); LRMS APCI m/z 458 [M+H]$^+$

EXAMPLE 12

5-[(3R)-3-(3-Methoxyphenoxy)pyrrolidin-1-yl]-5-methyl-2,2-diphenylhexanamide

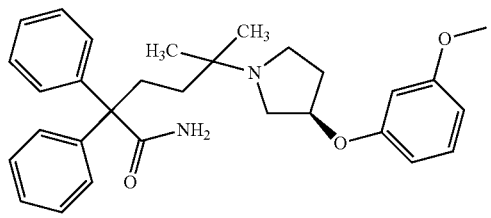 [SMILES: COc1cccc(O[C@@H]2CCN(C(C)(C)CCC(C(N)=O)(c3ccccc3)c3ccccc3)C2)c1]

A solution of triphenyl phosphine (272 mg, 1.04 mmol) in tetrahydrofuran (3 mL) and di-isopropylazodicarboxylate (0.20 mL, 1.04 mmol) were added to a solution of the product of preparation 16 (190 mg, 0.52 mmol) in tetrahydrofuran (2 mL) and the mixture was stirred at room temperature for 15 minutes. A solution of 3-methoxyphenol (129 mg, 1.04 mmol) in tetrahydrofuran (2 mL) was added and the mixture was stirred at room temperature for 2.5 hours. The reaction mixture was then concentrated in vacuo and the residue was purified by column chromatography on silica gel, eluting with dichloromethane:methanol, 95:5 to 90:10, to afford the title compound as a colourless oil in 7% yield, 20 mg.

$^1$HNMR(400 MHz, CD$_3$OD) δ: 1.05(s, 3H), 1.10(s, 3H), 1.18-1.37(m, 2H), 1.92-2.00(m, 1H), 2.10-2.16(m, 1H), 2.40-2.45(m, 2H), 2.72-2.95(m, 3H), 2.97-3.05(m, 1H), 3.74(s, 3H), 4.80-4.14(m, 1H), 6.38-6.40(m, 2H), 6.51(d, 1H), 7.12-7.16(m, 2H), 7.22-7.37(m, 9H); LRMS APCI m/z 472 [M+H]$^+$

EXAMPLE 13

5-[(3R)-3-(3-Hydroxyphenoxy)pyrrolidin-1-yl]-5-methyl-2,2-diphenylhexanamide

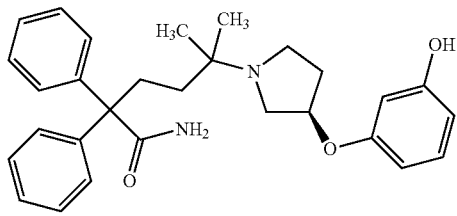 [SMILES: CC(C)(CCC(C(N)=O)(c1ccccc1)c1ccccc1)N1CC[C@@H](Oc2cccc(O)c2)C1]

Boron tribromide (1M in dichloromethane, 0.17 mL, 169 mmol) was added to a solution of the product of example 12 (20 mg, 42 mmol) in dichloromethane (2 mL) and the mixture was stirred at room temperature. The reaction was monitored by tlc analysis and portions of boron tribromide (1M in dichloromethane, 0.17 mL, 42 mmol) were added at regular intervals until all of the starting material had been consumed. After a period of 8 days, the reaction mixture was quenched with 0.88 ammonia solution, stirred at room temperature for 1 hour then extracted with dichloromethane (3×5 mL). The combined organic solution was dried over sodium sulfate, concentrated in vacuo and the residue was purified by column chromatography on silica gel, eluting with dichloromethane:methanol:0.88 ammonia, 95:5:0.5 to 92:8:0.8. The appropriate fractions were evaporated under reduced pressure and the residue was dissolved in ethanol. Ammonium formate (12 mg, 0.19 mmol) and 20% Pd(OH)$_2$/C (2 mg) were added and the mixture was heated under reflux for 4 hours. The reaction mixture was then cooled to room temperature, filtered through Arbocel® and the filtrate was concentrated in vacuo. The filtrate was partitioned between ethyl acetate (8 mL) and aqueous ammonia solution (2 mL) and the aqueous layer was separated and extracted with further ethyl acetate (2×3 mL). The combined organic solution was dried over sodium sulfate, concentrated in vacuo and the residue was purified by column chromatography on silica gel, eluting with dichloromethane:methanol:0.88 ammonia, 95:5:0.5, to afford the title compound as a colourless gum in 68% yield, 5.8 mg.

$^1$HNMR(400 MHz, CD$_3$OD) δ: 0.99(s, 3H), 1.05(s, 3H), 1.23-1.28(m, 2H), 1.85-1.90(m, 1H), 2.06-2.12(m, 1H), 2.40-2.45(m, 2H), 2.57-2.69(m, 2H), 2.72-2.79(m, 1H), 2.85-2.90 (m, 1H), 4.70-4.73(m, 1H), 6.26-6.30(m, 2H), 6.36(d, 1H), 7.00-7.04(m, 1H), 7.21-7.25(m, 2H), 7.27-7.31(m, 4H), 7.33-7.36(m, 4H); LRMS ESI m/z 459 [M+H]$^+$

EXAMPLE 14

5-Methyl-5-[(3S)-3-(3-methylphenoxy)pyrrolidin-1-yl]-2,2-diphenylhexanamide

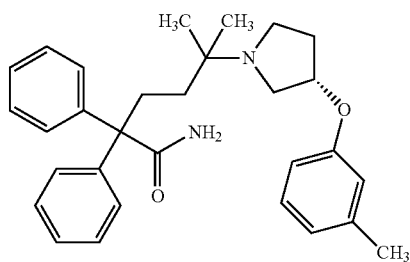 [SMILES: Cc1cccc(O[C@H]2CCN(C(C)(C)CCC(C(N)=O)(c3ccccc3)c3ccccc3)C2)c1]

Di-isopropylazodicarboxylate (65 μL, 0.34 mmol) and the product of preparation 17 (62 mg, 0.17 mmol) were added to a solution of triphenyl phosphine (89 mg, 0.34 mmol) in tetrahydrofuran (5 mL) and the mixture was stirred at room temperature for 15 minutes. A solution of 3-methylphenol (27 mg, 0.25 mmol) in tetrahydrofuran (1 mL) was added and the mixture was stirred at room temperature for 2 hours. The reaction mixture was then concentrated in vacuo and the residue was purified by column chromatography on silica gel, eluting with dichloromethane:methanol, 100:0 to 93:7, to afford the title compound as a colourless gum in 43% yield, 33 mg.

$^1$HNMR(400 MHz, CD$_3$OD) δ: 0.97(s, 3H), 1.03(s, 3H), 1.21-1.26(m, 2H), 1.82-1.90(m, 1H), 2.05-2.13(m, 1H), 2.27 (s, 3H), 2.40-2.45(m, 2H), 2.51-2.61(m, 2H), 2.68-2.74(m, 1H), 2.81-2.85(m, 1H), 4.71-4.75(m, 1H), 6.57-6.62(m, 2H), 6.72(d, 1H), 7.08-7.12(m, 1H), 7.35-7.20(m, 10H); LRMS APCI m/z 457 [M+H]$^+$

EXAMPLE 15

5-[(3R)-3-(1,3-Benzoxazol-6-yloxy)pyrrolidin-1-yl]-5-methyl-2,2-diphenylhexanamide

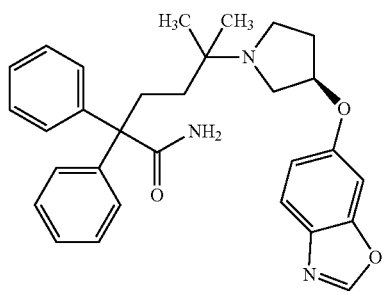 [SMILES: CC(C)(CCC(C(N)=O)(c1ccccc1)c1ccccc1)N1CC[C@@H](Oc2ccc3ncoc3c2)C1]

Diethyl azodicarboxylate (125 μL, 0.74 mmol) and a solution of 6-benzoxazolol [(100 mg, 0.74 mmol), US 613027, p 56] in tetrahydrofuran (2 mL) were added to an ice-cooled solution of triphenyl phosphine (195 mg, 0.74 mmol) in tetrahydrofuran (2 mL) and the mixture was stirred at 0° C. for 10 minutes and at room temperature for 90 minutes. A solution of the product of preparation 16 (238 mg, 0.65 mmol) in tetrahydrofuran (2 mL) was then added and the mixture was stirred at room temperature for 18 hours. The reaction mixture was then partitioned between ethyl acetate and dilute sodium carbonate solution and the aqueous layer was separated and extracted with ethyl acetate (×2). The combined organic solution was dried over magnesium sulfate, concentrated in vacuo and the residue was purified by column chromatography on silica gel, eluting with dichloromethane:methanol, 90:10 to afford the title compound in 29% yield, 90 mg.

LRMS APCI m/z 484 [M+H]$^+$

EXAMPLEs 16 and 17

The following compounds, of the general formula shown below, were prepared using the same method to that described for example 15, using the product of preparation 17 and commercially available phenols. The reactions were monitored by tlc analysis and were stirred at room temperature for 18-96 hours.

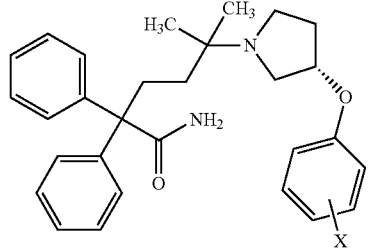

| No. | Data | Yield |
|---|---|---|
| 16 | X = 4-Cl<br>5-[(3S)-3-(4-Chlorophenoxy)pyrrolidin-1-yl]- | 35% |

-continued

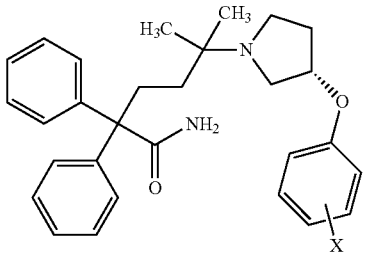

| No. | Data | Yield |
|---|---|---|
|  | 5-methyl-2,2-diphenylhexanamide ¹HNMR (400 MHz, CD₃OD) δ: 0.99(s, 3H), 1.05(s, 3H), 1.23-1.27(m, 2H), 1.85-1.92(m, 1H), 2.07-2.16(m,1H), 2.39-2.45(m, 2H), 2.57-2.67(m, 2H), 2.72-2.77(m, 1H), 2.85-2.89(m, 1H), 4.73-4.76(m, 1H), 6.80(d, 2H), 7.19-7.36(m, 12H); LRMS APCI m/z 477[M + H]⁺ |  |
| 17 | X = 3-Br 5-[(3S)-3-(3-Bromophenoxy)pyrrolidin-1-yl]-5-methyl-2,2-diphenylhexanamide ¹HNMR(400 MHz, CD₃OD) δ: 1.00(s, 3H), 1.05(s, 3H), 1.22-1.26(m, 2H), 1.85-1.93(m, 1H), 2.08-2.17(m, 1H), 2.36-2.49(m, 2H), 2.56-2.66(m, 2H), 2.71-2.79(m, 1H), 2.83-2.91(m, 1H), 4.76-4.79(m, 1H), 6.78-6.81(m, 1H), 6.99-7.35(m, 13H) | 38% |

EXAMPLE 18

5-{(3S)-3-[(3'-Hydroxybiphenyl-4-yl)oxy]pyrrolidin-1-yl}-5-methyl-2,2-diphenylhexanamide

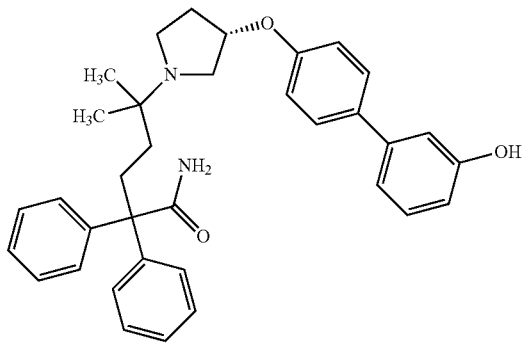 [SMILES: CC(C)(CCC(C(N)=O)(c1ccccc1)c1ccccc1)N1CC[C@H](Oc2ccc(-c3cccc(O)c3)cc2)C1]

Di-isopropylazodicarboxylate (0.21 mL, 1.09 mmol) and the product of preparation 17 (218 mg, 1.09 mmol) were added to a solution of triphenyl phosphine (286 mg, 1.09 mmol) in tetrahydrofuran (5 mL) and the mixture was stirred at room temperature for 15 minutes. A solution of 3-methoxy-1,1'-biphenyl-4-ol [(200 mg, 0.55 mmol) Bioinorganic and Medicinal Chemistry, 2003, 11, 2347] in tetrahydrofuran (2 mL) was added and the mixture was stirred at room temperature for 4 hours. The reaction mixture was then concentrated in vacuo and the residue was purified by column chromatography on silica gel, eluting with dichloromethane:methanol, 100:0 to 93:7. The appropriate fractions were evaporated under reduced pressure and the residue was further purified by column chromatography on silica gel, eluting with pentane:ethyl acetate/methanol/0.88 ammonia (90:10:1), 100:0 to 50:50. The appropriate fractions were concentrated in vacuo and the residue was dissolved in dichloromethane (2 mL). Boron tribromide (1M in dichloromethane, 0.58 mL, 0.58 mmol) was added and the mixture as stirred at room temperature for 90 minutes. The reaction was then quenched by the dropwise addition of 0.88 ammonia solution and the mixture was stirred at room temperature for a further 30 minutes. The reaction mixture was then extracted with dichloromethane (3×20 mL) and the combined organic solution was concentrated in vacuo. Purification of the residue by column chromatography on silica gel, eluting with pentane:ethyl acetate/methanol/0.88 ammonia (90:10:1), 100:0 to 50:50, to afford the title compound as a foam in 5% yield, 14 mg.

¹HNMR(400 MHz, CD₃OD) δ: 0.96(s, 3H), 1.04(s, 3H), 1.21-1.26(m, 2H), 1.86-1.93(m, 1H), 2.10-2.15(m, 1H), 2.39-2.46(m, 2H), 2.52-2.57(m, 1H), 2.62(dd, 1H), 2.70-2.76(m, 1H), 2.83(dd, 1H), 4.73-4.79(m, 1H), 6.70-6.72(dd, 1H), 6.84-6.87(m, 2H), 6.97-7.02(m, 2H), 7.18-7.57(m, 13H); LRMS APCI m/z 535 [M+H]⁺

EXAMPLE 19

5-{(3S)-3-[(3'-Hydroxybiphenyl-3-yl)oxy]pyrrolidin-1-yl}-5-methyl-2,2-diphenylhexanamide

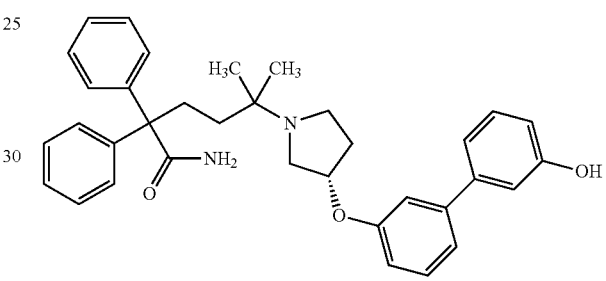

The title compound was prepared from the product of preparation 17 and 3-methoxy-1,1'-biphenyl-3-ol [WO 2003 006437, p 45], using the same method as that described for example 18, as a colourless gum in 16% yield.

¹HNMR(400 MHz, CD₃OD) δ: 0.98(s, 3H), 1.03(s, 3H), 1.21-1.25(m, 2H), 1.87-1.94(m, 1H), 2.09-2.18(m, 1H), 2.40-2.45(m, 2H), 2.53-2.58(m, 1H), 2.61-2.64(dd, 1H), 2.71-2.76(m, 1H), 2.82-2.87(dd, 1H), 4.80-4.83(m, 1H), 6.76-6.76(m, 2H), 6.97-7.04(m, 3H), 7.12(d, 1H), 7.16-7.35(m, 12H); LRMS APCI m/z 535 [M+H]⁺

EXAMPLE 20

5-{(3S)-3-[(6-Hydroxy-2-naphthyl)oxy]pyrrolidin-1-yl}-5-methyl-2,2-diphenylhexanamide

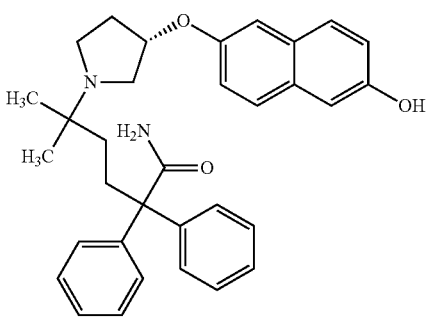 [SMILES: CC(C)(CCC(C(N)=O)(c1ccccc1)c1ccccc1)N1CC[C@H](Oc2ccc3cc(O)ccc3c2)C1]

Ammonium fluoride (27 mg, 0.738 mmol) was added to a solution of the product of preparation 19 (46 mg, 0.0738 mmol) in methanol (3 mL) and water (0.3 mL) and the mixture stirred at room temperature for 18 hours. The mixture was concentrated in vacuo and the residue purified using a RediSep® silica gel cartridge eluting with dichloromethane:methanol:0.88 ammonia (100:0:0 to 92:8:0.8). Appropriate fractions were concentrated in vacuo and the residue was dissolved in diethyl ether (30 ml), washed with water (2×10 ml), dried over magnesium sulphate and concentrated in vacuo to afford the title compound as an off-white foam in 35% yield, 14 mg.

$^1$HNMR(400 MHz, CD$_3$OD) δ: 0.97(s, 3H), 1.06(s, 3H), 1.17-1.26(m, 2H), 1.88-1.98(m, 1H), 2.09-2.25(m, 1H), 2.33-2.51(m, 2H), 2.54-2.62(m, 1H), 2.63-2.68(m, 1H), 2.71-2.80 (m, 1H), 2.81-2.91(m, 1H), 4.80-4.95(m, 1H), 6.89-7.00(m, 2H), 7.00-7.06(m, 2H), 7.10-7.26(m, 6H), 7.26-7.35(m, 4H), 7.47-7.54(m, 1H), 7.56-7.62(m, 1H); LRMS APCI m/z 509 [M+H]$^+$

EXAMPLE 21

5-[(3S)-3-(2-Hydroxyphenoxy)pyrrolidin-1-yl]-5-methyl-2,2-diphenylhexanamide

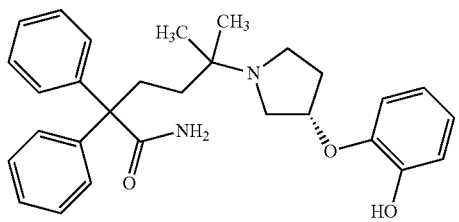 [SMILES: CC(C)(CCC(C(N)=O)(c1ccccc1)c1ccccc1)N1CC[C@H](Oc2ccccc2O)C1]

Di-isopropylazodicarboxylate (0.22 mL, 1.12 mmol) was added to an ice-cooled solution of the product of preparation 17 (205 mg, 0.56 mmol), triphenyl phosphine (293 mg, 1.12 mmol), and 2-hydroxyphenol (616 mg, 5.59 mmol) in tetrahydrofuran (4 mL) the solution was stirred with ice cooling for 2 hours. Triphenyl phosphine (293 mg, 1.12 mmol) and di-isopropylazodicarboxylate (0.22 mL, 1.12 mmol) were added and the resulting solution was stirred at room temperature for 16 hours. Di-isopropylazodicarboxylate (0.22 mL, 1.12 mmol) was added and the solution was stirred at room temperature for 4 hours. Tlc analysis indicated complete reaction. The reaction mixture was then concentrated in vacuo and the residue was purified using an (solute® SCX-2 cartridge, eluting with methanol followed by 1M ammonia in methanol. The basic fractions were evaporated under reduced pressure and the residue was purified by column chromatography on silica gel, eluting with pentane:(ethyl acetate:methanol:0.88 ammonia, 90:10:1) 1:0 to 1:1, to afford the title compound as a brown gum in 38% yield, 98 mg.

$^1$HNMR(400 MHz, CD$_3$OD) δ: 1.02(s, 3H), 1.06(s, 3H), 1.25-1.29(m, 2H), 1.87-1.94(m, 1H), 2.03-2.11(m, 1H), 2.41-2.45(m, 2H), 2.51-2.57(m, 1H), 2.66-2.70(dd, 1H), 2.75-2.84 (m, 2H), 4.80-4.85(m, 1H), 6.71-6.84(m, 4H), 7.21-7.37(m, 10H); LRMS APCI m/z 459 [M+H]$^+$ 458 [M−1]$^-$

EXAMPLE 22

5-[(3S)-3-(4-methoxyphenoxy)pyrrolidin-1-yl]-5-methyl-2,2-diphenylhexanamide

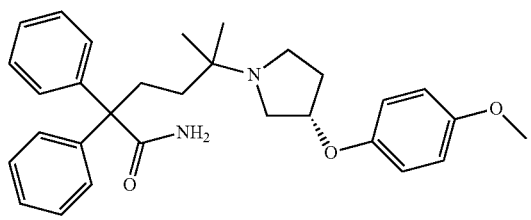 [SMILES: COc1ccc(O[C@H]2CCN(C(C)(C)CCC(C(N)=O)(c3ccccc3)c3ccccc3)C2)cc1]

Di-isopropylazodicarboxylate (0.21 mL, 1.09 mmol) was added to a solution of the product of preparation 17 (200 mg, 0.546 mmol), triphenyl phosphine (286 mg, 1.09 mmol), and 4-methoxyphenol (135 mg, 1.09 mmol) in tetrahydrofuran (3 mL) the solution was stirred at room temperature for 16 hours. The reaction mixture was then concentrated in vacuo and the residue was purified by column chromatography on silica gel, eluting with pentane:ethyl acetate, 100:0 to 50:50 The product containing fractions were evaporated under reduced pressure and the residue was further purified by column chromatography on silica gel, eluting with ethyl acetate:methanol:0.88 ammonia, 100:0:0 to 95:5:0.5 to afford the title compound as a white foam in 14% yield, 36 mg.

$^1$HNMR(400 MHz, CD$_3$OD) δ: 0.96(s, 3H), 1.02(s, 3H), 1.19-1.25(m, 2H), 1.81-1.91(m, 1H), 2.00-2.11(m, 1H), 2.35-2.60(m, 4H), 2.66-2.72(m, 1H), 2.77-2.81(m, 1H), 3.73(s, 3H), 4.64-4.69(m, 1H), 6.72-6.81(m, 4H), 7.20-7.39(m, 10H); LRMS APCI m/z 473 [M+H]$^+$

EXAMPLE 23

5-[(3S)-3-(4-hydroxyphenoxy)pyrrolidin-1-yl]-5-methyl-2,2-diphenylhexanamide

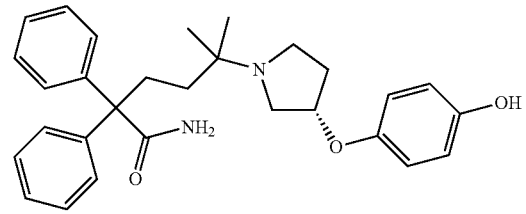 [SMILES: CC(C)(CCC(C(N)=O)(c1ccccc1)c1ccccc1)N1CC[C@H](Oc2ccc(O)cc2)C1]

Boron tribromide (1M in dichloromethane, 0.76 mL, 0.761 mmol) was added to a solution of the product of example 22 (36 mg, 0.0761 mmol) in dichloromethane (3 mL) and the mixture was stirred at room temperature for 1 hour. Tlc analysis indicated complete reaction. The reaction mixture was quenched via dropwise addition of 0.88 ammonia (2 mL) and stirred for 30 minutes to allow gas evolution. The reaction mixture was partitioned and aqueous was extracted with dichloromethane (2×5 mL). Combined organic fractions were concentrated in vacuo and the residue was purified by column chromatography on silica gel, eluting with ethyl

EXAMPLE 24

5-[(3S)-3-(4-trifluoromethyl-phenoxy)pyrrolidin-1-yl]-5-methyl-2,2-diphenylhexanamide

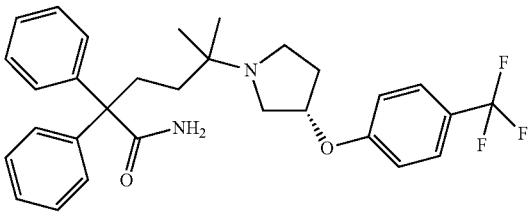 [SMILES: CC(C)(CCC(C(N)=O)(c1ccccc1)c1ccccc1)N1CC[C@H](Oc2ccc(C(F)(F)F)cc2)C1]

Di-isopropylazodicarboxylate (0.11 mL, 0.546 mmol) was added to a solution of the product of preparation 17 (100 mg, 0.273 mmol), triphenyl phosphine (143 mg, 0.546 mmol), and 4-trifluoromethylphenol (88 mg, 0.546 mmol) in tetrahydrofuran (3 mL) the solution was stirred at room temperature for 4 hours. The reaction mixture was then concentrated in vacuo and the residue was purified by column chromatography on silica gel, eluting with pentane:(ethyl acetate:methanol:0.88 ammonia, 90:10:1), 1:0 to 1:1 to afford the title compound as a white foam in 34% yield, 48 mg.

$^1$HNMR(400 MHz, CD$_3$OD) δ: 0.97(s, 3H), 1.03(s, 3H), 1.21-1.26(m, 2H), 1.84-1.92(m, 1H), 2.11-2.20(m, 1H), 2.35-2.50(m, 2H), 2.52-2.62(m, 2H), 2.69-2.75(m, 1H), 2.85-2.89 (m, 1H), 4.81-4.86(m, 1H), 6.93-6.96(d, 2H), 7.20-7.35(m, 10H), 7.52-7.54(d, 2H); LRMS APCI m/z 511 [M+H]$^+$ 510 [M−1]$^−$

EXAMPLE 25

5-[(3R)-3-(4-Trifluoromethyl-phenoxy)pyrrolidin-1-yl]-5-methyl-2,2 diphenylhexanenitrile

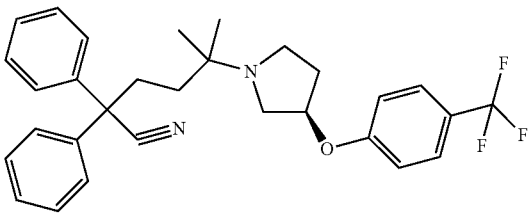 [SMILES: CC(C)(CCC(C#N)(c1ccccc1)c1ccccc1)N1CC[C@@H](Oc2ccc(C(F)(F)F)cc2)C1]

Sodium hydride (60% dispersion in mineral oil, 23 mg, 0.574 mmol) was added to an ice-cooled solution of the product of preparation 20 (100 mg, 0.287 mmol) in N,N-dimethylformamide (1.5 mL) and the mixture was stirred at 0° C. for 30 minutes. 4-fluorobenzotrifluoride (71 mg, 0.431 mmol) in N,N-dimethylformamide (0.5 mL) was added and the mixture was stirred for 16 hours, allowing the temperature to rise to 25° C. The solution was stirred at 50° C. for 24 hours and then stirred at 25° C. for 48 hours. Sodium hydride (60% dispersion in mineral oil, 23 mg, 0.574 mmol) was added and the solution was stirred for 1.25 hours at 50° C. The reaction mixture was then cooled to 25° C. and quenched with water (8 mL), concentrated in vacuo and the aqueous residue was partitioned between ethyl acetate (10 mL) and water (10 mL). The aqueous layer was separated and extracted with ethyl acetate (2×15 mL). The combined organic solution was washed with brine (5 mL), concentrated in vacuo and the residue was purified by column chromatography on silica gel, eluting with pentane: ethyl acetate, 3:1 to 0:1, to afford the title compound as a colourless gum in 70% yield, 10 mg.

$^1$HNMR(400 MHz, CD$_3$OD) δ: 1.02(s, 3H), 1.07(s, 3H), 1.44-1.48(m, 2H), 1.88-1.95(m, 1H), 2.16-2.25(m, 1H), 2.49-2.53(m, 2H), 2.56-2.62(m, 1H), 2.67-2.70(m, 1H), 2.75-2.80 (q, 1H), 2.89-2.93(dd, 1H), 4.85-4.89(m, 1H), 6.96-6.98(d, 2H), 7.42-7.45(m, 10H), 7.53-7.55(d, 2H); LRMS APCI m/z 493 [M+H]$^+$

EXAMPLE 26

5-[(3R)-3-(4-trifluoromethyl-phenoxy)pyrrolidin-1-yl]-5-methyl-2,2-diphenylhexanamide

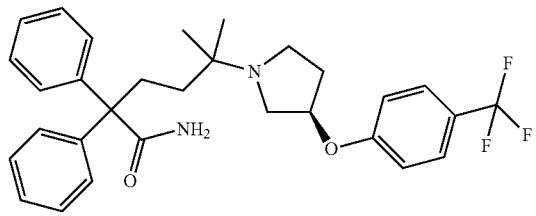 [SMILES: CC(C)(CCC(C(N)=O)(c1ccccc1)c1ccccc1)N1CC[C@@H](Oc2ccc(C(F)(F)F)cc2)C1]

Potassium hydroxide (23 mg, 0.406 mmol) was added to a solution of example 25 (10 mg, 0.0203 mmol) in 3-methyl-3-pentanol (2 mL) and the mixture was heated under reflux for 16 hours. The solution was cooled to 25° C. and potassium hydroxide (23 mg, 0.406 mmol) was added and the solution was heated under reflux for an additional 24 hours. The reaction mixture was then cooled to room temperature, concentrated in vacuo and the residue was purified by column chromatography on silica gel, eluting with ethyl acetate: methanol:0.88 ammonia, 95:5:0.5. to afford the title compound as a colourless gum in 68% yield, 7 mg.

$^1$HNMR(400 MHz, CD$_3$OD) δ: 0.97(s, 3H), 1.03(s, 3H), 1.20-1.25(m, 2H), 1.84-1.91(m, 1H), 2.10-2.20(m, 1H), 2.34-2.49(m, 2H), 2.52-2.61(m, 2H), 2.69-2.74(m, 1H), 2.84-2.88 (dd, 1H), 4.81-4.85(m, 1H), 6.94-6.96(d, 2H), 7.20-7.35(m, 10H), 7.53-7.55(d, 2H); LRMS APCI m/z 511 [M+H]$^+$ 510 [M−1]$^−$

EXAMPLE 27

5-[(3R)-3-(3-chloro-4-methoxy-phenoxy)pyrrolidin-1-yl]-5-methyl-2,2-diphenylhexanenitrile

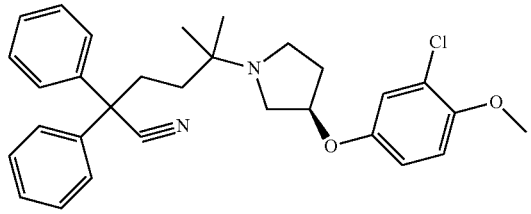 [SMILES: COc1ccc(O[C@@H]2CCN(C(C)(C)CCC(C#N)(c3ccccc3)c3ccccc3)C2)cc1Cl]

Sodium hydride (60% dispersion in mineral oil, 31 mg, 0.776 mmol) was added to an ice-cooled solution of the product of preparation 20 (135 mg, 0.388 mmol) in N,N-dimethylformamide (4 mL) and the mixture was stirred at 0° C. for 15 minutes. 2-chloro-4-fluoro-anisole (93 mg, 0.582 mmol) in N,N-dimethylformamide (1 mL) was added and the mixture was stirred for 16 hours, at 50° C. The solution was cooled to 25° C. and sodium hydride (60% dispersion in mineral oil, 62 mg, 1.55 mmol) was added and the solution was stirred for 16 hours at 80° C. The reaction mixture was then cooled to 25° C. and quenched with water (3 mL), concentrated in vacuo and the aqueous residue was partitioned between ethyl acetate (20 mL) and water (5 mL). The aqueous layer was separated and extracted with ethyl acetate (2×20 mL). The combined organic solution was washed with brine (10 mL), concentrated in vacuo and the residue was purified by column chromatography on silica gel, eluting with pentane:(ethyl acetate:methanol:0.88 ammonia, 90:10:1), 3:1 to 1:1. The product containing fractions were evaporated under reduced pressure and the residue was further purified using an Isolute® SCX-2 cartridge, eluting with methanol followed by 1M ammonia in methanol. The basic fractions were evaporated to afford the title compound as a yellow gum in 32% yield, 61 mg.

$^1$HNMR(400 MHz, CD$_3$OD) δ: 1.03(s, 3H), 1.08(s, 3H), 1.28-1.31(m, 2H), 1.76-1.80(m, 1H), 1.86-1.93(m, 1H), 2.09-2.18(m, 1H), 2.49-2.63(m, 2H), 2.67-2.70(m, 1H), 2.76-2.87(m, 2H), 3.80(s, 3H), 4.71-4.75(m, 1H), 6.74-6.77(dd, 1H), 6.89-6.95(dd, 1H), 7.24-7.46(m, 10H), 8.45-8.59(m, 1H); LRMS APCI m/z 489 [M+H]$^+$

EXAMPLE 28

5-[(3R)-3-(3-chloro-4-methoxy-phenoxy)pyrrolidin-1-yl]-5-methyl-2,2-diphenylhexanamide

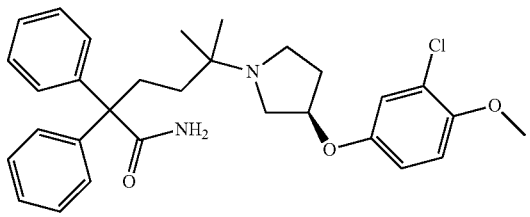 [SMILES: COc1ccc(O[C@@H]2CCN(C(C)(C)CCC(C(N)=O)(c3ccccc3)c3ccccc3)C2)cc1Cl]

Potassium hydroxide (140 mg, 2.49 mmol) was added to a solution of the product of example 27 (61 mg, 0.125 mmol) in 3-methyl-3-pentanol (5 mL) and the mixture was heated under reflux for 16 hours. The solution was cooled to room temperature, concentrated in vacuo and the residue was partitioned between dichloromethane (10 mL) and water (5 mL), aqueous was extracted with dichloromethane (3×10 mL). Combined organics were concentrated under reduced pressure and the residue purified by column chromatography on silica gel, eluting with ethyl acetate:methanol:0.88 ammonia, 90:10:1. The product containing fractions were evaporated under reduced pressure to afford the title compound as a colourless gum in 33% yield, 21 mg.

$^1$HNMR(400 MHz, CD$_3$OD) δ: 1.03(s, 3H), 1.09(s, 3H), 1.26-1.30(m, 2H), 1.88-1.96(m, 1H), 2.05-2.14(m, 1H), 2.35-2.49(m, 2H), 2.70-2.75(m, 2H), 2.82-2.88(m, 1H), 2.91-2.96(m, 1H), 3.81(s, 3H), 4.72-4.76(m, 1H), 6.73-6.76(dd, 1H), 6.88-6.89(d, 1H), 6.94-6.96(d, 1H), 7.24-7.36(m, 10H); LRMS APCI m/z 507 [M+H]$^+$ 505 [M−1]$^−$

EXAMPLE 29

5-[(3S)-3-(3-Hydroxy-5-methyl-phenoxy)-pyrrolidin-1-yl]-5-methyl-2,2-diphenyl-hexanoic acid amide

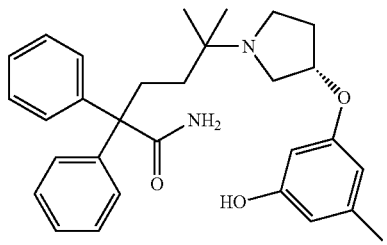 [SMILES: Cc1cc(O)cc(O[C@H]2CCN(C(C)(C)CCC(C(N)=O)(c3ccccc3)c3ccccc3)C2)c1]

Diisopropyl azodicarboxylate (212 μL, 1.093 mmol) was added in three portions to an ice-cooled solution of triphenyl phosphine (287 mg, 1.093 mmol), 5-methylresorcinol (678 mg, 5.464 mmol) and product from preparation 17 (200 mg, 0.546 mmol) in tetrahydrofuran (8 mL) and the mixture was stirred at 0° C. to room temperature for 2 hours. The reaction mixture was concentrated in vacuo and residue purified using an Isolute® SCX-2 cartridge, eluting with methanol followed by 1M ammonia in methanol. Basic fractions were concentrated in vacuo and the residue was purified by column chromatography on silica gel, eluting with ethyl acetate:methanol:0.88 ammonia, 98:2:0.2 to 94:6:0.6 to afford the title compound as a white foam in 27% yield, 70 mg.

$^1$HNMR(400 MHz, CD$_3$OD) δ: 1.00(s, 3H), 1.06(s, 3H), 1.24-1.27(m, 2H), 1.87-1.93(m, 1H), 2.05-2.13(m, 1H), 2.19(s, 3H), 2.39-2.45(m, 2H), 2.61-2.69(m, 2H), 2.75-2.81(m, 1H), 2.85-2.90(m, 1H), 4.69-4.73(m, 1H), 6.07(s, 1H), 6.13(s, 1H), 6.21(s, 1H), 7.21-7.35(m, 10H); LRMS ESI m/z 473 [M+H]$^+$

EXAMPLE 30

5-[(3S)-3-(3-Hydroxy-2-methyl-phenoxy)-pyrrolidin-1-yl]-5-methyl-2,2-diphenyl-hexanoic acid amide

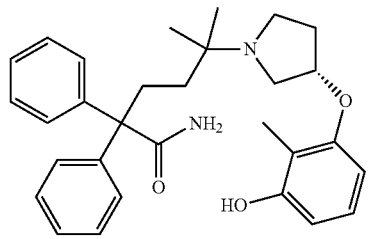 [SMILES: Cc1c(O)cccc1O[C@H]1CCN(C(C)(C)CCC(C(N)=O)(c2ccccc2)c2ccccc2)C1]

The title compound was prepared from the product of preparation 17 and 2-methylresorcinol, using the same method as that described for example 29, to afford an off-white foam in 68% yield.

$^1$HNMR(400 MHz, CD$_3$OD) δ: 0.99(s, 3H), 1.04(s, 3H), 1.23-1.28(m, 2H), 1.86-1.93(m, 1H), 1.98(s, 3H), 2.02-2.11(m, 1H), 2.41-2.45(m, 2H), 2.57-2.67(m, 2H), 2.71-2.78(m,

1H), 2.88-2.92(m, 1H), 4.69-4.72(m, 1H), 6.26-6.28(d, 1H), 6.38-6.40(d, 1H), 6.87-6.91(t, 1H), 7.21-7.24(m, 2H), 7.27-7.30(t, 4H), 7.34-7.36(m, 4H); LRMS ESI m/z 473 [M+H]+

EXAMPLE 31

5-[(3S)-3-(2,4-Dichloro-5-Hydroxy-phenoxy)-pyrrolidin-1-yl]-5-methyl-2,2-diphenyl-hexanoic acid amide

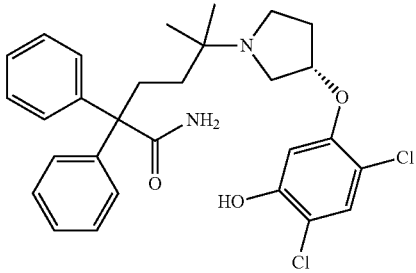 [SMILES: CC(C)(CCC(C(N)=O)(c1ccccc1)c1ccccc1)N1CC[C@H](Oc2cc(O)c(Cl)cc2Cl)C1]

The title compound was prepared from the product of preparation 17 and 4,6-dichlororesorcinol using the same method as that described for example 29, with the addition of further triphenyl phosphine (2 eq) and diisopropyl azodicarboxylate (2 eq) after both 18 hrs and 24 hrs, and subsequent stirring for an additional 24 hrs, to afford an off-white foam in 21% yield.

$^1$HNMR(400 MHz, CD$_3$OD) δ: 0.99(s, 3H), 1.06(s, 3H), 1.24-1.28(m, 2H), 1.89-1.96(m, 1H), 2.05-2.14(m, 1H), 2.38-2.49(m, 2H), 2.59-2.70(m, 2H), 2.75-2.81(m, 1H), 2.89-2.93 (m, 1H), 4.71-4.74(m, 1H), 6.48(s, 1H), 7.21-7.24(m, 3H), 7.26-7.31(t, 4H), 7.34-7.37(m, 4H); LRMS APCI m/z 527 [M+H]+

EXAMPLE 32

5-[(3S)-3-(4,5-Dichloro-2-Hydroxy-phenoxy)-pyrrolidin-1-yl]-5-methyl-2,2-diphenyl-hexanoic acid amide

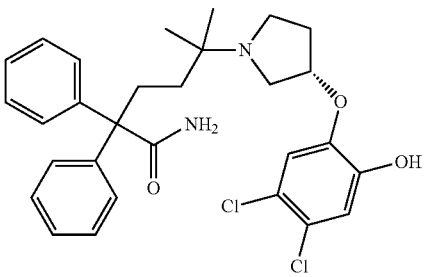 [SMILES: CC(C)(CCC(C(N)=O)(c1ccccc1)c1ccccc1)N1CC[C@H](Oc2cc(Cl)c(Cl)cc2O)C1]

The title compound was prepared from the product of preparation 17 and 4,5-dichlorocatechol, using the same method as that described for example 29, with the addition of further triphenyl phosphine (2 eq) and diisopropyl azodicarboxylate (2 eq) after both 18 hrs and 24 hrs, and subsequent stirring for an additional 24 hrs, to afford an off-white foam in 18% yield.

$^1$HNMR(400 MHz, CD$_3$OD) δ: 1.03(s, 3H), 1.09(s, 3H), 1.19-1.31(m, 2H), 1.90-1.97(m, 1H), 2.05-2.14(m, 1H), 2.34-2.49(m, 2H), 2.61-2.67(m, 1H), 2.69-2.73(m, 1H) 2.76-2.79 (m, 1H), 2.86-2.92(m, 1H), 4.78-4.83(m, 1H), 6.85 (s, 1H), 6.94(s, 1H), 7.21-7.40(m, 10H); LRMS ESI m/z 527 [M+H]+

EXAMPLE 33

5-[(3S)-3-(3-Chloro-5-methoxy-phenoxy)-pyrrolidin-1-yl]-5-methyl-2,2-diphenyl-hexanoic acid amide

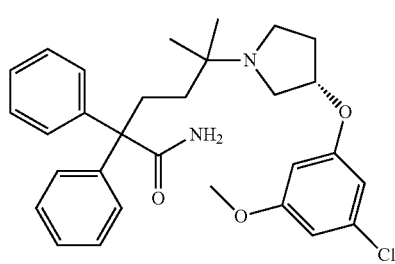 [SMILES: COc1cc(Cl)cc(O[C@H]2CCN(C(C)(C)CCC(C(N)=O)(c3ccccc3)c3ccccc3)C2)c1]

Diisopropyl azodicarboxylate (160 µL, 0.820 mmol) was added in three portions to an ice-cooled solution of triphenyl phosphine (215 mg, 0.820 mmol), 3-chloro-5-methoxyphenol (325 mg, 2.049 mmol) and the product from preparation 17 (150 mg, 0.410 mmol) in tetrahydrofuran (8 mL) and the mixture was stirred at 0° C. to room temperature for 18 hours. The reaction mixture was concentrated in vacuo and purified using an Isolute® SCX-2 cartridge, eluting with methanol, then with 2M ammonia in methanol. Basic fractions were concentrated in vacuo and the residue was purified by column chromatography on silica gel, eluting with dichloromethane:methanol:0.88 ammonia, 98:2:0.2 to 94:6:0.6 to afford the title compound as a green gum in 97% yield, 200 mg.

$^1$HNMR(400 MHz, CD$_3$OD) δ: 0.97(s, 3H), 1.03(s, 3H), 1.20-1.25(m, 2H), 1.81-1.89(m, 1H), 2.06-2.14(m, 1H), 2.35-2.49(m, 2H), 2.51-2.60(m, 2H), 2.67-2.73(m, 1H), 2.79-2.83 (m, 1H), 3.75(s, 3H), 4.70-4.74(m, 1H), 6.29-6.30(t, 1H), 6.41-6.42(t, 1H), 6.51-6.52(t, 1H), 7.20-7.24(m, 2H), 7.26-7.30(t, 4H), 7.33-7.35(m, 4H); LRMS ESI m/z 507 [M+H]+

EXAMPLE 34

5-[(3S)-3-(3-Chloro-5-hydroxy-phenoxy)-pyrrolidin-1-yl]-5-methyl-2,2-diphenyl-hexanoic acid amide

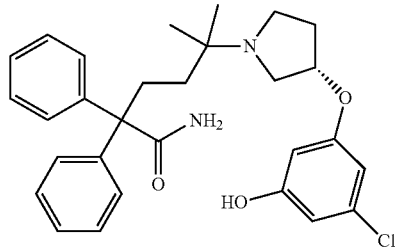 [SMILES: CC(C)(CCC(C(N)=O)(c1ccccc1)c1ccccc1)N1CC[C@H](Oc2cc(O)cc(Cl)c2)C1]

Boron tribromide (1M in dichloromethane, 1.97 mL, 1.976 mmol) was added to an ice-cooled solution of the product of example 33 (200 mg, 0.395 mmol) in dichloromethane (10 mL) and the mixture was stirred at 0° C. to room temperature for 18 hours. The reaction was quenched with 0.88 ammonia solution and stirred at room temperature for 90 minutes. The reaction mixture was extracted with dichloromethane (3×10 mL) and the combined organic solution was dried over sodium sulfate and concentrated in vacuo. Purification of the residue by column chromatography on silica gel, eluting with dichloromethane:methanol:0.88 ammonia, 95:5:0.5, afforded the title compound as a white foam in 45% yield, 88 mg.

¹HNMR(400 MHz, CD$_3$OD) δ: 1.01(s, 3H), 1.06(s, 3H), 1.24-1.28(m, 2H), 1.85-1.93(m, 1H), 2.06-2.15(m, 1H), 2.38-2.46(m, 2H), 2.61-2.69(m, 2H), 2.74-2.81(m, 1H), 2.87-2.92(m, 1H), 4.70-4.74(m, 1H), 6.18-6.19(t, 1H), 6.30-6.31(t, 1H), 6.38-6.39(t, 1H), 7.22-7.26(m, 2H), 7.28-7.31(t, 4H), 7.33-7.36(m, 4H); LRMS ESI m/z 493 [M+H]$^+$

EXAMPLE 35

5-[(3S)-3-(4-Chloro-2-Methoxy-phenoxy)-pyrrolidin-1-yl]-5-methyl-2,2-diphenyl-hexanoic acid amide

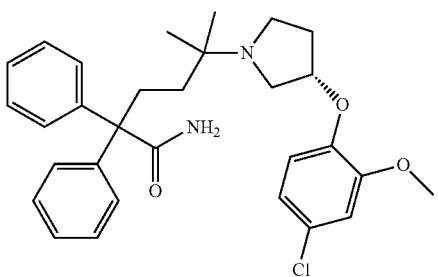 [SMILES: COc1cc(Cl)ccc1O[C@H]1CCN(C(C)(C)CCC(C(N)=O)(c2ccccc2)c2ccccc2)C1]

The title compound was prepared from the product of preparation 17 and 4-chloro-2-methoxyphenol, using the same method as that described for example 33, with stirring for 2 hrs and Isolute® SCX cartridge purification to afford a colourless gum in 100% yield.

¹HNMR(400 MHz, CD$_3$OD) δ: 0.96(s, 3H), 1.02(s, 3H), 1.21-1.25(m, 2H), 1.83-1.90(m, 1H), 2.02-2.11(m, 1H), 2.42-2.46(m, 2H), 2.48-2.54(m, 1H), 2.62-2.66(dd, 1H), 2.69-2.80(m, 2H), 3.73(s, 3H), 4.68-4.73(m, 1H), 6.75-6.77(d, 1H), 6.82-6.85(dd, 1H), 6.91-6.92(d, 1H), 7.20-7.23(m, 2H), 7.26-7.29(t, 4H), 7.33-7.37(m, 4H); LRMS ESI m/z 473 [M+H]$^+$

EXAMPLE 36

5-[(3S)-3-(4-Chloro-2-Hydroxy-phenoxy)-pyrrolidin-1-yl]-5-methyl-2,2-diphenyl-hexanoic acid amide

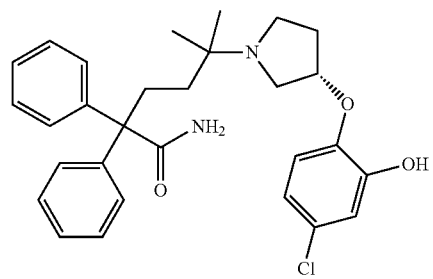 [SMILES: CC(C)(CCC(C(N)=O)(c1ccccc1)c1ccccc1)N1CC[C@H](Oc2ccc(Cl)cc2O)C1]

The title compound was prepared from the product of example 35, using the same method as that described for example 34, with stirring for 3 hours and purification by column chromatography on silica gel, eluting with ethyl acetate:methanol:ammonia, 98:2:0.2 to 94:6:0.6 to afford a white foam in 72% yield.

¹HNMR(400 MHz, CD$_3$OD) δ: 0.96(s, 3H), 1.02(s, 3H), 1.21-1.25(m, 2H), 1.83-1.90(m, 1H), 2.02-2.11(m, 1H), 2.42-2.46(m, 2H), 2.48-2.54(m, 1H), 2.62-2.66(dd, 1H), 2.69-2.80(m, 2H), 4.68-4.73(m, 1H), 6.75-6.77(d, 1H), 6.82-6.85(dd, 1H), 6.91-6.92(d, 1H), 7.20-7.23(m, 2H), 7.26-7.29(t, 4H), 7.33-7.37(m, 4H); LRMS ESI m/z 473 [M+H]$^+$

EXAMPLE 37

5-[(3S)-3-(2-Chloro-3-Methoxy-phenoxy)-pyrrolidin-1-yl]-5-methyl-2,2-diphenyl-hexanoic acid amide

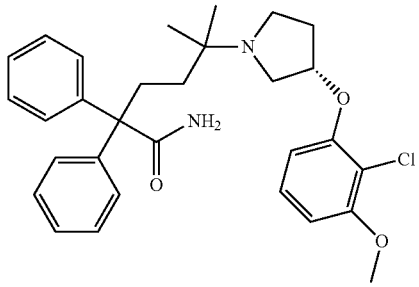 [SMILES: COc1cccc(O[C@H]2CCN(C(C)(C)CCC(C(N)=O)(c3ccccc3)c3ccccc3)C2)c1Cl]

The title compound was prepared from the product of preparation 17 and the product of preparation 21, using the same method as that described for example 33, with (solute® SCX cartridge purification to afford a white foam in 100% yield.

¹HNMR(400 MHz, CD$_3$OD) δ: 0.99(s, 3H), 1.04(s, 3H), 1.23-1.28(m, 2H), 1.88-1.95(m, 1H), 2.04-2.13(m, 1H), 2.42-2.46(m, 2H), 2.56-2.63(m, 1H), 2.65-2.70(m, 1H), 2.72-2.79(m, 1H), 2.88-2.93(m, 1H), 3.85(s, 3H), 4.79-4.81(m, 1H), 6.54-6.57(dd, 1H), 6.67-6.69(dd, 1H), 7.14-7.18(t, 1H) 7.20-7.24(m, 2H), 7.27-7.30(t, 4H), 7.33-7.37(m, 4H); LRMS ESI m/z 507 [M+H]$^+$

EXAMPLE 38

5-[(3S)-3-(2-Chloro-3-Hydroxy-phenoxy)-pyrrolidin-1-yl]-5-methyl-2,2-diphenyl-hexanoic acid amide

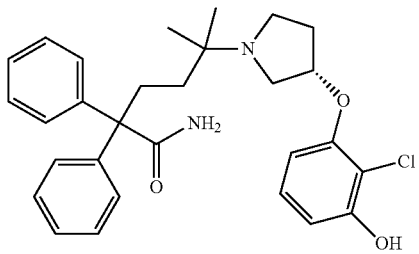 [SMILES: CC(C)(CCC(C(N)=O)(c1ccccc1)c1ccccc1)N1CC[C@H](Oc2cccc(O)c2Cl)C1]

The title compound was prepared from the product of example 37, using the same method as that described for example 34, to afford a white foam in 37% yield.

¹HNMR(400 MHz, CD$_3$OD) δ: 1.08(s, 3H), 1.12(s, 3H), 1.31-1.36(m, 2H), 1.97-2.05(m, 1H), 2.07-2.16(m, 1H), 2.44-

2.48(m, 2H), 2.77-2.96(m, 3H), 3.05-3.10(q, 1H), 4.82-4.87 (m, 1H), 6.43-6.45(dd, 1H), 6.54-6.57(dd, 1H), 7.01-7.05(t, 1H), 7.22-7.26(m, 2H), 7.29-7.33(t, 4H), 7.36-7.39(m, 4H); LRMS ESI m/z 493 [M+H]$^+$

EXAMPLE 39 & 40

The following compounds were prepared from the product of preparation 17 and 2-chlororesorcinol, using the same method as that described for example 33, with the addition of further triphenyl phosphine (2 eq) and diisopropyl azodicarboxylate (2 eq) after 18 hrs, and subsequent stirring for an additional 3 hrs. Crude material was purified by column chromatography on silica gel, eluting with ethyl acetate: methanol:0.88 ammonia, 98:2:0.2 to 94:6:0.6, to yield a mixture of regioisomers that were separated by HPLC on a Luna C8(2) acidic column, eluting with acetonitrile:water:diethylamine, 1:1:0.05 to afford the title compounds as white solids in 12% and 1% yield respectively.

EXAMPLE 39

5-[(3S)-3-(4-Chloro-3-Hydroxy-phenoxy)-pyrrolidin-1-yl]-5-methyl-2,2-diphenyl-hexanoic acid amide

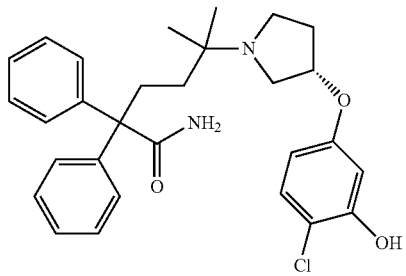 [SMILES: CC(C)(CCC(C(N)=O)(c1ccccc1)c1ccccc1)N1CC[C@H](Oc2ccc(Cl)c(O)c2)C1]

$^1$HNMR(400 MHz, CD$_3$OD) δ: 0.98(s, 3H), 1.04(s, 3H), 1.23-1.27(q, 2H), 1.87-1.95(m, 1H), 2.05-2.13(m, 1H), 2.41-2.47(m, 2H), 2.54-2.60(m, 1H), 2.62-2.66(dd, 1H), 2.71-2.77 (q, 1H), 2.86-2.90(q, 1H), 4.69-4.74(m, 1H), 6.32-6.36(m, 2H), 7.07-7.09(d, 1H), 7.20-7.24(m 2H), 7.27-7.30(t, 4H), 7.35-7.37(m, 4H); LRMS ESI m/z 493 [M+H]$^+$

EXAMPLE 40

5-[(3S)-3-(2-Chloro-5-Hydroxy-phenoxy)-pyrrolidin-1-yl]-5-methyl-2,2-diphenyl-hexanoic acid amide

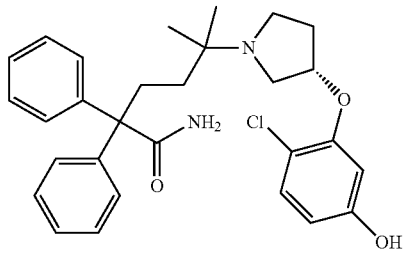 [SMILES: CC(C)(CCC(C(N)=O)(c1ccccc1)c1ccccc1)N1CC[C@H](Oc2cc(O)ccc2Cl)C1]

$^1$HNMR(400 MHz, CD$_3$OD) δ: 0.99(s, 3H), 1.04(s, 3H), 1.21-1.26(m, 2H), 1.82-1.90(m, 1H), 2.05-2.15(m, 1H), 2.35-2.46(m, 2H), 2.53-2.62(m, 2H), 2.69-2.75(q, 1H), 2.81-2.86 (q, 1H), 4.66-4.71(m, 1H), 6.27-6.30(dd, 1H), 6.39-6.40(d, 1H), 7.09-7.11(d, 1H), 7.21-7.36(m, 10H); LRMS ESI m/z 493 [M+H]$^+$

EXAMPLE 41

5-[(3R)-3-(3-Chloro-2-Methoxy-phenoxy)-pyrrolidin-1-yl]-5-methyl-2,2-diphenyl-hexanenitrile

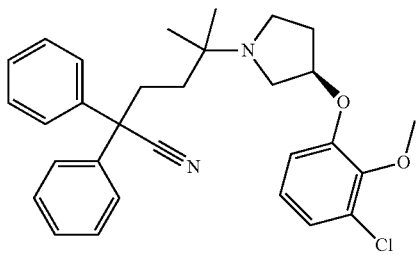 [SMILES: COc1c(Cl)cccc1O[C@@H]1CCN(C(C)(C)CCC(C#N)(c2ccccc2)c2ccccc2)C1]

The product of preparation 20 (150 mg, 0.431 mmol) in dimethylformamide (3 ml) was added drop wise to an ice-cooled solution of sodium hydride (60% dispersion in mineral oil, 52 mg, 1.293 mmol) in dimethylformamide (1 ml). After stirring for 1 hour the product of preparation 22 (103 mg, 0.646 mmol) in dimethylformamide (1 ml) was added and the mixture was heated to 60° C. for 96 hours. The solution was concentrated in vacuo and partitioned between ethyl acetate (10 ml) and water (10 ml). The organic layer was extracted and washed again with water (10 ml), then dried over sodium sulphate and concentrated in vacuo, to afford the title compound as a brown oil in 74% yield, 156 mg.

$^1$HNMR(400 MHz, CD$_3$OD) δ: 1.03(s, 3H), 1.08(s, 3H), 1.44-1.49(m, 2H), 1.90-1.97(m, 1H), 2.12-2.21(m, 1H), 2.50-2.62(m, 3H), 2.74-2.83(m, 2H), 2.87-2.91(m, 1H), 3.74(s, 3H), 4.81-4.84(m, 1H), 6.83-6.85(dd, 1H), 6.93-7.00(m, 2H), 7.25-7.42(m, 10H); LRMS ESI m/z 489 [M+H]$^+$

EXAMPLE 42

5-[(3R)-3-(3-Chloro-2-Methoxy-phenoxy)-pyrrolidin-1-yl]-5-methyl-2,2-diphenyl-hexanoic acid amide

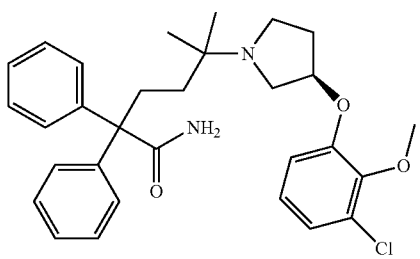 [SMILES: COc1c(Cl)cccc1O[C@@H]1CCN(C(C)(C)CCC(C(N)=O)(c2ccccc2)c2ccccc2)C1]

The title compound was prepared from the product of example 41, using the same method as that described for example 2. The crude compound was purified by column chromatography on silica gel, eluting with dichloromethane: methanol:0.88 ammonia, 95:5:0.5, to afford a white foam, in 50% yield.

¹HNMR(400 MHz, CD₃OD) δ: 1.00(s, 3H), 1.05(s, 3H), 1.23-1.27(q, 2H), 1.88-1.96(m, 1H), 2.07-2.16(m, 1H), 2.41-2.46(m, 2H), 2.56-2.61(m, 1H), 2.64-2.77(m, 2H), 2.86-2.92(m, 1H), 3.75(s, 3H), 4.77-4.82(m, 1H), 6.80-6.83(dd, 1H), 6.96-6.99(m, 2H), 7.21-7.25(m, 2H), 7.27-7.31(t, 4H), 7.34-7.36(m, 4H); LRMS ESI m/z 507 [M+H]⁺

EXAMPLE 43

5-[(3R)-3-(3-Chloro-2-Hydroxy-phenoxy)-pyrrolidin-1-yl]-5-methyl-2,2-diphenyl-hexanoic acid amide

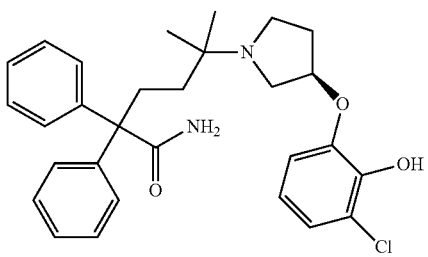 [SMILES: CC(C)(CCC(C(N)=O)(c1ccccc1)c1ccccc1)N1CC[C@@H](Oc2cccc(Cl)c2O)C1]

The title compound was prepared from the product of example 42, using the same method as that described for example 34, to afford a white foam in 65% yield.

¹HNMR(400 MHz, CD₃OD) δ: 1.05(s, 3H), 1.09(s, 3H), 1.28-1.32(m, 2H), 1.89-1.98(m, 1H), 2.03-2.13(m, 1H), 2.42-2.46(m, 2H), 2.59-2.67(m, 1H), 2.70-2.75(m, 1H), 2.81-2.93(m, 2H), 4.84-4.88(m, 1H), 6.66-6.70(t, 1H), 6.77-6.79(d, 1H), 6.88-6.91(d, 1H), 7.21-7.25(m, 2H), 7.28-7.32(t, 4H), 7.35-7.37(m, 4H); LRMS ESI m/z 493 [M+H]⁺

EXAMPLE 44

5-[(3S)-3-(3-Hydroxy-2,5-dimethyl-phenoxy)-pyrrolidin-1-yl]-5-methyl-2,2-diphenyl-hexanoic acid amide

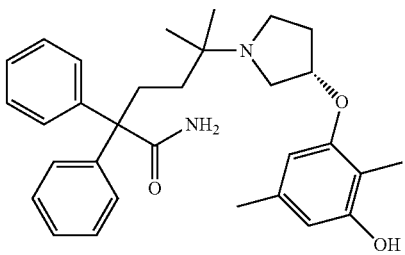 [SMILES: Cc1cc(O)c(C)c(O[C@H]2CCN(C(C)(C)CCC(C(N)=O)(c3ccccc3)c3ccccc3)C2)c1]

The title compound was prepared from the product of preparation 17 and 2,5-dimethylresorcinol, using the same method as that described for example 29, with the addition of further triphenyl phosphine (2 eq) and diisopropyl azodicarboxylate (2 eq) after 18 hrs, and subsequent stirring for 1 hour to afford a pale brown foam in 58% yield.

¹HNMR(400 MHz, CD₃OD) δ: 0.99(s, 3H), 1.04(s, 3H), 1.24-1.28(m, 2H), 1.85-1.92(m, 1H), 1.93(s, 3H), 2.01-2.10(m, 1H), 2.20(s, 3H), 2.41-2.45(m, 2H), 2.56-2.66(m, 2H), 2.70-2.78(m, 1H), 2.86-2.93(m, 1H), 4.67-4.873(m, 1H), 6.11(s, 1H), 6.24(s, 1H), 7.20-7.24(m, 2H), 7.26-7.30(t, 4H), 7.33-7.37(m, 4H); LRMS APCI m/z 487 [M+H]⁺

EXAMPLE 45

5-[(3S)-3-(3-Fluoro-5-Methoxy-phenoxy)-pyrrolidin-1-yl]-5-methyl-2,2-diphenyl-hexanoic acid amide

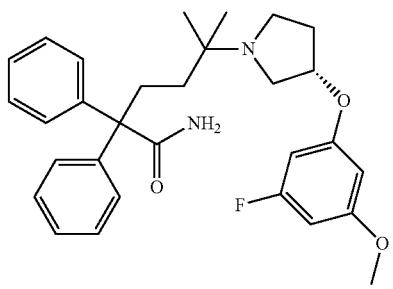 [SMILES: COc1cc(F)cc(O[C@H]2CCN(C(C)(C)CCC(C(N)=O)(c3ccccc3)c3ccccc3)C2)c1]

The title compound was prepared from the product of preparation 17 and the product of preparation 23, using the same method as that described for example 33, to afford the product as a colourless gum in 100% yield.

LRMS ESI m/z 491[M+H]⁺

EXAMPLE 46

5-[(3S)-3-(3-Fluoro-5-Hydroxy-phenoxy)-pyrrolidin-1-yl]-5-methyl-2,2-diphenyl-hexanoic acid amide

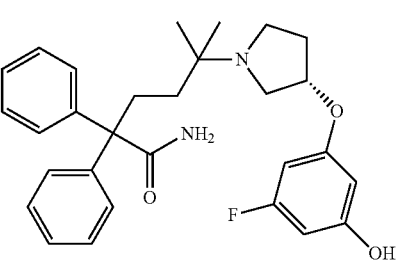 [SMILES: CC(C)(CCC(C(N)=O)(c1ccccc1)c1ccccc1)N1CC[C@H](Oc2cc(O)cc(F)c2)C1]

The title compound was prepared from the product of example 45, using the same method as that described for example 34, with the addition of further boron tribromide (1M in dichloromethane, 4 eq) after 3 hours, and subsequent stirring for 2 hrs. Crude material was purified by column chromatography on silica gel, eluting with ethyl acetate:methanol:0.88 ammonia, 98:2:0.2 to 94:6:0.6 to afford a white foam in 35% yield.

¹HNMR(400 MHz, CD₃OD) δ: 0.99(s, 3H), 1.04(s, 3H), 1.21-1.26(m, 2H), 1.82-1.90(m, 1H), 2.05-2.14(m, 1H), 2.39-2.45(m, 2H), 2.54-2.63(m, 2H), 2.69-2.75(m, 1H), 2.82-2.87

(q, 1H), 4.66-4.71(m, 1H), 6.02-6.11(m, 3H), 7.21-7.26(m, 2H), 7.27-7.31(t, 4H), 7.33-7.36(m, 4H); LRMS APCI m/z 477 [M+H]⁺

EXAMPLE 47

5-[(3R)-3-(3-Methoxy-5-trifluoromethyl-phenoxy)-pyrrolidin-1-yl]-5-methyl-2,2-diphenyl-hexanenitrile

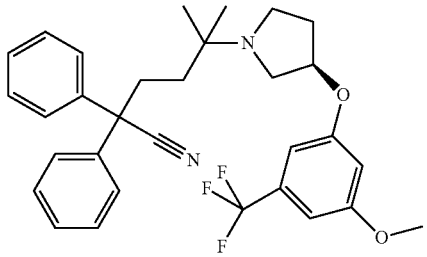 [SMILES: COc1cc(O[C@@H]2CCN(C(C)(C)CCC(C#N)(c3ccccc3)c3ccccc3)C2)cc(C(F)(F)F)c1]

The title compound was prepared from the product of preparation 20 and the product of preparation 24, using the same method as that described for example 41. The residue was purified by column chromatography on silica gel, eluting with dichloromethane:methanol:0.88 ammonia, 95:5:0.5, to afford a pale brown gum in 32% yield.

¹HNMR(400 MHz, CD₃OD) δ: 1.03(s, 3H), 1.08(s, 3H), 1.44-1.48(m, 2H), 1.87-1.90(m, 1H), 2.14-2.22(m, 1H), 2.49-2.54(m, 2H), 2.56-2.62(m, 1H), 2.67-2.70(d, 1H), 2.75-2.81 (q, 1H), 2.87-2.91(m, 1H), 3.80(s, 3H), 4.82-4.85(m, 1H), 6.61(s, 1H), 6.67(s, 1H), 6.74(s, 1H), 7.24-7.42(m, 10H); LRMS APCI m/z 523 [M+H]⁺

EXAMPLE 48

5-[(3R)-3-(3-Methoxy-5-trifluoromethyl-phenoxy)-pyrrolidin-1-yl]-5-methyl-2,2-diphenyl-hexanoic acid amide

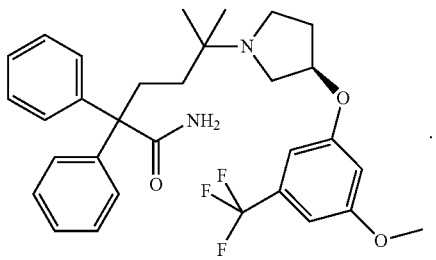 [SMILES: COc1cc(O[C@@H]2CCN(C(C)(C)CCC(C(N)=O)(c3ccccc3)c3ccccc3)C2)cc(C(F)(F)F)c1]

The title compound was prepared from the product of example 47, using the same method as that described for example 2, to afford product a colourless gum in 83% yield.

¹HNMR(400 MHz, CD₃OD) δ: 0.98(s, 3H), 1.02(s, 3H), 1.20-1.25(m, 2H), 1.82-1.89(m, 1H), 2.08-2.17(m, 1H), 2.39-2.46(m, 2H), 2.49-2.59(m, 2H), 2.66-2.72(q, 1H), 2.81-2.86 (m, 1H), 3.80(s, 3H), 4.76-4.81(m, 1H), 6.58-6.60(q, 1H), 6.64(s, 1H), 6.74(s, 1H), 7.18-7.36(m, 10H); LRMS APCI m/z 541 [M+H]⁺

EXAMPLE 49

5-[(3R)-3-(3-Hydroxy-5-trifluoromethyl-phenoxy)-pyrrolidin-1-yl]-5-methyl-2,2-diphenyl-hexanoic acid amide

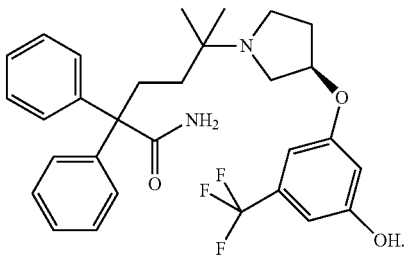 [SMILES: CC(C)(CCC(C(N)=O)(c1ccccc1)c1ccccc1)N1CC[C@@H](Oc2cc(O)cc(C(F)(F)F)c2)C1]

The title compound was prepared from the product of example 48, using the same method as that described for example 34, to afford a colourless gum in 40% yield.

¹HNMR(400 MHz, CD₃OD) δ: 0.99(s, 3H), 1.04(s, 3H), 1.22-1.27(m, 2H), 1.84-1.91(m, 1H), 2.08-2.16(m, 1H), 2.38-2.47(m, 2H), 2.54-2.63(m, 2H), 2.69-2.75(q, 1H), 2.85-2.89 (m, 1H), 4.73-4.78(m, 1H), 6.45-6.47(t, 1H), 6.52-6.53(s, 1H), 6.60-6.61(s, 1H), 7.21-7.24(m, 2H), 7.27-7.30(t, 4H), 7.34-7.36(m, 4H); LRMS APCI m/z 527 [M+H]⁺

EXAMPLE 50

5-[(3S)-3-(4-Fluoro-3-Methoxy-phenoxy)-pyrrolidin-1-yl]-5-methyl-2,2-diphenyl-hexanoic acid amide

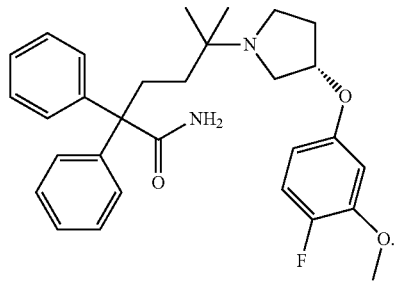 [SMILES: COc1cc(O[C@H]2CCN(C(C)(C)CCC(C(N)=O)(c3ccccc3)c3ccccc3)C2)ccc1F]

The title compound was prepared from the product of preparation 17 and the product of preparation 25, using the same method as that described for example 33, with the addition of further triphenyl phosphine (2 eq) and diisopropyl azodicarboxylate (2 eq) after both 16 hrs and 17 hrs, with subsequent stirring for an additional 1 hr and Isolute® SCX cartridge purification to afford a pale brown foam in 86% yield.

¹HNMR(400 MHz, CD₃OD) δ: 0.98(s, 3H), 1.03(s, 3H), 1.21-1.26(m, 2H), 1.82-1.89(m, 1H), 2.04-2.13(m, 1H), 2.37-2.47(m, 2H), 2.52-2.62(m, 2H), 2.68-2.74(q, 1H), 2.81-2.85 (m, 1H), 3.79(s, 3H), 4.69-4.73(m, 1H), 6.28-6.32(m, 1H), 6.52-6.56(dd, 1H), 6.90-6.95(dd, 1H), 7.20-7.24(m, 2H), 7.26-7.30(t, 4H), 7.33-7.36(m, 4H); LRMS APCI m/z 491 [M+H]$^+$

EXAMPLE 51

5-[(3S)-3-(2-Fluoro-3-Methoxy-phenoxy)-pyrrolidin-1-yl]-5-methyl-2,2-diphenyl-hexanoic acid amide

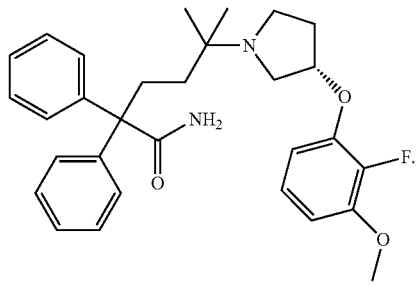 [SMILES: COc1cccc(O[C@H]2CCN(C(C)(C)CCC(C(N)=O)(c3ccccc3)c3ccccc3)C2)c1F]

The title compound was prepared from the product of preparation 17 and the product of preparation 26, using the same method as that described for example 33, with the addition of further triphenyl phosphine (2 eq) and diisopropyl azodicarboxylate (2 eq) after both 16 hrs and 17 hrs, with subsequent stirring for an additional 1 hr and Isolute® SCX cartridge purification to afford a pale yellow foam in 86% yield.

$^1$HNMR(400 MHz, CD$_3$OD) δ: 0.98(s, 3H), 1.02(s, 3H), 1.22-1.26(m, 2H), 1.85-1.93(m, 1H), 2.04-2.12(m, 1H), 2.40-2.45(m, 2H), 2.51-2.56(m, 1H), 2.62-2.65(m, 1H), 2.68-2.74 (q, 1H), 2.82-2.86(m, 1H), 3.83(s, 3H), 4.74-4.78(m, 1H), 6.53-6.57(t, 1H), 6.66-6.70(t, 1H), 6.93-6.98(td, 1H), 7.20-7.24(m, 2H), 7.27-7.30(t, 4H), 7.33-7.36(m, 4H); LRMS APCI m/z 491 [M+H]$^+$

EXAMPLE 52

5-[(3S)-3-(4-Fluoro-3-Hydroxy-phenoxy)-pyrrolidin-1-yl]-5-methyl-2,2-diphenyl-hexanoic acid amide

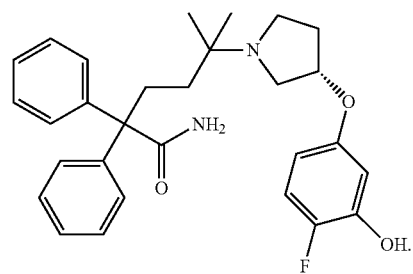 [SMILES: CC(C)(CCC(C(N)=O)(c1ccccc1)c1ccccc1)N1CC[C@H](Oc2ccc(F)c(O)c2)C1]

The title compound was prepared from the product of example 50, using the same method as that described for example 34, with stirring for 3 hours and purification by column chromatography on silica gel, eluting with ethyl acetate:methanol:0.88 ammonia, 98:2:0.2 to 94:6:0.6. to afford a white foam in 52% yield.

$^1$HNMR(400 MHz, CD$_3$OD) δ: 0.99(s, 3H), 1.04(s, 3H), 1.22-1.27(m, 2H), 1.82-1.90(m, 1H), 2.03-2.12(m, 1H), 2.38-2.46(m, 2H), 2.55-2.64(m, 2H), 2.70-2.76(q, 1H), 2.83-2.87 (m, 1H), 4.6-4.69(m, 1H), 6.19-6.23(dt, 1H), 6.38-6.40(dd, 1H), 6.85-6.90(dd, 1H), 7.21-7.25(m, 2H), 7.27-7.31(t, 4H), 7.33-7.36(m, 4H); LRMS APCI m/z 477 [M+H]$^+$

Example 53

5-[(3S)-3-(2-Fluoro-3-Hydroxy-phenoxy)-pyrrolidin-1-yl]-5-methyl-2,2-diphenyl-hexanoic acid amide

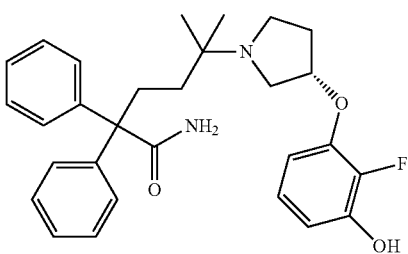 [SMILES: CC(C)(CCC(C(N)=O)(c1ccccc1)c1ccccc1)N1CC[C@H](Oc2cccc(O)c2F)C1]

The title compound was prepared from the product of example 51, using the same method as that described for example 34, with stirring for 3 hours and purification by column chromatography on silica gel, eluting with ethyl acetate:methanol:ammonia, 98:2:0.2 to 94:6:0.6 to afford a white foam in 26% yield.

$^1$HNMR(400 MHz, CD$_3$OD) δ: 1.00 (s, 3H), 1.04(s, 3H), 1.24-1.28(m, 2H), 1.88-1.95(m, 1H), 2.04-2.13(m, 1H), 2.41-2.47(m, 2H), 2.55-2.63(m, 1H), 2.66-2.71(m, 1H), 2.72-2.78 (q, 1H), 2.86-2.91(m, 1H), 4.73-4.77(m, 1H), 6.38-6.42(t, 1H), 6.48-6.53(t, 1H), 6.80-6.85(td, 1H), 7.21-7.25(m, 2H), 7.27-7.31(t, 4H), 7.34-7.37(m, 4H); LRMS ESI m/z 477 [M+H]$^+$

Example 54

5-[(3R)-3-(3-Hydroxy-benzyloxy)-pyrrolidin-1-yl]-5-methyl-2,2-diphenyl-hexanoic acid amide

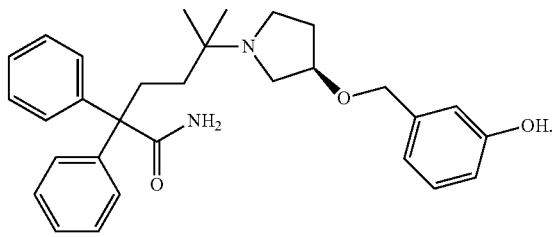 [SMILES: CC(C)(CCC(C(N)=O)(c1ccccc1)c1ccccc1)N1CC[C@@H](OCc2cccc(O)c2)C1]

4M Hydrochloric acid in dioxane (3 ml) and water (0.3 ml) were added to the product of preparation 29 (95 mg, 0.186 mmol) and the resulting solution was stirred at 60° C. for 20 minutes. The reaction was cooled to room temperature and partitioned between ethyl acetate (20 ml) and saturated sodium hydrogen carbonate solution (10 ml). The aqueous layer was extracted and washed with ethyl acetate (2×10 ml) and the combined organic layers dried over sodium sulphate and concentrated in vacuo. The residue was purified by column chromatography, eluting with ethyl acetate:methanol: 0.88 ammonia, 97:3:0.2 to 95:5:0.5, to afford the title compound as a colourless gum in 51% yield, 44 mg.

¹HNMR(400 MHz, CD₃OD) δ: 0.99(s, 3H), 1.00(s, 3H), 1.24-1.28(m, 2H), 1.74-1.81(m, 1H), 1.87-1.94(m, 1H), 2.40-2.44(m, 2H), 2.49-2.58(m, 2H), 2.61-2.67(m, 1H), 2.71-2.76(m, 1H), 3.98-4.03(m, 1H), 4.36(s, 2H), 6.67-6.69(d, 1H), 6.74-6.76(m, 2H), 7.09-7.13(t, 1H), 7.22-7.26(m, 2H), 7.29-7.32(t, 4H), 7.35-7.38(m, 4H); LRMS ESI m/z 473 [M+H]⁺

Example 55

5-{(3S)-3-[(3-Bromobenzyl)oxy]pyrrolidin-1-yl}-5-methyl-2,2-diphenylhexanenitrile

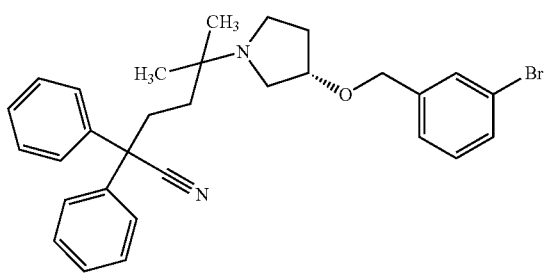 [SMILES: CC(C)(CCC(C#N)(c1ccccc1)c1ccccc1)N1CC[C@H](OCc2cccc(Br)c2)C1]

Sodium hydride (60% dispersion in mineral oil, 150 mg, 3.74 mmol) was added portionwise to an ice-cooled solution of the product of preparation 18 (1.3 g, 3.74 mmol) in N,N-dimethylformamide (20 mL) and the mixture was stirred at 0° C. for 1 hour. 3-Bromobenzylbromide (935 mg, 3.74 mmol) was added and the mixture was stirred for 4 hours, allowing the temperature to rise to 25° C. The reaction mixture was then quenched with water, concentrated in vacuo and the aqueous residue was partitioned between ethyl acetate (50 mL) and water (30 mL). The aqueous layer was separated and extracted with ethyl acetate (4×30 mL). The combined organic solution was dried over sodium sulfate, concentrated in vacuo and the residue was purified by column chromatography on silica gel, eluting with pentane:ethyl acetate, 50:50 to 100:0, to afford the title compound as a pale brown oil in 70% yield.

¹HNMR(400 MHz, CD₃OD) δ: 1.02(s, 3H), 1.04(s, 3H), 1.41-1.54(m, 2H), 1.77-1.85(m, 1H), 1.93-2.02(m, 1H), 2.49-2.54(m, 3H), 2.62-2.76(m, 3H), 4.02-4.07(m, 1H), 4.43(m, 2H), 7.18-7.50(m, 14H); LRMS APCI m/z 518 [M+H]⁺

Example 56

5-{(3S)-3-[(3'-Hydroxybiphenyl-3-yl)-methoxy]pyrrolidin-1-yl}-5-methyl-2,2-diphenylhexanenitrile

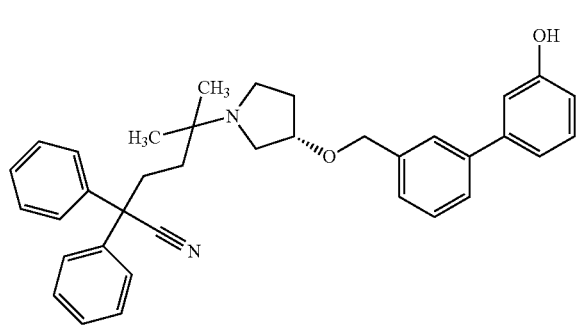 [SMILES: CC(C)(CCC(C#N)(c1ccccc1)c1ccccc1)N1CC[C@H](OCc2cccc(-c3cccc(O)c3)c2)C1]

[1,1'-Bis(diphenylphosphino)ferrocene]palladium(II) chloride (16 mg, 19 μmol) was added to a solution of the product of example 55 (205 mg, 0.38 mmol), 3-hydroxyphenylboronic acid (106 mg, 0.77 mmol) and sodium carbonate (81 mg, 0.77 mmol) in tetrahydrofuran (5 mL) and water (1 mL) and the mixture was heated under reflux for 16 hours. The cooled reaction mixture was then concentrated in vacuo and the residue was purified by column chromatography on silica gel, eluting with ethyl acetate:methanol, 98:2 to 96:4, to afford the title compound in 25% yield, 51 mg.

¹HNMR(CD₃OD, 400 MHz) δ: 1.04(s, 3H), 1.06(s, 3H), 1.46-1.52(m, 2H), 1.82-1.90(m, 1H), 1.96-2.03(m, 1H), 2.50-2.55(m, 3H), 2.67-2.80(m, 3H), 4.08-4.13(m, 1H), 4.52(s, 2H), 6.76(dd, 1H), 7.01(m, 1H), 7.05(d, 1H), 7.20-7.24(m, 1H), 7.27-7.42(m, 12H), 7.48(d, 1H), 7.54(s, 1H); LRMS ESI m/z 529[M−H]⁻

EXAMPLE 57

5-[(3S)-3-(Biphenyl-3-ylmethoxy)pyrrolidin-1-yl]-5-methyl-2,2-diphenylhexanenitrile

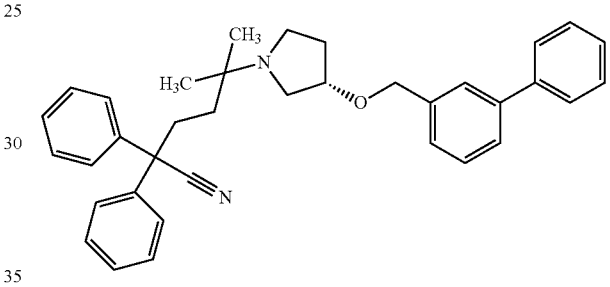

The title compound was prepared from the product of example 55 and benzeneboronic acid, using the same method as that described for example 56, as a green gum in 54% yield.

¹HNMR(400 MHz, CD₃OD) δ: 1.11(s, 3H), 1.13(s, 3H), 1.51-1.58(m, 2H), 1.94-2.03(m, 2H), 2.52-2.56(m, 2H), 2.70-2.77(m, 1H), 2.82-2.93(m, 3H), 4.08-4.13 & 4.13-4.18(2×m, 1H), 4.45 & 4.54(2×m, 2H), 7.26-7.43(m, 19H); LRMS APCI m/z 516 [M+H]⁺

EXAMPLE 58

5-{(3S)-3-[(2'-Hydroxybiphenyl-3-yl)methoxy]pyrrolidin-1-yl}-5-methyl-2,2-diphenylhexanenitrile

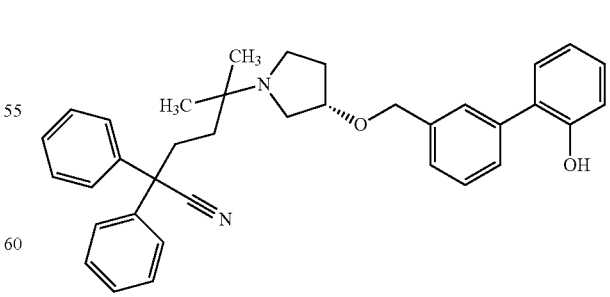

The title compound was prepared from the product of example 55 and 2-hydroxyphenylboronic acid, using the same method as that described for example 56. The crude compound was purified by column chromatography on silica gel, eluting with ethyl acetate followed by dichloromethane: methanol, 95:5, to afford the desired product as pale brown foam in 61% yield.

¹HNMR(CD₃OD, 400 MHz) δ: 1.03(s, 3H), 1.07(s, 3H), 1.47-1.53(m, 2H), 1.83-1.90(m, 1H), 1.94-2.03(m, 1H), 2.50-2.55(m, 2H), 2.57-2.64(m, 1H), 2.69-2.83(m, 3H), 4.09-4.14 (m, 1H), 4.51(s, 2H), 6.85-6.89(m, 2H), 7.14(m, 1H), 7.20-7.46(m, 14H), 7.51(s, 1H); LRMS ESI m/z 529 [M−H]⁻

EXAMPLE 59

5-{(3S)-3-[(4-Bromobenzyl)oxy]pyrrolidin-1-yl}-5-methyl-2,2-diphenylhexanenitrile

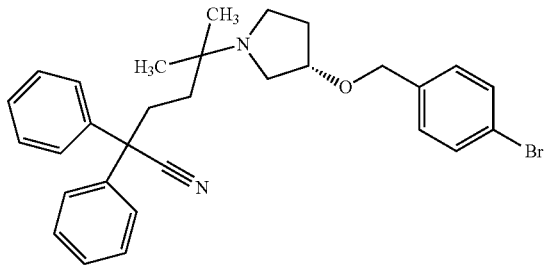 [SMILES: CC(C)(CCC(C#N)(c1ccccc1)c1ccccc1)N1CC[C@H](OCc2ccc(Br)cc2)C1]

Sodium hydride (60% dispersion in mineral oil, 35 mg, 0.88 mmol) was added portionwise to an ice-cooled solution of the product of preparation 18(205 mg, 0.59 mmol) in N,N-dimethylformamide (5 mL) and the mixture was stirred for 1 hour. 4-Bromobenzylbromide (220 mg, 0.88 mmol) was added and the mixture was stirred for 3 hours, allowing the temperature to rise to 25° C. The reaction mixture was then re-cooled to 0° C., further sodium hydride (60% dispersion in mineral oil, 220 mg, 0.88 mmol) was added and the mixture was stirred at room temperature. After 18 hours, the mixture was re-cooled to 0° C. and sodium hydride (60% dispersion in mineral oil, 293 mg, 1.17 mmol) was added. After stirring for 1 hour, further 4-bromobenzylbromide (220 mg, 0.88 mmol) was added and the mixture was stirred for 3 hours at room temperature. The reaction mixture was then quenched with water, concentrated in vacuo and the aqueous residue was partitioned between ethyl acetate (50 mL) and water (30 mL). The organic layer was separated, dried over sodium sulfate, concentrated in vacuo and the residue purified using an Isolute® SCX-2 cartridge, eluting with methanol followed by 0.5M ammonia in methanol. The basic fractions were evaporated under reduced pressure and the residue further purified by column chromatography on silica gel, eluting with dichloromethane: methanol:0.88 ammonia, 95:5:5 to afford the title compound as a pale orange gum.

¹HNMR(400 MHz, CD₃OD) δ: 1.02(s, 3H), 1.05(s, 3H), 1.40-1.53(m, 2H), 1.77-1.85(m, 1H), 1.93-2.02(m, 1H), 2.50-2.55(m, 3H), 2.64-2.78(m, 3H), 4.03-4.08(m, 1H), 4.42(s, 2H), 7.23(d, 2H), 7.28-7.44(m, 12H); LRMS APCI m/z 519 [M+H]⁺

EXAMPLE 60

5-{(3S)-3-[(3'-Hydroxybiphenyl-4-yl)methoxy]pyrrolidin-1-yl}-5-methyl-2,2-diphenylhexanenitrile

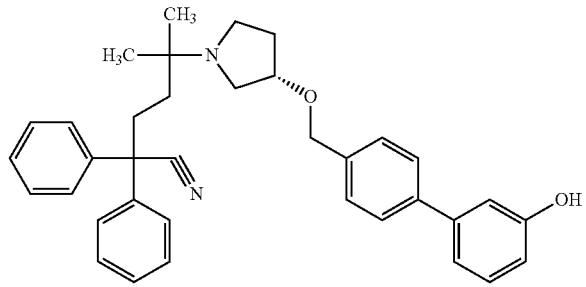 [SMILES: CC(C)(CCC(C#N)(c1ccccc1)c1ccccc1)N1CC[C@H](OCc2ccc(-c3cccc(O)c3)cc2)C1]

1,1'-Bis(diphenylphosphino)ferrocene]palladium(II) chloride (12 mg, 14 μmol) was added to a solution of the product of example 59 (150 mg, 0.29 mmol), 3-hydroxyphenylboronic acid (80 mg, 0.58 mmol) and sodium carbonate (62 mg, 0.58 mmol) in tetrahydrofuran (5.5 mL) and water (1 mL) and the mixture was heated under reflux for 18 hours. Further 1,1'-bis(diphenylphosphino)ferrocene]palladium(II) chloride (12 mg, 14 μmol) was added and the mixture was heated under reflux for 6 hours before cooling to room temperature. The reaction mixture was then concentrated in vacuo and the residue was purified by column chromatography on silica gel, eluting with dichloromethane:methanol:0.88 ammonia, 100:0:0 to 95:5:0.5, to afford the title compound as a pale brown foam in 47% yield, 73 mg.

LRMS ESI m/z 531 [M+H]⁺

EXAMPLE 61

5-{(3S)-3-[(3'-Hydroxybiphenyl-3-yl)methoxy]pyrrolidin-1-yl}-5-methyl-2,2-diphenylhexanamide

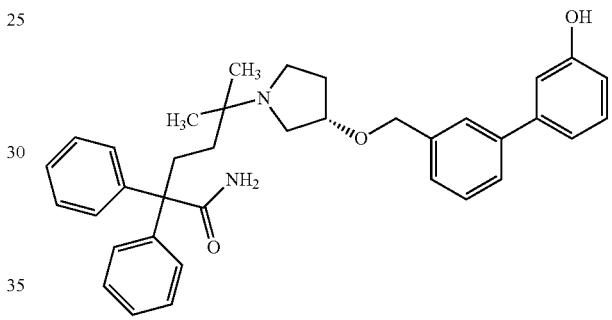

The title compound was prepared from the product of example 56, using the same method as that described for example 2, as a colourless gum in 17% yield.

¹HNMR(400 MHz, CD₃OD) δ: 1.22(s, 3H), 1.24(s, 3H), 1.42-1.47(m, 2H), 1.96-2.06(m, 1H), 2.11-2.19(m, 1H), 2.42-2.47(m, 2H), 3.14-3.23(m, 4H), 4.23-4.27(m, 1H), 4.56(m, 2H), 6.76-6.79(dd, 1H), 7.02(m, 1H), 7.06(d, 1H), 7.23-7.41 (m, 13H), 7.49-7.51(d, 1H), 7.54(s, 1H); LRMS ESI m/z 549 [M+H]⁺

EXAMPLE 62

5-{(3S)-3-[(4'-Hydroxybiphenyl-3-yl)methoxy]pyrrolidin-1-yl}-5-methyl-2,2-diphenylhexanenitrile

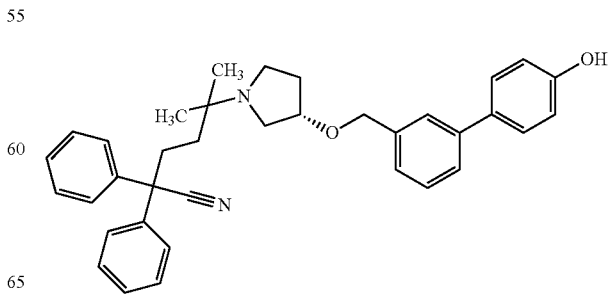

The title compound was prepared from the product of example 55 and 4-hydroxyphenylboronic acid, using the same method as that described for example 56. The crude compound was purified by column chromatography on silica gel, eluting with ethyl acetate. The appropriate fractions were evaporated under reduced pressure and the residue was further purified by column chromatography on silica gel, eluting with dichloromethane:methanol:0.88 ammonia, 98:2:0.2 to 95:5:0.5, to afford the desired compound as a pale brown gum in 78% yield.

¹HNMR(CD₃OD, 400 MHz) δ: 1.03(s, 3H), 1.06(s, 3H), 1.46-1.52(m, 2H), 1.80-1.88(m, 1H), 1.93-2.02(m, 1H), 2.49-2.60(m, 3H), 2.66-2.80(m, 3H), 4.04-4.09(m, 1H), 4.44(s, 2H), 6.80(d, 2H), 7.26-7.43(m, 15H), 7.50(s, 1H); LRMS ESI m/z 529 [M−H]⁻

EXAMPLE 63

5-{(3S)-3-[(4'-Hydroxybiphenyl-3-yl)methoxy]pyrrolidin-1-yl}-5-methyl-2,2-diphenylhexanamide

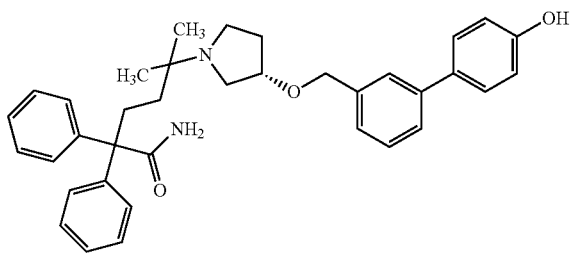 [SMILES: CC(C)(CCC(C(N)=O)(c1ccccc1)c1ccccc1)N1CC[C@H](OCc2cccc(-c3ccc(O)cc3)c2)C1]

The title compound was prepared from the product of example 62, using the same method as that described for example 2, in 6% yield.

¹HNMR(400 MHz, CD₃OD) δ: 1.00(s, 3H), 1.02(s, 3H), 1.25-1.29(m, 2H), 1.78-1.87(m, 1H), 1.88-1.99(m, 1H), 2.40-2.44(m, 2H), 2.52-2.59(m, 1H), 2.60-2.71(m, 2H), 2.72-2.78 (m, 1H), 4.03-4.08(m, 1H), 4.48(s, 2H), 6.84(d, 2H), 7.20-7.38(m, 12H), 7.41-7.45(m, 3H), 7.48(s, 1H); LRMS ESI m/z 549 [M+H]⁺

EXAMPLE 64

5-{(3S)-3-[(2'-Hydroxybiphenyl-3-yl)methoxy]pyrrolidin-1-yl}-5-methyl-2,2-diphenylhexanamide

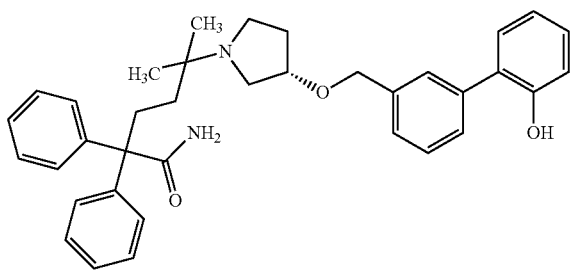 [SMILES: CC(C)(CCC(C(N)=O)(c1ccccc1)c1ccccc1)N1CC[C@H](OCc2cccc(-c3ccccc3O)c2)C1]

The title compound was prepared from the product of example 58, using the same method as that described for example 2. The crude was purified by column chromatography on silica gel, eluting with dichloromethane:methanol: 0.88 ammonia, 90:10:1 to 80:20:2, to afford the desired product as a white solid in 21% yield.

¹HNMR(400 MHz, CD₃OD) δ: 0.98(s, 3H), 1.00(s, 3H), 1.23-1.27(m, 2H), 1.75-1.84(m, 1H), 1.88-1.98(m, 1H), 2.39-2.44(m, 2H), 2.47-2.66(m, 3H), 2.71-2.75(m, 1H), 4.02-4.08 (m, 1H), 4.47(s, 2H), 6.86-6.89(m, 2H), 7.12-7.16(m, 1H), 7.20-7.37(m, 13H), 7.44(d, 1H), 7.49(s, 1H); LRMS ESI m/z 549 [M+H]⁺

EXAMPLE 65

5-{(3S)-3-[(3'-Hydroxybiphenyl-4-yl)methoxy]pyrrolidin-1-yl}-5-methyl-2,2-diphenylhexanamide

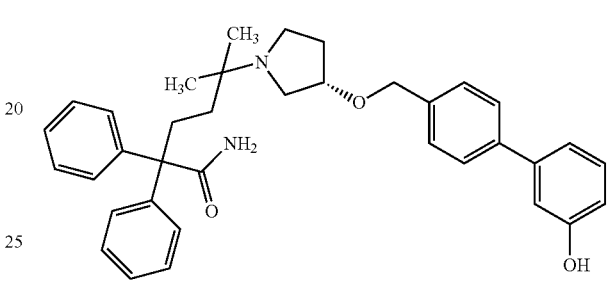

The title compound was prepared from the product of example 60, using the same method as that described for example 2. The crude was purified by column chromatography on silica gel, eluting with dichloromethane:methanol: 0.88 ammonia, 95:5:0.5 to 90:10:1, to afford the desired product as a white solid in 28% yield.

¹HNMR(400 MHz, CD₃OD) δ: 1.03(s, 3H), 1.05(s, 3H), 1.27-1.31(m, 1H), 1.52-1.56(m, 1H), 1.81-1.89(m, 1H), 1.90-2.00(m, 1H), 2.34-2.38(m, 1H), 2.41-2.45(m, 2H), 2.59-2.64 (m, 1H), 2.67-2.76(m, 1H), 2.79-2.83(m, 1H), 4.04-4.10(m, 1H), 4.47(m, 2H), 6.75(d, 1H), 7.01(m, 1H), 7.05(d, 1H), 7.18-7.38(m, 11H), 7.43(d, 2H), 7.53(d, 2H); LRMS ESI m/z 549 [M+H]⁺

EXAMPLE 66

5-[(3S)-3-(Biphenyl-3-ylmethoxy)pyrrolidin-1-yl]-5-methyl-2,2-diphenylhexanamide

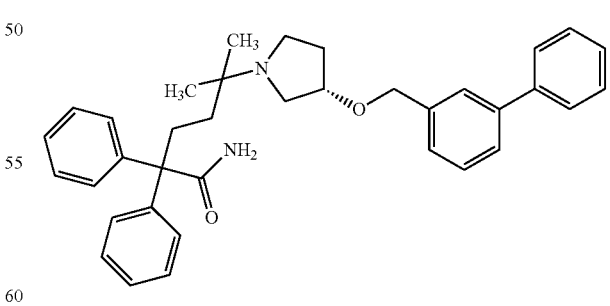

The title compound was prepared from the product of example 57, using the same method as that described for example 2, as a brown gum in 23% yield.

¹HNMR(400 MHz, CD₃OD) δ: 1.18(s, 3H), 1.20(s, 3H), 1.38-1.44(m, 2H), 1.97-2.04(m, 1H), 2.05-2.12(m, 1H), 2.41-2.46(m, 2H), 3.03-3.14(m, 4H), 4.21-4.24(m, 1H), 4.56(m,

2H), 7.23-7.44(m, 16H), 7.50-7.55(m, 1H), 7.57-7.60(m, 2H); LRMS APCI m/z 533 [M+H]⁺

EXAMPLE 67

5-[(3R)-3-(4-Fluoro-3-hydroxy-benzyloxy)-pyrrolidin-1-yl]-5-methyl-2,2-diphenylhexanamide

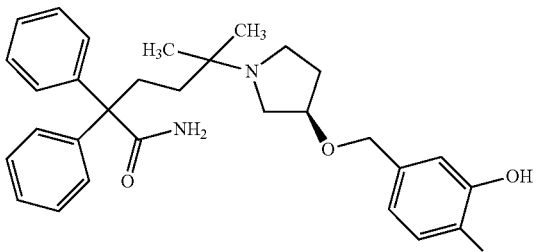

Hydrochloric acid in dioxane (4M, 4 ml) and water (0.5 ml) were added to the product of preparation 34 (150 mg, 0.248 mmol) and the resulting solution refluxed for 45 minutes. The solvent was removed in vacuo and the residue partitioned between ethyl acetate (10 ml) and saturated sodium hydrogen carbonate solution (3 ml). The aqueous layer was separated and extracted with further ethyl acetate (2×10 ml). The combined organic layers were washed with water (5 ml), brine (5 ml), dried over sodium sulphate and concentrated in vacuo. The residue was purified by column chromatography, eluting with dichloromethane:methanol:0.88 ammonia (95:5:0.5 to 93:7:0.7 to 90:10:1) to afford the title compound as an off-white foam in 44% yield, 54 mg.

¹HNMR(400 MHz, CD₃OD) δ: 1.05(s, 3H), 1.06(s, 3H), 1.28-1.33(m, 2H), 1.81-1.97(m, 2H), 2.41-2.45(m, 2H), 2.63-2.86(m, 4H), 4.02-4.07(m, 1H), 4.34(s, 2H), 6.70-6.74(m, 1H), 6.87-6.90(dd, 1H), 6.94-6.99(dd, 1H), 7.23-7.38(m, 10H); LRMS ESI m/z 491 [M+H]⁺

EXAMPLE 68

5-[(3S)-3-(3-Cyano-5-hydroxy-phenoxy)-pyrrolidin-1-yl]-5-methyl-2,2-diphenylhexanamide

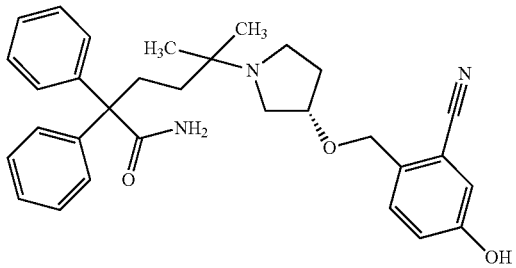 [SMILES: CC(C)(CCC(C(N)=O)(c1ccccc1)c1ccccc1)N1CC[C@H](OCc2ccc(O)cc2C#N)C1]

Ammonium formate (33 mg, 0.523 mmol) and 20% Pd(OH)₂\C (3 mg) were added to a solution of the product of preparation 36(30 mg, 0.0523 mmol) in ethanol (2 mL) and the mixture refluxed for 15 minutes. The reaction mixture was then filtered through Arbocel® and the filtrate was concentrated in vacuo. The residue was purified by column chromatography on silica gel, eluting with dichloromethane:methanol:0.88 ammonia (95:5:0.5) to afford the title compound as a yellow foam in 87% yield, 22 mg.

¹HNMR(400 MHz, CD₃OD) δ: 1.00(s, 3H), 1.04(s, 3H), 1.23-1.28(m, 2H), 1.84-1.93(m, 1H), 2.08-2.17(m, 1H), 2.36-2.50(m, 2H), 2.56-2.63(m, 2H), 2.71-2.77(q, 1H), 2.85-2.89(m, 1H), 4.73-4.79(m, 1H), 6.53-6.54(d, 1H), 6.60-6.61(d, 1H), 6.66-6.67(d, 1H), 7.22-7.36(m, 10H); LRMS ESI m/z 484 [M+H]⁺

EXAMPLE 69

5-[(3S)-3-(2-Cyano-5-methoxy-phenoxy)-pyrrolidin-1-yl]-5-methyl-2,2-diphenylhexanamide

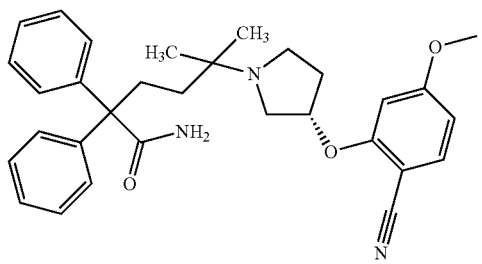 [SMILES: COc1ccc(C#N)c(O[C@H]2CCN(C(C)(C)CCC(C(N)=O)(c3ccccc3)c3ccccc3)C2)c1]

The title compound was prepared from the product of preparation 17 and 2-hydroxy-4-methoxybenzonitrile using the same method as that described for preparation 36, to afford an orange foam in 36% yield.

¹HNMR(400 MHz, CD₃OD) δ: 1.00(s, 3H), 1.04(s, 3H), 1.21-1.29(m, 2H), 1.89-1.98(m, 1H), 2.10-2.20(m, 1H), 2.35-2.51(m, 2H), 2.57-2.68(m, 2H), 2.73-2.83(m, 1H), 2.91-2.99(m, 1H), 3.86(s, 3H), 4.88-4.91(m, 1H), 6.51(d, 1H), 6.61-6.64(dd, 1H), 7.20-7.39(m, 10H), 7.48-7.50(d, 1H); LRMS ESI m/z 498 [M+H]⁺

EXAMPLE 70

5-{(3S)-3-[(7-Hydroxy-2-naphthyl)oxy]pyrrolidin-1-yl}-5-methyl-2,2-diphenylhexanamide

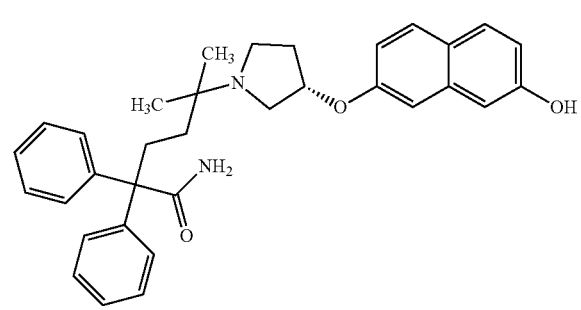 [SMILES: CC(C)(CCC(C(N)=O)(c1ccccc1)c1ccccc1)N1CC[C@H](Oc2ccc3ccc(O)cc3c2)C1]

Ammonium fluoride (53 mg, 1.44 mmol) was added to a solution of the product of preparation 37(90 mg, 0.144 mmol) in methanol (3 mL) and water (0.3 mL) and the mixture was heated at 50° C. for 18 hours. The mixture was concentrated in vacuo and the residue purified using a RediSep® silica gel cartridge eluting with dichloromethane:methanol:0.88 ammonia (100:0:0 to 90:10:1). Appropriate fractions were concentrated in vacuo and the residue further purified using a RediSep® silica gel cartridge eluting with dichloromethane:

methanol:0.88 ammonia (100:0:0 to 93:7:0.7) to afford the title compound as a colourless gum in 6% yield, 4.5 mg.

¹HNMR(400 MHz, CD₃OD) δ: 0.96(s, 3H), 1.06(s, 3H), 1.19-1.30(m, 2H), 1.88-1.98(m, 1H), 2.11-2.23(m, 1H), 2.34-2.52(m, 2H), 2.54-2.64(m, 1H), 2.64-2.68(m, 1H), 2.72-2.82 (m, 1H), 2.85-2.91(m, 1H), 4.82-4.89(m, 1H), 6.77-6.83(m, 1H), 6.85-6.87(m, 1H), 6.88-6.91(m, 1H), 6.98-7.01(m, 1H), 7.15-7.35(m, 10H), 7.54-7.62(m, 2H); LRMS APCI m/z 509 [M+H]⁺

EXAMPLE 71

5-[(3S)-3-(4-Phenylphenoxy)pyrrolidin-1-yl]-5-methyl-2,2-diphenylhexanamide

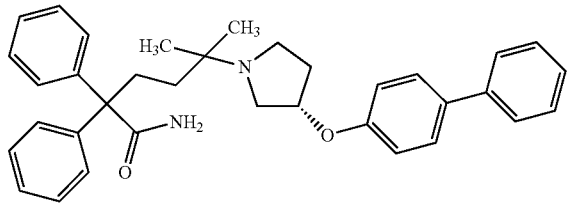 [SMILES: CC(C)(CCC(C(N)=O)(c1ccccc1)c1ccccc1)N1CC[C@H](Oc2ccc(-c3ccccc3)cc2)C1]

A solution of triphenylphosphine (143 mg, 0.546 mmol) in tetrahydrofuran (1 mL) and di-isopropylazodicarboxylate (0.11 mL, 0.546 mmol) were added to a solution of the product of preparation 17(100 mg, 0.273 mmol) in tetrahydrofuran (1 mL) and the mixture was stirred at room temperature for 15 minutes. 4-Phenylphenol (93 mg, 0.546 mmol) was added and the mixture was stirred at room temperature for 18 hours. Further triphenylphosphine (143 mg, 0.546 mmol) and di-isopropylazodicarboxylate (0.11 mL, 0.546 mmol) were added and the solution was stirred at room temperature for 72 hours. The mixture was concentrated in vacuo and the residue purified by column chromatography on silica gel, eluting with dichloromethane:methanol (100:0 to 95:5) to afford the title compound as a colourless oil in 28% yield, 40 mg.

¹HNMR(400 MHz, CD₃OD) δ: 0.99(s, 3H), 1.07(s, 3H), 1.23-1.26(m, 2H), 1.90-1.98(m, 1H), 2.10-2.19(m, 1H), 2.39-2.46(m, 2H), 2.58-2.68(m, 2H), 2.75-2.89(m, 2H), 4.80-4.84 (m, 1H), 6.88-6.90(d, 2H), 7.20-7.41(m, 13H), 7.49-7.56(dd, 4H); LRMS APCI m/z 519 [M+H]⁺

EXAMPLE 72

5-[(3R)-3-(3-chloro-4-hydroxyphenoxy)pyrrolidin-1-yl]-5-methyl-2,2-diphenylhexanamide

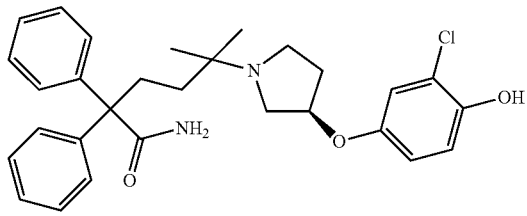 [SMILES: CC(C)(CCC(C(N)=O)(c1ccccc1)c1ccccc1)N1CC[C@@H](Oc2ccc(O)c(Cl)c2)C1]

Boron tribromide (1M in dichloromethane, 0.16 mL, 0.158 mmol) was added to a solution of the product of example 28(20 mg, 0.039 mmol) in dichloromethane (3 mL) and the mixture was stirred at room temperature for 72 hours. The reaction mixture was quenched via dropwise addition of 0.88 ammonia (5 mL) and stirred for 24 hours. The aqueous layer was separated and extracted with dichloromethane (3×20 mL). The combined organic layers were concentrated in vacuo and the residue was purified by column chromatography on silica gel, eluting with ethyl acetate:methanol:0.88 ammonia (100:0:0 to 95:5:0.5) to afford a colourless gum. This was further purified by HPLC using a Curosil PFP-Acid 150*21.2 stationary phase, eluting with 0.1% Formic acid (aq):(acetonitrile+0.1% Formic acid), 95:5 to 0:100. Appropriate fractions were concentrated in vacuo and the residue was partitioned between dichloromethane (15 ml) and water (5 ml), and the aqueous layer was separated and extracted with further dichloromethane (2×15 ml). The combined organic layers were washed with sodium hydroxide solution (1M, 5 ml), brine (10 ml) and concentrated in vacuo. The residue was further purified by preparative thin layer chromatography eluting with dichloromethane:methanol:0.88 ammonia (90:10:1). Clean product bands were washed from the silica gel using dichloromethane:methanol:0.88 ammonia (95:5:0.5), filtered and concentrated in vacuo to afford the title compound as a colourless gum in 16% yield, 3 mg.

¹HNMR(400 MHz, CD₃OD) δ: 1.18(s, 3H), 1.22(s, 3H), 1.28-1.30(m, 2H), 1.39-1.44(m, 2H), 2.08-2.14(m, 2H), 2.42-2.47(m, 2H), 3.04-3.27(m, 2H), 4.82-4.87(m, 1H), 6.66-6.70 (m, 1H), 6.82-6.87(m, 2H), 7.25-7.38(m, 10H); LRMS APCI m/z 493 [M+H]⁺ 491

EXAMPLE 73

5-[(3R)-3-(3-Fluoro-5-methoxy-phenoxy)-pyrrolidin-1-yl]-5-methyl-2,2-diphenylhexanamide

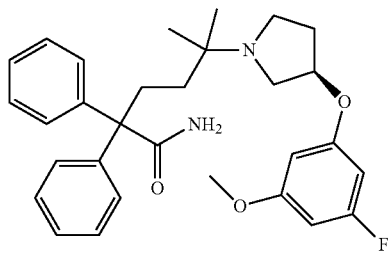 [SMILES: COc1cc(F)cc(O[C@@H]2CCN(C(C)(C)CCC(C(N)=O)(c3ccccc3)c3ccccc3)C2)c1]

Diisopropyl azodicarboxylate (160 μL, 0.822 mmol) was added in three portions to an ice-cooled solution of triphenyl phosphine (215 mg, 0.822 mmol), the product of preparation 23 (175 mg, 1.232 mmol) and the product of preparation 16 (150 mg, 0.411 mmol) in tetrahydrofuran (7 mL) and the mixture was stirred at room temperature for 2 hours. The reaction mixture was concentrated in vacuo and residue purified using an Isolute® SCX-2 cartridge, eluting with methanol followed by 2M ammonia in methanol. Basic fractions were concentrated in vacuo to afford the title compound as a pale brown foam in 75% yield, 150 mg.

¹HNMR(400 MHz, CD₃OD) δ: 0.98(s, 3H), 1.03(s, 3H), 1.21-1.26(m, 2H), 1.81-1.89(m, 1H), 2.06-2.15(m, 1H), 2.38-2.46(m, 2H), 2.50-2.61(m, 2H), 2.67-2.72(m, 1H), 2.78-2.85

(m, 1H), 3.74(s, 3H), 4.69-4.74(m, 1H), 6.14-6.19(m, 2H), 6.24-6.28(m, 1H), 7.21-7.36(m, 10H); LRMS ESI m/z 491 [M+H]+

EXAMPLE 74

5-[(3R)-3-(3-Fluoro-5-hydroxy-phenoxy)-pyrrolidin-1-yl]-5-methyl-2,2-diphenyl-hexanamide

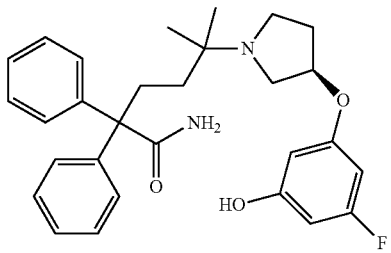 [SMILES: CC(C)(CCC(C(N)=O)(c1ccccc1)c1ccccc1)N1CC[C@@H](Oc2cc(O)cc(F)c2)C1]

Boron tribromide (1M in dichloromethane, 1.2 mL, 1.224 mmol) was added to an ice-cooled solution of the product of example 73 (150 mg, 0.306 mmol) in dichloromethane (4 mL) and the mixture was stirred at room temperature for 18 hours. The reaction was quenched with 0.88 ammonia solution and stirred at room temperature for 2 hours. The reaction mixture was adjusted to pH 8 by dropwise addition of 2N hydrochloric acid (aq) and extracted with dichloromethane (3×10 mL). The combined organic layers were dried over sodium sulfate and concentrated in vacuo. Purification of the residue by column chromatography on silica gel, eluting with dichloromethane:methanol:0.88 ammonia, 95:5:0.5, afforded the title compound as a pale brown foam in 49% yield, 71 mg.

$^1$HNMR(400 MHz, CD$_3$OD) δ: 1.01(s, 3H), 1.05(s, 3H), 1.24-1.28(m, 2H), 1.85-1.92(m, 1H), 2.07-2.15(m, 1H), 2.40-2.45(m, 2H), 2.59-2.67(m, 2H), 2.73-2.79(q, 1H), 2.87-2.91 (m, 1H), 4.68-4.72(m, 1H), 6.03-6.12(m, 3H), 7.21-7.26(m, 2H), 7.28-7.32(m, 4H), 7.33-7.37(m, 4H); LRMS ESI m/z 477 [M+H]+, 475 [M−H]−

EXAMPLE 75

5-[(3R)-3-(2-Fluoro-3-methoxy-phenoxy)-pyrrolidin-1-yl]-5-methyl-2,2-diphenylhexanamide

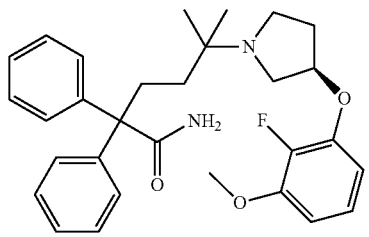 [SMILES: COc1cccc(O[C@@H]2CCN(C(C)(C)CCC(C(N)=O)(c3ccccc3)c3ccccc3)C2)c1F]

Diisopropyl azodicarboxylate (160 μL, 0.822 mmol) was added in three portions to an ice-cooled solution of triphenyl phosphine (215 mg, 0.822 mmol), the product of preparation 26 (160 mg, 1.127 mmol) and product from preparation 16 (150 mg, 0.411 mmol) in tetrahydrofuran (7 mL) and the mixture was stirred at 0° C. to room temperature for 16 hours. Additional triphenyl phosphine (215 mg, 0.822 mmol) and diisopropyl azodicarboxylate (160 μL, 0.822 mmol) were added and the mixture stirred for a further 48 hours. The reaction mixture was concentrated in vacuo and the residue purified using an Isolute® SCX-2 cartridge, eluting with methanol followed by 2M ammonia in methanol. Basic fractions were concentrated in vacuo to afford the title compound as a pale brown foam in 75% yield, 145 mg.

LRMS ESI m/z 491 [M+H]+

EXAMPLE 76

5-[(3R)-3-(2-Fluoro-3-hydroxy-phenoxy)-pyrrolidin-1-yl]-5-methyl-2,2-diphenylhexanamide

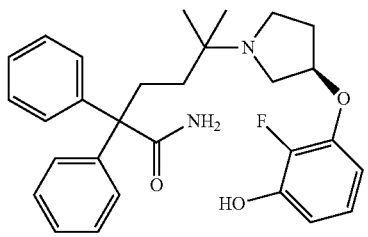 [SMILES: CC(C)(CCC(C(N)=O)(c1ccccc1)c1ccccc1)N1CC[C@@H](Oc2cccc(O)c2F)C1]

Boron tribromide (1M in dichloromethane, 1.1 mL, 1.224 mmol) was added to an ice-cooled solution of the product of example 75(140 mg, 0.286 mmol) in dichloromethane (4 mL) and the mixture was stirred at room temperature for 2 hours. The reaction was quenched with 0.88 ammonia solution and stirred at room temperature for 16 hours. The reaction mixture was adjusted to pH 8 by dropwise addition of 2N hydrochloric acid (aq) and extracted with dichloromethane (2×10 mL). The combined organic layers were dried over sodium sulfate and concentrated in vacuo. Purification of the residue by column chromatography on silica gel, eluting with dichloromethane:methanol:0.88 ammonia, 95:5:0.5, afforded the title compound as a pale yellow foam in 15% yield, 20 mg.

$^1$HNMR(400 MHz, CD$_3$OD) δ: 1.00(s, 3H), 1.04(s, 3H), 1.25-1.28(m, 2H), 1.85-1.93(m, 1H), 2.06-2.12(m, 1H), 2.42-2.46(m, 2H), 2.54-2.60(m, 1H), 2.65-2.75(m, 2H), 2.85-2.90 (q, 1H), 4.74-4.78(m, 1H), 6.38-6.42(t, 1H), 6.49-6.53(t, 1H), 6.80-6.85(t, 1H), 7.22-7.25(m, 2H), 7.28-7.32(m, 4H), 7.35-7.38(m, 4H); LRMS ESI m/z 477 [M+H]+ 475 [M−H]−

EXAMPLE 77

5-[(3R)-3-(2-Chloro-3-methoxy-phenoxy)-pyrrolidin-1-yl]-5-methyl-2,2-diphenylhexanamide

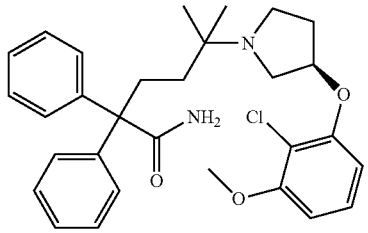 [SMILES: COc1cccc(O[C@@H]2CCN(C(C)(C)CCC(C(N)=O)(c3ccccc3)c3ccccc3)C2)c1Cl]

Diisopropyl azodicarboxylate (118 μL, 0.606 mmol) was added in three portions to an ice-cooled solution of triphenyl phosphine (160 mg, 0.606 mmol), the product of preparation 21 (120 mg, 0.757 mmol) and product from preparation 16

(111 mg, 0.411 mmol) in tetrahydrofuran (7 mL) and the mixture was stirred at 0° C. to room temperature for 3 hours. Additional triphenyl phosphine (160 mg, 0.606 mmol), and diisopropyl azodicarboxylate (118 μL, 0.606 mmol) were added and the mixture stirred for a further 16 hours. The reaction mixture was concentrated in vacuo and residue purified using an Isolute® SCX-2 cartridge, eluting with methanol followed by 2M ammonia in methanol. Basic fractions were concentrated in vacuo to afford the title compound as a pale brown foam in 82% yield, 124 mg.

$^1$HNMR(400 MHz, CD$_3$OD) δ: 1.00(s, 3H), 1.05(s, 3H), 1.24-1.29(m, 2H), 1.85-1.97(m, 1H), 2.05-2.15(m, 1H), 2.43-2.47(m, 2H), 2.58-2.64(m, 1H), 2.66-2.72(m, 1H), 2.73-2.80 (m, 1H), 2.89-2.95(m, 1H), 3.85(s, 3H), 4.79-4.81(m, 1H), 6.55-6.57(d, 1H), 6.67-6.70(d, 1H), 7.15-7.19(t, 1H), 7.21-7.24(m, 2H), 7.27-7.31(m, 4H), 7.34-7.38(m, 4H); LRMS ESI m/z 507 [M+H]$^+$

EXAMPLE 78

5-[(3R)-3-(2-Chloro-3-hydroxy-phenoxy)-pyrrolidin-1-yl]-5-methyl-2,2-diphenylhexanamide

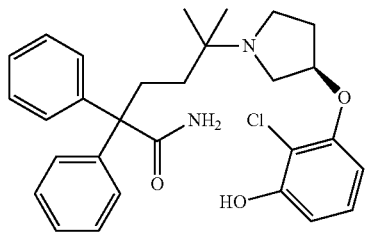 [SMILES: CC(C)(CCC(C(N)=O)(c1ccccc1)c1ccccc1)N1CC[C@@H](Oc2cccc(O)c2Cl)C1]

The title compound was prepared from the product of example 77, using the same method as that described for example 74, to afford a pale orange foam in 36% yield.

$^1$HNMR(400 MHz, CD$_3$OD) δ: 1.03(s, 3H), 1.07(s, 3H), 1.27-1.32(m, 2H), 1.92-1.99(m, 1H), 2.06-2.14(m, 1H), 2.43-2.47(m, 2H), 2.65-2.71(m, 1H), 2.74-2.78(d, 1H), 2.80-2.86 (q, 1H), 2.96-3.00(m, 1H), 4.79-4.82(m, 1H), 6.41-6.43(dd, 1H), 6.53-6.55(dd, 1H), 7.00-7.04(t, 1H), 7.21-7.25(m, 2H), 7.28-7.32(m, 4H), 7.36-7.39(m, 4H); LRMS ESI m/z 493 [M+H]$^+$ 491 [M−H]$^-$

EXAMPLE 79

5-[(3R)-3-(4-Chloro-3-hydroxy-benzyloxy)-pyrrolidin-1-yl]-5-methyl-2,2-diphenylhexanamide

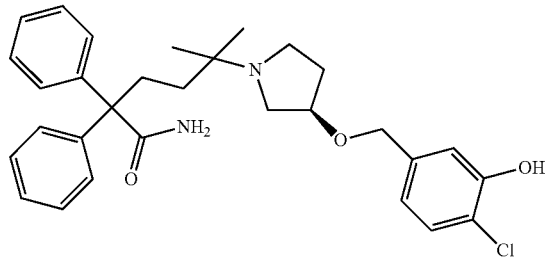 [SMILES: CC(C)(CCC(C(N)=O)(c1ccccc1)c1ccccc1)N1CC[C@@H](OCc2ccc(Cl)c(O)c2)C1]

Hydrochloric acid (4M in dioxan, 4 ml) and water (0.5 ml) were added to the product of preparation 44(161 mg, 0.295 mmol) and the mixture was heated under reflux for 30 minutes. The reaction mixture was then cooled to room temperature and partitioned between ethyl acetate (20 mL) and saturated aqueous sodium hydrogen carbonate solution (20 mL). The aqueous layer was separated, extracted with further ethyl acetate (20 mL) and the combined organic layers were dried over sodium sulfate and concentrated in vacuo. The residue was purified by column chromatography on silica gel, eluting with dichloromethane:methanol:0.88 ammonia, 95:5:0.5 to 90:10:1, to afford the title compound as a pale brown foam in 19% yield, 29 mg.

$^1$HNMR(400 MHz, CD$_3$OD) δ: 1.01(s, 3H), 1.02(s, 3H), 1.24-1.28(m, 2H), 1.75-1.82(m, 1H), 1.87-1.94(m, 1H), 2.40-2.44(m, 2H), 2.51-2.60(m, 2H), 2.63-2.69(q, 1H), 2.73-2.77 (q, 1H), 3.98-4.03(m, 1H), 4.34(s, 2H), 6.70-6.73(dd, 1H), 6.87-6.88(d, 1H), 7.18-7.21(d, 1H), 7.22-7.26(m, 2H), 7.29-7.33(m, 4H), 7.35-7.38(m, 4H); LRMS APCI m/z 505 [M−H]$^-$

EXAMPLE 80

5-[(3R)-3-(3-methoxy-4-chloro-phenoxy)pyrrolidin-1-yl]-5-methyl-2,2-diphenylhexanenitrile

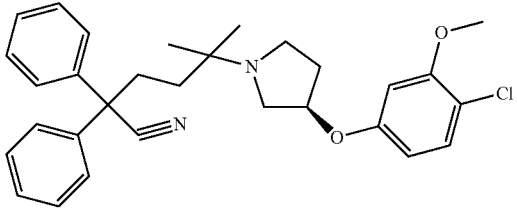 [SMILES: COc1cc(O[C@@H]2CCN(C(C)(C)CCC(C#N)(c3ccccc3)c3ccccc3)C2)ccc1Cl]

Sodium hydride (60% dispersion in mineral oil, 60 mg, 1.466 mmol) was added to an ice-cooled solution of the product of preparation 20(170 mg, 0.489 mmol) in N,N-dimethylformamide (5 mL) and the mixture was stirred at 0° C. for 30 minutes. 2-chloro-5-fluoro-anisole (73 μl, 0.586 mmol) was added and the mixture was stirred for 18 hours at room temperature. The mixture was then heated at 60° C. for 6 hours. The mixture was cooled to room temperature, further sodium hydride (60% dispersion in mineral oil, 60 mg, 1.466 mmol) was added and heating continued at 60° C. for 18 hours. The solution was cooled to 0° C., further sodium hydride (60% dispersion in mineral oil, 100 mg, 2.443 mmol) was added and the solution stirred for 30 minutes. Additional 2-chloro-5-fluoro-anisole (122 μl, 0.977 mmol) was added and mixture heated at 80° C. for 18 hours. The reaction mixture was then cooled to room temperature, quenched with water (3 mL), concentrated in vacuo and the aqueous residue was partitioned between ethyl acetate (10 mL) and water (5 mL). The aqueous layer was separated and extracted with further ethyl acetate (2×10 mL). The combined organic layers were washed with brine (10 mL), dried over sodium sulfate, concentrated in vacuo and the residue was purified by column chromatography on silica gel, eluting with ethyl acetate:methanol:0.88 ammonia, 99:1:0.1, to afford the title compound as a colourless gum in 34% yield, 80 mg.

$^1$HNMR(400 MHz, CD$_3$OD) δ: 1.03(s, 3H), 1.08(s, 3H), 1.44-1.49(m, 2H), 1.88-1.95(m, 1H), 2.12-2.21(m, 1H), 2.49-2.54(m, 2H), 2.56-2.62(m, 1H), 2.68-2.70(d, 1H), 2.76-2.82 (m, 1H), 2.85-2.89(m, 1H), 3.80(s, 3H), 4.79-4.81(m, 1H), 6.39-6.42(d, 1H), 6.54(s, 1H), 7.16-7.20(d, 1H), 7.26-7.42 (m, 10H); LRMS APCI m/z 489 [M+H]⁺

EXAMPLE 81

5-[(3R)-3-(3-methoxy-4-chloro-phenoxy)-pyrrolidin-1-yl]-5-methyl-2,2-diphenylhexanamide

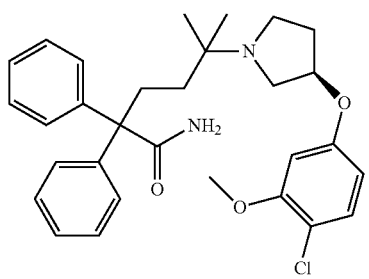 [SMILES: COc1cc(O[C@@H]2CCN(C(C)(C)CCC(C(N)=O)(c3ccccc3)c3ccccc3)C2)ccc1Cl]

Potassium hydroxide (185 mg, 3.275 mmol) was added to a solution of the product of example 80(80 mg, 0.163 mmol) in 3-methyl-3-pentanol (3 mL) and the mixture was heated under reflux for 24 hours. Further potassium hydroxide (93 mg, 1.638 mmol) was added and mixture heated at reflux for a further 5 hours. The reaction mixture was then cooled to room temperature, concentrated in vacuo and the residue was partitioned between ethyl acetate (15 mL) and water (10 mL). The aqueous layer was separated, extracted with further ethyl acetate (15 mL) and the combined organic layers were dried over sodium sulfate and concentrated in vacuo. The residue was purified by column chromatography in dichloromethane:methanol:0.88 ammonia, 97:3:0.3 to 94:6:0.6, to afford the title compound as a white foam in 64% yield, 53 mg.

¹HNMR(400 MHz, CD₃OD) δ: 0.98(s, 3H), 1.05(s, 3H), 1.20-1.26(m, 2H), 1.84-1.93(m, 1H), 2.07-2.16(m, 1H), 2.34-2.49(m, 2H), 2.53-2.65(m, 2H), 2.70-2.77(m, 1H), 2.81-2.88 (m, 1H), 3.80(s, 3H), 4.74-4.79(m, 1H), 6.36-6.38(dd, 1H), 6.51-6.52(d, 1H), 7.18-7.20(d, 1H), 7.21-7.35(m, 10H); LRMS APCI m/z 507 [M+H]⁺

EXAMPLE 82

5-[(3R)-3-(3-hydroxy-4-chloro-phenoxy)-pyrrolidin-1-yl]-5-methyl-2,2-diphenylhexanamide

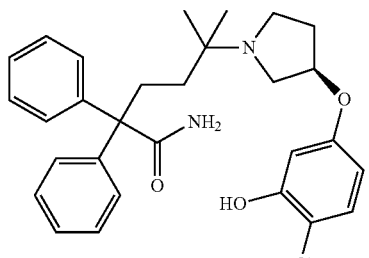

Boron tribromide (1M in dichloromethane, 0.4 mL, 0.4 mmol) was added to an ice-cooled solution of the product of example 81(50 mg, 0.099 mmol) in dichloromethane (2 mL) and the mixture was stirred at room temperature for 18 hours. Further boron tribromide (1M in dichloromethane, 0.2 mL, 0.2 mmol) was added and the mixture stirred at room temperature for a further 3 hours. The reaction was quenched with 0.88 ammonia solution and stirred at room temperature for 1 hour. The reaction mixture was acidified to pH 6 by dropwise addition of 2N hydrochloric acid (aq) and extracted with dichloromethane (2×10 ml). The combined organic layers were dried over sodium sulfate and concentrated in vacuo. Purification of the residue by column chromatography on silica gel, eluting with dichloromethane:methanol:0.88 ammonia, 97:3:0.3 to 94:6:0.6, afforded the title compound as a white foam in 70% yield, 34 mg.

¹HNMR(400 MHz, CD₃OD) δ: 1.00(s, 3H), 1.06(s, 3H), 1.24-1.28(m, 2H), 1.83-1.93(m, 1H), 2.06-2.15(m, 1H), 2.35-2.47(m, 2H), 2.60-2.68(m, 2H), 2.74-2.81(m, 1H), 2.87-2.91 (m, 1H), 4.68-4.73(m, 1H), 6.28-6.31(dd, 1H), 6.40-6.41(d, 1H), 7.10-7.12(d, 1H), 7.22-7.35(m, 10H); LRMS ESI m/z 493 [M+H]⁺ 491 [M−H]⁻

EXAMPLE 83

5-[(3R)-3-(3-hydroxy-4-cyano-phenoxy)-pyrrolidin-1-yl]-5-methyl-2,2-diphenylhexanamide

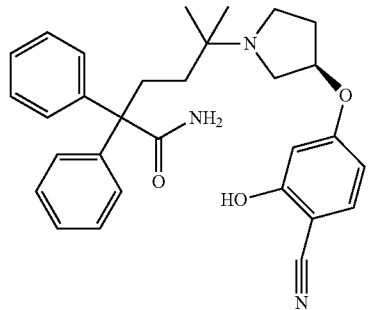 [SMILES: CC(C)(CCC(C(N)=O)(c1ccccc1)c1ccccc1)N1CC[C@@H](Oc2ccc(C#N)c(O)c2)C1]

Ammonium formate (44 mg, 0.698 mmol) and palladium hydroxide (20% on carbon, 8 mg) were added to a solution of the product of preparation 45(40 mg, 0.070 mmol) in ethanol (2 mL) and the mixture was stirred at reflux for 20 minutes. The reaction was cooled, the catalyst removed by filtration over Arbocel® and the filtrate concentrated in vacuo. Purification of the residue by column chromatography on silica gel, eluting with dichloromethane:methanol:0.88 ammonia, 95:5: 0.5 to 90:10:1, afforded the title compound as a white foam in 55% yield, 18 mg.

¹HNMR(400 MHz, CD₃OD) δ: 1.00(s, 3H), 1.06(s, 3H), 1.24-1.28(m, 2H), 1.87-1.94(m, 1H), 2.09-2.18(m, 1H), 2.35-2.49(m, 2H), 2.61-2.71(m, 2H), 2.75-2.82(q, 1H), 2.91-2.95 (q, 1H), 4.76-4.79(m, 1H), 6.32-6.35(m, 2H), 7.21-7.36(m, 11H); LRMS APCI m/z 484 [M+H]⁺

EXAMPLE 84

5-[(3S)-3-(3-methoxy-benzyloxy)pyrrolidin-1-yl]-5-methyl-2,2-diphenylhexanamide

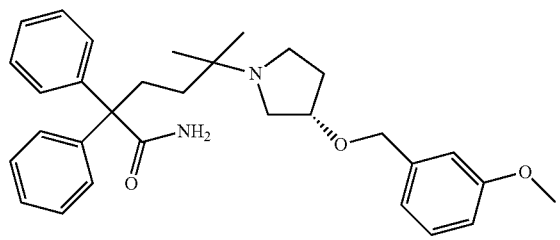 [SMILES: COc1cccc(CO[C@H]2CCN(C(C)(C)CCC(C(N)=O)(c3ccccc3)c3ccccc3)C2)c1]

Sodium hydride (60% dispersion in mineral oil, 26 mg, 0.638 mmol) was added to an ice-cooled solution of the product of preparation 18(185 mg, 0.532 mmol) in N,N-dimethylformamide (5 mL) and the mixture was stirred at 0° C. for 60 minutes. 3-Methoxybenzyl bromide (128 mg, 0.638 mmol) was added and the mixture was stirred for 3 hours at room temperature. Additional 3-methoxybenzyl bromide (160 mg, 0.797 mmol) was added and the mixture stirred for a further 2 hours. The reaction mixture was quenched with water (3 mL), concentrated in vacuo and the aqueous residue was partitioned between ethyl acetate (20 mL) and water (10 mL). The aqueous layer was separated and extracted with further ethyl acetate (2×10 mL). The combined organic layers were concentrated in vacuo and the residue was purified by column chromatography on silica gel, eluting with dichloromethane to afford a colourless oil, 180 mg.

Potassium hydroxide (430 mg, 7.692 mmol) was added to a solution of this colourless oil (180 mg, 0.385 mmol) in 3-methyl-3-pentanol (5 mL) and the mixture was heated under reflux for 24 hours. The reaction mixture was cooled to room temperature, concentrated in vacuo and the residue was partitioned between ethyl acetate (20 mL) and water (10 mL). The aqueous layer was separated, extracted with further ethyl acetate (10 mL) and the combined organic layers were dried over sodium sulfate and concentrated in vacuo. The residue was purified by column chromatography, eluting initially with pentane, then dichloromethane:methanol:0.88 ammonia, 95:5:0.5 up to 90:10:1, to afford the title compound as a white foam in 16% yield, 40 mg.

$^1$HNMR(400 MHz, CD$_3$OD) δ: 1.01(s, 3H), 1.03(s, 3H), 1.26-1.30(m, 2H), 1.77-1.85(m, 1H), 1.88-1.95(m, 1H), 2.40-2.45(m, 2H), 2.53-2.72(m, 3H), 2.75-2.79(m, 1H), 3.76(s, 3H), 4.00-4.05(m, 1H), 4.41(s, 2H), 6.80-6.83(d, 1H), 6.86-6.88(m, 2H), 7.16-7.37(m, 11H); LRMS ESI m/z 487 [M+H]$^+$

EXAMPLE 85

5-[(3R)-3-(2-Chloro-3-hydroxy-benzyloxy)-pyrrolidin-1-yl]-5-methyl-2,2-diphenylhexanamide

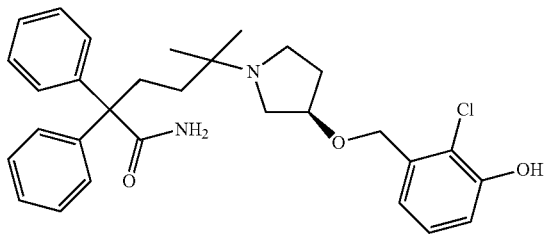 [SMILES: CC(C)(CCC(C(N)=O)(c1ccccc1)c1ccccc1)N1CC[C@@H](OCc2cccc(O)c2Cl)C1]

The title compound was prepared from the product of preparation 49, using the same method as that described for example 79, to afford a white foam in 34% yield.

$^1$HNMR(400 MHz, CD$_3$OD) δ: 1.11(s, 3H), 1.13(s, 3H), 1.34-1.38(m, 2H), 1.90-2.02(m, 2H), 2.41-2.45(m, 2H), 2.83-3.02(m, 4H), 4.14-4.18(m, 1H), 4.49-4.57(m, 2H), 6.84-6.87 (dd, 1H), 6.91-6.93(d, 1H), 7.06-7.10(t, 1H), 7.24-7.27(m, 2H), 7.30-7.38(m, 8H); LRMS APCI m/z 505 [M−H]$^-$

EXAMPLE 86

5-Methyl-5-(4-phenoxypiperidin-1-yl)-2,2-diphenyl-hexanenitrile

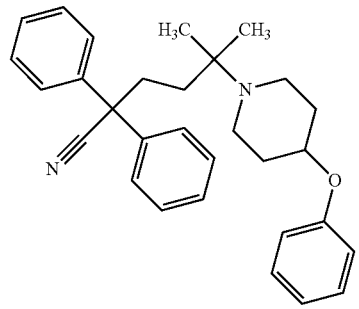 [SMILES: CC(C)(CCC(C#N)(c1ccccc1)c1ccccc1)N1CCC(Oc2ccccc2)CC1]

A solution of the product of preparation 50(9.03 g, 21 mmol) in tetrahydrofuran (270 mL) was cooled to −20° C. Zirconium tetrachloride (9.91 g, 43 mmol) was added and the reaction mixture was stirred at −20° C. for 1 hour. Methyl magnesium chloride (3M in tetrahydrofuran, 63.8 mL, 191 mmol) was then added dropwise and the mixture was stirred for 1 hour, with the temperature maintained below −10° C. The reaction was quenched with ethanol (20 mL), concentrated in vacuo and the residue was partitioned between 2N sodium hydroxide solution (200 mL) and ethyl acetate (250 mL). The aqueous layer was separated and extracted with ethyl acetate (2×200 mL), and the combined organic solution was dried over magnesium sulfate and concentrated in vacuo. The residue was purified by column chromatography on silica gel, eluting with pentane:ethyl acetate, 75:25 to 67:33. The appropriate fractions were evaporated under reduced pressure and the residue was further purified by using an Isolute® SCX-2 cartridge, methanol followed by 1M ammonia in methanol, to afford the title compound as a yellow gum in a 41% yield (3.83 g).

$^1$HNMR(400 MHz, CDCl$_3$) δ: 1.04(s, 6H), 1.54-1.58(m, 2H), 1.71-1.80(m, 2H), 1.99-2.02(m, 2H), 2.25(m, 2H), 2.53-2.57(m, 2H), 2.70-2.75(m, 2H), 4.22-4.28(m, 1H), 6.92-6.96 (m, 3H), 7.28-7.32(m, 4H), 7.35-7.39(m, 4H), 7.45-7.47(m, 4H); LRMS APCI m/z 439 [M+H]$^+$

EXAMPLE 87

5-{4-[(3-Bromobenzyl)oxy]piperidin-1-yl}-5-methyl-2,2-diphenylhexanenitrile

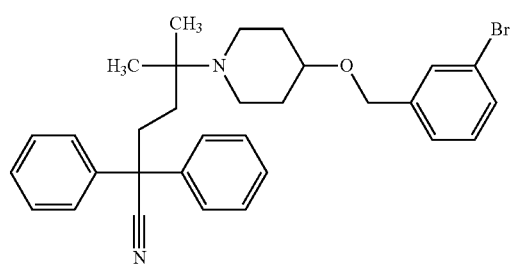 [SMILES: CC(C)(CCC(C#N)(c1ccccc1)c1ccccc1)N1CCC(OCc2cccc(Br)c2)CC1]

The title compound was prepared from the product of preparation 53, using the same method as that described for example 86, as a yellow gum in 33% yield.

¹HNMR(400 MHz, CDCl₃) δ: 0.98(s, 6H), 1.46-1.60(m, 4H), 1.88-1.91(m, 2H), 2.04-2.09(m, 2H), 2.46-2.50(m, 2H), 2.65-2.68(m, 2H), 3.28-3.34(m, 1H), 4.50(s, 2H), 7.18-7.42 (m, 13H), 7.51(s, 1H); LRMS ESI m/z 533 [M+H]⁺

EXAMPLE 88

5-{4-[(3-Hydroxybenzyl)oxy]piperidin-1-yl}-5-methyl-2,2-diphenylhexanenitrile

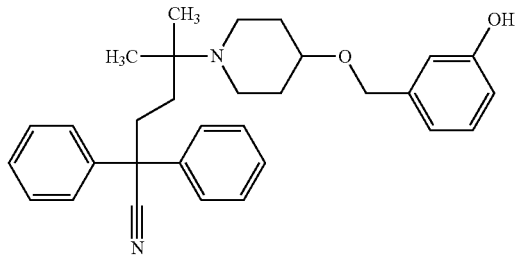 [SMILES: CC(C)(CCC(C#N)(c1ccccc1)c1ccccc1)N1CCC(OCc2cccc(O)c2)CC1]

n-Butyl lithium (2.5M in hexanes, 0.18 mL, 0.45 mmol) was added dropwise to a solution of the product of example 87 (200 mg, 0.38 mmol) in tetrahydrofuran (5 mL), cooled to −78° C., and the mixture was stirred for 15 minutes. Trimethylborate (0.13 mL, 1.13 mmol) was added and the mixture was stirred at −78° C. for 30 minutes and at room temperature for 2 hours. 4-methylmorpholine N-oxide (132 mg, 1.13 mmol) was added and the mixture was heated under reflux for 4 hours and stirred at room temperature for 18 hours. The reaction mixture was then partitioned between ethyl acetate (30 mL) and water (30 mL) and the organic layer was separated and washed with water (20 mL). The organic solution was dried over sodium sulfate, concentrated in vacuo and the residue was purified by column chromatography on silica gel, eluting with dichloromethane:methanol:0.88 ammonia, 100:0:0 to 90:10:1. The appropriate fractions were evaporated under reduced pressure and the residue was further purified by preparative tlc, eluting with dichloromethane:methanol:0.88 ammonia, 90:10:1, to afford the title compound as a gum in 3% yield, 5 mg.

¹HNMR(400 MHz, CD₃OD) δ: 1.02(s, 6H), 1.46-1.58(m, 4H), 1.86-1.90(m, 2H), 2.13-2.19(m, 2H), 2.49-2.53(m, 2H), 2.70-2.75(m, 2H), 3.33-3.39(m, 1H), 4.45(s, 2H), 6.67-6.70 (m, 1H), 6.77-6.79(m, 2H), 7.12(m, 1H), 7.28-7.43(m, 10H); LRMS ESI m/z 469 [M+H]⁺

EXAMPLE 89

5-[4-(Benzyloxy)piperidin-1-yl]-5-methyl-2,2-diphenylhexanenitrile

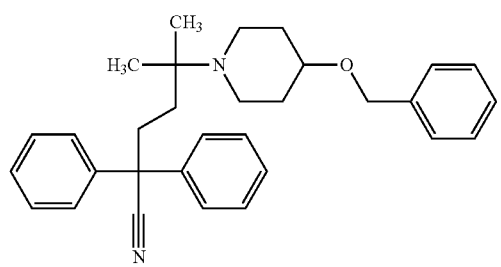 [SMILES: CC(C)(CCC(C#N)(c1ccccc1)c1ccccc1)N1CCC(OCc2ccccc2)CC1]

n-Butyl lithium (2.5M in hexanes, 0.23 mL, 0.56 mmol) was added dropwise to a solution of the product of example 87 (200 mg, 0.38 mmol) in tetrahydrofuran (8 mL), cooled to −78° C., and the mixture was stirred for 30 minutes. Carbon dioxide was then passed through the solution, with stirring at −78° C., for 3.5 hours before the mixture was allowed to warm to room temperature. The reaction mixture was concentrated in vacuo and the residue was partitioned between ethyl acetate (30 mL) and water (20 mL). The organic layer was separated, washed with water, dried over magnesium sulfate and concentrated in vacuo. Purification of the residue by column chromatography on silica gel, eluting with dichloromethane:methanol:0.88 ammonia, 100:0:0 to 98:2:0.2, afforded the title compound as a by-product, as an off white solid in 68% yield, 116 mg.

¹HNMR(400 MHz, CD₃OD) δ: 1.00(s, 6H), 1.45-1.49(m, 2H), 1.50-1.58(m, 2H), 1.86-1.90(m, 2H), 2.11-2.17(m, 2H), 2.48-2.53(m, 2H), 2.69-2.72(m, 2H), 3.33-3.39(m, 1H), 4.51 (s, 2H), 7.29-7.42(m, 15H); LRMS ESI m/z 453 [M+H]⁺

EXAMPLE 90

5-Methyl-5-(4-phenoxypiperidin-1-yl)-2,2-diphenylhexanamide

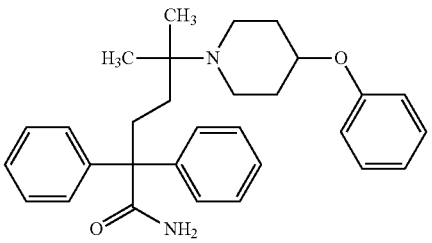

Potassium hydroxide (512 mg, 9.12 mmol) was added to a solution of the product of example 86(200 mg, 0.46 mmol) in 3-methyl-3-pentanol (4 mL) and the mixture was heated under reflux for 20 hours. The reaction mixture was then cooled to room temperature, concentrated in vacuo and the residue was partitioned between ethyl acetate (20 mL) and water (20 mL). The organic layer was separated, dried over magnesium sulfate and concentrated in vacuo. Purification of the residue by column chromatography on silica gel, eluting with dichloromethane:methanol:0.88 ammonia, 100:0 to 90:10:1, afforded the title compound as a colourless glass in 93% yield, 193 mg.

¹HNMR(400 MHz, CDCl₃) δ: 0.99(s, 6H), 1.25-1.29(m, 2H), 1.60-1.68(m, 2H), 1.89-1.93(m, 2H), 2.20-2.25(m, 2H), 2.42-2.46(m, 2H), 2.64-2.68(m, 2H), 4.20-4.27(m, 1H), 6.85-6.89(m, 3H), 7.20-7.26(m, 4H), 7.30-7.34(m, 4H), 7.37-7.40 (m, 4H); LRMS ESI m/z 457 [M+H]⁺

EXAMPLE 91

5-{4-[(3-Bromobenzyl)oxy]piperidin-1-yl}-5-methyl-2,2-diphenylhexanamide

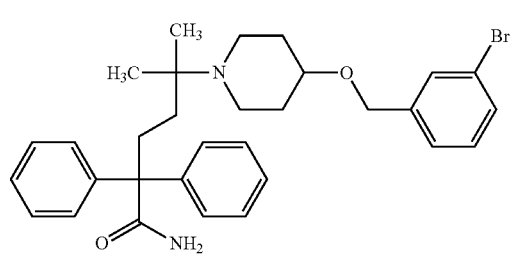 [SMILES: CC(C)(CCC(C(N)=O)(c1ccccc1)c1ccccc1)N1CCC(OCc2cccc(Br)c2)CC1]

The title compound was prepared from the product of example 87, using the same method as that described for example 90, as a colourless gum in 99% yield.

$^1$HNMR(400 MHz, CD$_3$OD) δ: 0.97(s, 6H), 1.23-1.27(m, 2H), 1.48-1.57(m, 2H), 1.82-1.87(m, 2H), 2.07-2.12(m, 2H), 2.40-2.44(m, 2H), 2.62-2.66(m, 2H), 3.29-3.37(m, 1H), 4.48 (s, 2H), 7.21-7.42(m, 13H), 7.49(s, 1H); LRMS ESI m/z 551 [M+H]$^+$

EXAMPLE 92

5-[4-(Benzyloxy)piperidin-1-yl]-5-methyl-2,2-diphenylhexanamide

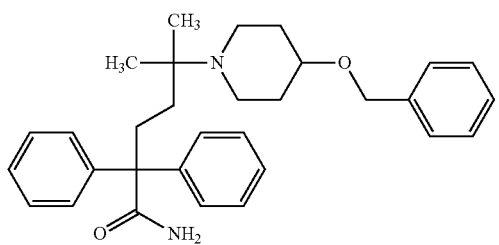 [SMILES: CC(C)(CCC(C(N)=O)(c1ccccc1)c1ccccc1)N1CCC(OCc2ccccc2)CC1]

The title compound was prepared from the product of example 89, using the same method as that described for example 90, as a colourless glass in 79% yield.

$^1$HNMR(400 MHz, CD$_3$OD) δ: 1.01(s, 6H), 1.26-1.30(m, 2H), 1.57-1.59(m, 2H), 1.86-1.89(m, 2H), 2.21(m, 2H), 2.40-2.45(m, 2H), 2.72(m, 2H), 3.38(m, 1H), 4.50(s, 2H), 7.23-7.39(m, 15H); LRMS APCI m/z 471 [M+H]$^+$

EXAMPLE 93

5-[4-(2,4-Dichloro-5-hydroxy-phenoxy)-piperidin-1-yl]-5-methyl-2,2-diphenylhexanoic acid amide

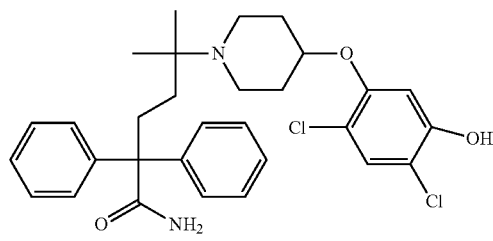 [SMILES: CC(C)(CCC(C(N)=O)(c1ccccc1)c1ccccc1)N1CCC(Oc2cc(O)c(Cl)cc2Cl)CC1]

Diisopropyl azodicarboxylate (0.05 mL, 0.26 mmol) was added dropwise to a mixture of preparation 54(50 mg, 0.13 mmol), 4,6-dichlorobenzene-1,3-diol (47 mg, 0.26 mmol) and triphenylphosphine (69 mg, 0.26 mmol) in tetrahydrofuran (1 mL) and the mixture left to stir for 7 days at room temperature. The solvent was concentrated in vacuo and the residue purified using an Isolute® SCX-2 cartridge, eluting with methanol followed by 1M ammonia in methanol. The appropriate fractions were combined, evaporated under reduced pressure and the residue further purified by column chromatography on silica gel, eluting with dichloromethane:methanol, 98:2 to 95:5, afforded the title compound as a colourless glass in 8% yield, 6 mg.

$^1$HNMR(400 MHz, CD$_3$OD) δ: 1.04(s, 6H), 1.28-1.32(m, 2H), 1.71-1.78(m, 2H), 1.86-1.92(m, 2H), 2.36-2.46(m, 4H), 2.69-2.75(m, 2H), 4.29 (m, 1H), 6.57(s, 1H), 7.21-7.39(m, 11H); LRMS ESI m/z 541 [M+H]$^+$

EXAMPLE 94

5-[4-(4-Cyano-2,5-difluoro-phenoxy)-piperidin-1-yl]-5-methyl-2,2-diphenylhexanoic acid amide

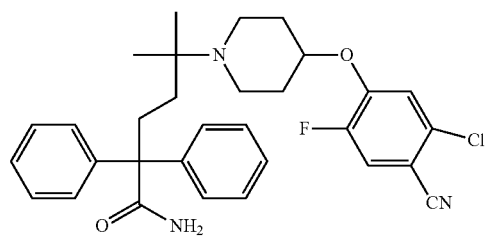 [SMILES: CC(C)(CCC(C(N)=O)(c1ccccc1)c1ccccc1)N1CCC(Oc2cc(Cl)c(C#N)cc2F)CC1]

Sodium hydride (60% dispersion in mineral oil, 12 mg, 0.29 mmol) was added to a solution of the product of preparation 54(100 mg, 0.26 mmol) in tetrahydrofuran (0.5 mL) at room temperature and allowed to stir for 20 minutes before cooling to −70° C. The mixture was added into a solution of 2,4,5-trifluorobenzonitrile (41 mg, 0.26 mmol) in tetrahydrofuran (0.5 mL) at −70° C. and stirred for 3 hours. The reaction was then allowed to warm to room temperature and stirred for a further 18 hours. The reaction was quenched with water (5 drops) and the solvent evaporated in vacuo. The residue was partitioned between ethyl acetate (40 mL) and water (20 mL), the organic layer was separated and washed with brine (20 mL). The organic phase was dried over magnesium sulfate, concentrated in vacuo and the residue purified by column chromatography on silica gel, eluting with dichloromethane:methanol:0.88 ammonia, 100:0:0 to 90:10:1. The appropriate fractions were evaporated under reduced pressure to afford the title compound as a colourless glass in 40% yield, 54 mg.

$^1$HNMR(400 MHz, CD$_3$OD) δ: 0.99(s, 6H), 1.25-1.29(m, 2H), 1.66-1.75(m, 2H), 1.92-1.97(m, 2H) 2.25-2.30(m, 2H) 2.42-2.46(m, 2H), 4.43-4.49(m, 1H), 7.13-7.52(m, 12H); LRMS APCI m/z 518 [M+H]$^+$

EXAMPLE 95

5-[4-(3-hydroxyphenoxy)piperidin-1-yl]-5-methyl-2,2-diphenylhexanamide

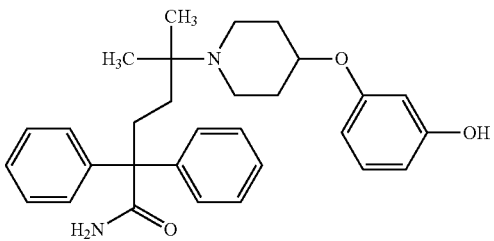 [SMILES: CC(C)(CCC(C(N)=O)(c1ccccc1)c1ccccc1)N1CCC(Oc2cccc(O)c2)CC1]

Diisopropyl azodicarboxylate (0.23 mL, 1.20 mmol) was added dropwise to an ice cold solution of the product of preparation 54(226 mg, 0.594 mmol), resorcinol (196 mg, 1.71 mmol) and triphenylphosphine (312 mg, 1.19 mmol) in tetrahydrofuran (2 mL) and the mixture stirred at room temperature for 12 hours. The solvent was removed under reduced pressure and the residue purified using an Isolute® SCX-2 cartridge, eluting with methanol, then with 1M ammonia in methanol. Basic fractions were concentrated in vacuo and further purified by chromatography on silica gel, eluting with dichloromethane:methanol:0.88 ammonia, 98:2: 0.2 to 95:5:0.5. Appropriate fractions were concentrated in vacuo and half of the residue obtained (55 mg) was further purified by preparative thin layer chromatography using a silica coated plate and eluting with dichloromethane:methanol:0.88 ammonia 80:20:2 to afford the title compound as a gum in 14% yield.

$^1$HNMR(400 MHz, CD$_3$OD) δ: 1.05 (s, 6H), 1.30-1.34 (m, 2H), 1.66-1.74 (m, 2H), 1.91-1.96 (m, 2H), 2.34-2.47 (m, 4H), 2.70-2.79 (m, 2H), 4.21-4.27 (m, 1H), 6.32-6.38 (m, 3H), 7.00-7.05 (m, 1H), 7.23-7.40 (m, 10H); LRMS APCI m/z 473 [M+H]$^+$

EXAMPLE 96

5-[4-(3-hydroxy-2-methylphenoxy)piperidin-1-yl]-5-methyl-2,2-diphenylhexanamide

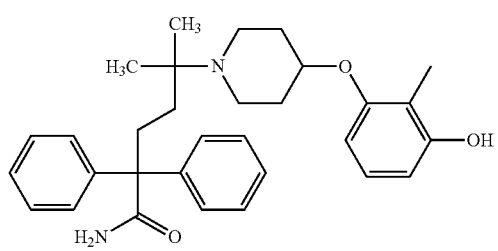 [SMILES: Cc1c(O)cccc1OC1CCN(C(C)(C)CCC(C(N)=O)(c2ccccc2)c2ccccc2)CC1]

Diisopropyl azodicarboxylate (0.1 mL, 0.53 mmol) was added dropwise to a solution of the product of preparation 54 (100 mg, 0.263 mmol), 2-methyl-resorcinol (130 mg, 1.05 mmol) and triphenylphosphine (139 mg, 0.53 mmol) in tetrahydrofuran (2 mL) and the mixture stirred at room temperature for 12 hours. The solvent was removed under reduced pressure and purified using an Isolute® SCX-2 cartridge, eluting with methanol, then with 1M ammonia in methanol. Basic fractions were concentrated in vacuo and further purified by chromatography on silica gel, eluting with dichloromethane:methanol:0.88 ammonia, 98:2:0.2 to 95:5:0.5. Appropriate fractions were concentrated in vacuo and the residue further purified using a Phenomenex Curosil PFP column (21.2*150 mm dimensions) on a preparative Agilent 1100 HPLC. The two mobile phases were 0.1% v/v Formic acid (aq) (A) and 0.1% v/v Formic acid in acetonitrile (B), eluting with a gradient of 20-80% B over 18 minutes at a flow rate of 18 ml/min. The peaks were detected using a UV detector at 225 nm and appropriate fractions concentrated in vacuo to afford the title compound as a gum in 9% yield.

$^1$HNMR(400 MHz, CD$_3$OD) δ: 1.06 (s, 6H), 1.28-1.34 (m, 2H), 1.71-1.81 (m, 2H), 1.89-1.94 (m, 2H), 2.02 (s, 3H), 2.37-2.46 (m, 4H), 2.68-2.77 (m, 2H), 4.24-4.31 (m, 1H), 6.37-6.41 (m, 2H), 6.86-6.90 (m, 1H), 7.23-7.40 (m, 10H); LRMS APCI m/z 487 [M+H]$^+$

EXAMPLE 97

5-{4-[(3'-hydroxybiphenyl-3-yl)methoxy]piperidin-1-yl}-5-methyl-2,2-diphenylhexanenitrile

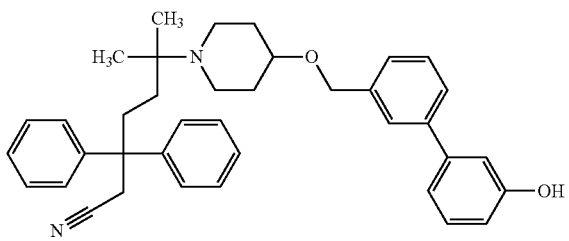 [SMILES: CC(C)(CCC(CC#N)(c1ccccc1)c1ccccc1)N1CCC(OCc2cccc(-c3cccc(O)c3)c2)CC1]

1,1'-Bis (diphenylphosphino)ferrocenedichloro palladium (II) (8 mg, 0.09 mmol) was added to a suspension of the product of example 87 (100 mg, 0.19 mmol), 3-hydroxyphenylboronic acid (52 mg, 0.038 mmol) and sodium carbonate (40 mg, 0.038 mmol) in tetrahydrofuran (5 mL) and water (1 mL) and the mixture was heated at 60° C. for 12 hours. The suspension was allowed to cool to room temperature and then evaporated to dryness under reduced pressure. The residue was purified by chromatography on silica gel, eluting with dichloromethane:methanol:0.88 ammonia, 99:1:0 to 98:2:0.2, to give the title compound as a gum in 72% yield.

$^1$HNMR(400 MHz, CD$_3$OD) δ: 1.09 (s, 6H), 1.52-1.56 (m, 2H), 1.61-1.68 (m, 2H), 1.93-1.96 (m, 2H), 2.24-2.42 (m, 2H), 2.51-2.55 (m, 2H), 2.81-2.84 (m, 2H), 3.45-3.49 (m, 1H), 4.58 (s, 2H), 6.75-6.78 (m, 1H), 7.02-7.07 (m, 2H), 7.21-7.43 (m, 13H), 7.47-7.50 (m, 1H), 7.54 (s, 1H); LRMS ESI m/z 545 [M+H]$^+$

EXAMPLE 98

5-{4-[(3'-hydroxybiphenyl-3-yl)methoxy]piperidin-1-yl}-5-methyl-2,2-diphenylhexanamide

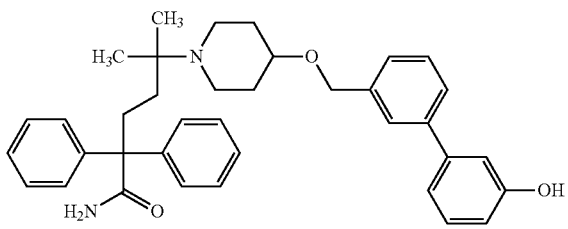 [SMILES: CC(C)(CCC(C(N)=O)(c1ccccc1)c1ccccc1)N1CCC(OCc2cccc(-c3cccc(O)c3)c2)CC1]

A suspension of the product of example 97 (70 mg, 0.13 mmol) and powdered potassium hydroxide (144 mg, 2.57 mmol) in 3-methyl-4-pentanol (4 mL) was heated under reflux for 36 hours. The reaction mixture was allowed to cool to room temperature and the solvent removed under reduced pressure. The residue was partitioned between ethyl acetate (30 mL) and water (20 mL). The organic layer was separated, dried over magnesium sulphate and concentrated in vacuo. The residue was purified by chromatography on silica gel, eluting with dichloromethane:methanol:0.88 ammonia, 95:5: 0.5 to 90:10:1. Appropriate fractions were concentrated in vacuo and the residue further purified by chromatography on silica gel, eluting with dichloromethane:methanol:0.88 ammonia, 98:2:0.2 to 95:5:0.5, to afford the title compound as a gum in 21% yield.

¹HNMR(400 MHz, CD₃OD) δ: 1.05 (s, 6H), 1.22-1.35(m, 2H), 1.62-1.68 (m, 2H), 1.85-1.93 (m, 2H), 2.35-2.45 (m, 4H), 2.78-2.82 (m, 2H), 3.43-3.49 (m, 1H), 4.57 (s, 2H), 6.75-6.78 (m, 1H), 7.02-7.07 (m, 2H), 7.21-7.40 (m, 13H), 7.47-7.50 (m, 1H), 7.54 (s, 1H); LRMS APCI m/z 563 [M+H]⁺

EXAMPLE 99

5-[3-(3-Methoxyphenoxy)azetidin-1-yl]-5-methyl-2,2-diphenylhexanenitrile

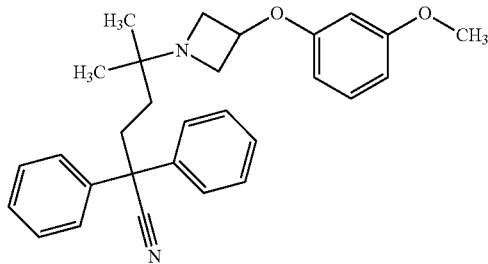 [SMILES: COc1cccc(OC2CN(C(C)(C)CCC(C#N)(c3ccccc3)c3ccccc3)C2)c1]

A mixture of the product of preparation 57(500 mg, 1.21 mmol), caesium carbonate (1.18 g, 3.64 mmol) and 3-methoxyphenol (0.41 mL, 3.64 mmol) in N,N-dimethylformamide (10 mL) was stirred at 80° C. for 18 hours. The reaction mixture was then concentrated in vacuo and the residue was partitioned between diethyl ether (50 mL) and water (20 mL). The aqueous layer was separated, extracted with diethyl ether (2×30 mL) and the combined organic solution was dried over magnesium sulfate and concentrated in vacuo. The residue was purified by column chromatography on silica gel, eluting with pentane:ethyl acetate, 90:10 to 75:25 then dichloromethane:methanol:0.88 ammonia, 100:0:0 to 95:5:0.5, to afford the title compound as a colourless gum in 71% yield, 380 mg.

¹HNMR(400 MHz, CDCl₃) δ: 0.90-1.03(m, 6H), 1.31-1.44(m, 2H), 2.41-2.56(m, 2H), 3.07-3.24(m, 2H), 3.42-3.54 (m, 2H), 3.77(s, 3H), 4.63-4.74(m, 1H), 6.28-6.38(m, 2H), 6.48-6.55(m, 1H), 7.26-7.49(m, 11H); LRMS APCI m/z 441 [M+H]⁺

EXAMPLE 100

5-[3-(3-Methoxyphenoxy)azetidin-1-yl]-5-methyl-2,2-diphenylhexanamide

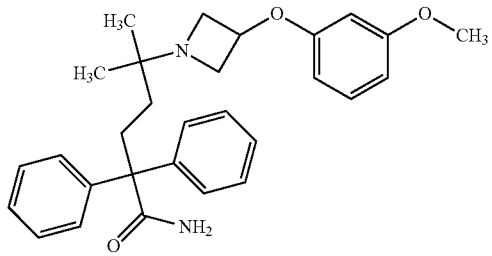 [SMILES: COc1cccc(OC2CN(C(C)(C)CCC(C(N)=O)(c3ccccc3)c3ccccc3)C2)c1]

Potassium hydroxide (215 mg, 3.83 mmol) was added to a solution of the product of example 99(85 mg, 0.19 mmol) in 3-methyl-3-pentanol (5 mL) and the mixture was heated under reflux for 24 hours. The reaction mixture was then cooled to room temperature, concentrated in vacuo and the residue was partitioned between ethyl acetate (20 mL) and water (5 mL). The aqueous layer was separated, extracted with ethyl acetate (20 mL) and the combined organic solution was dried over magnesium sulfate and concentrated in vacuo. Purification of the residue by column chromatography on silica gel, eluting with dichloromethane:methanol:0.88 ammonia, 100:0:0 to 93:7:0.7, afforded the title compound as a colourless gum in 74% yield, 65 mg.

¹HNMR(400 MHz, CDCl₃) δ: 0.92(s, 6H), 1.12-1.23(m, 2H), 2.40-2.50(m, 2H), 3.10-3.25(m, 2H), 3.44-3.58(m, 2H), 3.78(s, 3H), 4.62-4.72(m, 1H), 6.30-6.38(m, 2H), 6.47-6.54 (m, 1H), 7.10-7.18(m, 1H), 7.22-7.45(m, 10H); LRMS ESI m/z 459 [M+H]⁺

EXAMPLE 101

5-[3-(Benzyloxy)azetidin-1-yl]-5-methyl-2,2-diphenylhexanenitrile

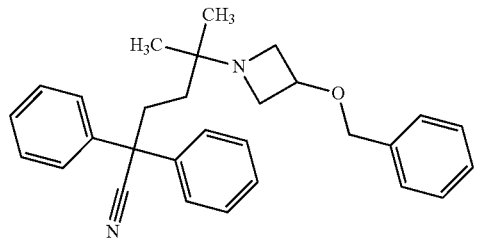 [SMILES: CC(C)(CCC(C#N)(c1ccccc1)c1ccccc1)N1CC(OCc2ccccc2)C1]

Sodium hydride (60% dispersion in mineral oil, 24 mg, 0.60 mmol) was added to an ice-cooled solution of the product of preparation 56(166 mg, 0.50 mmol) in N,N-dimethylformamide (5 mL) and the mixture was stirred for 30 minutes allowing the temperature to rise to 25° C. The reaction mixture was then re-cooled to 0° C., benzyl bromide (89 μL, 0.75 mmol) was added and the mixture was stirred at 0° C. for 30 minutes. The reaction was quenched with 2M hydrochloric acid (2 mL), basified to pH 8 with saturated sodium hydrogen carbonate solution and extracted with ethyl acetate (3×50 mL). The combined organic solution was dried over magnesium sulfate, concentrated in vacuo and the residue was purified by column chromatography on silica gel, eluting with dichloromethane:methanol:0.88 ammonia, 100:0:0 to 97:3:0.3, to afford the title compound as a colourless oil in 65% yield, 137 mg.

¹HNMR(400 MHz, CDCl₃) δ: 0.91(s, 6H), 0.90-0.97(m, 2H), 2.40-2.48(m, 2H), 2.97-3.06(m, 2H), 3.21-3.30(m, 2H), 4.07-4.17(m, 1H), 4.41(s, 2H), 7.26-7.46(m, 15H); LRMS APCI m/z 425 [M+H]⁺

EXAMPLE 102

5-[3-(Benzyloxy)azetidin-1-yl]-5-methyl-2,2-diphenylhexanamide

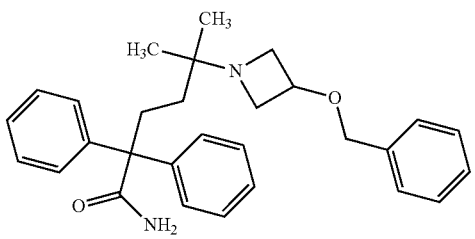 [SMILES: CC(C)(CCC(C(N)=O)(c1ccccc1)c1ccccc1)N1CC(OCc2ccccc2)C1]

The title compound was prepared from the product of example 101, using the same method as that described for example 100, as a colourless gum in 77% yield.

$^1$HNMR(400 MHz, CDCl$_3$) δ: 0.89(s, 6H), 1.05-1.13(m, 2H), 2.32-2.41(m, 2H), 2.95-3.05(m, 2H), 3.15-3.25(m, 2H), 4.02-4.13(m, 1H), 4.39(s, 2H), 7.21-7.42(m, 15H); LRMS APCI m/z 443 [M+H]$^+$

EXAMPLE 103

5-Methyl-5-(3-phenoxyazetidin-1-yl)-2,2-diphenyl-hexanenitrile

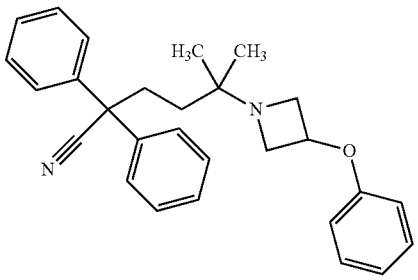 [SMILES: CC(C)(CCC(C#N)(c1ccccc1)c1ccccc1)N1CC(Oc2ccccc2)C1]

The title compound was prepared from the product of preparation 65, using the same method as that described for preparation 62, as a colourless oil in 38% yield.

$^1$HNMR(400 MHz, CDCl$_3$) δ: 0.95 (s, 6H), 1.34-1.41 (m, 2H), 2.43-2.54 (m, 2H), 3.15-3.22 (m, 2H), 3.45-3.55 (m, 2H), 4.65-4.75 (m, 1H), 6.73-6.78 (m, 2H), 6.90-6.98 (m, 1H), 7.22-7.45 (m, 12H); LRMS APCI m/z 411 [M+H]$^+$

EXAMPLE 104

5-Methyl-5-(3-phenoxyazetidin-1-yl)-2,2-diphenyl-hexanamide

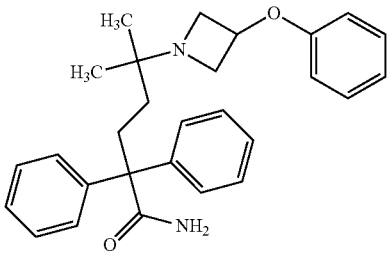 [SMILES: CC(C)(CCC(C(N)=O)(c1ccccc1)c1ccccc1)N1CC(Oc2ccccc2)C1]

The title compound was prepared from the product of example 103, using the same method as that described for example 100, as a white solid in 88% yield.

$^1$HNMR(400 MHz, CDCl$_3$) δ: 0.91(s, 6H), 1.12-1.20(m, 2H), 2.42-2.48(m, 2H), 3.12-3.18(m, 2H), 3.45-3.55(m, 2H), 4.62-4.73(m, 1H), 5.55(brs, 2H), 6.75-6.78(m, 2H), 6.92-6.96(m, 1H), 7.20-7.41(m, 12H); LRMS APCI m/z 429 [M+H]$^+$

EXAMPLE 105

5-[3-(4-Methoxyphenoxy)azetidin-1-yl]-5-methyl-2,2-diphenylhexanenitrile

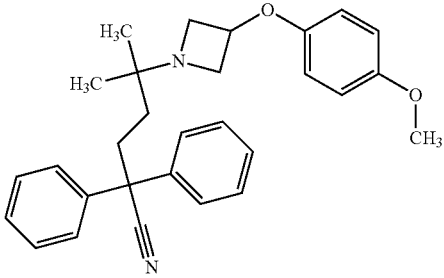 [SMILES: COc1ccc(OC2CN(C(C)(C)CCC(C#N)(c3ccccc3)c3ccccc3)C2)cc1]

The title compound was prepared from the product of preparation 57 and 4-methoxyphenol, using the same method as that described for example 99, as a colourless gum in 55% yield.

$^1$HNMR(400 MHz, CDCl$_3$) δ: 0.98(s, 6H), 1.33-1.45(m, 2H), 2.45-2.55(m, 2H), 3.14-3.24(m, 2H), 3.42-3.55(m, 2H), 3.78(s, 3H), 4.58-4.68(m, 1H), 6.66-6.74(m, 2H), 6.76-6.85(m, 2H), 7.25-7.47(m, 10H); LRMS APCI m/z 441 [M+H]$^+$

EXAMPLE 106

5-[3-(4-Methoxyphenoxy)azetidin-1-yl]-5-methyl-2,2-diphenylhexanamide

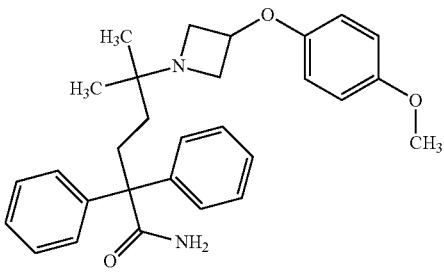 [SMILES: COc1ccc(OC2CN(C(C)(C)CCC(C(N)=O)(c3ccccc3)c3ccccc3)C2)cc1]

Potassium hydroxide (135 mg, 2.41 mmol) was added to a solution of the product of example 105(53 mg, 0.12 mmol) in 3-methyl-3-pentanol (5 mL) and the mixture was heated under reflux for 18 hours. The reaction mixture was then cooled to room temperature, concentrated in vacuo and the residue was partitioned between ethyl acetate (20 mL) and water (5 mL). The aqueous layer was separated, extracted with ethyl acetate (2×20 mL) and the combined organic solution was dried over magnesium sulfate and concentrated in vacuo to give a colourless oil in 96% yield, 53 mg.

¹HNMR(400 MHz, CDCl₃) δ: 0.92(s, 6H), 1.12-1.23(m, 2H), 2.40-2.50(m, 2H), 3.10-3.25(m, 2H), 3.44-3.58(m, 2H), 3.78(s, 3H), 4.62-4.72(m, 1H), 6.30-6.38(m, 2H), 6.47-6.54(m, 1H), 7.10-7.18(m, 1H), 7.22-7.45(m, 10H); LRMS ESI m/z 459 [M+H]⁺

EXAMPLE 107

5-[3-(4-hydroxyphenoxy)azetidin-1-yl]-5-methyl-2,2-diphenylhexanamide

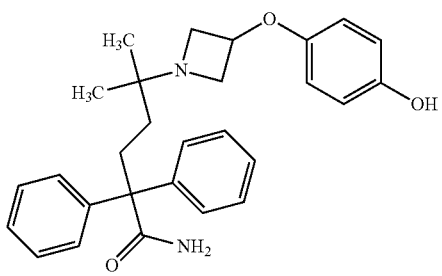 [SMILES: CC(C)(CCC(C(N)=O)(c1ccccc1)c1ccccc1)N1CC(Oc2ccc(O)cc2)C1]

The product of example 106(53 mg, 0.16 mmol) was dissolved in dichloromethane (5 mL) and the solution was cooled to 0° C. Boron tribromide (1M in dichloromethane, 0.52 mL, 0.52 mmol) was added and the solution was stirred at 0° C. for 35 minutes. Further boron tribromide (1M in dichloromethane, 0.52 mL, 0.52 mmol) was added and stirring continued at 0° C. for 30 minutes. The reaction was then quenched with saturated sodium hydrogen carbonate solution (20 mL) and stirred at room temperature for 18 hours. The aqueous layer was separated, extracted with ethyl acetate (25 mL) and the combined organic solution was dried over magnesium sulfate and concentrated in vacuo to give a gum. The gum was re-dissolved in dichloromethane (5 mL) and the solution was cooled to −10° C. Boron tribromide (1M in dichloromethane, 0.52 mL, 0.52 mmol) was added and the mixture was stirred at −10° C. for 1 hour. The reaction was then quenched with saturated sodium hydrogen carbonate solution (20 mL) and the organic layer was separated and extracted with ethyl acetate (20 mL). The combined organic solution was dried over magnesium sulfate, concentrated in vacuo and the residue was purified by column chromatography on silica gel, eluting with pentane:ethyl acetate/methanol/0.88 ammonia (90/10/1), 75:25 to 50:50, to afford the title compound as a colourless foam in 27% yield (14 mg).

¹HNMR(400 MHz, CDCl₃) δ: 0.92(s, 6H), 1.13-1.26(m, 2H), 2.40-2.50(m, 2H), 3.08-3.24(m, 2H), 3.42-3.58(m, 2H), 4.52-4.63(m, 1H), 5.50-5.68(brs, 2H), 6.53-6.62(m, 2H), 6.67-6.78(m, 2H), 7.21-7.42(m, 10H); LRMS APCI m/z 445 [M+H]⁺

EXAMPLE 108

5-[3-(3-Hydroxyphenoxy)azetidin-1-yl]-5-methyl-2,2-diphenylhexanamide

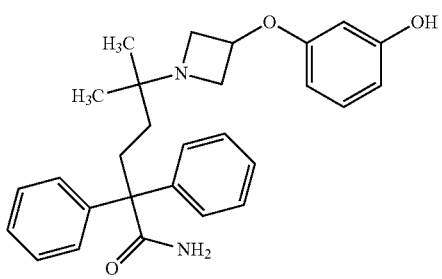 [SMILES: CC(C)(CCC(C(N)=O)(c1ccccc1)c1ccccc1)N1CC(Oc2cccc(O)c2)C1]

Boron tribromide (1M in dichloromethane, 1.75 mL, 1.75 mmol) was added to an ice-cooled solution of the product of example 100(200 mg, 0.44 mmol) in dichloromethane (5 mL) and the mixture was stirred at 0° C. for 1 hour. Further boron tribromide (1M in dichloromethane, 0.5 mL, 0.5 mmol) was added and the mixture was stirred at 0° C. for 30 minutes. The reaction was then quenched with 1M sodium hydroxide solution (5 mL), diluted with dichloromethane (20 mL) and stirred at room temperature for 40 minutes. The aqueous layer was separated, extracted with ethyl acetate (2×25 mL) and the combined organic solution was dried over magnesium sulfate and concentrated in vacuo. Purification of the residue by column chromatography on silica gel, eluting with pentane:ethyl acetate/methanol/0.88 ammonia (90/10/1), 75:25 to 50:50, afforded the title compound as a colourless foam in 91% yield, 176 mg.

¹HNMR(400 MHz, CDCl₃) δ: 1.10(s, 6H), 1.22-1.34(m, 2H), 2.42-2.55(m, 2H), 3.28-3.40(m, 2H), 3.65-3.88(m, 2H), 4.70-4.80(m, 1H), 5.55-5.70(brs, 2H), 6.23-6.36(m, 2H), 6.45-6.53(m, 1H), 7.03-7.12(m, 1H), 7.19-7.39(m, 10H); LRMS ESI m/z 445 [M+H]⁺

EXAMPLE 109

5-[3-(2-Hydroxyphenoxy)azetidin-1-yl]-5-methyl-2,2-diphenylhexanamide

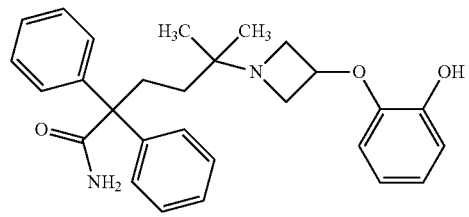 [SMILES: CC(C)(CCC(C(N)=O)(c1ccccc1)c1ccccc1)N1CC(Oc2ccccc2O)C1]

Ammonium formate (25 mg, 0.4 mmol) was added to a mixture of the product of preparation 63 (35 mg, 65 μmol) and 20% Pd(OH)₂/C (10 mg) in ethanol (10 mL) and the mixture was heated under reflux for 2 hours. The reaction mixture was cooled to room temperature, further ammonium formate (25 mg, 0.4 mmol) and 20% Pd(OH)₂/C (10 mg) were added and the mixture was re-heated under reflux for 2 hours. The reaction mixture was filtered through Arbocel®, washing through with methanol, and the filtrate was concentrated in vacuo. The residue was diluted with saturated sodium hydrogen carbonate solution extracted with ethyl acetate (2×20 mL) and the combined organic solution was dried over magnesium sulfate and concentrated in vacuo. Purification of the residue by column chromatography on silica gel, eluting with ethyl acetate:methanol, 95:5, then afforded the title compound as a colourless oil in quantitative yield, 30 mg.

¹HNMR(400 MHz, CDCl₃) δ: 1.02(s, 6H), 1.22-1.32(m, 2H), 2.31-2.49(m, 2H), 2.57-2.72(m, 2H), 3.98-4.04(m, 1H), 4.15-4.24(m, 2H), 5.40-5.70(brm, 2H), 6.77-6.86(m, 4H), 7.22-7.38(m, 10H); LRMS APCI m/z 445 [M+H]⁺

EXAMPLE 110

5-{3-(2,4-Dichloro-5-hydroxy-phenoxy)-azetidin-1-yl}-5-methyl-2,2-diphenylhexanamide

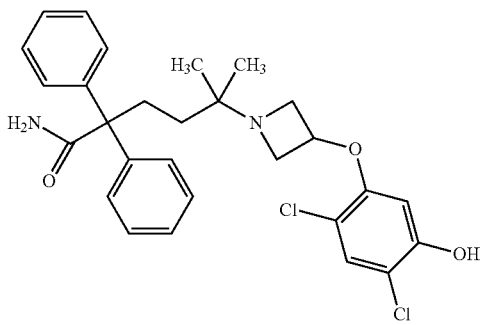 [SMILES: CC(C)(CCC(C(N)=O)(c1ccccc1)c1ccccc1)N1CC(Oc2cc(O)c(Cl)cc2Cl)C1]

Potassium hydroxide (523 mg, 9.33 mmol) was added to a solution of the product of preparation 68(250 mg, 0.46 mmol) in 3-methyl-3-pentanol (5 mL) and the mixture was heated under reflux for 18 hours. The reaction mixture was then cooled to room temperature, concentrated in vacuo and the residue was partitioned between ethyl acetate (20 mL) and water (20 mL). The aqueous layer was separated and extracted with ethyl acetate (20 mL) and the combined organic solution was dried over magnesium sulphate and concentrated in vacuo. The crude material was treated with 4M hydrochloric acid in dioxane (10 mL, 40 mmol) and the solution stirred at 60° C. for 30 minutes. The dioxane was removed in vacuo and the residue basified with 0.88 ammonia. The aqueous layer was extracted with ethyl acetate (2×20 mL). The combined organic solution was dried over magnesium sulphate and concentrated in vacuo. The residue was purified by column chromatography on silica gel, eluting with dichloromethane:methanol 100:1 to 10:1 to afford the title compound as a colourless oil in 61% yield, 147 mg.

$^1$HNMR(400 MHz, CDCl$_3$) δ: 0.98 (s, 6H), 1.18-1.25 (m, 2H), 2.41-2.55 (m, 2H), 3.32-3.38 (m, 2H), 3.75-3.82 (m, 2H), 4.68-4.75 (m, 1H), 5.65-5.75 (m, 1H), 5.95-6.05 (m, 1H), 6.43 (s, 1H), 7-20-7.40 (m, 11H); LRMS APCI m/z 513 [M+H]$^+$

EXAMPLE 111

5-{3-(4,5-Dichloro-2-hydroxy-phenoxy)-azetidin-1-yl}-5-methyl-2,2-diphenylhexanamide

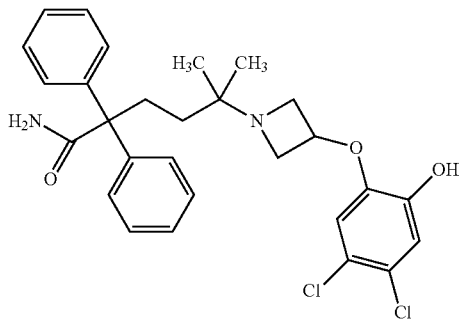 [SMILES: CC(C)(CCC(C(N)=O)(c1ccccc1)c1ccccc1)N1CC(Oc2cc(Cl)c(Cl)cc2O)C1]

The title compound was prepared from the product of preparation 70, using the same method as described for example 110, as a colourless oil in 53% yield.

$^1$HNMR(400 MHz, CDCl$_3$) δ: 1.02 (s, 6H), 1.22-1.30 (m, 2H), 2.35-2.50 (m, 2H), 2.60-2.75 (m, 2H), 3.95-4.01 (m, 1H), 4.10-4.25 (m, 2H), 5.40-5.60 (m, 2H), 6.92-6.98 (m, 2H), 7-20-7.40 (m, 10H); LRMS ESI m/z 513 [M+H]$^+$

EXAMPLE 112

5-[3-(4-Chloro-3-methoxy-phenoxy)-azetidin-1-yl]-5-methyl-2,2-diphenyl-hexanenitrile

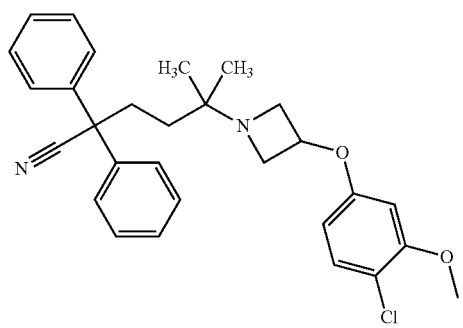 [SMILES: COc1cc(OC2CN(C(C)(C)CCC(C#N)(c3ccccc3)c3ccccc3)C2)ccc1Cl]

The title compound was prepared from 4-chloro-3-methoxyphenol (EP230379, p 52) and the product of preparation 57, using the same method as that described for example 99, as a colourless oil in 85% yield.

$^1$HNMR(400 MHz, CDCl$_3$) δ: 0.95 (s, 6H), 1.35-1.40 (m, 2H), 2.45-2.53 (m, 2H), 3.16-3.20 (m, 2H), 3.45-3.52 (m, 2H), 3.86 (s, 3H), 4.62-4.70 (m, 1H), 6.20-6.25 (m, 1H), 6.40-6.43 (m, 1H), 7-18-7.45 (m, 11H); LRMS APCI m/z 475 [M+H]$^+$

EXAMPLE 113

5-{3-(4-Chloro-3-methoxy-phenoxy)-azetidin-1-yl}-5-methyl-2,2-diphenylhexanamide

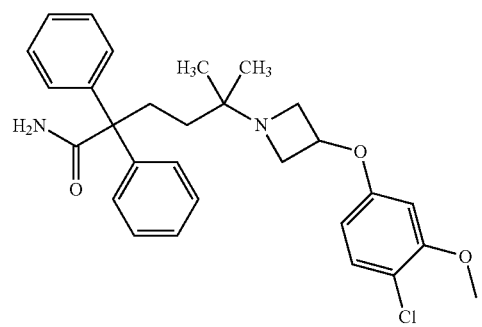 [SMILES: COc1cc(OC2CN(C(C)(C)CCC(C(N)=O)(c3ccccc3)c3ccccc3)C2)ccc1Cl]

The title compound was prepared from the product of example 112, using the same method as that described for example 100, as a colourless oil in 91% yield.

$^1$HNMR(400 MHz, CDCl$_3$) δ: 0.85 (s, 6H), 1.08-1.22 (m, 2H), 2.38-2.50 (m, 2H), 3.15-3.20 (m, 2H), 3.40-3.55 (m, 2H), 3.85 (s, 3H), 4.60-4.72 (m, 1H), 5.30-5.55 (m, 2H), 6.20-6.23 (m, 1H), 6.38-6.41 (m, 1H). 7-18-7.40 (m, 11H); LRMS APCI m/z 493 [M+H]+

EXAMPLE 114

5-{3-(4-Chloro-3-hydroxy-phenoxy)-azetidin-yl}-5-methyl-2,2-diphenylhexanamide

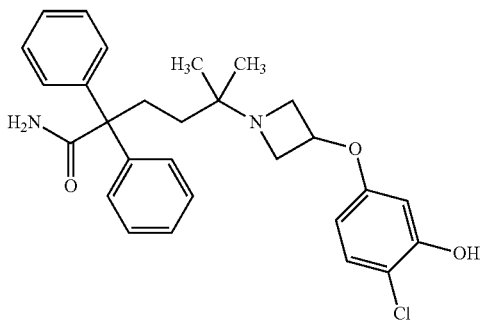 [SMILES: CC(C)(CCC(C(N)=O)(c1ccccc1)c1ccccc1)N1CC(Oc2ccc(Cl)c(O)c2)C1]

Boron tribromide (1M in dichloromethane, 1.75 mL, 1.75 mmol) was added to an ice-cooled solution of the product of example 113 (180 mg, 0.36 mmol) in dichloromethane (5 mL) and the mixture was stirred at 0° C. for 1.5 hour. The reaction was then quenched with 0.88 ammonia (30 mL) and the solution stirred at room temperature for 18 hours. The organic layer was separated, dried over magnesium sulfate and concentrated in vacuo. Purification of the residue by column chromatography on silica gel, eluting with dichloromethane to dichloromethane/methanol/0.88 ammonia (97:3:0.3), afforded the title compound as a colourless foam in 93% yield, 270 mg $^1$HNMR(400 MHz, CDCl$_3$) δ: 0.85 (s, 6H), 1.08-1.22 (m, 2H), 2.40-2.50 (m, 2H), 3.10-3.20 (m, 2H), 3.50-3.58 (m, 2H), 4.58-4.66 (m, 1H), 5.45-5.55 (m, 1H), 5.75-5.90 (m, 1H), 6.25-6.32 (m, 1H), 6.38-6.40 (m, 1H). 7-15-7.40 (m, 11H); LRMS APCI m/z 479 [M+H]+

EXAMPLE 115

5-[3-(3-Hydroxy-benzyloxy)-azetidin-1-yl]-5-methyl-2,2-diphenyl-hexanoic acid amide

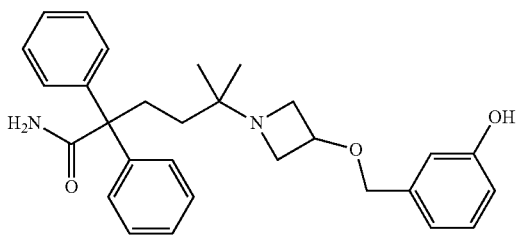 [SMILES: CC(C)(CCC(C(N)=O)(c1ccccc1)c1ccccc1)N1CC(OCc2cccc(O)c2)C1]

The product of preparation 73 (65 mg, 0.131 mmol) was treated with 4M hydrochloric acid in dioxane (2 mL, 8 mmol), water (0.2 ml) was added and the solution stirred at 85° C. for 30 minutes. The dioxane was removed in vacuo and the residue partitioned between ethyl acetate (25 ml) and saturated sodium hydrogen carbonate solution (20 mL). The aqueous layer was extracted with ethyl acetate (20 mL). The combined organic solution was dried over magnesium sulphate and concentrated in vacuo. The residue was purified by column chromatography on silica gel, eluting with pentane:ethyl acetate:methanol:0.88 ammonia (90/10/1), 75:25 to 50:50, to afford the title compound as a colourless foam in 70% yield, 42 mg.

$^1$HNMR(400 MHz, CDCl$_3$) δ: 0.90(s, 6H), 1.16-1.25(m, 2H), 2.38-2.48(m, 2H), 3.02-3.12 (m, 2H), 3.28-3.40(m, 2H), 4.06-4.17(m, 1H), 4.31(s, 2H), 5.58-5.74 (br s, 2H), 6.72-6.83 (m, 3H), 7.12-7.20(m, 1H), 7.21-7.40 (m, 10H); LRMS APCI m/z 459 [M+H]+

EXAMPLE 116

5-[3-(2-Chloro-5-methoxy-phenoxy)-azetidin-1-yl]-5-methyl-2,2-diphenyl-hexanenitrile

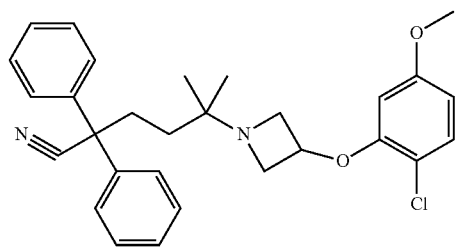 [SMILES: COc1ccc(Cl)c(OC2CN(C(C)(C)CCC(C#N)(c3ccccc3)c3ccccc3)C2)c1]

The title compound was prepared from the product of preparation 57 and 2-chloro-5-methoxyphenol, using the same method as that described for example 99, as a brown gum in 55% yield.

$^1$HNMR(400 MHz, CDCl$_3$) δ: 0.96 (s, 6H), 1.31-1.44(m, 2H), 2.40-2.57 (m, 2H), 3.14-3.35 (m, 2H), 3.40-3.60 (m, 2H), 3.77(s, 3H), 4.64-4.79 (m, 1H), 6.20-6.25 (m, 1H), 6.39-6.47(m, 1H), 7.20-7.48(m, 11H); LRMS APCI m/z 475 [M+H]+

EXAMPLE 117

5-[3-(2-Chloro-5-methoxy-phenoxy)-azetidin-1-yl]-5-methyl-2,2-diphenyl-hexanoic acid amide

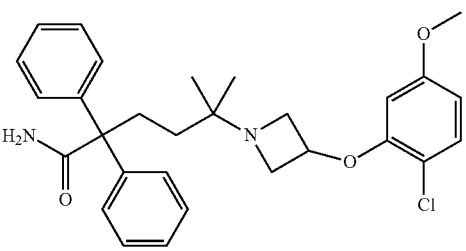 [SMILES: COc1ccc(Cl)c(OC2CN(C(C)(C)CCC(C(N)=O)(c3ccccc3)c3ccccc3)C2)c1]

The title compound was prepared from the product of example 116, using the same method as that described for example 100, as a colourless gum in 61% yield.

$^1$HNMR(400 MHz, CDCl$_3$) δ: 0.92 (s, 6H), 1.11-1.20 (m, 2H), 2.40-2.48 (m, 2H), 3.15-3.24 (m, 2H), 3.42-3.55 (m, 2H), 3.76 (s, 3H), 4.64-4.72 (m, 1H), 5.48-5.75 (m, 2H), 6.20-6.25 (m, 1H), 6.38-6.45 (m, 1H). 7.20-7.41 (m, 11H); LRMS APCI m/z 493 [M+H]+

EXAMPLE 118

5-[3-(2-Chloro-5-hydroxy-phenoxy)-azetidin-1-yl]-5-methyl-2,2-diphenyl-hexanoic acid amide

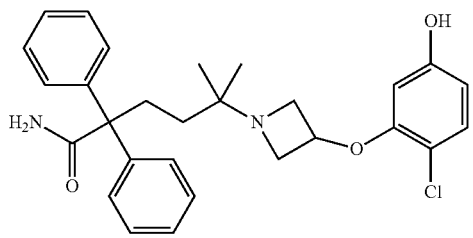 [SMILES: CC(C)(CCC(C(N)=O)(c1ccccc1)c1ccccc1)N1CC(Oc2cc(O)ccc2Cl)C1]

Boron tribromide (1M in dichloromethane, 1.42 mL, 1.42 mmol) was added to an ice-cooled solution of the product of example 117 (70 mg, 0.142 mmol) in dichloromethane (5 mL) and the mixture was stirred at 0° C. for 1 hour. The reaction was then quenched with 0.88 ammonia (20 mL) and the solution stirred at room temperature for 18 hours. The organic layer was separated. The aqueous layer was extracted with dichloromethane (20 mls). The combined organic solution was washed with saturated sodium hydrogen carbonate solution (10 mL) and dried over magnesium sulfate and concentrated in vacuo. Purification of the residue by column chromatography on silica gel, eluting with pentane:ethyl acetate:methanol:0.88 ammonia (90/10/1), 85:15 to 50:50. The resulting gum was dissolved in methanol (5 mls) and 1N hydrochloric acid in diethyl ether (0.5 ml) added. The solution was evaporated and the solid recrystallised from ethyl acetate/methanol to give the title compound hydrochloride salt as a purple solid in 30% yield, 22 mgs.

$^1$HNMR (400 MHz, CD$_3$OD) δ: 1.28 (s, 6H), 1.33-1.44 (m, 2H), 2.40-2.48 (m, 2H), 4.02-4.30 (m, 2H), 4.33-4.62 (m, 2H), 4.95-5.06 (m, 1H), 6.20-6.28 (m, 1H), 6.44-6.49 (m, 1H), 7-15-7.20 (m, 1H), 7.24-7.41 (m, 10H); LRMS APCI m/z 479 [M+H]+

EXAMPLE 119

5-[3-(3-Fluoro-5-methoxy-phenoxy)-azetidin-1-yl]-5-methyl-2,2-diphenyl-hexanenitrile

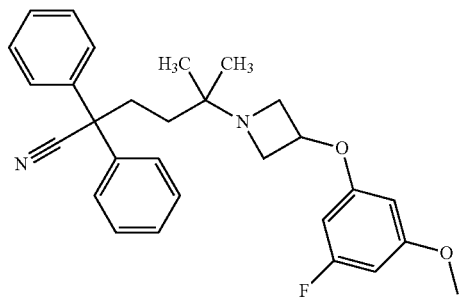 [SMILES: COc1cc(F)cc(OC2CN(C(C)(C)CCC(C#N)(c3ccccc3)c3ccccc3)C2)c1]

The title compound was prepared from 3-fluoro-5-methoxyphenol (WO2005037763, p 95) and the product of preparation 57, using the same method as that described for example 99, as a colourless oil in 90% yield.

$^1$HNMR (400 MHz, CDCl$_3$) δ: 0.95 (s, 6H), 1.35-1.40 (m, 2H), 2.45-2.53 (m, 2H), 3.06-3.15 (m, 2H), 3.40-3.48 (m, 2H), 3.75 (s, 3H), 4.58-4.64 (m, 1H), 6.05-6.12 (m, 2H), 6.20-6.26 (m, 1H), 7-22-7.45 (m, 10H); LRMS APCI m/z 459 [M+H]+

EXAMPLE 120

5-[3-(3-Fluoro-5-methoxy-phenoxy)-azetidin-1-yl]-5-methyl-2,2-diphenylhexanamide

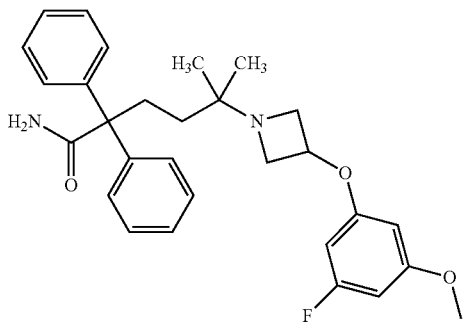 [SMILES: COc1cc(F)cc(OC2CN(C(C)(C)CCC(C(N)=O)(c3ccccc3)c3ccccc3)C2)c1]

The title compound was prepared from the product of example 119, using the same method as that described for example 100, as a colourless oil in 90% yield.

$^1$HNMR (400 MHz, CDCl$_3$) δ: 0.95 (s, 6H), 1.42-1.55 (m, 2H), 2.40-2.48 (m, 2H), 3.06-3.15 (m, 2H), 3.40-3.45 (m, 2H), 3.78 (s, 3H), 4.58-4.66 (m, 1H), 5.40-5.55 (m, 2H), 6.03-6.12 (m, 2H), 6.20-6.25 (m, 1H), 7.22-7.45 (m, 10H).

EXAMPLE 121

5-{3-(3-Fluoro-5-hydroxy-phenoxy)-azetidin-1-yl}-5-methyl-2,2-diphenylhexanamide

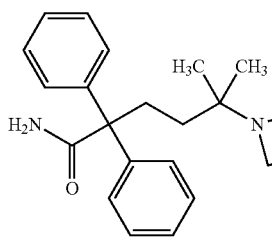

The title compound was prepared from the product of example 120, using the same method as that described for example 108, as a colourless oil in 25% yield.

$^1$HNMR (400 MHz, CDCl$_3$) δ: 0.95 (s, 6H), 1.20-1.26 (m, 2H), 2.40-2.46 (m, 2H), 3.20-3.28 (m, 2H), 3.60-3.65 (m, 2H), 4.64-4.70 (m, 1H), 5.50-5.60 (m, 1H), 6.00 (s, 1H), 6.02-6.06 (m, 1H), 6.18-6.23 (m, 1H), 6.25-6.35 (m, 1H), 7.20-7.35 (m, 10H); LRMS APCI m/z 463 [M+H]+

EXAMPLE 122

5-[3-(3-Chloro-5-methoxy-phenoxy)-azetidin-1-yl]-5-methyl-2,2-diphenyl-hexanenitrile

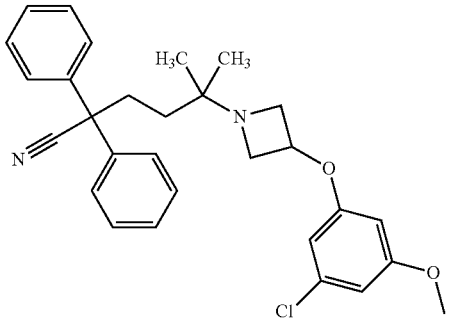 [SMILES: COc1cc(Cl)cc(OC2CN(C(C)(C)CCC(C#N)(c3ccccc3)c3ccccc3)C2)c1]

The title compound was prepared from 3-chloro-5-methoxyphenol and the product of preparation 57, using the same method as that described for example 99, as a colourless oil in 75% yield.

$^1$HNMR(400 MHz, CDCl$_3$) δ: 0.95 (s, 6H), 1.35-1.40 (m, 2H), 2.45-2.53 (m, 2H), 3.06-3.15 (m, 2H), 3.40-3.48 (m, 2H), 3.78 (s, 3H), 4.58-4.66 (m, 1H), 6.20 (s, 2H), 6.35 (s, 1H), 6.50 (s, 1H), 7-22-7.45 (m, 10H); LRMS APCI m/z 475 [M+H]+

EXAMPLE 123

5-[3-(3-Chloro-5-methoxy-phenoxy)-azetidin-1-yl]-5-methyl-2,2-diphenylhexanamide

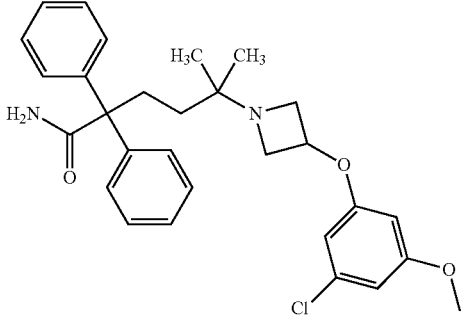 [SMILES: COc1cc(Cl)cc(OC2CN(C(C)(C)CCC(C(N)=O)(c3ccccc3)c3ccccc3)C2)c1]

The title compound was prepared from the product of example 122, using the same method as that described for example 100, as a colourless oil in 90% yield.

$^1$HNMR(400 MHz, CDCl$_3$) δ: 0.95 (s, 6H), 1.15-1.20 (m, 2H), 2.38-2.45 (m, 2H), 3.02-3.10 (m, 2H), 3.37-3.43 (m, 2H), 3.75 (s, 3H), 4.55-4.63 (m, 1H), 5.40-5.65 (m, 2H), 6.18 (s, 1H), 6.30 (s, 1H), 6.48 (s, 1H), 7.20-7.40 (m, 10H); LRMS APCI m/z 493 [M+H]+

EXAMPLE 124

5-{3-(3-Chloro-5-hydroxy-phenoxy)-azetidin-1-yl}-5-methyl-2,2-diphenylhexanamide

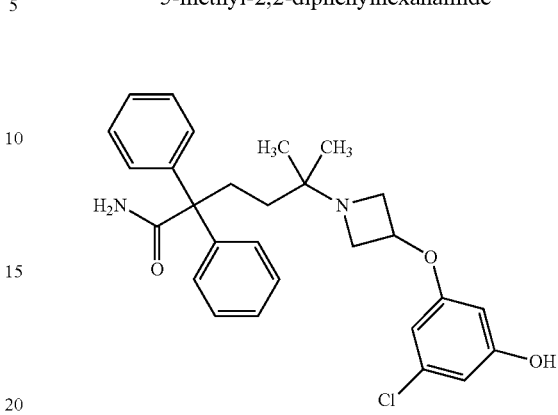

The title compound was prepared from the product of example 123, using the same method as that described for example 114, as a colourless oil in 92% yield.

$^1$HNMR(400 MHz, CDCl$_3$) δ: 0.90 (s, 6H), 1.08-1.18 (m, 2H), 2.35-2.45 (m, 2H), 3.06-3.15 (m, 2H), 3.40-3.46 (m, 2H), 4.55-4.60 (m, 1H), 5.45 (brs, 2H), 6.15 (s, 1H), 6.25 (s, 1H), 6.40 (s, 1H), 7.20-7.40 (m, 10H)

EXAMPLE 125

5-[3-(4-Fluoro-2-methoxy-phenoxy)-azetidin-1-yl]-5-methyl-2,2-diphenyl-hexanenitrile

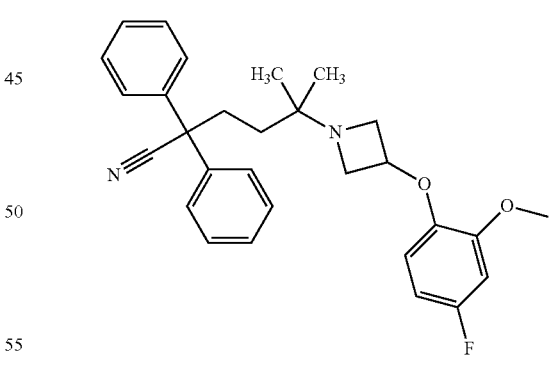

The title compound was prepared from 4-fluoro-2-methoxyphenol and the product of preparation 57, using the same method as that described for example 99, as a colourless oil in 72% yield.

$^1$HNMR(400 MHz, CDCl$_3$) δ: 0.95 (s, 6H), 1.35-1.40 (m, 2H), 2.45-2.53 (m, 2H), 3.20-3.25 (m, 2H), 3.42-3.48 (m, 2H), 3.83 (s, 3H), 4.58-4.66 (m, 1H), 6.53-6.65 (m, 3H), 7-22-7.45 (m, 10H); LRMS APCI m/z 459 [M+H]+

EXAMPLE 126

5-[3-(4-Fluoro-2-methoxy-phenoxy)-azetidin-1-yl]-5-methyl-2,2-diphenylhexanamide

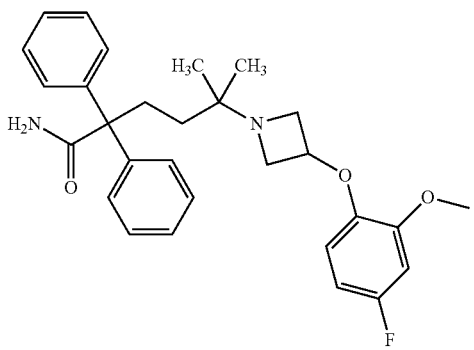 [SMILES: COc1cc(F)ccc1OC1CN(C(C)(C)CCC(C(N)=O)(c2ccccc2)c2ccccc2)C1]

The title compound was prepared from the product of example 125, using the same method as that described for example 100, as a colourless oil in 87% yield.

¹HNMR(400 MHz, CDCl₃) δ: 0.95 (s, 6H), 1.10-1.18 (m, 2H), 2.40-2.48 (m, 2H), 3.15-3.20 (m, 2H), 3.40-3.46 (m, 2H), 3.80 (s, 3H), 4.58-4.66 (m, 1H), 5.50-5.75 (m, 2H), 6.48-6.65 (m, 3H), 7-22-7.40 (m, 10H); LRMS APCI m/z 477 [M+H]⁺

EXAMPLE 127

5-{3-(4-Fluoro-2-hydroxy-phenoxy)-azetidin-1-yl}-5-methyl-2,2-diphenylhexanamide

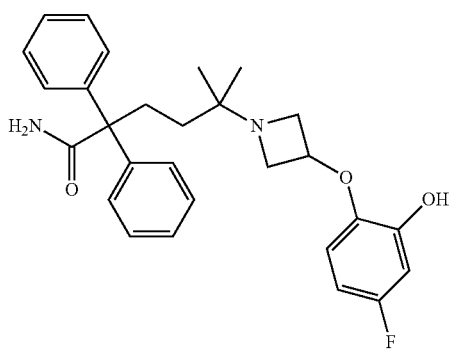 [SMILES: CC(C)(CCC(C(N)=O)(c1ccccc1)c1ccccc1)N1CC(Oc2ccc(F)cc2O)C1]

The title compound was prepared from the product of example 126, using the same method as that described for example 114, as a colourless oil in 32% yield.

¹HNMR(400 MHz, CDCl₃) δ: 0.98 (s, 6H), 1.20-1.28 (m, 2H), 2.35-2.48 (m, 2H), 2.56-2.68 (m, 2H), 3.95-3.42 (m, 1H), 4.05-4.18 (m, 1H), 4.18-4.25 (m, 1H), 5.40-5.65 (m, 2H), 6.45-6.53 (m, 1H), 6.55-6.60 (m, 1H), 6.72-6.78 (m, 1H), 7.20-7.35 (m, 10H); LRMS APCI m/z 463 [M+H]⁺

EXAMPLE 128

5-[3-(2,6-Dichloro-3-hydroxy-benzyloxy)-azetidin-1-yl]-5-methyl-2,2-diphenyl-hexanoic acid amide

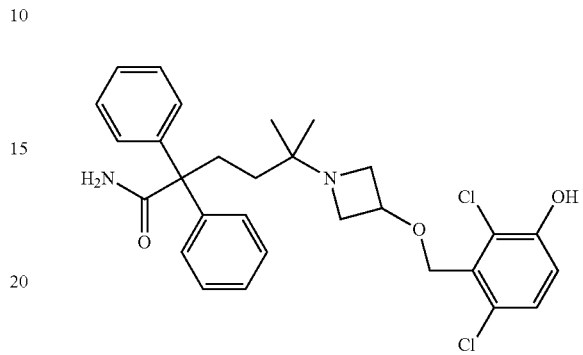

The product of preparation 78(150 mg, 0.265 mmol) was treated with 4M hydrochloric acid in dioxane (5 mL, 20 mmol) and water (0.5 ml) and the solution stirred at 70° C. for 25 minutes. The dioxane was removed in vacuo and the residue partitioned between ethyl acetate (30 ml) and saturated sodium hydrogen carbonate solution (20 mL). The aqueous layer was extracted with ethyl acetate (20 mL). The combined organic solution was dried over magnesium sulphate and concentrated in vacuo. The residue was purified by column chromatography on silica gel, eluting with pentane:ethyl acetate/methanol/0.88 ammonia (90/10/1), 5:1 to 1:3, to afford the title compound in 52% yield, 73 mg.

¹HNMR(400 MHz, CDCl₃) δ: 1.22 (s, 6H), 1.44-1.53 (m, 2H), 2.60-2.68 (m, 2H), 3.60-3.68 (m, 2H), 4.26-4.37 (m, 2H), 4.57-4.64 (m, 1H), 4.70 (s, 2H), 5.48-5.55 (br m, 1H), 5.78-5.84 (br m, 1H), 7.06-7.12 (m, 1H), 7.18-7.23 (m, 1H), 7.23-7.38 (m, 10H); LRMS APCI m/z 527[M+H]⁺

EXAMPLE 129

4-{1-[3-(3-Methoxy-phenoxy)-azetidin-1-yl]-cyclopentyl}-2,2-diphenyl-butyronitrile

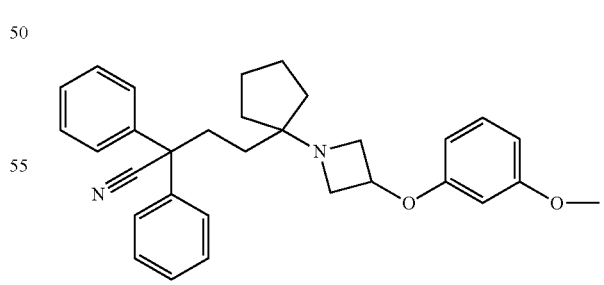

The title compound was prepared from the product of preparation 84 and 3-methoxyphenol, using a similar method to that described in example 99, in 73% yield.

¹HNMR(400 MHz, CDCl₃) δ: 1.25-1.38 (m, 2H), 1.40-1.65 (m, 6H), 1.66-1.76 (m, 2H), 2.46-2.57 (m, 2H), 3.06-3.16 (m, 2H), 3.48-3.57 (m, 2H), 3.78 (s, 3H), 4.64-4.72 (m,

1H), 6.34 (s, 1H), 6.33-6.37 (m, 1H), 6.48-6.53 (m, 1H), 7.13-7.19 (m, 1H), 7.27-7.46 (m, 10H); LRMS APCI m/z 467 [M+H]+

EXAMPLE 130

4-{1-[3-(3-Methoxy-phenoxy)-azetidin-1-yl]-cyclopentyl}-2,2-diphenyl-butyramide

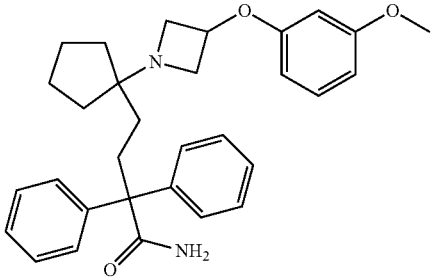 [SMILES: COc1cccc(OC2CN(C3(CCC(C(N)=O)(c4ccccc4)c4ccccc4)CCCC3)C2)c1]

The title compound was prepared from the product of example 129 using a similar method to that described for example 106, in 48% yield.

¹HNMR(400 MHz, CDCl₃) δ: 1.22-1.70 (m, 10H), 2.46-2.53 (m, 2H), 3.07-3.15 (m, 2H), 3.47-3.59 (m, 2H), 3.77 (s, 3H), 4.63-4.73 (m, 1H), 5.44-5.60 (br m, 2H), 6.33 (s, 1H), 6.33-6.36 (m, 1H), 6.48-6.53 (m, 1H), 7.11-7.18 (m, 1H), 7.20-7.40 (m, 10H); LRMS APCI m/z 485[M+H]+

EXAMPLE 131

4-{1-[3-(3-Hydroxy-phenoxy)-azetidin-1-yl]-cyclopentyl}-2,2-diphenyl-butyramide

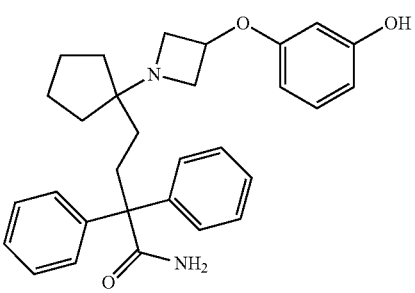 [SMILES: NC(=O)C(CCC1(N2CC(Oc3cccc(O)c3)C2)CCCC1)(c1ccccc1)c1ccccc1]

The title compound was prepared from the product of example 130 using a similar method to that described for example 108, in 53% yield.

¹HNMR(400 MHz, CDCl₃) δ: 1.31-1.47 (m, 6H), 1.48-1.60 (m, 2H), 1.63-1.77 (m, 2H), 2.45-2.54 (m, 2H), 3.22-3.28 (m, 2H), 3.73-3.80 (m, 2H), 4.75-4.83 (m, 1H), 5.40-5.55 (br m, 1H), 6.24 (s, 1H), 6.36-6.39 (m, 1H), 6.48-6.55 (m, 1H), 6.56-6.67 (br m, 1H), 7.08-7.7.16 (m, 1H), 7.17-7.38 (m, 10H); LRMS APCI m/z 471[M+H]+

EXAMPLE 132

5-[3-(2-Fluoro-3-methoxy-phenoxy)-azetidin-1-yl]-5-methyl-2,2-diphenyl-hexanenitrile

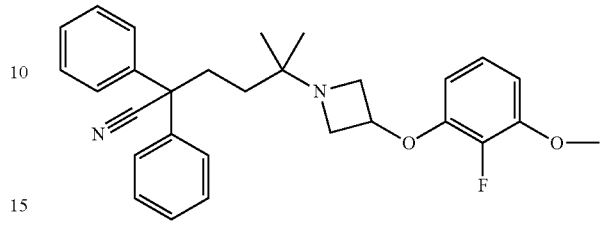

The title compound was prepared from the product of preparation 57 and 2-fluoro-3-methoxyphenol (J. Comb. Chem. 2002, 4, 329), using a similar method to that described for example 99, in 73% yield.

¹HNMR(400 MHz, CDCl₃) δ: 0.95 (s, 6H), 1.34-1.40 (m, 2H), 2.44-2.53 (m, 2H), 3.20-3.27 (m, 2H), 3.43-3.52 (m, 2H), 3.88 (s, 3H), 4.65-4.74 (m, 1H), 6.34-6.39 (m, 1H), 6.58-6.64 (m, 1H), 6.88-6.95 (m, 1H), 7.25-7.47 (m, 10H); LRMS APCI m/z 459 [M+H]+

EXAMPLE 133

5-[3-(2-Fluoro-3-methoxy-phenoxy)-azetidin-1-yl]-5-methyl-2,2-diphenyl-hexanoic acid amide

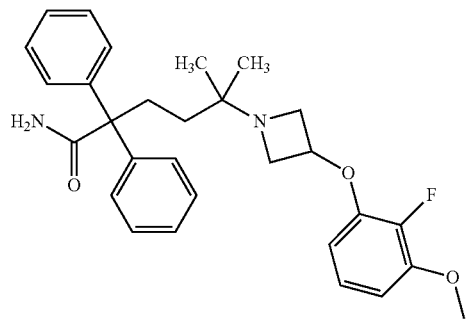 [SMILES: COc1cccc(OC2CN(C(C)(C)CCC(C(N)=O)(c3ccccc3)c3ccccc3)C2)c1F]

The title compound was prepared from the product of example 132, using the same method as that described for example 100, as a colourless oil in 72% yield.

¹HNMR(400 MHz, CDCl₃) δ: 0.95 (s, 6H), 1.17-1.25 (m, 2H), 2.40-2.48 (m, 2H), 3.20-3.28 (m, 2H), 3.50-3.60 (m, 2H), 4.65-4.74 (m, 1H), 5.46-5.75 (br m, 2H), 6.20-6.27 (m, 1H), 6.56-6.63 (m, 1H), 6.80-6.86 (m, 1H), 7.25-7.40 (m, 10H); LRMS APCI m/z 477 [M+H]+

EXAMPLE 134

5-[3-(2-Fluoro-3-hydroxy-phenoxy)-azetidin-1-yl]-5-methyl-2,2-diphenyl-hexanoic acid amide

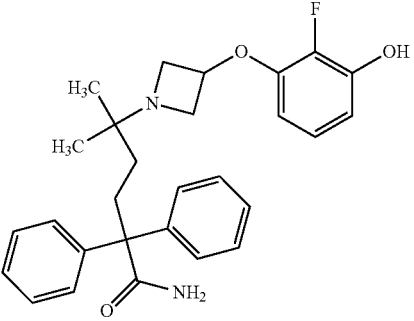 [SMILES: CC(C)(CCC(C(N)=O)(c1ccccc1)c1ccccc1)N1CC(Oc2cccc(O)c2F)C1]

Boron tribromide (1M in dichloromethane, 1.5 mL, 1.5 mmol) was added to an ice-cooled solution of the product of example 133(45 mg, 0.094 mmol) in dichloromethane (5 mL) and the mixture was stirred at 0° C. for 45 minutes. The reaction was warmed to room temperature. After 15 min, a further 1.5 mL boron tribromide was added. After 20 minutes, the reaction was quenched with 0.88 ammonia (20 mL) and the solution stirred at room temperature for 18 hours. The organic layer was separated and washed with saturated sodium hydrogen carbonate solution (10 mL) and dried over magnesium sulfate and concentrated in vacuo. Purification of the residue by column chromatography on silica gel, eluting with dichloromethane:methanol:0.88 ammonia 100:0:0 to 98:2:0.2 to give the title compound in 100% yield (44 mg).

$^1$HNMR(400 MHz, CDCl$_3$) δ: 0.95 (s, 6H), 1.17-1.26 (m, 2H), 2.43-2.49 (m, 2H), 3.20-3.28 (m, 2H), 3.45-3.60 (m, 2H), 4.65-4.74 (m, 1H), 5.49-5.76 (br m, 2H), 6.20-6.27 (m, 1H), 6.57-6.62 (m, 1H), 6.80-6.85 (m, 1H), 7.23-7.38 (m, 10H); LRMS APCI m/z 463 [M+H]$^+$

EXAMPLE 135

5-[3-(2-Fluoro-5-methoxy-phenoxy)-azetidin-1-yl]-5-methyl-2,2-diphenyl-hexanenitrile

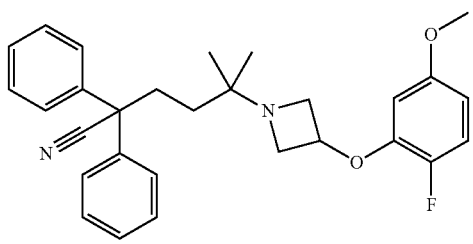 [SMILES: COc1ccc(F)c(OC2CN(C(C)(C)CCC(C#N)(c3ccccc3)c3ccccc3)C2)c1]

The title compound was prepared from the product of preparation 57 and 2-fluoro-5-methoxyphenol (J. Can. Chem. 1988, 66, 1479), using a similar method to that described for example 99, in 68% yield.

$^1$HNMR(400 MHz, CDCl$_3$) δ: 0.95 (s, 6H), 1.36-1.42 (m, 2H), 2.44-2.53 (m, 2H), 3.20-3.27 (m, 2H), 3.43-3.52 (m, 2H), 3.77 (s, 3H), 4.65-4.74 (m, 1H), 6.27-6.34 (m, 1H), 6.38-6.42 (m, 1H), 6.95-7.02 (m, 1H), 7.25-7.47 (m, 10H); LRMS APCI m/z 459 [M+H]$^+$

EXAMPLE 136

5-[3-(2-Fluoro-5-methoxy-phenoxy)-azetidin-1-yl]-5-methyl-2,2-diphenyl-hexanoic acid amide

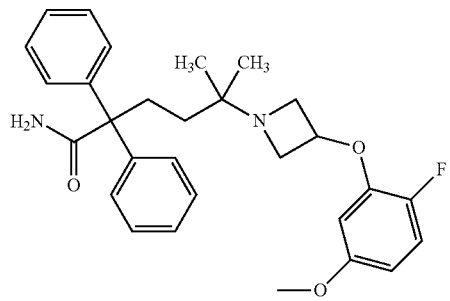 [SMILES: COc1ccc(F)c(OC2CN(C(C)(C)CCC(C(N)=O)(c3ccccc3)c3ccccc3)C2)c1]

The title compound was prepared from the product of example 135, using the same method as that described for example 100, as a colourless oil in 96% yield.

$^1$HNMR(400 MHz, CDCl$_3$) δ: 0.92 (s, 6H), 1.12-1.20 (m, 2H), 2.40-2.48 (m, 2H), 3.16-3.21 (m, 2H), 3.43-3.50 (m, 2H), 3.76 (s, 3H), 4.60-4.72 (m, 1H), 5.46-5.60 (br m, 1H), 5.65-5.75 (br m, 1H), 6.25-6.33 (m, 1H), 6.34-6.40 (m, 1H), 6.91-6.99 (m, 1H), 7.22-7.40 (m, 10H); LRMS APCI m/z 477 [M+H]$^+$

EXAMPLE 137

5-[3-(2-Fluoro-5-hydroxy-phenoxy)-azetidin-1-yl]-5-methyl-2,2-diphenyl-hexanoic acid amide

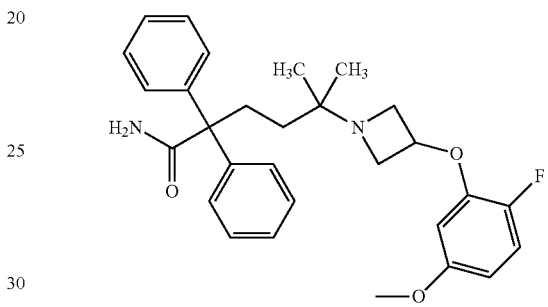

The title compound was prepared from the product of example 136 using the same method as that described for example 118, as a colourless oil in 51% yield.

$^1$HNMR(400 MHz, CDCl$_3$) δ: 1.04 (s, 6H), 1.22-1.33 (m, 2H), 2.46-2.57 (m, 2H), 3.43-3.55 (m, 2H), 3.92-4.00 (m, 2H), 4.75-4.86 (m, 1H), 5.72-5.82 (br m, 1H), 6.35-6.48 (m, 3H), 6.83-6.92 (m, 1H), 7.20-7.38 (m, 10H); LRMS APCI m/z 463 [M+H]$^+$

EXAMPLE 138

5-[3-(4-Chloro-3-hydroxy-benzyloxy)-azetidin-1-yl]-5-methyl-2,2-diphenyl-hexanoic acid amide

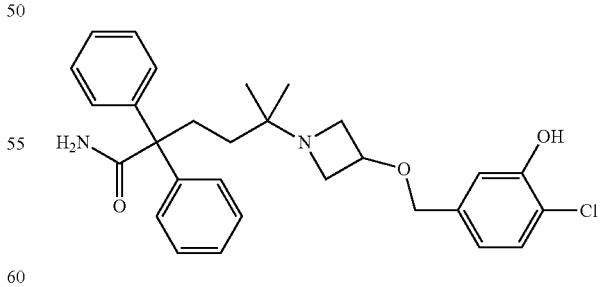

The title compound was prepared from the product of preparation 86, using the same method as that described for example 115, as a colourless oil in 37% yield.

$^1$HNMR(400 MHz, CDCl$_3$) δ: 0.88 (s, 6H), 1.15-1.20 (m, 2H), 2.38-2.45 (m, 2H), 3.00-3.08 (m, 2H), 3.26-3.36 (m,

2H), 4.03-4.15 (m, 1H), 4.27 (s, 2H), 5.55-5.80 (br m, 2H), 6.73-6.78 (m, 1H), 6.95 (s, 1H), 7.20-7.38 (m, 11H); LRMS APCI m/z 493 [M+H]+

EXAMPLE 139

4-{1-[3-(4-Chloro-3-hydroxy-phenoxy)-azetidin-1-yl]-cyclopentyl}-2,2-diphenyl-butyramide

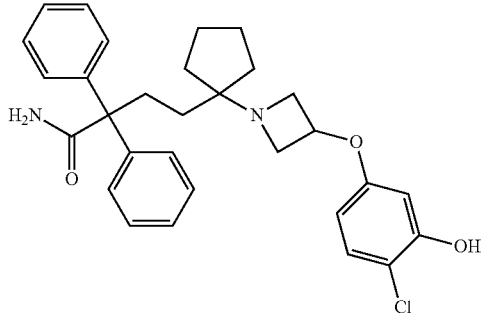 [SMILES: NC(=O)C(CCC1(N2CC(Oc3ccc(Cl)c(O)c3)C2)CCCC1)(c1ccccc1)c1ccccc1]

The title compound was prepared from the product of preparation 88, using the same method as that described for example 115, as a colourless oil in 20% yield.

$^1$HNMR(400 MHz, CDCl$_3$) δ: 1.22-1.60 (m, 8H), 1.60-1.73 (m, 2H), 2.43-2.55 (m, 2H), 3.14-3.20 (m, 2H), 3.60-3.68 (m, 2H), 4.62-4.73 (m, 1H), 5.48-5.62 (br m, 1H), 6.11-6.25 (br m, 1H), 6.26-6.35 (m, 1H), 6.36-6.40 (m, 1H), 7.15-7.38 (m, 11H); LRMS APCI m/z 505 [M+H]+

EXAMPLE 140

5-[3-(3-Bromo-5-methoxy-phenoxy)-azetidin-1-yl]-5-methyl-2,2-diphenyl-hexanenitrile

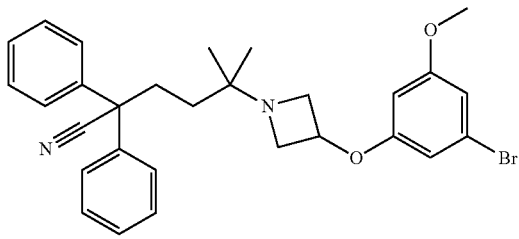 [SMILES: COc1cc(Br)cc(OC2CN(C(C)(C)CCC(C#N)(c3ccccc3)c3ccccc3)C2)c1]

The title compound was prepared from the product of preparation 57 and the product of preparation 89, using a similar method to that described for example 99, in 90% yield.

$^1$HNMR(400 MHz, CDCl$_3$) δ: 0.95 (s, 6H), 1.33-1.40 (m, 2H), 2.42-2.53 (m, 2H), 3.06-3.18 (m, 2H), 3.38-3.50 (m, 2H), 3.75 (s, 3H), 4.60-4.66 (m, 1H), 6.25 (s, 1H), 6.48 (s, 1H), 6.67 (s, 1H), 7.24-7.46 (m, 10H); LRMS ESI m/z 519 [M+H]+

EXAMPLE 141

5-[3-(3-Bromo-5-methoxy-phenoxy)-azetidin-1-yl]-5-methyl-2,2-diphenyl-hexanoic acid amide

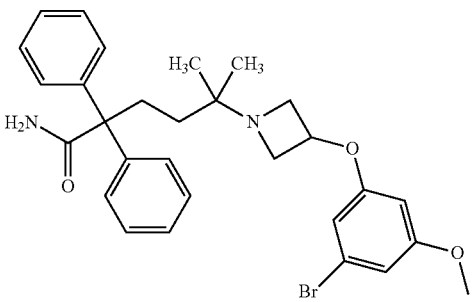 [SMILES: COc1cc(Br)cc(OC2CN(C(C)(C)CCC(C(N)=O)(c3ccccc3)c3ccccc3)C2)c1]

The title compound was prepared from the product of example 140, using the same method as that described for example 100, as a colourless oil in 80% yield.

$^1$HNMR(400 MHz, CDCl$_3$) δ: 0.92 (s, 6H), 1.12-1.18 (m, 2H), 2.38-2.46 (m, 2H), 3.05-3.13 (m, 2H), 3.37-3.44 (m, 2H), 3.75 (s, 3H), 4.56-4.63 (m, 1H), 5.45-5.58 (br m, 1H), 5.95-6.08 (br m, 1H), 6.23 (s, 1H), 6.48 (s, 1H), 6.65 (s, 1H), 7.20-7.40 (m, 10H); LRMS ESI m/z 539 [M+H]+

EXAMPLE 142

5-[3-(3-Bromo-5-hydroxy-phenoxy)-azetidin-1-yl]-5-methyl-2,2-diphenyl-hexanoic acid amide

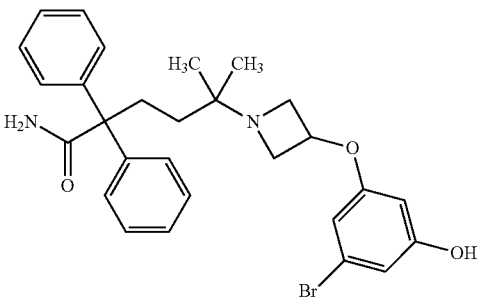 [SMILES: CC(C)(CCC(C(N)=O)(c1ccccc1)c1ccccc1)N1CC(Oc2cc(O)cc(Br)c2)C1]

The title compound was prepared from the product of example 141, using the same method as that described for example 114, as a colourless foam in 27% yield.

$^1$HNMR(400 MHz, CDCl$_3$) δ: 0.95 (s, 6H), 1.18-1.25 (m, 2H), 2.38-2.46 (m, 2H), 3.19-3.26 (m, 2H), 3.55-3.63 (m, 2H), 4.60-4.66 (m, 1H), 5.45-5.58 (br m, 1H), 6.13 (s, 1H), 6.20-6.35 (br m, 1H), 6.48 (s, 1H), 6.65 (s, 1H), 7.20-7.35 (m, 10H); LRMS ESI m/z 525 [M+H]+

EXAMPLE 143

4-{1-[3-(3-Fluoro-4-methoxy-phenoxy)-azetidin-1-yl]-cyclopentyl}-2,2-diphenyl-butyronitrile

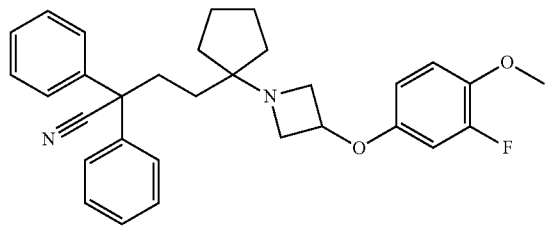 [SMILES: COc1ccc(OC2CN(C3(CCC(C#N)(c4ccccc4)c4ccccc4)CCCC3)C2)cc1F]

The title compound was prepared from the product of preparation 84 and 3-fluoro-4-methoxyphenol (J. Het. Chem., 1989, 26, 1547) using a similar method to that described for example 99, in 75% yield.

$^1$HNMR(400 MHz, CDCl$_3$) δ: 1.25-1.39 (m, 2H), 1.40-1.65 (m, 6H), 1.65-1.77 (m, 2H), 2.47-2.58 (m, 2H), 3.12-3.22 (m, 2H), 3.46-3.57 (m, 2H), 3.77 (s, 3H), 4.66-4.74 (m, 1H), 6.27-6.33 (m, 1H), 6.35-6.43 (m, 1H), 6.94-7.03 (m, 1H), 7.24-7.48 (m, 10H); LRMS ESI m/z 485 [M+H]$^+$

EXAMPLE 144

4-{1-[3-(3-Fluoro-4-methoxy-phenoxy)-azetidin-1-yl]-cyclopentyl}-2,2-diphenyl-butyramide

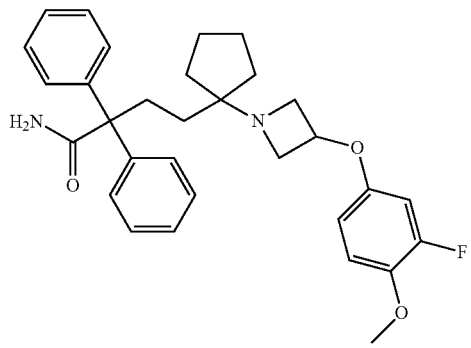 [SMILES: COc1ccc(OC2CN(C3(CCC(C(N)=O)(c4ccccc4)c4ccccc4)CCCC3)C2)cc1F]

The title compound was prepared from the product of example 143, using the same method as that described for example 100, as a colourless foam in 65% yield.

$^1$HNMR(400 MHz, CDCl$_3$) δ: 1.20-1.37 (m, 4H), 1.39-1.58 (m, 4H), 1.58-1.67 (m, 2H), 2.40-2.53 (m, 2H), 3.06-3.15 (m, 2H), 3.46-3.53 (m, 2H), 3.75 (s, 3H), 4.60-4.71 (m, 1H), 5.50-5.67 (br m, 1H), 6.17-6.38 (m, 3H), 6.88-6.98 (m, 1H), 7.18-7.40 (m, 10H); LRMS APCI m/z 503 [M+H]$^+$

EXAMPLE 145

4-{1-[3-(3-Fluoro-4-hydroxy-phenoxy)-azetidin-1-yl]-cyclopentyl}-2,2-diphenyl-butyramide

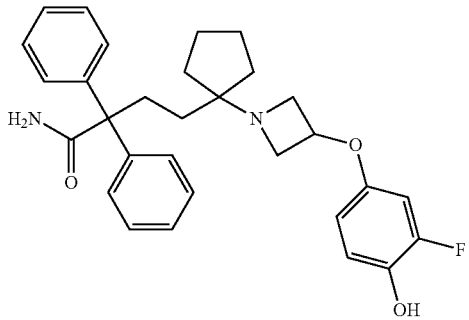 [SMILES: NC(=O)C(CCC1(N2CC(Oc3ccc(O)c(F)c3)C2)CCCC1)(c1ccccc1)c1ccccc1]

The title compound was prepared from the product of example 144, using a similar method to that described for example 114, as a colourless foam in 25% yield.

$^1$HNMR(400 MHz, CDCl$_3$) δ: 1.31-1.47 (m, 6H), 1.48-1.62 (m, 2H), 1.64-1.78 (m, 2H), 2.43-2.54 (m, 2H), 3.27-3.37 (m, 2H), 3.76-3.85 (m, 2H), 4.75-4.84 (m, 1H), 5.44-5.56 (br m, 1H), 6.22-6.28 (m, 1H), 6.38-6.44 (m, 1H), 6.84-7.00 (m, 2H), 7.16-7.34 (m, 10H).

EXAMPLE 146

5-[3-(3-Chloro-4-hydroxy-benzyloxy)-azetidin-1-yl]-5-methyl-2,2-diphenyl-hexanoic acid amide

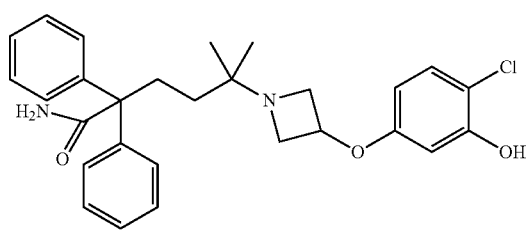 [SMILES: CC(C)(CCC(C(N)=O)(c1ccccc1)c1ccccc1)N1CC(Oc2ccc(Cl)c(O)c2)C1]

The product of preparation 94(100 mg, 0.19 mmol) was dissolved in tetrahydrofuran (10 mL) and sodium borohydride (47 mg, 1.2 mmol) and tetrakis(triphenylphosphine)palladium(0) (22 mg, 0.02 mmol) were added. After stirring at 45° C. for 30 minutes, the reaction was cooled to room temperature and quenched with a few drops of glacial acetic acid. The reaction was basified with saturated sodium hydrogen carbonate solution. The organics were extracted with ethyl acetate (20 mL) the organic solution was dried over magnesium sulfate and concentrated in vacuo. Purification of the residue by column chromatography on silica gel, eluting with dichloromethane:methanol:0.88 ammonia, 100:0:0 to 95:5:0.5, afforded the title compound in 38% yield, 35 mg.

$^1$HNMR(400 MHz, CDCl$_3$) δ: 0.90 (s, 6H), 1.12-1.20 (m, 2H), 2.38-2.45 (m, 2H), 2.98-3.07 (m, 2H), 3.28-3.39 (m, 2H), 4.06-4.15 (m, 1H), 4.26 (s, 2H), 5.53-5.65 (br m, 2H), 6.88-6.95 (m, 1H), 7.02-7.06 (m, 1H), 7.20-7.37 (m, 11H); LRMS APCI m/z 493 [M+H]+

EXAMPLE 147

5-[3-(4-Chloro-2-hydroxy-benzyloxy)-azetidin-1-yl]-5-methyl-2,2-diphenyl-hexanoic acid amide

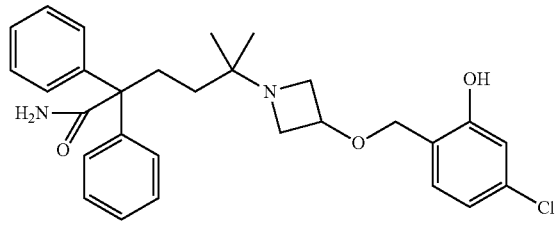 [SMILES: CC(C)(CCC(C(N)=O)(c1ccccc1)c1ccccc1)N1CC(OCc2ccc(Cl)cc2O)C1]

The title compound was prepared from the product of preparation 98 using a similar method to that described for example 146, in 19% yield.
$^1$HNMR(400 MHz, CDCl$_3$) δ: 0.92 (s, 6H), 1.12-1.20 (m, 2H), 2.40-2.46 (m, 2H), 3.04-3.15 (m, 2H), 3.35-3.43 (m, 2H), 4.13-4.20 (m, 1H), 4.47 (s, 2H), 5.56-5.74 (br m, 2H), 6.75-6.80 (m, 1H), 7.03 (s, 1H), 7.08-7.14 (m, 1H), 7.23-7.38 (m, 10H); LRMS ESI m/z 493 [M+H]+

EXAMPLE 148

5-[3-(2-Chloro-3-hydroxy-benzyloxy)-azetidin-1-yl]-5-methyl-2,2-diphenyl-hexanoic acid amide

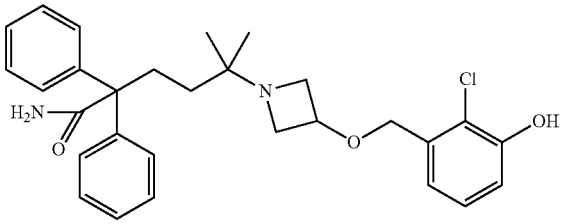 [SMILES: CC(C)(CCC(C(N)=O)(c1ccccc1)c1ccccc1)N1CC(OCc2cccc(O)c2Cl)C1]

The title compound was prepared from the product of preparation 103 using a similar method to that described for example 128, in 25% yield.
$^1$HNMR(400 MHz, CDCl$_3$) δ: 0.95 (s, 6H), 1.12-1.24 (m, 2H), 2.38-2.45 (m, 2H), 3.02-3.12 (m, 2H), 3.28-3.39 (m, 2H), 4.13-4.20 (m, 1H), 4.45 (s, 2H), 5.37-5.60 (br m, 2H), 6.94-6.99 (m, 2H), 7.12-7.18 (m, 1H), 7.20-7.40 (m, 10H); LRMS APCI m/z 493 [M+H]+

EXAMPLE 149

5-[3-(3,5-Dihydroxy-phenoxy)-azetidin-1-yl]-5-methyl-2,2-diphenyl-hexanoic acid amide

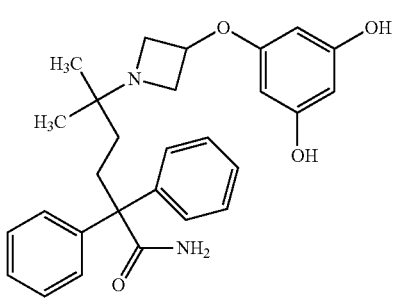 [SMILES: CC(C)(CCC(C(N)=O)(c1ccccc1)c1ccccc1)N1CC(Oc2cc(O)cc(O)c2)C1]

1,3,5-trihydroxybenzene dihydrate (10 g, 79 mmol) was placed in a round bottomed flask equipped with a Dean Stark trap and dehydrated using 23 mL toluene. After removal of the water and concentration in vacuo, the dry phenol was isolated as a white solid.

A mixture of caesium carbonate (107 mg, 0.33 mmol) and anhydrous 1,3,5-trihydroxybenzene (125 mg, 0.99 mmol) in N,N-dimethylformamide (3 mL) was stirred at 80° C. for 10 minutes. The product of preparation 104 (142 mg, 0.33 mmol) was added and the reaction mixture was stirred at 80° C. for 10 minutes. The crude material was partitioned between ethyl acetate (20 mL) and water (30 mL), the organic layer was separated and the aqueous re-extracted with ethyl acetate (2×20 mL). The combined organics were dried over magnesium sulphate, filtered and concentrated in vacuo. The residue was purified by column chromatography on silica gel, eluting with pentane: (90:10:1 ethyl acetate:methanol:0.88 ammonia), 100:1 to 30:70, to afford the title compound as a colourless gum in 5% yield, 7 mg.
$^1$HNMR(400 MHz, CDCl$_3$) δ: 0.95 (s, 6H), 1.20-1.28 (m, 2H), 2.35-2.48 (m, 2H), 3.15-3.24 (m, 2H), 3.52-3.60 (m, 2H), 4.48-4.58 (m, 1H), 5.62-5.65 (br s, 1H), 5.78 (s, 2H), 6.06 (s, 1H), 6.35-6.40 (br s, 1H), 7.15-7.28 (m, 10H); LRMS APCI m/z 461[M+H]+

EXAMPLE 150

5-[3-(3-Hydroxy-phenoxy)-azetidin-1-yl]-5-methyl-2,2-diphenyl-hexanenitrile

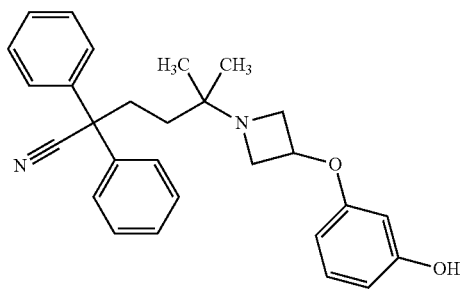 [SMILES: CC(C)(CCC(C#N)(c1ccccc1)c1ccccc1)N1CC(Oc2cccc(O)c2)C1]

The title compound was prepared from the product of preparation 105, using the same method as that described in example 109, as a colourless oil in 73% yield.
$^1$HNMR(400 MHz, CDCl$_3$) δ: 0.98 (s, 6H), 1.35-1.40 (m, 2H), 2.42-2.48 (m, 2H), 3.16-3.22 (m, 2H), 3.45-3.57 (m, 2H), 4.64-4.72 (m, 1H), 6.25 (s, 1H), 6.30-6.35 (m, 1H), 6.42-6.48 (m, 1H), 7.05-7.15 (m, 1H), 7.25-7.42 (m, 10H); LRMS APCI m/z 427 [M+H]+

EXAMPLE 151

5-{3-[(4-Hydroxybenzyl)oxy]azetidin-1-yl}-5-methyl-2,2-diphenylhexanenitrile

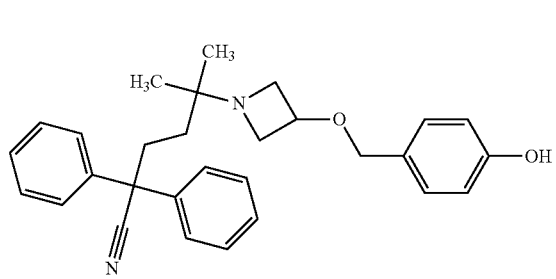 [SMILES: CC(C)(CCC(C#N)(c1ccccc1)c1ccccc1)N1CC(OCc2ccc(O)cc2)C1]

The title compound was prepared from the products of preparations 56 and 66, using the same method as that described for example 101, in 15% yield.

$^1$HNMR(400 MHz, CDCl$_3$) δ: 0.95(s, 6H), 1.32-1.40(m, 2H), 2.40-2.48(m, 2H), 3.04-3.08(m, 2H), 3.26-3.35(m, 2H), 4.05-4.15(m, 1H), 4.32(s, 2H), 6.72-6.76(m, 2H), 7.10-7.15 (m, 2H), 7.18-7.46(m, 10H)

EXAMPLE 152

5-[3-(4-Hydroxy-benzyloxy)-azetidin-1-yl]-5-methyl-2,2-diphenyl-hexanoic acid amide

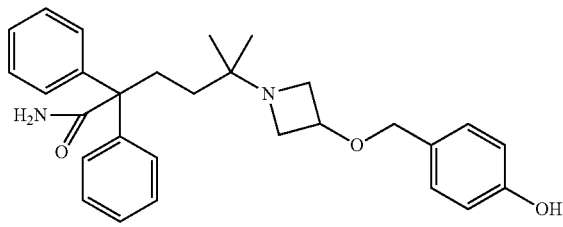 [SMILES: CC(C)(CCC(C(N)=O)(c1ccccc1)c1ccccc1)N1CC(OCc2ccc(O)cc2)C1]

The title compound was prepared from the product of preparation 108 using a similar method to that described for example 146, in 53% yield.

$^1$HNMR(400 MHz, MeOD) δ: 0.95 (s, 6H), 1.23-1.28 (m, 2H), 2.35-2.45 (m, 2H), 2.96-3.05 (m, 2H), 3.22-3.28 (m, 2H), 4.01-4.18 (m, 1H), 4.30 (s, 2H), 5.55-5.65 (br s, 2H), 6.70-6.75 (m, 2H), 7.05-7.12 (m, 2H), 7.20-7.35 (m, 10H); LRMS ESI m/z 459 [M+H]$^+$

Potency Assay

M$_3$ potency was determined in CHO-K1 cells transfected with the NFAT-Betalactamase gene. CHO (Chinese Hamster Ovary) cells recombinantly expressing the human muscarinic M$_3$ receptor were transfected with the NFAT_β-Lac_Zeo plasmid. Cells were grown in DMEM with Glutamax-1, supplemented with 25 mM HEPES (Life Technologies 32430-027), containing 10% FCS (Foetal Calf Serum; Sigma F-7524), 1 nM Sodium pyruvate (Sigma S-8636), NEAA (non-Essential Amino Acids; Invitrogen 11140-035) and 200 µg/ml Zeocin (Invitrogen R250-01).

hM$_3$ β-Lac Assay Protocol

Cells were harvested for assay when they reached 80-90% confluency using enzyme free cell Dissociation Solution (Life technologies 13151-014) incubated with the cells for 5 min at 37° C. in an atmosphere containing 5% CO$_2$. Detached cells were collected in warmed growth media and centrifuged at 2000 rpm for 10 min, washed in PBS (Phosphate Buffered Saline; Life Technologies 14190-094) and centrifuged again as just described. The cells were re-suspended at 2×10$^5$ cells/ml in growth medium (composition as described above). 200 of this cell suspension was added to each well of a 384 well black clear bottomed plate (Greiner Bio One 781091-PFI). The assay buffer used was PBS supplemented with 0.05% Pluronic F-127 (Sigma 9003-11-6) and 2.5% DMSO. Muscarinic M$_3$ receptor signalling was stimulated using 80 nM carbamyl choline (Aldrich N240-9) incubated with the cells for 4 h at 37° C./5% CO$_2$ and monitored at the end of the incubation period using a Tecan SpectraFluor+plate reader (λ-excitation 405 nm, emission 450 nm and 503 nm). M$_3$ receptor antagonists under test were added to the assay at the beginning of the 4 h incubation period and compound activity measured as the concentration dependent inhibition of the carbamyl choline induced signal. Inhibition curves were plotted and IC$_{50}$ values generated using a 4-parameter sigmoid fit and converted to Ki values using the Cheng-Prusoff correction and the K$_D$ value for carbamyl choline in the assay.

It has thus been found that carboxamide derivatives of formula (I) according to the present invention that have been tested in the above assay show M$_3$ receptor antagonist activity as listed in the table below:

| Example Number | Cell based β-lactamase M$_3$ Ki (nM) |
|---|---|
| 1 | 8.34 |
| 2 | 0.251 |
| 4 | 1.55 |
| 6 | 1.02 |
| 7 | 0.212 |
| 9 | 1.87 |
| 11 | 3.27 |
| 12 | 0.300 |
| 13 | 0.512 |
| 14 | 1.32 |
| 15 | 4.25 |
| 16 | 1.85 |
| 17 | 5.11 |
| 18 | 6.96 |
| 19 | 5.56 |
| 20 | 108 |
| 21 | 0.155 |
| 23 | 0.762 |
| 24 | 20.7 |
| 26 | 1.67 |
| 28 | 47.4 |
| 29 | 2.26 |
| 30 | 0.333 |
| 31 | 45.1 |
| 32 | 36.4 |
| 34 | 6.57 |
| 35 | 7.28 |
| 36 | 17.6 |
| 37 | 5.01 |
| 38 | 0.996 |
| 39 | 1.97 |
| 40 | 6.09 |
| 42 | 22.1 |
| 43 | 5.35 |
| 44 | 32.2 |
| 46 | 1.74 |
| 49 | 48.5 |
| 50 | 3.18 |
| 51 | 0.623 |
| 52 | 2.16 |
| 53 | 0.334 |
| 54 | 3.62 |
| 58 | 1580 |
| 61 | 9.85 |
| 62 | 57.4 |
| 63 | 28.7 |
| 64 | 65.6 |
| 65 | 62.7 |
| 66 | 45.4 |
| 67 | 10.7 |
| 68 | 9.88 |
| 69 | 111 |
| 70 | 19.1 |
| 71 | 113 |
| 72 | 1.23 |
| 73 | 0.852 |
| 74 | <0.560 |
| 76 | 0.582 |
| 77 | 4.96 |
| 78 | 0.917 |
| 79 | 16.2 |
| 81 | 35.4 |
| 82 | 7.96 |
| 83 | 30.0 |
| 84 | 6.97 |
| 85 | 3.19 |
| 86 | 1.26 |

-continued

| Example Number | Cell based β-lactamase $M_3$ Ki (nM) |
|---|---|
| 88 | 71.9 |
| 89 | 159 |
| 90 | 0.268 |
| 91 | 22.6 |
| 92 | 2.13 |
| 93 | 26.8 |
| 94 | 12.4 |
| 95 | 2.25 |
| 96 | 6.51 |
| 98 | 139 |
| 99 | 65.7 |
| 100 | 0.430 |
| 102 | 0.0636 |
| 104 | 0.0488 |
| 105 | 1.94 |
| 107 | 0.132 |
| 108 | 0.201 |
| 109 | 10.8 |
| 110 | 7.33 |
| 111 | 76.9 |
| 113 | 7.22 |
| 114 | 1.94 |
| 115 | 0.176 |
| 118 | 40.7 |
| 121 | 0.604 |
| 124 | 0.223 |
| 127 | 110 |
| 128 | 8.19 |
| 131 | 0.728 |
| 134 | 0.258 |
| 137 | 0.713 |
| 138 | 0.468 |
| 139 | 5.39 |
| 142 | 8.05 |
| 145 | 10.8 |
| 146 | 0.247 |
| 147 | 33.4 |
| 148 | 0.353 |
| 149 | 0.714 |
| 150 | 1.05 |
| 151 | 0.191 |
| 152 | 0.229 |

Guinea Pig Trachea Assay

Male, Dunkin-Hartley guinea-pigs weighing 350-450 g are culled in a rising concentration of $CO_2$, followed by exsanguinations of the vena cava. Tracheas are dissected from the larynx to the entry point into the chest cavity and then placed in fresh, oxygenated, modified Krebs buffer solution (Krebs containing 10 μM propranolol, 10 μM guanethidine and 3 μM indomethacin) at room temperature. The tracheas are opened by cutting through the cartilage opposite the trachealis muscle. Strips approximately 3-5 cartilage rings wide are cut. A cotton thread is attached to the cartilage at one end of the strip for attachment to the force transducer and a cotton loop made at the other end to anchor the tissue in the organ bath. The strips are mounted in 5 ml organ baths filled with warm (37° C.) aerated modified Krebs. The pump flow rate is set to 1.0 ml/min and the tissues washed continuously. Tissues are placed under an initial tension of 1000 mg. Tissues are re-tensioned after 15 and 30 minutes, then allowed to equilibrate for a further 30-45 minutes. Tissues are subjected to electrical field stimulation (EFS) of the following parameters: 10 s trains every 2 minutes, 0.1 ms pulse width, 10 Hz and 10-30V. The voltage is raised 5V every 10 min within the stated range until a maximum contractile response for each tissue is observed. This just maximum voltage for each tissue is then used throughout the remainder of the experiment. Following equilibration to EFS for 20 min, the pump is stopped, and after 15 min control readings are taken over a 8-10 min period (4-5 responses). Compound is then added to each tissue as a bolus dose at 30 xKi (determined at the human $M_3$ receptor expressed in CHO cells in a filtration binding assay), and left to incubate for 2 h. Compound is then washed from tissues using a rapid wash with modified Krebs for 1 min and flow is restored to 1 ml/min for the remainder of the experiment. At the end of the experiment tissues are challenged with histamine (10/1) to determine viability. Readings taken during the experiment are automatically collected using Notocord® software. The raw data are converted into percent response taking into account measurements of inhibition of the EFS response. After starting washout, the times taken for the tissue to recover by 25% from the inhibition induced are recorded and used as a measure of compound duration of action. Tissue viability limits the duration of the experiment to 16 h post-compound washout. Compounds are typically tested at n=2 to 5 to estimate duration of action.

Alternatively the Following Guinea Pig Trachea Assay can Also be Used:

Trachea were removed from male Dunkin-Hartley guinea-pigs (wt 350-450 g) and following removal of adherent connective tissue, an incision was made through the cartilage opposite the trachealis muscle and tracheal strips 3-5 cartilage rings wide prepared. The tracheal strips were suspended between an isometric strain gauge and a fixed tissue hook with the muscle in the horizontal plane in 5 ml tissue baths under an initial tension of 1 g and bathed in warmed (37° C.) aerated (95% $O_2$ 15% $CO_2$) Krebs solution containing 3 μM indomethacin and 10 μM guanethidine. The tissues were positioned between parallel platinum wire electrodes (~1 cm gap). A constant 1 ml/min flow of fresh Krebs solution (of the above composition) was maintained through the tissue baths using peristaltic pumps. The tissues were allowed to equilibrate for an hour with re-tensioning to 1 g at 15 min and 30 min from the start of the equilibration period. At the end of the equilibration, tissues were electrically field stimulated (EFS) using the following parameters: 10 y, 10 Hz 0.1 ms pulse width with 10 sec trains every 2 min. In each tissue a voltage response curve was constructed over the range 10 v-30V (keeping all other stimulation parameters constant) to determine a just maximal stimulation. Using these stimulation parameters EFS responses were 100% nerve mediated and 100% cholinergic as confirmed by blockade by 1 μM tetrodotoxin or 1 μM atropine. Tissues were then repeatedly stimulated at 2 min intervals until the responses were reproducible. The peristaltic pump was stopped 20 min prior to the addition of the study compound and the average twitch contraction over the last 10 min recorded as the control response. The study compound was added to the tissue baths, with each tissue receiving a single concentration of compound and allowed to equilibrate for 2 h. At 2 h post addition the inhibition of the EFS response was recorded and $IC_{50}$ curves generated using a range of compound concentrations over tracheal strips from the same animal. The tissues were then rapidly washed and the 1 ml/min perfusion with Krebs solution re-established. Tissues were stimulated for a further 16 h and recovery of the EFS response recorded. At the end of the 16 h, 10 μM histamine was added to the baths to confirm tissue viability. The just max concentration (tested concentration giving a response >70% inhibition but less than 100%) of antagonist was identified from the $IC_{50}$ curve and the time to 25% recovery of the induced inhibition ($T_{25}$) calculated in tissues receiving this concentration. Compounds are typically tested at n=2 to 5 to estimate duration of action.

What is claimed is:

1. A kit comprising
   a) a pharmaceutical composition comprising a combination of a compound of formula (I):

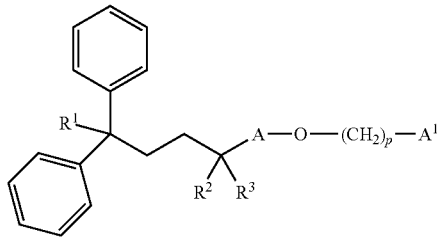

or a pharmaceutically acceptable salt thereof, wherein:
   $R^1$ is CN or $CONH_2$;
   A is selected from

wherein * and  represent the attachment points,  being linked to the oxygen,
   $R^2$ and $R^3$ are methyl or where A is a group of formula

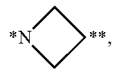

$R^2$ and $R^3$ may also together form with the carbon atom to which they are linked a cyclopentane ring;
   p is 0 or 1;
   $A^1$ is selected from
   a) phenyl optionally substituted with 1, 2 or 3 groups independently selected from halo, CN, $CF_3$, $OR^4$, $SR^4$, $OCF_3$, $(C_1-C_4)$alkyl and phenyl optionally substituted with OH;
   b) naphthyl optionally substituted with 1 or 2 groups selected from halo, CN, $CF_3$, $OR^4$, $SR^4$, $OCF_3$ and $(C_1-C_4)$alkyl;
   c) a 9 or 10-membered bicyclic aromatic heterocyclic group, containing from 1, 2 or 3 heteroatoms independently selected from O, S or N, said heterocyclic group being optionally substituted with 1 or 2 substituents independently selected from $OR^4$, $(C_1-C_4)$ alkyl and halo; and
   $R^4$ is H or $(C_1-C_4)$alkyl;
   and a pharmaceutically acceptable carrier or diluent; and
   b) a pharmaceutical composition comprising a long acting $\beta_2$ agonist selected from the group consisting of: salbutamol, terbutaline, bambuterol, fenoterol, salmeterol, formoterol, tulobuterol or a salt thereof and a pharmaceutically acceptable carrier or diluent.

2. A kit of claim 1 wherein the compound of formula (I) is 5-[3-(3-Hydroxyphenoxy)azetidin-1-yl]-5-methyl-2,2-diphenylhexanamide, having the structure:

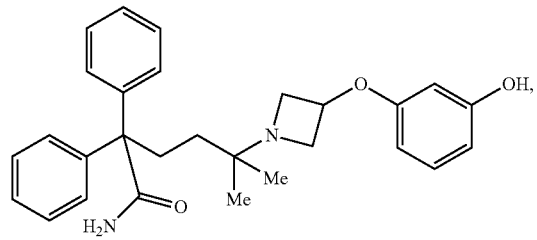 [SMILES: CC(C)(CCC(C(N)=O)(c1ccccc1)c1ccccc1)N1CC(Oc2cccc(O)c2)C1]

or a pharmaceutically acceptable salt thereof.

3. A method of treating asthma or chronic obstructive pulmonary disease (COPD) in a mammal in need thereof, said method comprising administering to said mammal an effective amount of a kit of claim 1.

4. A method of treating asthma or chronic obstructive pulmonary disease (COPD) in a mammal in need thereof, said method comprising administering to said mammal an effective amount of a kit of claim 2.

* * * * *